United States Patent
Nishino et al.

(10) Patent No.: US 8,658,686 B2
(45) Date of Patent: Feb. 25, 2014

(54) PYRAZOLE COMPOUNDS HAVING THERAPEUTIC EFFECT ON MULTIPLE MYELOMA

(75) Inventors: Taito Nishino, Chiyoda-ku (JP); Katsuaki Miyaji, Chiyoda-ku (JP); Shunsuke Iwamoto, Funabashi (JP); Takumi Mikashima, Funabashi (JP); Koichiro Saruhashi, Funabashi (JP); Yo Kishikawa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/991,024

(22) PCT Filed: Dec. 1, 2011

(86) PCT No.: PCT/JP2011/077829
§ 371 (c)(1),
(2), (4) Date: May 31, 2013

(87) PCT Pub. No.: WO2012/074067
PCT Pub. Date: Jun. 7, 2012

(65) Prior Publication Data
US 2013/0253204 A1  Sep. 26, 2013

(30) Foreign Application Priority Data

Dec. 1, 2010 (JP) ................................ 2010-268758
Sep. 30, 2011 (JP) ................................ 2011-217818

(51) Int. Cl.
*A61K 31/415* (2006.01)
*C07D 231/10* (2006.01)

(52) U.S. Cl.
USPC ...................... 514/407; 548/357.5; 548/366.1

(58) Field of Classification Search
USPC .............................. 548/357.5, 366.1; 514/407
See application file for complete search history.

(56) References Cited

U.S. PATENT DOCUMENTS

| 2002/0111353 A1 | 8/2002 | Ledeboer et al. |
| 2009/0093444 A1 | 4/2009 | Black et al. |

FOREIGN PATENT DOCUMENTS

| JP | 62 77371 | 4/1987 |
| WO | 01 85685 | 11/2001 |
| WO | 02 46184 | 6/2002 |
| WO | 2007 003056 | 1/2007 |
| WO | 2008 073825 | 6/2008 |

OTHER PUBLICATIONS

Kumar, S.K. et al., "Improved survival in multiple myeloma and the impact of novel therapies", Blood, vol. 111, No. 5, pp. 2516 to 2520, (Mar. 1, 2008).
Palumbo, A., et al., "How to treat elderly patients with multiple myeloma: combination of therapy or sequencing", American Society of Hematology, Hematology, pp. 566 to 575, (2009).
Stewart, A. K., "Novel therapies for relapsed myeloma", American Society of Hematology, Hematology, pp. 578 to 586, (2009).
Kuhn, D. et al., "Potent activity of carfilzomib, a novel, irreversible inhibitor of the ubiquitin-proteasome pathway, against preclinical models of multiple myeloma", Blood, vol. 110, No. 9, pp. 3281 to 3290, (Nov. 1, 2007).
Badros, A. et al., "Phase I Study of Vorinostat in Combination with Bortezomib for Relapsed and Refractory Multiple Myeloma", Clin. Cancer Res. vol. 15, No. 16, pp. 5250 to 5257, (Aug. 15, 2009).
Pirkle, W.H. et al., "Persistent Cyclic Diacylhydrazyl Radicals from Urazoles and Pyrazolidine-3,5-diones", J. Org. Chem., American Chemical Society, vol. 43, No. 5, pp. 808 to 815, (1978).
Kluge, R. et al., "Radikalreaktionen cyclischer 1,2-Diacylhydrazine", Chemische Berichte, vol. 125, pp. 2075 to 2079, (1992).
Khimiya Geterotsiklicheskikh Soedinenii, vol. 5, p. 710, (1988).
International Search Report Issued Jan. 24, 2012 in PCT/JP11/77829 Filed Dec. 1, 2011.
U.S. Appl. No. 13/990,959, filed May 31, 2013, Nishino, et al.

*Primary Examiner* — Samantha Shterengarts
(74) *Attorney, Agent, or Firm* — Oblon, Spivak, McClelland, Maier & Neustadt, L.L.P.

(57) ABSTRACT

Novel therapeutic agents for myeloma are provided.
A therapeutic agent for multiple myeloma containing a pyrazole compound represented by the formula (1):

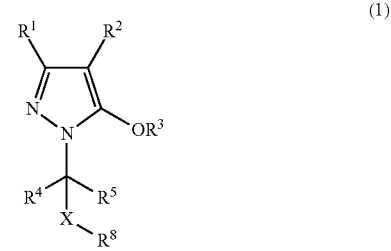

(1)

wherein $R^1$ is $C_1$-$C_6$ alkyl, $C_1$-$C_6$ alkyl substituted with $R^{17}$, $C_1$-$C_6$ haloalkyl, phenyl, phenyl substituted with a $R^{11}$'s or the like, $R^2$ is a hydrogen atom, $C_1$-$C_6$ alkyl, phenyl or phenyl optionally substituted with e $R^{21}$'s or the like, $R^3$ is a hydrogen atom or the like, X is a single bond or —$(CR^6R^7)_n$—, each of $R^4$ and $R^5$ is independently $C_1$-$C_6$ alkyl or the like, $R^6$ and $R^7$ are hydrogen atoms or $C_1$-$C_6$ alkyl, $R^8$ is phenyl, phenyl optionally substituted with k $R^{81}$'s or the like, a tautomer of the compound or a pharmaceutically acceptable salt or solvate thereof, as an active ingredient.

10 Claims, No Drawings

PYRAZOLE COMPOUNDS HAVING THERAPEUTIC EFFECT ON MULTIPLE MYELOMA

TECHNICAL FIELD

The present invention relates to pyrazole compounds having growth inhibitory activity on multiple myeloma cells and therapeutic agents for myeloma using the compounds.

BACKGROUND ART

Multiple myeloma is a tumor resulting from malignant transformation of plasma cells, immunocytes in the bone marrow due to genetic abnormalities or the like. These malignant plasma cells (myeloma cells) migrate through the bloodstream and accumulate in the bone marrow where they proliferate, causing bone damage, hypercalcemia, renal failure, anemia, neuropathy and infections. Bone damage is caused by rapid proliferation of myeloma cells and resorption and breakdown of bones by osteoclasts stimulated by interleukin-6 (IL-6) which is released by myeloma cells. Bone damage can also cause the level of calcium in the bloodstream to rise, a condition called hypercalcemia. Hypercalcemia injures the kidneys, resulting in reduced calcium excretion, increased urine production and the potential for dehydration. As myeloma cells crowd out normal cells in the bone marrow, the production of normal blood cells is also impaired. A reduction in leukocyte count can increase the high risk of infections due to immunodeficiency, and decreased erythrocyte counts can result in anemia. A reduction in platelets can prevent normal blood clotting. In addition, excess globulin and light chain proteins produced by myeloma cells can thicken the blood (hyperviscosity syndrome) and can cause circulatory problems in the kidneys. These proteins can also damage the kidneys and cause acute renal failure and chronic renal failure. Invasion of myeloma cells into the spinal canal can cause pain through spinal cord compression and can progress to paralysis. Accumulation of the amyloid protein derived from the M proteins secreted from myeloma cells can injure peripheral nerves (amyloidosis). Because multiple myeloma affects many tissues and organs in patients, the symptoms and signs are variable.

As mentioned above, multiple myeloma is a lethal disease associated with various complications, and there is no treatment that results in complete and permanent recovery from the disease with no or little side effect so fart. Therefore, there is a need for new treatment methods for multiple myeloma, and treatment of multiple myeloma with low molecular weight compounds having growth inhibitory effects on myeloma cells has been studied. However, no low molecular weight compounds having satisfying therapeutic effect on multiple myeloma have been found so far (Non-Patent Documents 1 to 5).

Meanwhile, pyrazole compounds are reported to have various bioactivities, and many pyrazole-based compounds have been developed for agricultural and medicinal use (Patent Document 1 and 2 and Non-Patent Documents 6 to 8).

PRIOR ART DOCUMENT

Patent Documents

Patent Document 1: WO2001/085685
Patent Document 2: WO2008/073825

Non-Patent Documents

Non-Patent Document 1: Blood. 2008, vol. 111, p. 2516.
Non-Patent Document 2 Hematology Am. Soc. Hematol. Educ. Program. 2009, p. 566
Non-Patent Document 3: Hematology Am. Soc. Hematol. Educ. Program. 2009, p. 578
Non-Patent Document 4: Blood. 2007, vol. 110, p. 3281.
Non-Patent Document 5: Clin. Cancer Res. 2009, vol. 15, p. 5250.
Non-Patent Document 6: J. Org. Chem. 1978, vol. 43, p. 808.
Non-Patent Document 7: Chemische Berichte 1992, vol. 125, vol. 9, p. 2075
Non-Patent Document 8: Khimiya Geterotsiklicheskikh Soedinenii 1988, vol. 5, p. 710

DISCLOSURE OF THE INVENTION

Technical Problem

The object of the present invention is to solve the above-mentioned problems with prior art by providing pyrazole compounds and therapeutic agents using them against myeloma cells.

Solution to Problems

As a result of extensive studies on pyrazole compounds and inhibition of myeloma cell growth by them, the present inventors succeeded in synthesis of novel pyrazole compounds and found these compounds inhibit growth of myeloma cells. The present invention was accomplished on the basis of the discovery.

Namely, the present invention provides the following [1] to [10].

[1] A pyrazole compound represented by the formula (1):

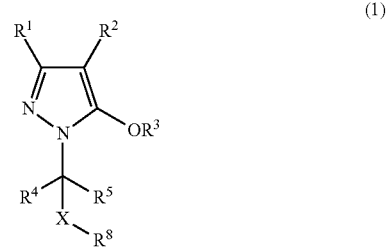

(1)

[wherein $R^1$ is a hydrogen atom, $C_1$-$C_{10}$ alkyl, $C_1$-$C_{10}$ alkyl substituted with $R^{17}$, $C_1$-$C_{10}$ haloalkyl, $C_3$-$C_{10}$ cycloalkyl, $C_3$-$C_{10}$ halocycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, C($R^{12}$)=NO$R^{13}$, D1 to D23, cyano, phenyl, phenyl substituted with a $R^{11}$'s, benzyl or benzyl having a benzene ring which may be substituted with a $R^{11}$'s, when a is an integer of at least 2, each $R^{11}$ may be identical with or different from one another, and when there are two neighboring $R^{11}$'s, the two neighboring $R^{11}$'s may form —CH$_2$CH$_2$CH$_2$—, —CH$_2$CH$_2$O—, —CH$_2$OCH$_2$—, —CH$_2$CH$_2$S—, —CH$_2$SCH$_2$—, —CH$_2$CH$_2$N($R^{3'}$)—, —CH$_2$N($R^{3'}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O, —OCH$_2$CH$_2$S—, —CH$_2$CH=CH—, —OCH=CH—, —SCH=CH—, —N($R^{3'}$)CH=CH—, —OCH=N—, —SCH=N—, —N($R^{3'}$)CH=N—, —N($R^{3'}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is a hydrogen atom, a halogen atom, cyano, $C_1$-$C_{10}$ alkyl, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, —C($R^{12}$)=NO$R^{13}$, D1 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^y$)—, —CH$_2$N($R^y$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH=CH—CH—, —OCH=CH—, —SCH=CH—, —N($R^y$)CH=CH—, —OCH=N—, —SCH=N—, —N($R^y$)CH=N—, —N($R^y$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_6$ alkyl, $C_3$-$C_6$ cycloalkyl, $C_1$-$C_6$ alkoxy$C_1$-$C_6$ alkyl, $C_2$-$C_6$ alkenyl, $C_2$-$C_6$ alkenyl optionally substituted with $R^{31}$, $C_2$-$C_6$ alkynyl, $C_2$-$C_6$ alkynyl optionally substituted with $R^{31}$, —C(O)$R^{12}$, —C(O)O$R^{12}$, —C(O)N($R^{12}$)$R^{13}$, —Si($R^{32}$)($R^{33}$)$R^{34}$, benzyl or benzyl having a benzene ring which may be substituted with g $R^{15}$'s, and when g is an integer of at least 2, each $R^{15}$ may be identical with or different from one another, X is a single bond or —(C$R^6$$R^7$)$_n$— each of $R^4$ and $R^5$ is independently $C_1$-$C_6$ alkyl or $C_3$-$C_6$ cycloalkyl, and $R^4$ and $R^5$ may form —CH$_2$CH$_2$—, —CH$_2$CH$_2$CH$_2$—, —CH$_2$CH$_2$CH$_2$CH$_2$— or —CH$_2$CH$_2$CH$_2$CH$_2$CH$_2$— to form a 3-membered, 4-membered, 5-membered or 6-membered ring together with the carbon atoms attached to $R^4$ and $R^5$, each of $R^6$ and $R^7$ is independently a hydrogen atom or $C_1$-$C_6$ alkyl, $R^8$ is D1 to D23, E1 to E8, M1 to M9, $C_3$-$C_{10}$ cycloalkyl, F1, F2, $C_3$-$C_{10}$ cycloalkenyl, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^y$)—, —CH$_2$N($R^y$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^y$)CH=CH—, —OCH=N—, —SCH=N—, —N($R^y$)CH=N—, —N($R^y$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, D1 to D23 are aromatic heterocyclic rings represented by the following structural formulae, respectively,

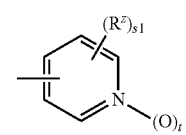

D1

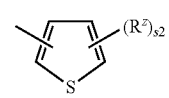

D2

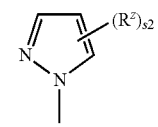

D3

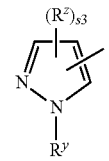

D4

D5

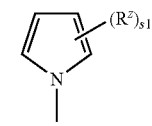

D6

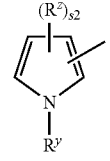

D7

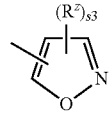

D8

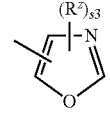

D9

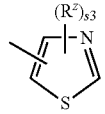

D10

-continued
D11 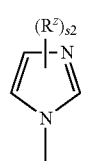
D12 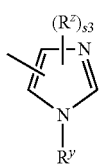
D13 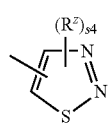
D14 
D15 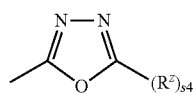
D16 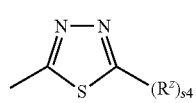
D17 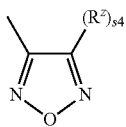
D18 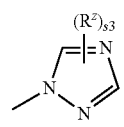
D19 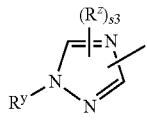
D20 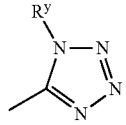
D21 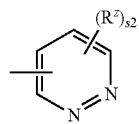
D22 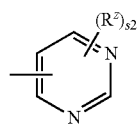
-continued
D23 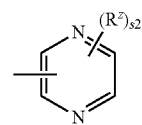
E1 to E8 are saturated heterocyclic rings represented by the following structural formulae, respectively,
E1 
E2 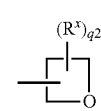
E3 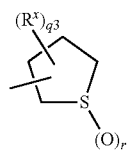
E4 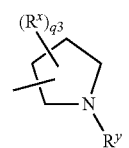
E5 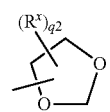
E6 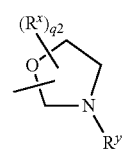
E7 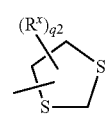
E8 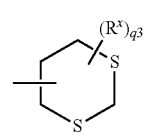
M1 to M9 are partially unsaturated aromatic heterocyclic rings represented by the following formulae, respectively,
M1 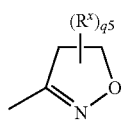

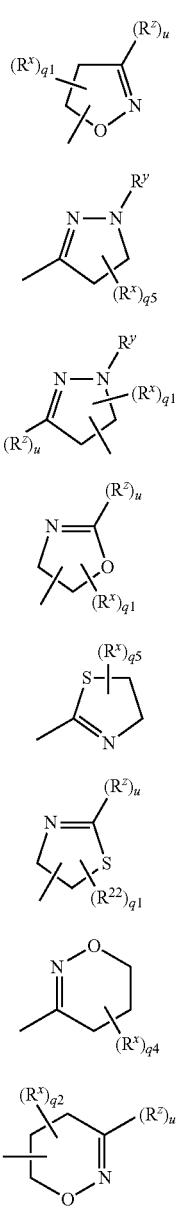

F1 to F2 are rings represented by the following formulae, respectively,

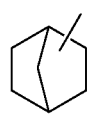

$R^x$ is a hydrogen atom, $C_1$-$C_6$ alkyl, $C_1$-$C_6$ haloalkyl, $C_3$-$C_6$ cycloalkyl, $C_3$-$C_6$ halocycloalkyl, —$OR^{82}$, —$C(O)R^{12}$, —$C(O)OR^{12}$, phenyl, phenyl which may be substituted with d $R^{15}$'s, benzyl or benzyl having a benzene ring which may be substituted with d $R^{15}$'s, and when d is an integer of at least 2, each $R^{15}$ may be identical with or different from one another, $R^y$ is $C_1$-$C_{10}$ alkyl, $C_1$-$C_{10}$ haloalkyl, $C_3$-$C_{10}$ cycloalkyl, $C_3$-$C_{10}$ halocycloalkyl, phenyl, phenyl which may be substituted with d $R^{15}$'s, benzyl or benzyl having a benzene ring which may be substituted with d $R^{15}$'s, and when d is an integer of at least 2, each $R^{15}$ may be identical with or different from one another, $R^z$ is a halogen atom, cyano, nitro, $C_1$-$C_{10}$ alkyl, $C_1$-$C_{10}$ haloalkyl, $C_1$-$C_{10}$ alkoxy, $C_1$-$C_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —$C(O)NH_2$, —$C(S)NH_2$, —$S(O)_2NH_2$, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, and when there are two neighboring $R^z$'s, the two neighboring $R^z$'s, may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH=CH$—, —$OCH=CH$—, —$SCH=CH$—, —$N(R^y)CH=CH$—, —$OCH=N$—, —$SCH=N$—, —$N(R^y)CH=N$—, —$N(R^y)N=CH$—, —$CH=CHCH=CH$—, —$OCH_2CH=CH$—, —$N=CHCH=CH$—, —$N=CHCH=N$— or —$N=CHN=CH$— to form, together with the carbon atoms attached to the two neighboring $R^z$'s, a 5-membered or 6-membered ring which may have one or more hydrogen atoms on the ring-constituting carbon atoms replaced by one or more Z's which may be identical with or different from one another, if two or more Z's are present, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, $C_1$-$C_6$ alkoxy($C_1$-$C_6$) alkyl, $C_1$-$C_6$ alkoxy($C_1$-$C_6$) alkoxy, nitro, cyano or phenyl, each of $R^{12}$ and $R^{13}$ is independently a hydrogen atom, $C_1$-$C_{10}$ alkyl, $C_3$-$C_{10}$ cycloalkyl, $C_1$-$C_{10}$ haloalkyl, $C_3$-$C_{10}$ halocycloalkyl, D1 to D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, and when there are two neighboring $R^{14}$'s, the two neighboring $R^{14}$'s may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH=CH$—, —$OCH=CH$—, —$SCH=CH$—, —$N(R^y)CH=CH$—, —$OCH=N$—, —$SCH=N$—, —$N(R^y)CH=N$—, —$N(R^y)N=CH$—, —$CH=CHCH=CH$—, —$OCH_2CH=CH$—, —$N=CHCH=CH$—, —$N=CHCH=N$— or —$N=CHN=CH$— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present, $R^{14}$ is a halogen atom, nitro, cyano, $C_1$-$C_{10}$ alkyl, $C_1$-$C_{10}$ haloalkyl, $C_1$-$C_{10}$ alkoxy, $C_1$-$C_{10}$ haloalkoxy, phenoxy or phenyl, $R^{15}$ is a halogen atom, $C_1$-$C_6$ alkyl, $C_1$-$C_6$ alkoxy, $C_1$-$C_6$ haloalkyl, $C_1$-$C_6$ haloalkoxy, $C_3$-$C_6$ cycloalkyl, $C_3$-$C_6$ cycloalkoxy, $C_3$-$C_6$ halocycloalkyl, $C_3$-$C_6$ halocycloalkoxy, nitro, cyano or phenyl, $R^{16}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, nitro, cyano or phenyl, and when there are two neighboring $R^{16}$'s, the two neighboring $R^{16}$'s may form —OCH$_2$O— to form a 5-membered ring together with the carbon atoms to the two $R^{16}$'s, $R^{17}$ is —C(O)OR$^{12}$, phenyl or phenyl substituted with a $R^{11}$'s, and when a is an integer of at least 2, each $R^{11}$ may be identical with or different from one another, $R^{21}$ is a halogen atom, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_6$ alkoxy($C_1$-$C_6$) alkyl, —OR$^{23}$, —C(O)R$^{24}$, —C(O)OR$^{24}$, —NR$^{24}$R$^{25}$, —C(O)NR$^{24}$R$^{25}$, —S(O)$_2$NR$^{24}$R$^{25}$, phenyl or phenyl which may be substituted with f $R^{22}$'s, and when f is an integer of at least 2, each $R^{22}$ may be identical with or different from one other, and when there are two neighboring $R^{22}$'s, the two neighboring $R^{22}$'s may form —CH$_2$CH$_2$CH$_2$—, —CH$_2$CH$_2$O—, —CH$_2$OCH$_2$—, OCH$_2$O—, —CH$_2$CH$_2$S—, —CH$_2$SCH$_2$—, —CH$_2$CH$_2$N(R$^{y}$)—, —CH$_2$N(R$^{y}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{y}$)CH=CH—, —OCH=N—, —SCH=N—, —N(R$^{y}$)CH=N—, —N(R$^{y}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{22}$'s, a 5-membered or 6-membered ring which may have one or more hydrogen atoms on the ring-constituting carbon atoms replaced by one or more Z's which may be identical with or different from one another, if two or more Z's are present, $R^{22}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, nitro, cyano or phenyl, $R^{23}$ is a hydrogen atom, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_6$ alkoxy ($C_1$-$C_6$) alkyl, phenyl, phenyl which may be substituted with f $R^{22}$'s, benzyl or benzyl having a benzene ring which may be substituted with f $R^{22}$'s, when f is an integer of at least 2, each $R^{22}$ may be identical with different from one another, each of $R^{24}$ and $R^{25}$ is independently a hydrogen atom, $C_1$-$C_{10}$ alkyl, $C_3$-$C_{10}$ cycloalkyl, $C_1$-$C_{10}$ haloalkyl, $C_3$-$C_{10}$ halocycloalkyl, benzyl, benzyl having a benzene ring which may optionally be substituted with b $R^{14}$'s, 1-phenethyl, 1-phenethyl having a benzene ring which may optionally be substituted with b $R^{14}$'s, 2-phenethyl, 2-phenethyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{31}$ is a halogen atom or phenyl, each of $R^{32}$, $R^{33}$ and $R^{34}$ is independently $C_1$-$C_{10}$ alkyl, $C_3$-$C_{10}$ cycloalkyl, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{81}$ is a halogen atom, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_6$ alkoxy($C_1$-$C_6$) alkyl, —OR$^{23}$, —C(R$^{83}$)=NR$^{84}$, —C(R$^{83}$)=NOR$^{84}$, —C(O)R$^{24}$, —C(O)OR$^{24}$, S(O)cR$^{24}$, —OS(O)$_2$R$^{24}$, —NR$^{24}$R$^{25}$, C(O)NR$^{24}$R$^{25}$, —C(S)NH$_2$, —S(O)$_2$NR$^{24}$R$^{25}$, phenyl or phenyl which may be substituted with m $R^{22}$'s, and when m is an integer of at least 2, each $R^{22'}$ may be identical with or different from one another, $R^{82}$ is a hydrogen atom, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy($C_1$-$C_6$) alkyl, phenyl, phenyl which may be substituted with d $R^{15}$'s, benzyl or benzyl having a benzene ring which may be substituted with d $R^{15}$'s, and when d is an integer of at least 2, each $R^{15'}$ may be identical with or different from one another, each of $R^{83}$ and $R^{84}$ is independently a hydrogen atom, $C_1$-$C_6$ alkyl, $C_1$-$C_6$ haloalkyl, $C_3$-$C_6$ cycloalkyl, $C_3$-$C_6$ halocycloalkyl, phenyl, phenyl which may be substituted with d $R^{15}$'s, benzyl or benzyl having a benzene ring which may be substituted with d $R^{15}$'s, and when d is an integer of at least 2, each $R^{15'}$ may be identical with or different from one another, Z is a halogen atom, cyano, nitro, $C_1$-$C_{10}$ alkyl, $C_1$-$C_{10}$ haloalkyl, $C_1$-$C_{10}$ alkoxy, $C_1$-$C_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —C(O)NH$_2$, —C(S)NH$_2$, or —S(O)$_2$NH$_2$, a, b, d, e, f, g, k and m are integers of from 1 to 5, c is an integer of from 0 to 2,
q1 is an integer of from 0 to 3,
q2 is an integer of from 0 to 5,
q3 is an integer of from 0 to 7,
q4 is an integer of from 0 to 6,
q5 is an integer of from 0 to 4,
r is an integer of from 0 to 2,
s1 is an integer of from 0 to 4,
s2 is an integer of from 0 to 3,
s3 is an integer of from 0 to 2,
s4 is an integer of 0 or 1,
n is an integer of 1,
t is an integer of from 0 or 1,
u is an integer of 0 or 1], a tautomer of the compound or a pharmaceutically acceptable salt or solvate thereof.

[2] The pyrazole compound according to [1], wherein X is —(CR$^6$R$^7$)$_n$—, a tautomer of the compound or a pharmaceutically acceptable salt or solvate thereof.

[3] The pyrazole compound according to [2], wherein $R^1$ is $C_1$-$C_{10}$ alkyl, $C_1$-$C_{10}$ alkyl substituted with $R^{17}$, $C_1$-$C_6$ haloalkyl, $C_3$-$C_6$ cycloalkyl, —C(O)R$^{12}$, —C(O)OR$^{12}$, —C(O)N(R$^{13}$)R$^{12}$, —C(R$^{12}$)=NR$^{13}$, —C(R$^{12}$)=NOR$^{13}$, D1 to D12, D18, D19, D21 to D23, phenyl or phenyl substituted with a $R^{11}$'s, and when a is an integer of at least 2, each $R^{11}$ may be identical with or different from one another, when there are two neighboring $R^{11}$'s, the two neighboring $R^{11}$'s may form —OCH$_2$O—, —OCH$_2$CH$_2$O—, —OCH=CH—, —CH=CHCH=CH— or —N=CHCH=CH— to form, together with the carbon atoms attached to the two $R^{11}$'s, a 5-membered or 6-membered ring which may have one or more hydrogen atoms on the ring-constituting carbon atoms optionally replaced by one or more Z's which may be identical with or different from one another, if two or more Z's are present, $R^2$ is a hydrogen atom, a halogen atom, $C_1$-$C_6$ alkyl, $C_3$-$C_6$ cycloalkyl, D1, D2, D4 to D12, D18, D19, D21 to D23, —C(O)$R^{12}$, —C(O)O$R^{12}$, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$, —C(O)N($R^{12}$)$R^{13}$, —Si($R^{32}$)($R^{33}$)$R^{34}$, benzyl or benzyl having a benzene ring which may be substituted with g $R^{15}$'s, and when g is an integer of at least 2, each $R^{15}$ may be identical with or different from one another, each of $R^4$ and $R^5$ is independently $C_1$-$C_4$ alkyl, each of $R^6$ and $R^7$ is a hydrogen atom, $R^8$ is D1, D2, D4, D5, D7 to D12, D19, D22, D23, E1 to E8, F1, F2, $C_3$-$C_{10}$ cycloalkyl, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —OCH$_2$O—, —CH$_2$CH$_2$CH$_2$—, —OCH$_2$CH$_2$O—, —OCH=CH—, —CH=CHCH=CH— or —N=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^x$ is a hydrogen atom, $C_1$-$C_6$ alkyl, $C_1$-$C_6$ haloalkyl or phenyl, $R^y$ is $C_1$-$C_6$ alkyl, $C_3$-$C_6$ cycloalkyl, phenyl or phenyl which may be substituted with d $R^{15}$'s, and when d is an integer of at least 2, each $R^{15}$ may be identical with or different from one another, $R^z$ is a halogen atom, $C_1$-$C_6$ alkyl, phenoxy, phenyl or phenyl which may be substituted with m $R^{16}$'s and when m is an integer of at least 2, each $R^{16}$ may be identical with or different from one another, and when s1, s2 or s3 is an integer of at least 2, each $R^z$ may be identical with or different from one another, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl, each of $R^{12}$ and $R^{13}$ is independently a hydrogen atom, $C_1$-$C_6$ alkyl, $C_3$-$C_6$ cycloalkyl, $C_1$-$C_6$ haloalkyl, $C_1$-$C_6$ halocycloalkyl, D2, D4, D5, D7, D21, D22, D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, when there are two neighboring $R^{14}$'s, the two neighboring $R^{14}$'s may form —OCH$_2$O—, —OCH$_2$CH$_2$O—, —OCH=CH—, —CH=CHCH=CH— or —N=CHCH=CH— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present, $R^{14}$ is a halogen atom, nitro, cyano, $C_1$-$C_6$ alkyl, $C_1$-$C_6$ haloalkyl, $C_1$-$C_6$ alkoxy, $C_1$-$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy, and when there are two neighboring $R^{16}$'s, the two neighboring $R^{16}$'s may form —OCH$_2$O— to form a 5-membered ring together with the carbon atoms to the two $R^{16}$'s, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one other, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$'s, the two neighboring $R^{22}$'s may form —OCH$_2$O— to form, together with the carbon atoms attached to the two $R^{22}$'s, a 5-membered ring each of $R^{32}$, $R^{33}$ and $R^{34}$ is independently $C_1$-$C_6$ alkyl, $C_3$-$C_6$ cycloalkyl, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl, a tautomer of the compound or a pharmaceutically acceptable salt or solvate thereof.

[4] The pyrazole compound according to [3], wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —C(O)O$R^{12}$, D2, D4, D5, D7, D21 to D23, phenyl or phenyl substituted with a $R^{11}$'s, and when a is an integer of at least 2, each $R^{11}$ may be identical with or different from one another, when there are two neigh $R^{11}$'s, the two neighboring $R^{11}$'s may form —CH=CHCH=CH— to form, together with the carbon atoms attached to the two $R^{11}$'s, a 6-membered ring which may have one or more hydrogen atoms on the ring-constituting carbon atoms replaced by one or more Z's which may be identical with or different from one another, if two or more Z's are present, $R^2$ is a hydrogen atom, a halogen atom, $C_1$-$C_6$ alkyl, $C_3$-$C_6$ cycloalkyl, D2, D7, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$, —C(O)N($R^{12}$)$R^{13}$, —Si($R^{32}$)($R^{33}$)$R^{34}$ or benzyl, $R^8$ is D2, D7, D23, F1, F2, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, each of $R^{12}$ and $R^{13}$ is independently a hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, $R^{17}$ is —C(O)O$R^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, each of $R^{32}$, $R^{33}$ and $R^{34}$ is independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy, a tautomer of the compound or a pharmaceutically acceptable salt or solvate thereof.

[5] The pyrazole compound according to [4], wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, and when a is an integer of at least 2, each $R^{11}$ may be identical with or different from one another, $R^2$ is a hydrogen atom, a halogen atom, $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $R^8$ is D2, F1, F2, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, $R^{12}$ is $C_1$-$C_6$ alkyl, $R^{17}$ is —C(O)O$R^{12}$ or phenyl, $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and $R^{81}$ is a halogen atom, $C_1$-$C_6$ alkyl, $C_1$-$C_6$ haloalkyl, $C_1$-$C_6$ alkoxy, phenyl or phenoxy, a tautomer of the compound or a pharmaceutically acceptable salt or solvate thereof.

[6] The pyrazole compound according to [1], wherein $R^2$ is a hydrogen atom, a halogen atom, cyano, $C_1$-$C_{10}$ alkyl, $C_1$-$C_{10}$ alkyl substituted with $R^{17}$, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C($R^{12}$)=N$R^{13}$, —C($R^{12}$)=NO$R^{13}$, D1 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^{y}$)—, —CH$_2$N($R^{y}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{y}$)CH=CH—, —OCH=N—, —SCH=N—, —N($R^{y}$)CH=N—, —N($R^{y}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, X is a single bond, a tautomer of the compound or a pharmaceutically acceptable salt or solvate thereof.

[7] The pyrazole compound according to [6], wherein $R^1$ is $C_1$-$C_{10}$ alkyl, $C_1$-$C_{10}$ alkyl substituted with $R^{17}$, $C_1$-$C_6$ haloalkyl, $C_3$-$C_6$ cycloalkyl, —C(O)$R^{12}$, —C(O)O$R^{12}$, —C(O)N($R^{13}$)$R^{12}$, —C($R^{12}$)=NO$R^{13}$, D1 to D12, D18, D19, D21 to D23, phenyl or phenyl substituted with a $R^{11}$'s, when a is an integer of at least 2, each $R^{11}$ may be identical with or different from one another, and when there are two neighboring $R^{11}$'s, the two neighboring $R^{11}$'s may form —OCH$_2$O—, —OCH$_2$CH$_2$O—, —OCH=CH—, —CH=CHCH=CH— or —N=CHCH=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is $C_1$-$C_6$ alkyl, $C_3$-$C_6$ cycloalkyl, D1, D2, D4 to D12, D18, D19, D21 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$ cycloalkyl, alkoxy($C_1$-$C_4$) alkyl, —C(O)$R^{12}$, —C(O)O$R^{12}$, —C(O)N($R^{12}$)$R^{13}$, —Si($R^{32}$)($R^{33}$)$R^{34}$, benzyl or benzyl having a benzene ring which may be substituted with g $R^{15}$'s, and when g is an integer of at least 2, each $R^{15}$ may be identical with or different from one another, each of $R^4$ and $R^5$ is independently $C_1$-$C_4$ alkyl, $R^8$ is D1, D2, D4, D5, D7 to D12, D19, D22, D23, E1 to E9, F1, F2, $C_3$-$C_{10}$ cycloalkyl, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —$OCH_2O$—, —$CH_2CH_2CH_2$—, —$OCH_2CH_2O$—, —OCH=CH—, —CH=CHCH=CH— or —N=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^x$ is a hydrogen atom, $C_1$-$C_6$ alkyl, $C_1$-$C_6$ haloalkyl or phenyl, $R^y$ is $C_1$-$C_6$ alkyl, $C_3$-$C_6$ cycloalkyl, phenyl or phenyl which may be substituted with d $R^{15}$'s, benzyl or benzyl having a benzene ring which may be substituted with d $R^{15}$'s, and when d is an integer of at least 2, each $R^{15}$ may be identical with or different from one another, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl, each of $R^{12}$ and $R^{13}$ is independently a hydrogen atom, $C_1$-$C_6$ alkyl, $C_3$-$C_6$ cycloalkyl, $C_1$-$C_6$ haloalkyl, $C_3$-$C_6$ halocycloalkyl, D2, D4, D5, D7, D21, D22, D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, and when there are two neighboring $R^{14}$'s, the two neighboring $R^{14}$'s may form —$OCH_2O$—, —$OCH_2CH_2O$—, —OCH=CH—, —CH=CHCH=CH— or —N=CHCH=CH— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present, $R^{14}$ is a halogen atom, nitro, cyano, $C_1$-$C_6$ alkyl, $C_1$-$C_6$ haloalkyl, $C_1$-$C_6$ alkoxy, $C_1$-$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{16}$'s, the two neighboring $R^{16}$'s may form —$OCH_2O$— to form a 5-membered ring together with the carbon atoms to the two $R^{16}$'s, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one other, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$'s, the two neighboring $R^{22}$'s may form —$OCH_2O$— to form, together with the carbon atoms attached to the two $R^{22}$'s, a 5-membered ring, each of $R^{32}$, $R^{33}$ and $R^{34}$ is independently $C_1$-$C_6$ alkyl, $C_3$-$C_6$ cycloalkyl, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl, a tautomer of the compound or a pharmaceutically acceptable salt or solvate thereof.

[8] The pyrazole compound according to [7], wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —C(O)O$R^{12}$, D2, D4, D5, D7, D21, D23, phenyl or substituted with a $R^{11}$'s, when a is an integer of at least 2, each $R^{11}$ may be identical with or different from one another, and when there are two neighboring $R^{11}$'s, the two neighboring $R^{11}$'s may form —CH=CHCH=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is $C_1$-$C_6$ alkyl, $C_3$-$C_6$ cycloalkyl, D2, D7, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$, —C(O)N($R^{12}$)$R^{13}$, —Si($R^{32}$)($R^{33}$)$R^{34}$ or benzyl, $R^8$ is D2, D7, D23, F1, F2, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —OCH$_2$O—, —CH$_2$CH$_2$CH$_2$— or —CH═CHCH═CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 or s3 is an integer of at least 2, each $R^z$ may be identical with or different from one another, each of $R^{12}$ and $R^{13}$ is independently hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ loalkyl or $C_1$-$C_6$ haloalkoxy, $R^{17}$ is —C(O)O$R^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, each of $R^{32}$, $R^{33}$ and $R^{34}$ is independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl or phenoxy, a tautomer of the compound or a pharmaceutically acceptable salt or solvate thereof.

[9] The pyrazole compound according to [8], wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, when a is an integer of at least 2, each $R^{11}$ may be identical with or different from one another, $R^2$ is $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O— or —CH═CHCH═CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $R^8$ is D2, F1, F2, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —OCH$_2$O—, —CH$_2$CH$_2$CH$_2$— or —CH═CHCH═CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, $R^{12}$ is $C_1$-$C_6$ alkyl, $R^{17}$ is —C(O)O$R^{12}$ or phenyl, $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and $R^{81}$ is a halogen atom, $C_1$-$C_6$ alkyl, $C_1$-$C_6$ haloalkyl, $C_1$-$C_6$ alkoxy or phenoxy, a tautomer of the compound or a pharmaceutically acceptable salt or solvate thereof.

[10] A therapeutic agent for multiple myeloma containing the pyrazole compound as defined in any one of [1] to [9], a tautomer of the compound or a pharmaceutically acceptable salt or solvate thereof as an active ingredient.

Advantageous Effects of Invention

The compounds of the present invention have growth inhibitory effect on multiple myeloma cells. Therefore, they are useful as therapeutic agents for multiple myeloma and can be used as preventive, therapeutic and improving agents for the disease.

DESCRIPTION OF EMBODIMENTS

Now, the present invention will be described in further detail.

The terms used herein are defined below.

The present invention is used when use of a compound having growth inhibitory action on myeloma cells is expected to improve pathological conditions. Multiple myeloma is a disease as a target of treatment with therapeutic agents containing the compounds of the present invention. Multiple myeloma is a tumor of plasma cells and can be staged by using the international staging system (ISS): stage I: serum β2 microglobulin<3.5 mg/L and serum albumin≥3.5 g/dL, stage II neither stage I nor III, stage III: serum β2 microglobulin≥5.5 mg.L.

Multiple myeloma is also classified as asymptomatic or symptomatic. Asymptomatic myeloma patients meet the criteria for myeloma with high levels of M proteins and a myeloma cell proportion in the bone marrow of 10% or more, but do not show no related tissue or organ impairment or symptoms. Asymptomatic myeloma includes smoldering multiple myeloma, indolent multiple myeloma and stage I multiple myeloma. Multiple myeloma is symptomatic if there is any of the associated organ or tissue disorders such as hypercalcemia, renal dysfunction, anemia, infections, hyperviscosity syndrome, amyloidosis and bone lesions. Other diseases classified as associated with multiple myeloma include nonsecretory myeloma characterized by no detection of M proteins in blood or urine, plasmacytoma accompanied by formation of a single lesion in a bone, extramedullary plasmacytoma defined as a cancer formed outside the bone marrow by myeloma cells and plasmacytic leukemia characterized by the presence of a detectable amount of plasma cells in peripheral blood.

Multiple myeloma is also therapeutically categorized as follows.

Responsive type: refers to myeloma which is responding to therapy. There has been a decrease in M proteins of at least 50%.

Stable type: refers to myeloma which has not responded to treatment (i.e., the decrease in M proteins has not reached 50%) but has not recognizably progressed.

Progressive type: refers to active myeloma which is worsening (i.e., increasing M proteins and worsening organ or tissue impairment).

Relapsed type: refers to myeloma which initially responded to treatment but has then begun to progress again. Patients may be further classified as having relapsed after initial therapy or after subsequent therapy.

Refractory type: refers to myeloma which has not responded to initial therapy, as well as relapsed myeloma which does not respond to subsequent treatment.

The multiple myeloma to be treated with the compounds of the present invention can be in any stages, in any classes, with any associated diseases, in any categories or in any disease statuses as described above.

A compound of the present invention can be used alone or in combination with at least one other therapeutic agent to ease at least one symptoms of multiple myeloma. A compound of the present invention may be administered at the same time as or prior to or subsequent to administration of the other therapeutic agent. A compound of the present invention may be administered through the same or different administration route as the other therapeutic agent. Such a therapeutic agent may be a chemotherapeutic agent, a supportive therapeutic agent or a combinations thereof.

As used herein, a chemotherapeutic agent is a substance which inhibits growth of cancer cells, such as bortezomib (Velcade (registered trademark)), melphalan, Predisone, vincristine, carmustine, cyclophosphamide, dexamethasone, thalidomide, doxorubicin, cicplatin, etoposide, cytarabine, but it is not restricted thereto.

A "supportive therapeutic agent" is an active substance which reduces the symptoms and complications of multiple myeloma. Examples of supportive therapeutic agent include antibiotics, bisphosphonates, blood cell growth factors, diuretics and analgesics.

Examples of antibiotics include sulfa drugs, penicillin, Phenethicillin, Methicillin, Oxacillin, Cloxacillin, Dicloxacillin, Flucloxacillin, Nafcillin, Ampicillin, Amoxicillin, Cyclacillin, Carbenicillin, Ticarcillin, Piperacillin, Azlocillin, Mezlocillin, Mecillinam, Amdinocillin, Cephalosporin and derivatives thereof, Oxolinic acid, Amifloxacin, Temafloxacin, Nalidixic acid, Piromidic acid, Ciprofloxacin, Cinoxacin, Norfloxacin, Perfloxacin, Rosaxacin, Ofloxacin, Enoxacin, Pipemidic acid, Sulbactam, Clavulinic acid, β-Bromopenicillanic acid, β-Chloropenicillanic acid, 6-Acetylmethylenepenicillanic acid, Cephoxazole, Sultampicillin, Formaldehyde Hudrate Ester of Adinocillin and Sulbactam, Tazobactam, Aztreonam, Sulfazethin, Isosulfazethin, Norcardicins, m-Carboxyphenyl Phenylacetamidomethylphosphonate, Chlortetracycline, Oxytetracyline, Tetracycline, Demeclocycline, Doxycycline, Methacycline and Minocycline.

Examples of bisphosphonates include etidronate (Didronel), pamidronate (Aredia), alendronate (Fosamax), risedronate (Actonel), zoledronate (Zometa), ibandronate (Boniva).

Examples of diuretics include thiazide derivatives such as amiloride, chlorothiazide, hydrochlorothiazide, methylchlorothiazide, and chlorthalidon.

Examples of blood cell growth factors include granulocyte colony-stimulating factor (G-CSF), granulocyte-macrophage colony-stimulating factor (GM-CSF), macrophage colony-stimulating factor (M-CSF), erythropoietin, thrombopoietin, Oncostatin M and various interleukins.

Examples of analgesics include an opioid, a COX-2 inhibitor (e.g., Rofecoxib, Valdecoxib and Celecoxib), salicylates (e.g., ASPIRIN, choline magnesium trisalicylate, salsalate, dirunisal and sodium salicylate), propionic acid derivatives (e.g., fenoprofen calcium, ibuprofen, ketoprofen, naproxen and naproxen sodium), indoleacetic acid derivatives (e.g., indomethacin, sulfindac, etodalac and tolmetin), fenamates (e.g., mefenamic acid and meclofenamate), benzothiazine derivatives or oxicams (e.g., mobic or piroxicam) and pyrrolacetic acid (e.g., ketorolac).

As used herein "treating" includes achieving, partially or substantially, one or more of the following results: partially or totally reducing the extent of the disease; ameliorating or improving a clinical symptom or indicator associated with the disease; or delaying, inhibiting or preventing the progression or onset of the disease.

A "subject" as the target of treatment with a compound of the present invention is a mammal, preferably a human, but can also be a pet animal (such as a dog or a cat) or a farm animal (such as a cow, a sheep, a pig or a horse).

The therapeutic agents containing the compounds of the present invention as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the therapeutic agents containing the compounds of the present invention for administration to human is usually about from 0.1 to 1000 mg/human/day in the case of oral drugs or rectal administration and about from 0.05 mg to 500 mg/human/day in the case of injections, though it depends on the symptoms of the patient. The above-mentioned ranges are mere examples, and the dose should be determined from the conditions of the patient.

When $R^3$ is a hydrogen atom, the compounds of the present invention represented by the formula (1) can have tautomers (2) to (4) which undergo endocyclic or exocyclic isomerization, and the present invention covers these tautomers (2) to (4) and mixtures containing them in any ratios.

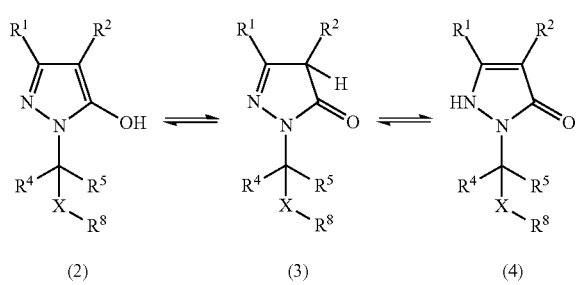

(2)  (3)  (4)

When the compounds of the present invention have an asymmetric center, whether or not resulting from an isomerization, the present invention covers both resolved optical isomers and mixtures containing them in any ratios.

The compounds of the present invention can have geometrical isomers such as E-isomers and Z-isomers, whether or not resulting from an isomerization, depending on the substituents, and the present invention covers both these geometrical isomers and mixtures containing hem in any ratios.

The compounds of the present invention represented by the formula (1) may be converted to pharmaceutically acceptable salts or may be liberated from the resulting salts, if necessary. Some of the compounds of the present invention can be converted, by ordinary methods, to acid addition salts with hydrogen halides such as hydrofluoric acid, hydrochloric acid, hydrobromic acid and hydriodic acid, with inorganic acids such as nitric acid, sulfuric acid, phosphoric acid, chloric acid and perchloric acid, with sulfonic acids such as methanesulfonic acid, ethanesulfonic acid, trifluoromethanesulfonic acid, benzenesulfonic acid and p-toluenesulfonic acid, with carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, with amino acids such as glutamic acid asparatic acid.

Some of the compounds of the present invention can be converted, by ordinary methods, to metal salts with alkali metals such as lithium sodium and potassium, with alkaline earth metals such as calcium, barium and magnesium, with metals suchas aluminum zinc and copper.

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985). In the present invention, when the compound has a hydroxy group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO(m-CO$_2$Na—Ph), —OCOCH$_2$CH$_2$CO$_2$Na, —OCOCH(NH$_2$)CH$_3$, —OCOCH$_2$N(CH$_3$)$_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

Next, specific examples of each substituent used herein will be given below. "n" denotes normal, "i" denotes iso, "s" denotes secondary, "t" or "tert" denotes tertiary, and "Ph" denotes phenyl.

As a halogen atom in the compounds of the present invention, a fluorine atom, a chlorine atom, a bromine atom or an iodine atom may be mentioned. Herein, the expression "halo" also means such a halogen atom.

The expression $C_\alpha$-$C_\beta$ alkyl herein means a linear or branched hydrocarbon group containing from $\alpha$ to $\beta$ carbon atoms such as a methyl group, an ethyl group, a n-propyl group, an i-propyl group, a n-butyl group, an i-butyl group, a s-butyl group, a t-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 1,1-dimethylbutyl group, a 1,3-dimethylbutyl group, a heptyl group, an octyl group, a nonyl group, a decyl group, an undecyl group or a dodecyl group, and those within the designated carbon number range are selected.

The expression $C_\alpha$-$C_\beta$ haloalkyl herein means a linear or branched hydrocarbon group containing from a to $\beta$ carbon atoms in which hydrogen atom(s) on carbon atom(s) are optionally substituted with halogen atom(s) which may be identical with or different from one another if two or more halogen atoms are present, such as a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a difluoroiodomethyl group, a 2-fluoroethyl group, a 2-chloroethyl group, a 2-bromoethyl group, a 2,2-difluoroethyl group, a 2-chloro2-fluoroethyl group, a 2,2-dichloroethyl group, a 2-bromo2-fluoroethyl group, a 2,2,2-trifluoroethyl group, a 2-chloro-2,2-difluoroethyl group, a 2,2-dichloro2-fluoroethyl group, a 2,2,2-trichloroethyl group, a 2-bromo-2,2-difluoroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 1-bromo-1,2,2,2-tetrafluoroethyl group, a 2-bromo-1,1,2,2-tetrafluoroethyl group, a 2-fluoropropyl group, a 2-chloropropyl group, a 2,3-dichloropropyl group, a 3,3,3-trifluoropropyl group, a 3-bromo-3,3-difluoropropyl group, 2,2,3,3-tetrafluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluorol-methylethyl group, a 2-chloro1-methylethyl group, a 2-bromo-1-methylethyl group, a 2,2,2-trifluoro1-(trifluoromethyl) ethyl group, a 1,2,2,2-tetrafluoro1-(trifluoromethyl)ethyl group or a nonafluorobutyl group, and those within the designated carbon number range are selected.

The expression $C_\alpha$-$C_\beta$ cycloalkyl herein means a cyclic hydrocarbon group containing from a to $\beta$ carbon atoms in the form of a 3- to 6-membered monocyclic or polycyclic ring which may optionally be substituted with an alkyl group as long as the number of carbon atoms does not exceed the designated carbon number range, such as a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a cyclohexyl group, a cycloheptyl group, a cyclooctyl group, a bicyclo [2.2.1]heptan-2-yl group, a 1-adamantyl group or a 2-adamantyl group, and those within the designated carbon number range are selected.

The expression $C_\alpha$-$C_\beta$ halocycloalkyl means a cyclic hydrocarbon group containing from α to β carbon atoms in the form of a 3- to 6-membered monocyclic or complex ring which may optionally be substituted with an alkyl group as long as the number of carbon atoms does not exceed the designated carbon number range, in which hydrogen atom(s) on carbon atom(s) in a ring moiety and/or in a side chain are optionally substituted with halogen atom(s) which may be identical with or different from one another if two or more halogen atoms are present, such as a 2-fluorocyclopropyl group, a 2-chlorocyclopropyl group, a 2,2-difluorocyclopropyl group, a 2,2-dichlorocyclopropyl group, a 2,2-dibromocyclopropyl group, a 2,2-difluoro1-methylcyclopropyl group, a 2,2-dichloro1-methylcyclopropyl group, a 2,2,3,3-tetrafluorocyclobutyl group or a 2-chloro-2,3,3-trifluorocyclobutyl group, and those within the designated carbon atom range are selected.

The expression $C_\alpha$-$C_\beta$ alkenyl herein means a linear or branched unsaturated hydrocarbon group containing from α to β carbon atoms and having one or more double bonds in the molecule such as a vinyl group, a 1-propenyl group, a 2-propenyl group, a 1-methylethenyl group, a butenyl group, a 1-methyl-2-propenyl group, a 2-methyl-2-propenyl group, a 2-pentenyl group, a 2-methyl-2-butenyl group, a 3-methyl-2-butenyl group, a 2-ethyl2-propenyl group, a 1,1-dimethyl-2-propenyl group, a 2-hexenyl group, a 2-methyl-2-pentenyl group, a 2,4-dimethyl-2,6-heptadienyl group or a 3,7-dimethyl-2,6-octadienyl group, and those within the designated carbon atom range are selected.

The expression $C_\alpha$-$C_\beta$ alkynyl herein means a linear or branched unsaturated hydrocarbon group containing from a to β carbon atoms and having one or more triple bonds in the molecule such as an ethylene group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group or a 2-hexynyl group, and those within the designated carbon atom range are selected.

The expression $C_\alpha$-$C_\beta$ alkoxy herein means an alkyl-O— group in which the alkyl is a previously mentioned alkyl group containing from a to βcarbon atoms, such as a methoxy group, an ethoxy group, a n-propyloxy group, an i-propyloxy group, a n-butyloxy group, an i-butyloxy group, a s-butyloxy group, a t-butyloxy group, a n-pentyloxy group, a n-hexyloxy group, and those within the designated carbon atom range are selected.

The expression $C_\alpha$-$C_\beta$ haloalkoxy herein means a haloalkyl-O— group in which the haloalkyl is a previously mentioned haloalkyl group containing from α to β carbon atoms, such as a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2,-tetrafluoroethoxy group, a 2-chloro-1,1,2-trifluoroethoxy group, a 2-bromo-1,1,2-trifluoroethoxy group, a pentafluoroethoxy group, a 2,2-dichloro-1,1,2-trifluoroethoxy group, a 2,2,2-trichloro1,1-difluoroethoxy group, a 2-bromo-1,1,2,2-tetrafluoroethoxy group, a 2,2,3,3,3-tetrafluoropropyloxy group, a 1,1,2,3,3,3-hexafluoropropyloxy group, a 2,2,2-trifluoro1-(trifluoromethyl)ethoxy group, a heptafluoropropyloxy group or a 2-bromo-1,1,2,3,3,3-hexafluoropropyloxy group, and those within the designated carbon atom range are selected.

The expression $C_\alpha$-$C_\beta$ alkylthio herein means an alkyl-S— group in which the alkyl is a previously mentioned alkyl group containing from α to β carbon atoms, such as a methylthio group, an ethylthio group, a n-propylthio group, an i-propylthio group, a n-butylthio group, an i-butylthio group, a s-butylthio group, a t-butylthio group, a n-pentylthio group or a n-hexylthio group, and those within the designated carbon atom range are selected.

The expression $C_\alpha$-$C_\beta$ haloalkylthio herein means a haloalkyl-S— group in which the haloalkyl is a previously mentioned haloalkyl group containing from α to β carbon atoms, such as a difluoromethylthio group, a trifluoromethylthio group, a chlorodifluoroethylthio group, a bromodifluoroethylthio group, a 2,2,2-trifluoroethylthio group, a 1,1,2,2-tetrafluoroethylthio group, a 2-chloro-1,1,2-trifluoroethylthio group, a pentafluoroethylthio group, a 2-bromo-1,1,2,2-tetrafluoroethylthio group, a 1,1,2,3,3,3-hexafluoropropylthio group, a heptafluoropropylthio group, a 1,2,2,2-tetrafluoro1-(trifluoromethyl)ethylthio group or a nonafluorobutylthio group, and those within the designated carbon atom range are selected.

The expression $C_\alpha$-$C_\beta$ alkylsulfinyl herein means an alkyl-S(O)— group in which the alkyl is a previously mentioned alkyl group containing from α to β carbon atoms, such as a methylsulfinyl group, an ethylsulfinyl group, a n-propylsulfinyl group, an i-propylsulfinyl group, a n-butylsulfinyl group, an i-butylsulfinyl group, a s-butylsulfinyl group or a t-butylsulfinyl group, and those within the designated carbon atom range are selected.

The expression $C_\alpha$-$C_\beta$ haloalkylsulfinyl herein means a haloalkyl-S(O)— group in which the haloalkyl is a previously mentioned haloalkyl group containing from α to β carbon atoms, such as a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 2-bromo-1,1,2,2-tetrafluoroethylsulfinyl group, a 1,2,2,2-tetrafluoro-1-(trifluoromethyl)ethylsulfinyl group or a nonafluorobutylsulfinyl group, and those within the designated carbon atom range are selected.

The expression $C_\alpha$-$C_\beta$ alkylsulfonyl herein means an alkyl-$SO_2$— group in which the haloalkyl is a previously mentioned haloalkyl group containing from α to β carbon atoms, such as a methylsulfonyl group, an ethylsulfonyl group, a n-propylsulfonyl group, an i-propylsulfonyl group, a n-butylsulfonyl group, an i-butylsulfonyl group, a s-butylsulfonyl group, a t-butylsulfonyl group, a n-pentylsulfonyl group or a n-hexylsulfonyl group, and those within the designated carbon atom range are selected.

The expression $C_\alpha$-$C_\beta$ haloalkylsulfonyl herein means a haloalkyl-$SO_2$— group in which the haloalkyl is a previously mentioned haloalkyl group containing from α to β carbon atoms, such as adifluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group, a 2-chloro-1,1,2-trifluoroethylsulfonyl group or a 2-bromo-1,1,2,2-tetrafluoroethylsulfonyl group, and those within the designated carbon atom range are selected.

The expression $C_\alpha$-$C_\beta$ alkylamino herein means an amino group in which either hydrogen atom is replaced by a previously mentioned alkyl group containing from α to β carbon atoms, such as a methylamino group, an ethylamino group, a n-propylamino group, an i-propylamino group, a n-butylamino group, an i-butylamino group or a t-butylamino group, and those within the designated carbon atom range are selected.

The expression di($C_\alpha$-$C_\beta$ alkyl)amino herein means an amino group in which both hydrogen atoms are replaced by previously mentioned alkyl groups containing from $\alpha$ to $\beta$ carbon atoms which may be identical with or different from each other, such as a dimethylamino group, an ethyl(methyl)amino group, a diethylamino group, a n-propyl(methyl)amino group, an i-propyl(methyl)amino group, a di(n-propyl)amino group, a n-butyl(methyl)amino group, an i-butyl(methyl)amino group or a t-butyl(methyl)amino group, and those within the designated carbon atom range are selected.

The expression $C_\alpha$-$C_\beta$ alkylimino herein means an alkyl-N= group in which the alkyl means a previously mentioned alkyl group containing from $\alpha$ to $\beta$ carbon atoms, such as a methylimino group, an ethylimino group, a n-propylimino group, an i-propylimino group, a n-butylimino group, an i-butylimino group, a s-butylimino group, a n-pentylimino group or a n-hexylimino group, and those within the designated carbon atom range are selected.

The expression $C_\alpha$-$C_\beta$ alkoxyimino herein means an alkoxy-N= group in which the alkoxy means a previously mentioned alkoxy group containing from $\alpha$ to $\beta$ carbon atoms, such as a methoxyimino group, an ethoxyimino group, a n-propyloxyimino group, an i-propyloxyimino group, a n-butyloxyimino group, a n-pentyloxyimino group or a n-hexyloxyimino group, and those within the designated carbon atom range are selected.

The expression $C_\alpha$-$C_\beta$ alkylcarbonyl herein means an alkyl-C(O)— group in which the alkyl means a previously mentioned alkyl group containing from $\alpha$ to $\beta$ carbon atoms, such as an acetyl group, a propionyl group, a butyryl group, an isobutyryl group, a valeryl group, an isovaleryl group, a 2-methylbutanoyl group, a pivaloyl group, a hexanoyl group or a heptanoyl group, and those within the designated carbon atom range are selected.

The expression $C_\alpha$-$C_\beta$ haloalkylcarbonyl herein means a haloalkyl-C(O)— group in which the haloalkyl means a previously mentioned haloalkyl group containing from a to $\beta$ carbon atoms, such as a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group or a 3-chloro-2,2-dimethylpropanoyl group, and those within the designated carbon atom range are selected.

The expression $C_\alpha$-$C_\beta$ alkoxycarbonyl herein means an alkyl-O—C(O)— group in which the alkyl means a previously mentioned alkoxy group containing from $\alpha$ to $\beta$ carbon atoms, such as a methoxycarbonyl group, an ethoxycarbonyl group, a n-propyloxycarbonyl group, an i-propyloxycarbonyl group, a n-butoxycarbonyl group, an i-butoxycarbonyl group or a t-butoxycarbonyl group, and those within the designated carbon atom range are selected.

The expression $C_\alpha$-$C_\beta$ haloalkoxycarbonyl herein means a haloalkyl-O—C(O)— group in which the haloalkyl means a previously mentioned haloalkyl group containing from $\alpha$ to $\beta$ carbon atoms, such as a 2-chloroethoxycarbonyl group, a 2,2-difluoroethoxycarbonyl group, a 2,2,2-trifluoroethoxycarbonyl group or a 2,2,2-trichloroethoxycarbonyl group, and those within the designated carbon atom range are selected.

The expression $C_\alpha$-$C_\beta$ alkylaminocarbonyl herein means a carbamoyl group in which either hydrogen atom is replaced by a previously mentioned alkyl group containing from $\alpha$ to $\beta$ carbon atoms, such as a methylcarbamoyl group, an ethylcarbamoyl group, a n-propylcarbamoyl group, an i-propylcarbamoyl group, a n-butylcarbamoyl group, an i-butylcarbamoyl group, a s-butylcarbamoyl group or a t-butylcarbamoyl group, and those within the designated carbon atom range are selected.

The expression $C_\alpha$-$C_\beta$ haloalkylaminocarbonyl herein means a carbamoyl group in which either hydrogen atom is replaced by a previously mentioned haloalkyl group containing from $\alpha$ to $\beta$ carbon atoms, such as a 2-fluoroethylcarbamoyl group, a 2-chloroethylcarbamoyl group, a 2,2-difluoroethylcarbamoyl group or a 2,2,2-trifluoroethylcarbamoyl group, and those within the designated carbon atom range are selected.

The expression di($C_\alpha$-$C_\beta$ alkyl)aminocarbonyl herein means a carbamoyl group in which both hydrogen atoms are replaced by previously mentioned alkyl groups containing from $\alpha$ to $\beta$ carbon atoms which may be identical with or different from each other, such as an N,N-dimethylcarbamoyl group, an N-ethyl-N-methylcarbamoyl group, an N,N-diethylcarbamoyl group, an N,N-di-n-propylcarbamoyl group or an N,N-di-n-butylcarbamoyl group, and those within the designated carbon atom range are selected.

The expression $C_\alpha$-$C_\beta$ alkylaminosulfonyl herein means a sulfamoyl group in which either hydrogen atom is replaced by a previously mentioned alkyl group containing from $\alpha$ to $\beta$ carbon atoms, such as a methylsulfamoyl group, an ethylsulfamoyl group, a n-propylsulfamoyl group, an i-propylsulfamoyl group, a n-butylsulfamoyl group, an i-butylsulfamoyl group, a s-butylsulfamoyl group or a t-butylsulfamoyl group, and those within the designated carbon atom range are selected.

The expression di($C_\alpha$-$C_\beta$ alkyl)aminosulfonyl herein means a sulfamoyl group in which both hydrogen atoms are replaced by previously mentioned alkyl groups containing from $\alpha$ to $\beta$ carbon atoms which may be identical with or different from each other, such as an N,N-dimethylsulfamoyl group, an N-ethyl-N-methylsulfamoyl group, an N,N-diethylsulfamoyl group, an N,N-di-n-propylsulfamoyl group or an N,N-di-n-butylsulfamoyl group, and those within the designated carbon atom range are selected.

The expression tri($C_\alpha$-$C_\beta$ alkyl)silyl herein means a silyl group substituted with previously mentioned alkyl groups containing from $\alpha$ to $\beta$ carbon atoms which may be identical with or different from one another, such as a trimethylsilyl group, a triethylsilyl group, a tri(n-propyl)silyl group, an ethyldimethylsilyl group, a n-propyldimethylsilyl group, a n-butyldimethylsilyl group, an i-butyldimethylsilyl group or a t-butyldimethylsilyl group, and those within the designated carbon atom range are selected.

The expression $C_\alpha$-$C_\beta$ alkylsulfonyloxy herein means an alkylsulfonyl-O— group in which the alkylsulfonyl means a previously mentioned alkylsulfonyl group containing from $\alpha$ to $\beta$ carbon atoms, such as a methylsulfonyloxy group, an ethylsulfonyloxy group, a n-propylsulfonyloxy group or an i-propylsulfonyloxy group, and those within the designated carbon atom range are selected.

The expression $C_\alpha$-$C_\beta$ haloalkylsulfonyloxy herein means a haloalkylsulfonyl-O— group in which the haloalkylsulfonyl means a previously mentioned haloalkylsulfonyl group containing from $\alpha$ to $\beta$ carbon atoms, such as a difluoromethylsulfonyloxy group, a trifluoromethylsulfonyloxy group, a chlorodifluoromethylsulfonyloxy group or a bromodifluoromethylsulfonyloxy group, and those within the designated carbon atom range are selected.

The expression $C_\alpha$-$C_\beta$ alkoxy ($C_\delta$-$C_\epsilon$) alkyl herein means a previously mentioned alkyl group containing from $\delta$ to $\epsilon$ carbon atoms in which hydrogen atom(s) on carbon atom(s) are optionally substituted with previously mentioned alkoxy group(s) containing from α to β carbon atoms, and those within the designated carbon atom range are selected.

The expression $C_\alpha$-$C_\beta$ alkoxy($C_\delta$-$C_\epsilon$) alkoxy herein means a previously mentioned alkoxy group containing from δ to ε carbon atoms in which hydrogen atom(s) on carbon atom(s) are optionally substituted with previously mentioned alkoxy group(s) containing from α to β carbon atoms, and those within the designated carbon atom range are selected.

The expression ($C_\alpha$-$C_\beta$) alkenyl optionally substituted with a halogen atom or ($C_\alpha$-$C_\beta$) alkenyl optionally substituted with $R^{31}$ herein means a previously mentioned alkynyl group containing from α to β carbon atoms in which hydrogen atom(s) on carbon atom(s) are substituted with optional halogen atom(s) or $R^{31}$, and those within the designated carbon atom range are selected. When there are two or more halogen atoms or the substituent $R^{31}$'s on an ($C_\alpha$-$C_\beta$) alkenyl group, the $R^{31}$'s or the halogen atoms may be identical with or different from one another.

The expression benzyl having a benzene ring optionally substituted with e $R^{21}$'s, benzyl having a benzene ring which may be substituted with f $R^{22}$'s or benzyl having a benzene ring which may be substituted with g $R^{15}$'s herein means a previously mentioned benzyl group in which the hydrogen atoms on e, f or g carbon atom(s) in the benzene ring are optionally substituted with optional $R^{21}$'s, $R^{22}$'s or $R^{15}$'s. When there are two or more $R^{21}$'s, $R^{22}$'s or $R^{15}$'s in the benzene ring, they may be identical with or different from one another.

The expression phenyl optionally substituted with e $R^{21}$'s, phenyl which may be substituted with f $R^{22}$'s or phenyl optionally substituted with k $R^{81}$'s herein means a previously mentioned phenyl group in which the hydrogen atoms on e, f, or k carbon atoms in the benzene ring are optionally substituted with optional $R^{21}$'s, $R^{22}$'s or $R^{81}$'s. When there are two or more $R^{21}$'s, $R^{22}$'s or $R^{81}$'s in the benzene ring, they may be identical with or different from one another.

The expression 1-phenethyl having a benzene ring which may optionally be substituted with b $R^{14}$'s herein means a 1-phenethyl group having a benzene ring in which the hydrogen atoms on b carbon atoms are optionally substituted with optional $R^{14}$'s. When there are two or more $R^{14}$'s in the benzene ring, they may be identical with or different from one another.

The expression 2-phenethyl having a benzene ring which may optionally be substituted with b $R^{14}$'s herein means a 2-phenethyl group having a benzene ring in which the hydrogen atoms on b carbon atoms are optionally substituted with optional $R^{14}$'s. When there are two or more $R^{14}$'s in the benzene ring, they may be identical with or different from one another.

The expression ($C_\alpha$-$C_\beta$) alkyl substituted with $R^{17}$ herein means a previously mentioned alkyl group containing from α to β carbon atoms in which hydrogen atom(s) on carbon atom(s) are optionally substituted with $R^{17}$, and those within the designated carbon atom range are selected. When there are two or more $R^{17}$'s on an alkyl group on the ($C_\alpha$-$C_\beta$) alkyl group, the $R^{17}$'s may be identical with or different from one another.

As the scope of the substituent represented by $R^1$ in the compounds which fall within the present invention, the following sets may, for example, be mentioned.

$R^1$-I: $C_1$-$C_6$ alkyl.

$R^1$-II: $C_1$-$C_6$ alkyl, $C_1$-$C_6$ alkyl substituted with $R^{17}$, $C_1$-$C_6$ haloalkyl, $C_3$-$C_6$ cycloalkyl, phenyl and phenyl substituted with a $R^{11}$'s [wherein $R^{11}$ is a halogen atom, $C_1$-$C_6$ alkyl or $C_1$-$C_6$ alkoxy, and when a is an integer of at least two, each $R^{11}$ may be identical with or different from one another, $R^{12}$ is $C_1$-$C_6$ alkyl, $R^{17}$ is —C(O)O$R^{12}$ or phenyl, and a is an integer of from 1 to 5].

$R^1$-III: $C_1$-$C_6$ alkyl, $C_1$-$C_6$ alkyl substituted with $R^{17}$, $C_1$-$C_6$ haloalkyl, $C_3$-$C_6$ cycloalkyl, D5, phenyl and phenyl substituted with a $R^{11}$'s [wherein $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, and when a is an integer of at least two, each $R^{11}$ may be identical with or different from one another, and when there are two neighboring $R^{11}$'s, the two neighboring $R^{11}$'s may form —CH=CHCH=CH— to form a 6-membered ring together with the carbon atoms attached to the two $R^{11}$'s, $R^z$ is a halogen atom or $C_1$-$C_6$ alkyl, $R^{12}$ is $C_1$-$C_6$ alkyl, $R^{17}$ is —C(O)O $R^{12}$ or phenyl, a is an integer of from 1 to 5, and s2 is an integer of from 0 to 3].

$R^1$-IV: $C_1$-$C_6$ alkyl, $C_1$-$C_6$ alkyl substituted with $R^{17}$, $C_1$-$C_6$ haloalkyl, $C_3$-$C_6$ cycloalkyl, —C(O)O $R^{12}$, D2, D4, D5, D7, D21, D22, D23, phenyl and phenyl substituted with a $R^{11}$'s [wherein $R^{11}$ is a halogen atom, $C_1$-$C_{10}$ alkyl, $C_1$-$C_{10}$ alkoxy, $C_1$-$C_{10}$haloalkyl, $C_1$-$C_{10}$ haloalkoxy, nitro or phenyl, $R^{12}$ is a hydrogen atom, $C_1$-$C_6$ alkyl or $C_3$-$C_6$ cycloalkyl, and when a is an integer of at least 2, each $R^{11}$ may be identical with or different from one another, and when there are two neighboring $R^{11}$'s, the two neighboring $R^{11}$'s may form, together with the carbon atoms attached to the two $R^{11}$'s, —CH=CHCH=CH— to form a 6-membered ring which may have one or more hydrogen atoms on the ring-constituting carbon atoms replaced by one or more Z's which may be identical with or different from one another, if two or more Z's are present, $R^{12}$ is a hydrogen atom, $C_1$-$C_6$ alkyl or $C_3$-$C_6$ cycloalkyl, $R^{17}$ is —C(O)O$R^{12}$ or phenyl, Z is a halogen atom or $C_1$-$C_6$ alkyl, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, and when m is an integer of at least 2, each $R^{16}$ may be identical with or different from one another, when s2 or s3 is an integer of at least 2, each $R^z$ may be identical with or different from one another, a is an integer of from 1 to 5, m is an integer of from 1 to 5, s2 is an integer of from 0 to 3, and s3 is an integer of from 0 to 2].

As the scope of the substituent represented by $R^2$ in the compounds which fall within the present invention, the following sets may, for example, be mentioned.

$R^2$-I: a hydrogen atom, $C_1$-$C_6$ alkyl, phenyl and phenyl optionally substituted with e $R^{21}$'s [wherein $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl or phenyl, and when e is an integer of at least 2, each $R^{21}$ may be identical with or different from one another, and e is an integer of from 1 to 5].

$R^2$-II: a hydrogen atom, $C_1$-$C_6$ alkyl, D2, benzyl, benzyl having a benzene ring optionally substituted with e $R^{21}$'s, phenyl and phenyl optionally substituted with e $R^{21}$'s [wherein $R^{21}$ is a halogen atom, $C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, when e is an integer of at least 2, each $R^{21}$ may be identical with or different from one another, and when there are two neighboring $R^{21}$'s, the two neighboring $R^{21}$'s may form —OCH$_2$O—, —OCH$_2$CH$_2$O— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, Z is a halogen atom or $C_1$-$C_6$ alkyl, $R^z$ is $C_1$-$C_6$ alkyl, phenoxy or phenyl, and when s2 is an integer of at least 2, each $R^z$ may be identical with or different from one another, e is an integer of from 1 to 5, and s2 is an integer of from 0 to 3].

$R^2$-III: a hydrogen atom, $C_1$-$C_6$ alkyl, D2, D7, benzyl, benzyl having a benzene ring optionally substituted with e $R^{21}$'s, phenyl and phenyl optionally substituted with e $R^{21}$'s [wherein $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one another, and when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, Z is a halogen atom or $C_1$-$C_6$ alkyl, and when f is an integer of at least 2, each $R^{22}$ may be identical with or different from one another, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R_z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, e is an integer of from 1 to 5, f is an integer of from 1 to 5, m is an integer of from 1 to 5, and s2 is an integer of from 0 to 3].

$R^2$-IV: a hydrogen atom, $C_1$-$C_6$ alkyl, $C_3$-$C_6$ cycloalkyl, D2, D7, benzyl, benzyl having a benzene ring optionally substituted with e $R^{21}$'s, phenyl and phenyl optionally substituted with e $R^{21}$'s [wherein $R^{21}$ is a halogen atom, $C_1$-$C_{10}$ alkyl, $C_{30}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one another, and when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, Z is a halogen atom or $C_1$-$C_6$ alkyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, e is an integer of from 1 to 5, f is an integer of from 1 to 5, e is an integer of from 1 to 5, and s2 is an integer of from 0 to 3].

As the scope of the substituent represented by $R^3$ in the compounds which fall within the present invention, the following sets may, for example, be mentioned.

$R^3$-I: a hydrogen atom.

$R^3$-II: a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$ and —C(O)N($R^{12}$)$R^{13}$ [wherein each of $R^{12}$ and $R^{13}$ is independently a hydrogen atom, $C_1$-$C_6$ alkyl or $C_3$-$C_6$ cycloalkyl], —Si($R^{32}$)($R^{33}$)$R^{34}$ [wherein each of $R^{32}$, $R^{33}$ and $R^{34}$ is independently $C_1$-$C_6$ alkyl or $C_3$-$C_6$ cycloalkyl].

$R^3$-III: a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$ and —C(O)N($R^{12}$)$R^{13}$ [wherein each of $R^{12}$ and $R^{13}$ is independently a hydrogen atom, $C_1$-$C_6$ alkyl or $C_3$-$C_6$ cycloalkyl], —Si($R^{32}$)($R^{33}$)$R^{34}$ [wherein each of $R^{32}$, $R^{33}$ and $R^{34}$ is independently $C_1$-$C_6$ alkyl or $C_3$-$C_6$ cycloalkyl], benzyl or benzyl having a benzene ring which may be substituted with g $R^{15}$'s [wherein $R^{15}$ is a halogen atom, $C_1$-$C_6$ alkyl, $C_1$-$C_6$ alkoxy or $C_1$-$C_6$ haloalkyl, and when g is an integer of at least 2, each $R^{15}$ may be identical with or different from one another, and g is an integer of from 1 to 5].

As the scope of the substituent represented by $R^4$ in the compounds which fall within the present invention, the following sets may, for example, be mentioned.

$R^4$-I: $C_1$-$C_4$ alkyl.

As the scope of the substituent represented by $R^5$ in the compounds which fall within the present invention, the following sets may, for example, be mentioned.

$R^5$-I: $C_1$-$C_4$ alkyl$_o$

As the scope of the substituent represented by $R^4$ and $R^5$ in the compounds which fall within the present invention, the following sets may, for example, be mentioned.

$R^4$+$R^5$: —$CH_2CH_2$—, —$CH_2CH_2CH_2$—, —$CH_2CH_2CH_2CH_2$— or —$CH_2CH_2CH_2CH_2CH_2$—, which forms a 3-membered, 4-membered, 5-membered or 6-membered ring together with the carbon atoms attached to $R^4$ and $R^5$.

As the scope of the substituent represented by $R^8$ in the compounds which fall within the present invention, the following sets may, for example, be mentioned.

$R^8$-I: F1, phenyl, 1-naphthyl or 2-naphthyl.

$R^8$-II: D2, F1, phenyl and phenyl optionally substituted with k $R^{81}$'s [wherein $R^{81}$ is a halogen atom, $C_1$-$C_6$ alkyl, $C_1$-$C_6$ haloalkyl, $C_1$-$C_6$ alkoxy, phenyl or phenoxy, and when k is an integer of at least 2, each $R^{81}$ may be identical with or different from one another, and when there are two neighboring $R^{81}$'s, the two neighboring $R^{81}$'s may form —$OCH_2O$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, k is an integer of from 1 to 5, and s2 is an integer of from 0 to 3].

$R^8$-III: D2, F1, phenyl and phenyl optionally substituted with k $R^{81}$'s [wherein $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy, and when k is an integer of at least 2, each $R^{81}$ may be identical with or different from one another, and when there are two neighboring $R^{81}$'s, the two neighboring $R^{81}$'s may form —$OCH_2O$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom or $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, k is an integer of from 1 to 5, m is an integer of from 1 to 5, and s2 is an integer of from 0 to 3].

$R^8$-IV: D2, D7, D23, F1, F2, phenyl and phenyl optionally substituted with k $R^{81}$s [wherein $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy, and when k is an integer of at least 2, each $R^{81}$ may be identical with or different from one another, and when there are two neighboring $R^{81}$'s, the two neighboring $R^{81}$'s may form —OCH$_2$O— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, k is an integer of from 1 to 5, m is an integer of from 1 to 5, and s2 is an integer of from 0 to 3].

As the scope of the substituent represented by X in the compounds which fall within the present invention, the following sets may, for example, be mentioned.

X-1: a single bond.
X-2: —CH$_2$—.

The sets indicating the scope of each substituent in the compounds which fall within the present invention may be combined arbitrarily to indicate the scope of the compounds of the present invention. The scope of $R^1$, $R^2$, $R^3$, $R^8$ or X may be combined, for example, as shown in Table 1. The combinations shown in Table 1 merely exemplify the present invention, and the present invention is by no means restricted thereto.

TABLE 1

| $R^1$ | $R^2$ | $R^3$ | $R^8$ | X |
|---|---|---|---|---|
| $R^1$-I | $R^2$-I | $R^3$-I | $R^8$-I | X-1 |
| $R^1$-I | $R^2$-I | $R^3$-I | $R^8$-II | X-1 |
| $R^1$-I | $R^2$-I | $R^3$-I | $R^8$-III | X-1 |
| $R^1$-I | $R^2$-I | $R^3$-I | $R^8$-IV | X-1 |
| $R^1$-I | $R^2$-I | $R^3$-II | $R^8$-I | X-1 |
| $R^1$-I | $R^2$-I | $R^3$-II | $R^8$-II | X-1 |
| $R^1$-I | $R^2$-I | $R^3$-II | $R^8$-III | X-1 |
| $R^1$-I | $R^2$-I | $R^3$-II | $R^8$-IV | X-1 |
| $R^1$-I | $R^2$-I | $R^3$-III | $R^8$-I | X-1 |
| $R^1$-I | $R^2$-I | $R^3$-III | $R^8$-II | X-1 |
| $R^1$-I | $R^2$-I | $R^3$-III | $R^8$-III | X-1 |
| $R^1$-I | $R^2$-I | $R^3$-III | $R^8$-IV | X-1 |
| $R^1$-I | $R^2$-II | $R^3$-I | $R^8$-I | X-1 |
| $R^1$-I | $R^2$-II | $R^3$-I | $R^8$-II | X-1 |
| $R^1$-I | $R^2$-II | $R^3$-I | $R^8$-III | X-1 |
| $R^1$-I | $R^2$-II | $R^3$-I | $R^8$-IV | X-1 |
| $R^1$-I | $R^2$-II | $R^3$-II | $R^8$-I | X-1 |
| $R^1$-I | $R^2$-II | $R^3$-II | $R^8$-II | X-1 |
| $R^1$-I | $R^2$-II | $R^3$-II | $R^8$-III | X-1 |
| $R^1$-I | $R^2$-II | $R^3$-II | $R^8$-IV | X-1 |
| $R^1$-I | $R^2$-II | $R^3$-III | $R^8$-I | X-1 |
| $R^1$-I | $R^2$-II | $R^3$-III | $R^8$-II | X-1 |
| $R^1$-I | $R^2$-II | $R^3$-III | $R^8$-III | X-1 |
| $R^1$-I | $R^2$-II | $R^3$-III | $R^8$-IV | X-1 |
| $R^1$-I | $R^2$-III | $R^3$-I | $R^8$-I | X-1 |
| $R^1$-I | $R^2$-III | $R^3$-I | $R^8$-II | X-1 |
| $R^1$-I | $R^2$-III | $R^3$-I | $R^8$-III | X-1 |
| $R^1$-I | $R^2$-III | $R^3$-I | $R^8$-IV | X-1 |
| $R^1$-I | $R^2$-III | $R^3$-II | $R^8$-I | X-1 |
| $R^1$-I | $R^2$-III | $R^3$-II | $R^8$-II | X-1 |
| $R^1$-I | $R^2$-III | $R^3$-II | $R^8$-III | X-1 |
| $R^1$-I | $R^2$-III | $R^3$-II | $R^8$-IV | X-1 |
| $R^1$-I | $R^2$-III | $R^3$-III | $R^8$-I | X-1 |
| $R^1$-I | $R^2$-III | $R^3$-III | $R^8$-II | X-1 |
| $R^1$-I | $R^2$-III | $R^3$-III | $R^8$-III | X-1 |
| $R^1$-I | $R^2$-III | $R^3$-III | $R^8$-IV | X-1 |
| $R^1$-I | $R^2$-IV | $R^3$-I | $R^8$-I | X-1 |
| $R^1$-I | $R^2$-IV | $R^3$-I | $R^8$-II | X-1 |
| $R^1$-I | $R^2$-IV | $R^3$-I | $R^8$-III | X-1 |
| $R^1$-I | $R^2$-IV | $R^3$-I | $R^8$-IV | X-1 |
| $R^1$-I | $R^2$-IV | $R^3$-II | $R^8$-I | X-1 |
| $R^1$-I | $R^2$-IV | $R^3$-II | $R^8$-II | X-1 |
| $R^1$-I | $R^2$-IV | $R^3$-II | $R^8$-III | X-1 |
| $R^1$-I | $R^2$-IV | $R^3$-II | $R^8$-IV | X-1 |
| $R^1$-I | $R^2$-IV | $R^3$-III | $R^8$-I | X-1 |
| $R^1$-I | $R^2$-IV | $R^3$-III | $R^8$-II | X-1 |
| $R^1$-I | $R^2$-IV | $R^3$-III | $R^8$-III | X-1 |
| $R^1$-I | $R^2$-IV | $R^3$-III | $R^8$-IV | X-1 |
| $R^1$-II | $R^2$-I | $R^3$-I | $R^8$-I | X-1 |
| $R^1$-II | $R^2$-I | $R^3$-I | $R^8$-II | X-1 |
| $R^1$-II | $R^2$-I | $R^3$-I | $R^8$-III | X-1 |
| $R^1$-II | $R^2$-I | $R^3$-I | $R^8$-IV | X-1 |
| $R^1$-II | $R^2$-I | $R^3$-II | $R^8$-I | X-1 |
| $R^1$-II | $R^2$-I | $R^3$-II | $R^8$-II | X-1 |
| $R^1$-II | $R^2$-I | $R^3$-II | $R^8$-III | X-1 |
| $R^1$-II | $R^2$-I | $R^3$-II | $R^8$-IV | X-1 |
| $R^1$-II | $R^2$-I | $R^3$-III | $R^8$-I | X-1 |
| $R^1$-II | $R^2$-I | $R^3$-III | $R^8$-II | X-1 |
| $R^1$-II | $R^2$-I | $R^3$-III | $R^8$-III | X-1 |
| $R^1$-II | $R^2$-I | $R^3$-III | $R^8$-IV | X-1 |
| $R^1$-II | $R^2$-II | $R^3$-I | $R^8$-I | X-1 |
| $R^1$-II | $R^2$-II | $R^3$-I | $R^8$-II | X-1 |
| $R^1$-II | $R^2$-II | $R^3$-I | $R^8$-III | X-1 |
| $R^1$-II | $R^2$-II | $R^3$-I | $R^8$-IV | X-1 |
| $R^1$-II | $R^2$-II | $R^3$-II | $R^8$-I | X-1 |
| $R^1$-II | $R^2$-II | $R^3$-II | $R^8$-II | X-1 |
| $R^1$-II | $R^2$-II | $R^3$-II | $R^8$-III | X-1 |
| $R^1$-II | $R^2$-II | $R^3$-II | $R^8$-IV | X-1 |
| $R^1$-II | $R^2$-II | $R^3$-III | $R^8$-I | X-1 |
| $R^1$-II | $R^2$-II | $R^3$-III | $R^8$-II | X-1 |
| $R^1$-II | $R^2$-II | $R^3$-III | $R^8$-III | X-1 |
| $R^1$-II | $R^2$-II | $R^3$-III | $R^8$-IV | X-1 |
| $R^1$-II | $R^2$-III | $R^3$-I | $R^8$-I | X-1 |
| $R^1$-II | $R^2$-III | $R^3$-I | $R^8$-II | X-1 |
| $R^1$-II | $R^2$-III | $R^3$-I | $R^8$-III | X-1 |
| $R^1$-II | $R^2$-III | $R^3$-I | $R^8$-IV | X-1 |
| $R^1$-II | $R^2$-III | $R^3$-II | $R^8$-I | X-1 |
| $R^1$-II | $R^2$-III | $R^3$-II | $R^8$-II | X-1 |
| $R^1$-II | $R^2$-III | $R^3$-II | $R^8$-III | X-1 |
| $R^1$-II | $R^2$-III | $R^3$-II | $R^8$-IV | X-1 |
| $R^1$-II | $R^2$-III | $R^3$-III | $R^8$-I | X-1 |
| $R^1$-II | $R^2$-III | $R^3$-III | $R^8$-II | X-1 |
| $R^1$-II | $R^2$-III | $R^3$-III | $R^8$-III | X-1 |
| $R^1$-II | $R^2$-III | $R^3$-III | $R^8$-IV | X-1 |
| $R^1$-II | $R^2$-IV | $R^3$-I | $R^8$-I | X-1 |
| $R^1$-II | $R^2$-IV | $R^3$-I | $R^8$-II | X-1 |
| $R^1$-II | $R^2$-IV | $R^3$-I | $R^8$-III | X-1 |
| $R^1$-II | $R^2$-IV | $R^3$-I | $R^8$-IV | X-1 |
| $R^1$-II | $R^2$-IV | $R^3$-II | $R^8$-I | X-1 |
| $R^1$-II | $R^2$-IV | $R^3$-II | $R^8$-II | X-1 |
| $R^1$-II | $R^2$-IV | $R^3$-II | $R^8$-III | X-1 |
| $R^1$-II | $R^2$-IV | $R^3$-II | $R^8$-IV | X-1 |
| $R^1$-II | $R^2$-IV | $R^3$-III | $R^8$-I | X-1 |
| $R^1$-II | $R^2$-IV | $R^3$-III | $R^8$-II | X-1 |
| $R^1$-II | $R^2$-IV | $R^3$-III | $R^8$-III | X-1 |
| $R^1$-II | $R^2$-IV | $R^3$-III | $R^8$-IV | X-1 |
| $R^1$-III | $R^2$-I | $R^3$-I | $R^8$-I | X-1 |
| $R^1$-III | $R^2$-I | $R^3$-I | $R^8$-II | X-1 |

TABLE 1-continued

| R¹ | R² | R³ | R⁸ | X |
|---|---|---|---|---|
| R¹-III | R²-I | R³-I | R⁸-III | X-1 |
| R¹-III | R²-I | R³-I | R⁸-IV | X-1 |
| R¹-III | R²-I | R³-II | R⁸-I | X-1 |
| R¹-III | R²-I | R³-II | R⁸-II | X-1 |
| R¹-III | R²-I | R³-II | R⁸-III | X-1 |
| R¹-III | R²-I | R³-II | R⁸-IV | X-1 |
| R¹-III | R²-I | R³-III | R⁸-I | X-1 |
| R¹-III | R²-I | R³-III | R⁸-II | X-1 |
| R¹-III | R²-I | R³-III | R⁸-III | X-1 |
| R¹-III | R²-I | R³-III | R⁸-IV | X-1 |
| R¹-III | R²-II | R³-I | R⁸-I | X-1 |
| R¹-III | R²-II | R³-I | R⁸-II | X-1 |
| R¹-III | R²-II | R³-I | R⁸-III | X-1 |
| R¹-III | R²-II | R³-I | R⁸-IV | X-1 |
| R¹-III | R²-II | R³-II | R⁸-I | X-1 |
| R¹-III | R²-II | R³-II | R⁸-II | X-1 |
| R¹-III | R²-II | R³-II | R⁸-III | X-1 |
| R¹-III | R²-II | R³-II | R⁸-IV | X-1 |
| R¹-III | R²-II | R³-III | R⁸-I | X-1 |
| R¹-III | R²-II | R³-III | R⁸-II | X-1 |
| R¹-III | R²-II | R³-III | R⁸-III | X-1 |
| R¹-III | R²-II | R³-III | R⁸-IV | X-1 |
| R¹-III | R²-III | R³-I | R⁸-I | X-1 |
| R¹-III | R²-III | R³-I | R⁸-II | X-1 |
| R¹-III | R²-III | R³-I | R⁸-III | X-1 |
| R¹-III | R²-III | R³-I | R⁸-IV | X-1 |
| R¹-III | R²-III | R³-II | R⁸-I | X-1 |
| R¹-III | R²-III | R³-II | R⁸-II | X-1 |
| R¹-III | R²-III | R³-II | R⁸-III | X-1 |
| R¹-III | R²-III | ³-II | R⁸-IV | X-1 |
| R¹-III | R²-III | R³-III | R⁸-I | X-1 |
| R¹-III | R²-III | R³-III | R⁸-II | X-1 |
| R¹-III | R²-III | R³-III | R⁸-III | X-1 |
| R¹-III | R²-III | R³-III | R⁸-IV | X-1 |
| R¹-III | R²-IV | R³-I | R⁸-I | X-1 |
| R¹-III | R²-IV | R³-I | R⁸-II | X-1 |
| R¹-III | R²-IV | R³-I | R⁸-III | X-1 |
| R¹-III | R²-IV | R³-I | R⁸-IV | X-1 |
| R¹-III | R²-IV | R³-II | R⁸-I | X-1 |
| R¹-III | R²-IV | R³-II | R⁸-II | X-1 |
| R¹-III | R²-IV | R³-II | R⁸-III | X-1 |
| R¹-III | R²-IV | R³-II | R⁸-IV | X-1 |
| R¹-III | R²-IV | R³-III | R⁸-I | X-1 |
| R¹-III | R²-IV | R³-III | R⁸-II | X-1 |
| R¹-III | R²-IV | R³-III | R⁸-III | X-1 |
| R¹-III | R²-IV | R³-III | R⁸-IV | X-1 |
| R¹-IV | R²-I | R³-I | R⁸-I | X-1 |
| R¹-IV | R²-I | R³-I | R⁸-II | X-1 |
| R¹-IV | R²-I | R³-I | R⁸-III | X-1 |
| R¹-IV | R²-I | R³-I | R⁸-IV | X-1 |
| R¹-IV | R²-I | R³-II | R⁸-I | X-1 |
| R¹-IV | R²-I | R³-II | R⁸-II | X-1 |
| R¹-IV | R²-I | R³-II | R⁸-III | X-1 |
| R¹-IV | R²-I | R³-II | R⁸-IV | X-1 |
| R¹-IV | R²-I | R³-III | R⁸-I | X-1 |
| R¹-IV | R²-I | R³-III | R⁸-II | X-1 |
| R¹-IV | R²-I | R³-III | R⁸-III | X-1 |
| R¹-IV | R²-I | R³-III | R⁸-IV | X-1 |
| R¹-IV | R²-II | R³-I | R⁸-I | X-1 |
| R¹-IV | R²-II | R³-I | R⁸-II | X-1 |
| R¹-IV | R²-II | R³-I | R⁸-III | X-1 |
| R¹-IV | R²-II | R³-I | R⁸-IV | X-1 |
| R¹-IV | R²-II | R³-II | R⁸-I | X-1 |
| R¹-IV | R²-II | R³-II | R⁸-II | X-1 |
| R¹-IV | R²-II | R³-II | R⁸-III | X-1 |
| R¹-IV | R²-II | R³-II | R⁸-IV | X-1 |
| R¹-IV | R²-II | R³-III | R⁸-I | X-1 |
| R¹-IV | R²-II | R³-III | R⁸-II | X-1 |
| R¹-IV | R²-II | R³-III | R⁸-III | X-1 |
| R¹-IV | R²-II | R³-III | R⁸-IV | X-1 |
| R¹-IV | R²-III | R³-I | R⁸-I | X-1 |
| R¹-IV | R²-III | R³-I | R⁸-II | X-1 |
| R¹-IV | R²-III | R³-I | R⁸-III | X-1 |
| R¹-IV | R²-III | R³-I | R⁸-IV | X-1 |
| R¹-IV | R²-III | R³-II | R⁸-I | X-1 |
| R¹-IV | R²-III | R³-II | R⁸-II | X-1 |
| R¹-IV | R²-III | R³-II | R⁸-III | X-1 |
| R¹-IV | R²-III | R³-II | R⁸-IV | X-1 |
| R¹-IV | R²-III | R³-III | R⁸-I | X-1 |
| R¹-IV | R²-III | R³-III | R⁸-II | X-1 |
| R¹-IV | R²-III | R³-III | R⁸-III | X-1 |
| R¹-IV | R²-III | R³-III | R⁸-IV | X-1 |
| R¹-IV | R²-IV | R³-I | R⁸-I | X-1 |
| R¹-IV | R²-IV | R³-I | R⁸-II | X-1 |
| R¹-IV | R²-IV | R³-I | R⁸-III | X-1 |
| R¹-IV | R²-IV | R³-I | R⁸-IV | X-1 |
| R¹-IV | R²-IV | R³-II | R⁸-I | X-1 |
| R¹-IV | R²-IV | R³-II | R⁸-II | X-1 |
| R¹-IV | R²-IV | R³-II | R⁸-III | X-1 |
| R¹-IV | R²-IV | R³-II | R⁸-IV | X-1 |
| R¹-IV | R²-IV | R³-III | R⁸-I | X-1 |
| R¹-IV | R²-IV | R³-III | R⁸-II | X-1 |
| R¹-IV | R²-IV | R³-III | R⁸-III | X-1 |
| R¹-IV | R²-IV | R³-III | R⁸-IV | X-1 |
| R¹-I | R²-I | R³-I | R⁸-I | X-2 |
| R¹-I | R²-I | R³-I | R⁸-II | X-2 |
| R¹-I | R²-I | R³-I | R⁸-III | X-2 |
| R¹-I | R²-I | R³-I | R⁸-IV | X-2 |
| R¹-I | R²-I | R³-II | R⁸-I | X-2 |
| R¹-I | R²-I | R³-II | R⁸-II | X-2 |
| R¹-I | R²-I | R³-II | R⁸-III | X-2 |
| R¹-I | R²-I | R³-II | R⁸-IV | X-2 |
| R¹-I | R²-I | R³-III | R⁸-I | X-2 |
| R¹-I | R²-I | R³-III | R⁸-II | X-2 |
| R¹-I | R²-I | R³-III | R⁸-III | X-2 |
| R¹-I | R²-I | R³-III | R⁸-IV | X-2 |
| R¹-I | R²-II | R³-I | R⁸-I | X-2 |
| R¹-I | R²-II | R³-I | R⁸-II | X-2 |
| R¹-I | R²-II | R³-I | R⁸-III | X-2 |
| R¹-I | R²-II | R³-I | R⁸-IV | X-2 |
| R¹-I | R²-II | R³-II | R⁸-I | X-2 |
| R¹-I | R²-II | R³-II | R⁸-II | X-2 |
| R¹-I | R²-II | R³-II | R⁸-III | X-2 |
| R¹-I | R²-II | R³-II | R⁸-IV | X-2 |
| R¹-I | R²-II | R³-III | R⁸-I | X-2 |
| R¹-I | R²-II | R³-III | R⁸-II | X-2 |
| R¹-I | R²-II | R³-III | R⁸-III | X-2 |
| R¹-I | R²-II | R³-III | R⁸-IV | X-2 |
| R¹-I | R²-III | R³-I | R⁸-I | X-2 |
| R¹-I | R²-III | R³-I | R⁸-II | X-2 |
| R¹-I | R²-III | R³-I | R⁸-III | X-2 |
| R¹-I | R²-III | R³-I | R⁸-IV | X-2 |
| R¹-I | R²-III | R³-II | R⁸-I | X-2 |
| R¹-I | R²-III | R³-II | R⁸-II | X-2 |
| R¹-I | R²-III | R³-II | R⁸-III | X-2 |
| R¹-I | R²-III | R³-II | R⁸-IV | X-2 |
| R¹-I | R²-III | R³-III | R⁸-I | X-2 |
| R¹-I | R²-III | R³-III | R⁸-II | X-2 |
| R¹-I | R²-III | R³-III | R⁸-III | X-2 |
| R¹-I | R²-III | R³-III | R⁸-IV | X-2 |
| R¹-I | R²-IV | R³-I | R⁸-I | X-2 |
| R¹-I | R²-IV | R³-I | R⁸-II | X-2 |
| R¹-I | R²-IV | R³-I | R⁸-III | X-2 |
| R¹-I | R²-IV | R³-I | R⁸-IV | X-2 |
| R¹-I | R²-IV | R³-II | R⁸-I | X-2 |
| R¹-I | R²-IV | R³-II | R⁸-II | X-2 |
| R¹-I | R²-IV | R³-II | R⁸-III | X-2 |
| R¹-I | R²-IV | R³-II | R⁸-IV | X-2 |
| R¹-I | R²-IV | R³-III | R⁸-I | X-2 |
| R¹-I | R²-IV | R³-III | R⁸-II | X-2 |
| R¹-I | R²-IV | R³-III | R⁸-III | X-2 |
| R¹-I | R²-IV | R³-III | R⁸-IV | X-2 |
| R¹-II | R²-I | R³-I | R⁸-I | X-2 |
| R¹-II | R²-I | R³-I | R⁸-II | X-2 |
| R¹-II | R²-I | R³-I | R⁸-III | X-2 |
| R¹-II | R²-I | R³-I | R⁸-IV | X-2 |
| R¹-II | R²-I | R³-II | R⁸-I | X-2 |
| R¹-II | R²-I | R³-II | R⁸-II | X-2 |
| R¹-II | R²-I | R³-II | R⁸-III | X-2 |
| R¹-II | R²-I | R³-II | R⁸-IV | X-2 |
| R¹-II | R²-I | R³-III | R⁸-I | X-2 |
| R¹-II | R²-I | R³-III | R⁸-II | X-2 |
| R¹-II | R²-I | R³-III | R⁸-III | X-2 |
| R¹-II | R²-I | R³-III | R⁸-IV | X-2 |
| R¹-II | R²-II | R³-I | R⁸-I | X-2 |
| R¹-II | R²-II | R³-I | R⁸-II | X-2 |

TABLE 1-continued

| R¹ | R² | R³ | R⁸ | X |
|---|---|---|---|---|
| R¹-II | R²-II | R³-I | R⁸-III | X-2 |
| R¹-II | R²-II | R³-I | R⁸-IV | X-2 |
| R¹-II | R²-II | R³-II | R⁸-I | X-2 |
| R¹-II | R²-II | R³-II | R⁸-II | X-2 |
| R¹-II | R²-II | R³-II | R⁸-III | X-2 |
| R¹-II | R²-II | R³-II | R⁸-IV | X-2 |
| R¹-II | R²-II | R³-III | R⁸-I | X-2 |
| R¹-II | R²-II | R³-III | R⁸-II | X-2 |
| R¹-II | R²-II | R³-III | R⁸-III | X-2 |
| R¹-II | R²-II | R³-III | R⁸-IV | X-2 |
| R¹-II | R²-III | R³-I | R⁸-I | X-2 |
| R¹-II | R²-III | R³-I | R⁸-II | X-2 |
| R¹-II | R²-III | R³-I | R⁸-III | X-2 |
| R¹-II | R²-III | R³-I | R⁸-IV | X-2 |
| R¹-II | R²-III | R³-II | R⁸-I | X-2 |
| R¹-II | R²-III | R³-II | R⁸-II | X-2 |
| R¹-II | R²-III | R³-II | R⁸-III | X-2 |
| R¹-II | R²-III | R³-II | R⁸-IV | X-2 |
| R¹-II | R²-III | R³-III | R⁸-I | X-2 |
| R¹-II | R²-III | R³-III | R⁸-II | X-2 |
| R¹-II | R²-III | R³-III | R⁸-III | X-2 |
| R¹-II | R²-III | R³-III | R⁸-IV | X-2 |
| R¹-II | R²-IV | R³-I | R⁸-I | X-2 |
| R¹-II | R²-IV | R³-I | R⁸-II | X-2 |
| R¹-II | R²-IV | R³-I | R⁸-III | X-2 |
| R¹-II | R²-IV | R³-I | R⁸-IV | X-2 |
| R¹-II | R²-IV | R³-II | R⁸-I | X-2 |
| R¹-II | R²-IV | R³-II | R⁸-II | X-2 |
| R¹-II | R²-IV | R³-II | R⁸-III | X-2 |
| R¹-II | R²-IV | R³-II | R⁸-IV | X-2 |
| R¹-II | R²-IV | R³-III | R⁸-I | X-2 |
| R¹-II | R²-IV | R³-III | R⁸-II | X-2 |
| R¹-II | R²-IV | R³-III | R⁸-III | X-2 |
| R¹-II | R²-IV | R³-III | R⁸-IV | X-2 |
| R¹-III | R²-I | R³-I | R⁸-I | X-2 |
| R¹-III | R²-I | R³-I | R⁸-II | X-2 |
| R¹-III | R²-I | R³-I | R⁸-III | X-2 |
| R¹-III | R²-I | R³-I | R⁸-IV | X-2 |
| R¹-III | R²-I | R³-II | R⁸-I | X-2 |
| R¹-III | R²-I | R³-II | R⁸-II | X-2 |
| R¹-III | R²-I | R³-II | R⁸-III | X-2 |
| R¹-III | R²-I | R³-II | R⁸-IV | X-2 |
| R¹-III | R²-I | R³-III | R⁸-I | X-2 |
| R¹-III | R²-I | R³-III | R⁸-II | X-2 |
| R¹-III | R²-I | R³-III | R⁸-III | X-2 |
| R¹-III | R²-I | R³-III | R⁸-IV | X-2 |
| R¹-III | R²-II | R³-I | R⁸-I | X-2 |
| R¹-III | R²-II | R³-I | R⁸-II | X-2 |
| R¹-III | R²-II | R³-I | R⁸-III | X-2 |
| R¹-III | R²-II | R³-I | R⁸-IV | X-2 |
| R¹-III | R²-II | R³-II | R⁸-I | X-2 |
| R¹-III | R²-II | R³-II | R⁸-II | X-2 |
| R¹-III | R²-II | R³-II | R⁸-III | X-2 |
| R¹-III | R²-II | R³-II | R⁸-IV | X-2 |
| R¹-III | R²-II | R³-III | R⁸-I | X-2 |
| R¹-III | R²-II | R³-III | R⁸-II | X-2 |
| R¹-III | R²-II | R³-III | R⁸-III | X-2 |
| R¹-III | R²-II | R³-III | R⁸-IV | X-2 |
| R¹-III | R²-III | R³-I | R⁸-I | X-2 |
| R¹-III | R²-III | R³-I | R⁸-II | X-2 |
| R¹-III | R²-III | R³-I | R⁸-III | X-2 |
| R¹-III | R²-III | R³-I | R⁸-IV | X-2 |
| R¹-III | R²-III | R³-II | R⁸-I | X-2 |
| R¹-III | R²-III | R³-II | R⁸-II | X-2 |
| R¹-III | R²-III | R³-II | R⁸-III | X-2 |
| R¹-III | R²-III | R³-II | R⁸-IV | X-2 |
| R¹-III | R²-III | R³-III | R⁸-I | X-2 |
| R¹-III | R²-III | R³-III | R⁸-II | X-2 |
| R¹-III | R²-III | R³-III | R⁸-III | X-2 |
| R¹-III | R²-III | R³-III | R⁸-IV | X-2 |
| R¹-III | R²-IV | R³-I | R⁸-I | X-2 |
| R¹-III | R²-IV | R³-I | R⁸-II | X-2 |
| R¹-III | R²-IV | R³-I | R⁸-III | X-2 |
| R¹-III | R²-IV | R³-I | R⁸-IV | X-2 |
| R¹-III | R²-IV | R³-II | R⁸-I | X-2 |
| R¹-III | R²-IV | R³-II | R⁸-II | X-2 |
| R¹-III | R²-IV | R³-II | R⁸-III | X-2 |
| R¹-III | R²-IV | R³-II | R⁸-IV | X-2 |

TABLE 1-continued

| R¹ | R² | R³ | R⁸ | X |
|---|---|---|---|---|
| R¹-III | R²-IV | R³-III | R⁸-I | X-2 |
| R¹-III | R²-IV | R³-III | R⁸-II | X-2 |
| R¹-III | R²-IV | R³-III | R⁸-III | X-2 |
| R¹-III | R²-IV | R³-III | R⁸-IV | X-2 |
| R¹-IV | R²-I | R³-I | R⁸-I | X-2 |
| R¹-IV | R²-I | R³-I | R⁸-II | X-2 |
| R¹-IV | R²-I | R³-I | R⁸-III | X-2 |
| R¹-IV | R²-I | R³-I | R⁸-IV | X-2 |
| R¹-IV | R²-I | R³-II | R⁸-I | X-2 |
| R¹-IV | R²-I | R³-II | R⁸-II | X-2 |
| R¹-IV | R²-I | R³-II | R⁸-III | X-2 |
| R¹-IV | R²-I | R³-II | R⁸-IV | X-2 |
| R¹-IV | R²-I | R³-III | R⁸-I | X-2 |
| R¹-IV | R²-I | R³-III | R⁸-II | X-2 |
| R¹-IV | R²-I | R³-III | R⁸-III | X-2 |
| R¹-IV | R²-I | R³-III | R⁸-IV | X-2 |
| R¹-IV | R²-II | R³-I | R⁸-I | X-2 |
| R¹-IV | R²-II | R³-I | R⁸-II | X-2 |
| R¹-IV | R²-II | R³-I | R⁸-III | X-2 |
| R¹-IV | R²-II | R³-I | R⁸-IV | X-2 |
| R¹-IV | R²-II | R³-II | R⁸-I | X-2 |
| R¹-IV | R²-II | R³-II | R⁸-II | X-2 |
| R¹-IV | R²-II | R³-II | R⁸-III | X-2 |
| R¹-IV | R²-II | R³-II | R⁸-IV | X-2 |
| R¹-IV | R²-II | R³-III | R⁸-I | X-2 |
| R¹-IV | R²-II | R³-III | R⁸-II | X-2 |
| R¹-IV | R²-II | R³-III | R⁸-III | X-2 |
| R¹-IV | R²-II | R³-III | R⁸-IV | X-2 |
| R¹-IV | R²-III | R³-I | R⁸-I | X-2 |
| R¹-IV | R²-III | R³-I | R⁸-II | X-2 |
| R¹-IV | R²-III | R³-I | R⁸-III | X-2 |
| R¹-IV | R²-III | R³-I | R⁸-IV | X-2 |
| R¹-IV | R²-III | R³-II | R⁸-I | X-2 |
| R¹-IV | R²-III | R³-II | R⁸-II | X-2 |
| R¹-IV | R²-III | R³-II | R⁸-III | X-2 |
| R¹-IV | R²-III | R³-II | R⁸-IV | X-2 |
| R¹-IV | R²-III | R³-III | R⁸-I | X-2 |
| R¹-IV | R²-III | R³-III | R⁸-II | X-2 |
| R¹-IV | R²-III | R³-III | R⁸-III | X-2 |
| R¹-IV | R²-III | R³-III | R⁸-IV | X-2 |
| R¹-IV | R²-IV | R³-I | R⁸-I | X-2 |
| R¹-IV | R²-IV | R³-I | R⁸-II | X-2 |
| R¹-IV | R²-IV | R³-I | R⁸-III | X-2 |
| R¹-IV | R²-IV | R³-I | R⁸-IV | X-2 |
| R¹-IV | R²-IV | R³-II | R⁸-I | X-2 |
| R¹-IV | R²-IV | R³-II | R⁸-II | X-2 |
| R¹-IV | R²-IV | R³-II | R⁸-III | X-2 |
| R¹-IV | R²-IV | R³-II | R⁸-IV | X-2 |
| R¹-IV | R²-IV | R³-III | R⁸-I | X-2 |
| R¹-IV | R²-IV | R³-III | R⁸-II | X-2 |
| R¹-IV | R²-IV | R³-III | R⁸-III | X-2 |
| R¹-IV | R²-IV | R³-III | R⁸-IV | X-2 |

The compounds of the present invention can be produced, for example, by the following processes.

Process A

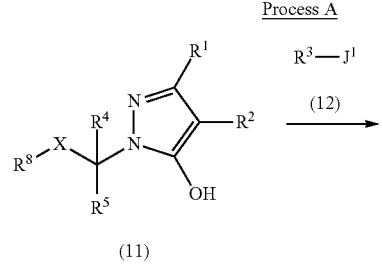

(11) (12)

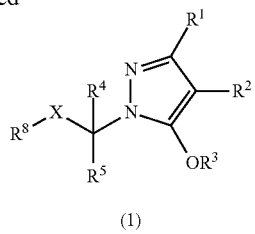

(1)

A compound represented by the formula (11) [wherein $R^1$, $R^2$, $R^4$, $R^5$, $R^8$ and X are the same as defined above] and a compound represented by the formula (12)[wherein $R^3$ is the same as defined above, and $J^1$ is a chlorine atom, a bromine atom, an iodine atom, a halosulfonyloxy group (such as a fluorosulfonyloxy group), a $C_1$-$C_4$ haloalkylsulfonyloxy group (such as a trifluoromethanesulfonyloxy group) or an arylsulfonyloxy group (such as a benzenesulfonyloxy group)] may be reacted, if necessary in the presence of a base, if necessary by using a solvent inert to the reaction, to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (12) may be used per 1 equivalent of the compound represented by the formula (11).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (11).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using from 1 to 10 equivalents of a compound represented by the formula (12) per 1 equivalent of a compound represented by the formula (11) in a solvent such as tetrahydrofuran, 1,4-dioxane, acetonitrile, N,N-dimethylformamide, chloroform, methylene chloride or toluene, if necessary by using from 1 to 3 equivalents of a base such as sodium hydride, potassium t-butoxide, potassium hydroxide, potassium carbonate, triethylamine or pyridine per 1 equivalent of the compound represented by the formula (11) at 0~100° C. for 10 minutes to 24 hours.

Process B

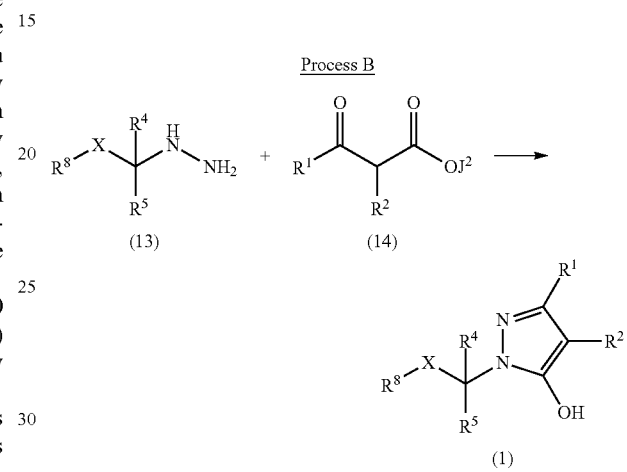

A compound represented by the formula (13) [wherein $R^4$, $R^5$, $R^8$ and X are the same as defined above] and a compound represented by the formula (14) [wherein $R^1$ and $R^2$ are the same as defined above, and $J^2$ is an alkyl group such as a methyl group or an ethyl group] are reacted, if necessary in the presence of an acid, if necessary by using a solvent inert to the reaction, by a known method disclosed in the literature such as WO 2005/061462 to obtain a compound of the present invention represented by the formula (1) [wherein $R^1$, $R^2$, $R^4$, $R^5$, $R^8$ and X are the same as defined above].

Regarding the amounts of the reactants, from 1 to 50 equivalents of the compound represented by the formula (13) may be used per 1 equivalent of the compound represented by the formula (14).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As an acid, if used, a mineral acid such as hydrochloric acid or sulfuric acid, a carboxylic acid such as formic acid, acetic acid, trifluoroacetic acid, mandelic acid or tartaric acid, a sulfonic acid such as methanesulfonic acid, p-toluenesulfonic acid, benzensulfonic acid, trifluoromethanesulfonic acid or camphor sulfonic acid, phosphorus oxychloride, Amberlite IR-120 (type H) or the like may be used in an amount of from 1 to 10 equivalents per 1 equivalent of a compound represented by the formula (14).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using from 1 to 10 equivalents of a compound represented by the formula (13) per 1 equivalent of a compound represented by the formula (14) in a solvent such as ethanol, toluene, tetrahydrofuran, 1,4-dioxane, acetonitrile, N,N-dimethylformamide, chloroform or methylene chloride, if necessary by using from 1 to 3 equivalents of an acid such as acetic acid, p-toluenesulfonic acid or hydrochloric acid at 0~100° C. for 10 minutes to 24 hours.

Some of the keto esters represented by the formula (15) used herein are known compounds, and some of them are commercially available. The rest of them can be readily synthesized from known compounds by known methods disclosed in the literature such as JP-A-2002-020366, J. Med. Chem., 2005, vol. 48, pages 3400.

Process C

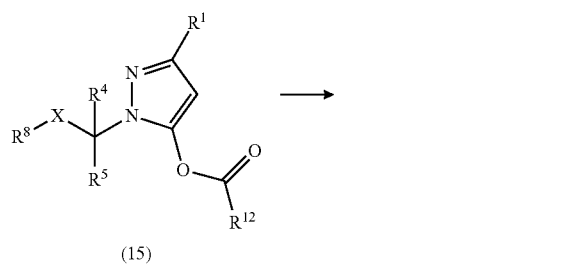

(15)

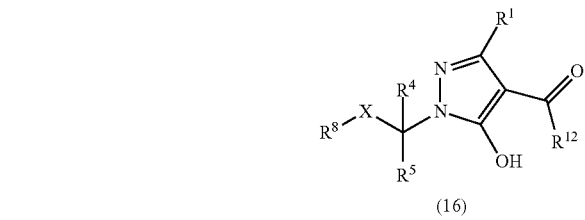

(16)

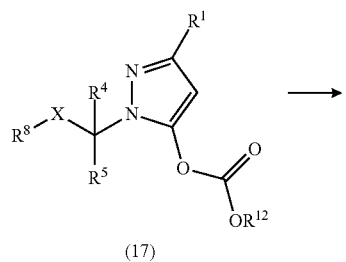

(17)

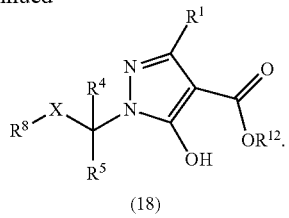

(18)

A compound represented by the formula (15) obtainable by Process A and a compound represented by the formula (17) [wherein $R^1$, $R^4$, $R^5$, $R^8$, $R^{12}$ and X are the same as defined above] are reacted, if necessary in the presence of a base, if necessary by using a solvent inert to the reaction, by a known method disclosed in the literature such as WO2007/142308 to obtain a compound of the present invention represented by the formula (16) [wherein $R^{11}$, $R^4$, $R^5$, $R^8$, $R^{12}$ and X are the same as defined above].

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide suchas dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diidopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (15) or (17).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using 1 equivalent of a compound represented by the formula (15) or (17) in a solvent such as ethanol, toluene, tetrahydrofuran, 1,4-dioxane, acetonitrile, N,N-dimethylformamide, chloroform or methylene chloride, if necessary by using from 1 to 3 equivalents of a base such as sodium hydride, potassium t-butoxide, potassium hydroxide, potassium carbonate, triethylamine or pyridine per 1 equivalent of the compound represented by the formula (15) or (17) at 0~100° C. for 10 minutes to 24 hours.

Process D

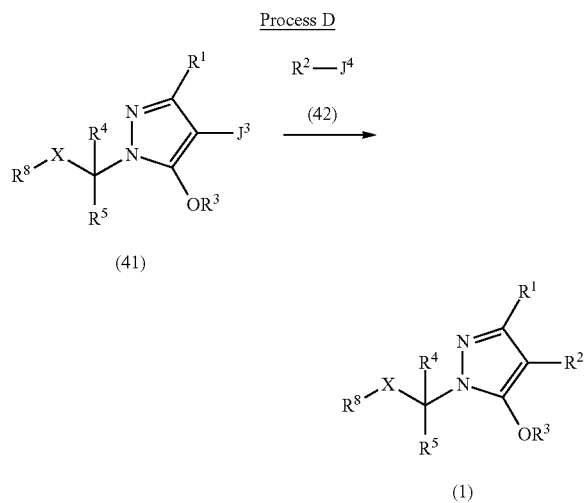

A compound represented by the formula (41) [wherein $R^1$, $R^3$, $R^4$, $R^5$, $R^8$ and X are the same as defined above, and $J^3$ is a chlorine atom, a bromine atom, an iodine atom or the like] and a compound represented by the formula (42) [wherein $R^2$ is the same as defined above, and $J^4$ is dihydroxyborane or the like] are reacted, if necessary in the presence of a metal catalyst, if necessary in the presence of a base, if necessary by using a solvent inert to the reaction, by a known method disclosed in the literature such as WO 2010/0794432 to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (42) may be used per 1 equivalent of the compound represented by the formula (41).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide suchas dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diidopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (41) or (42).

As the metal catalyst, if use, a palladium hydroxide catalyst such as $Pd(OH)_2$, a palladium oxide catalyst such as PdO, a palladium halide catalyst such as $PdBr_2$, $PdCl_2$ or $PdI_2$, a palladium acetate catalyst suchas palladium acetate (Pd $(OAc)_2$) or palladium trifluoroacetate $(Pd(OCOCF_3)_2)$, a palladium metal complex catalyst having a ligand such as $Pd(RNC)_2Cl_2$, $Pd(acac)_2$, diacetate bis(triphenylphosphine) palladium $[Pd(OAc)_2 (PPh_3)_2]$, $Pd(PPh_3)$, $Pd_2 (dba)_3$, $Pd(NH_3)_2$, $Pd(CH_3CN)_2Cl_2$, dichlorobis (benzonitrile)palladium $[Pd(PhCN)_2Cl_2]$, $Pd(dppe)Cl_2$, $Pd(dppf)Cl_2$, $Pd[PCy_3]_2Cl_2$, $Pd(PPh_3)_2Cl_2$, $Pd[P(o-tolyl)_3]_2Cl_2$, $Pd(cod)_2Cl_2$, $Pd(PPh_3)(CH_3CN)_2Cl_2$, Bis(di-tert-butyl(4-dimethylaminophenyl)phosphine)dichloropalladium(II) or the like may, for example, be mentioned.

Such a metal catalyst may be used in an amount of from 1 to 10 equivalents per 1 equivalent of a compound represented by the formula (41) or (42).

Process E

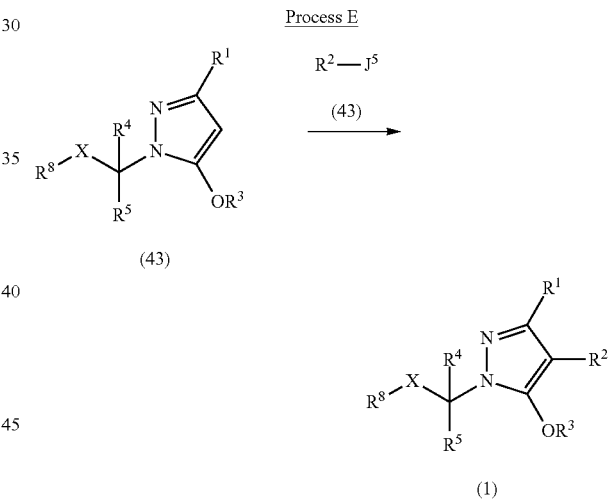

A compound represented by the formula (43) [wherein $R^1$, $R^3$, $R^4$, $R^5$, $R^8$ and X are the same as defined above] and a compound represented by the formula (44) [wherein $R^2$ is the same as defined above, and $J^5$ is a chlorine atom, a bromine atom, an iodine atom or the like] are reacted, if necessary in the presence of a base, if necessary by using a solvent inert to the reaction, by a known method disclosed in the literature such as Bioorganic & Medicinal Chemistry, 2006, vol. 14, p. 5061 to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (44) may be used per 1 equivalent of the compound represented by the formula (43).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide, potassium hydroxide or calcium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (43) or (44).

Process F

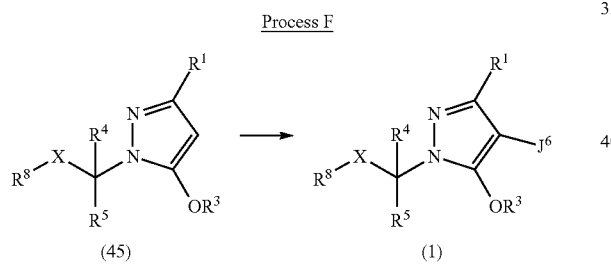

A compound represented by the formula (45) [wherein $R^1$, $R^3$, $R^4$, $R^6$, $R^8$ and X are the same as defined above] is reacted, if necessary by using a solvent inert to the reaction, by a known method disclosed in the literature such as Bioorganic & Medicinal Chemistry, 2006, vol. 14, p. 5061 to obtain a compound of the present invention represented by the formula (1) [wherein $R^1$, $R^3$, $R^4$, $R^6$, $R^8$ and X are the same as defined above, and $J^6$ is a chlorine atom, a bromine atom, an iodine atom or the like].

As the halogenation reagent, N-bromosuccinimide, N-chlorosuccinimide, chlorine, bromine, potassium iodide, sodium iodide or the like may be used.

Regarding the amounts of the reactants, from 1 to 50 equivalents of a halogenations reagent may be used per 1 equivalent of a compound represented by the formula (45).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide suchas dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions.

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

Process G

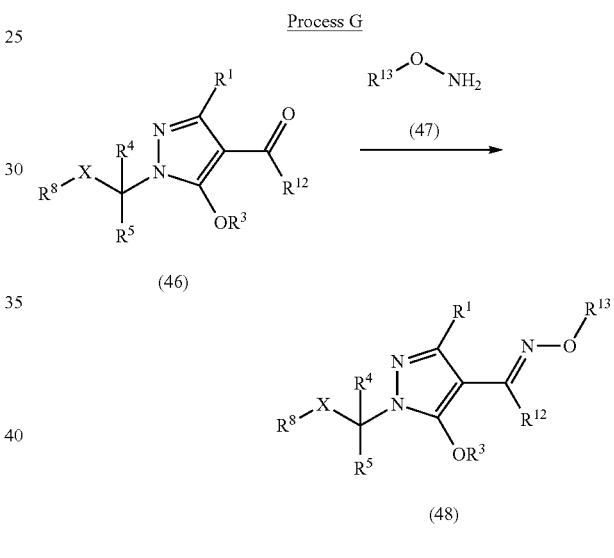

A compound represented by the formula (46) [wherein $R^1$, $R^3$, $R^4$, $R^5$, $R^8$, $R^{12}$ and X are the same as defined above] and a compound represented by the formula (47) are reacted, if necessary in the presence of a base, if necessary by using a solvent inert to the reaction, by a known method disclosed in the literature such as European Journal of Organic Chemistry, 2003, vol. 7, p. 1209 and Organic Letters, 2008, vol. 10, p. 1695 to obtain a compound of the present invention represented by the formula (48) [wherein $R^1$, $R^3$, $R^4$, $R^5$, $R^8$, $R^{12}$, $R^{13}$ and X are the same as defined above].

Regarding the amounts of the reactants, from 1 to 50 equivalents of the compound represented by the formula (47) may be used per 1 equivalent of the compound represented by the formula (46).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide suchas dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions.

As the base, if used, an alkali metal hydride such as sodium hydride or potassium hydride, an alkali metal hydroxide such as hydroxide, potassium hydroxide, calcium hydroxide or sodium acetate, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (46) or (47).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using 1 equivalent of a compound represented by the formula (46) and a compound represented by the formula (47) in a solvent such as ethanol, toluene, tetrahydrofuran, 1,4-dioxane, acetonitrile, N, N-dimethylformamide, chloroform or methylene chloride, if necessary by using from 1 to 3 equivalents of a base suchas sodium hydride, potassium t-butoxdie, potassium hydroxide, potassium carbonate, sodium acetate, triethylamine or pyrimidine per 1 equivalent of the compound represented by the formula (46) or (47) at 0~100° C. for 10 minutes to 24 hours.

Some of the amine compounds represented by the formula (47) used herein are known compounds, and some of them are commercially available. The rest of them can be readily synthesized from known compounds by known methods disclosed in the literature such as J. Am. Chem. Soc, 2011, vol. 133, p. 8704.

In Processes A, B, C, D, F and G, the reaction mixture obtained after the reaction is worked up by ordinary operations such as direct concentration, dissolution in an organic solvent followed by washing with water and concentration, or addition to ice-cold water followed by extraction with an organic solvent and concentration to obtain a compound of the present invention as intended. If purification is needed, it may be isolated or purified by a certain method such as recrystallization, column chromatography, thin layer chromatography and liquid chromatography.

The compound represented by the formula (13) used in Process B can be synthesized, for example, as follows.

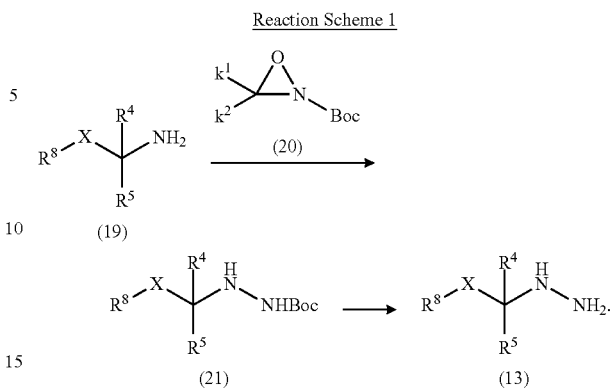

Reaction Scheme 1

A known substituted amine represented by the formula (19) [wherein $R^4$, $R^5$, $R^8$ and X are the same as defined above] and a compound represented by the formula (20) [wherein $k^1$ and $k^2$ are hydrogen atoms, trichloromethyl groups, cyclohexyl groups, phenyl groups, p-cyanophenyl groups, ethoxycarbonyl groups or the like, and Boc is a t-butoxycarbonyl group are reacted, if necessary by using a solvent inert to the reaction, by a known method disclosed in the literature such as Tetrahedron Lett., 1989, vol. 39, p. 6845 to obtain a compound represented by the formula (13) [wherein $R^4$, $R^5$, $R^8$ and X are the same as defined above].

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

Some of the compounds represented by the formula (19) used herein are known compounds, and some of them are commercially available. The rest of them can be readily synthesized from known compounds by known methods disclosed in the literature such as Journal of Medicinal Chemistry, 2009, vol. 52, p. 3982, Chem. Commun., 2001, p. 1792, and Synthesis 2000, vol. 12, p. 1709.

The compound represented by the formula (20) used herein can be synthesized readily from a known compound in accordance with Journal of Medicinal Chemistry, 2009, vol. 52, p. 1471 [52(5), 1471-1476; 2009] or WO2008/073987.

The compound represented by the formula (13) used in Process B can be synthesized in accordance with J. Chem. Soc., Chem. Commun., 1986, p. 176, or J. Chem. Soc., Chem. Commun., 1983, p. 1040, for example, as follows.

Reaction Scheme 2

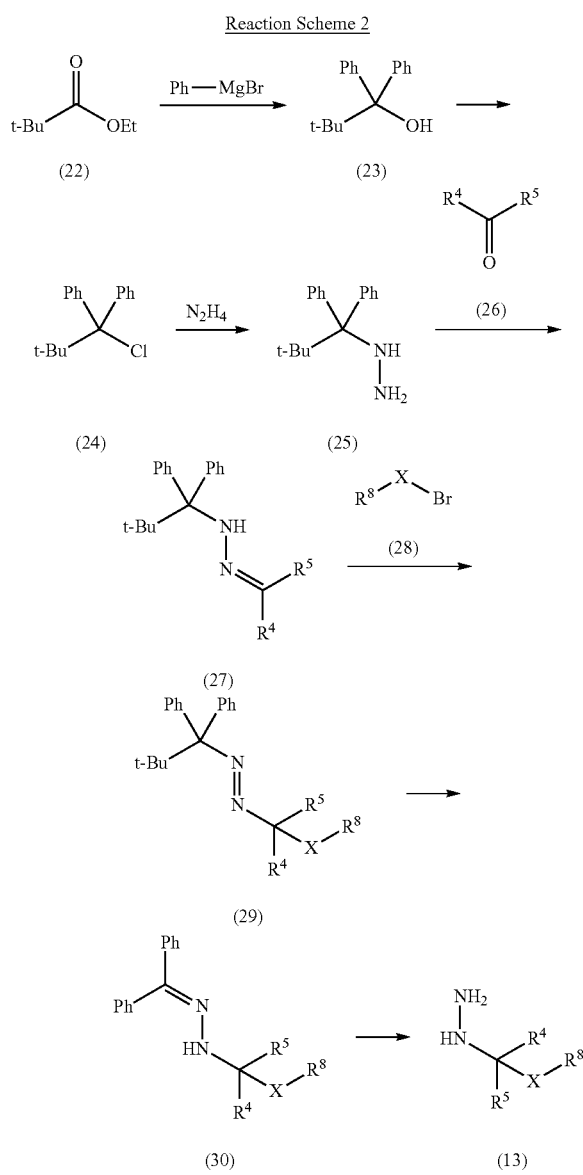

An ethyl pivalate represented by the formula (22) and a phenyl Grignard reagent by the formula are reacted, if necessary by using a solvent inert to the reaction, the resulting alcohol compound represented by the formula (23) is halogenated, and the resulting halide compound represented by the formula (24) is reacted with hydrazine to obtain a hydrazine compound represented by the formula (25).

The resulting hydrazine compound represented by the formula (25) is reacted with a carbonyl compound represented by the formula (26), if necessary by using a solvent inert to the reaction, the resulting hydrazine compound represented by the formula (27) is reacted with a halide compound represented by the formula (28), if necessary in the presence of a base, if necessary by using a solvent inert to the reaction, and the resulting hydrazine compound represented by the formula (29) is reacted in the presence of an acid, if necessary by using a solvent inert to the reaction to obtain a hydrazine compound represented by the formula (30).

The resulting hydrazinecompound represented by the formula (30) is reacted in the presence of an acid, if necessary by using a solvent inert to the reaction to obtain a hydrazine compound represented by the formula (13).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide suchas dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (27).

As the acid, if used, a mineral acid such as hydrochloric acid or sulfuric acid, a carboxylic acid such as formic acid, acetic acid, trifluoroacetic acid, mandelic acid or tartaric acid, a sulfonic acid such as methanesulfonic acid, p-toluenesulfonic acid, benzensulfonic acid, trifluoromethanesulfonic acid or camphor sulfonic acid, phosphorus oxychloride, Amberlite IR-120 (type H) or the like may be used in an amount of from 1 to 10 equivalents per 1 equivalent of a compound represented by the formula (29) or (30).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

Some of the compounds represented by the formula (22) used herein are known compounds, and some of them are commercially available. The rest of them can be readily synthesized by ordinary methods for synthesis of ester compounds disclosed in the literature.

Some of the compounds represented by the formula (26) used herein are known compounds, and some of them are commercially available. The rest of them can be readily synthesized by ordinary methods for synthesis of carbonyl compounds disclosed in the literature.

Some of the compounds represented by the formula (28) used herein are known compounds, and some of them are commercially available. The rest of them can be readily synthesized by ordinary methods for synthesis of halide compounds disclosed in the literature.

The compound represented by the formula (12) used in Process B can be synthesized in accordance with J. Am. Chem. Soc., 1958, vol. 80, p. 6562, for example, as follows.

Reaction Scheme 3

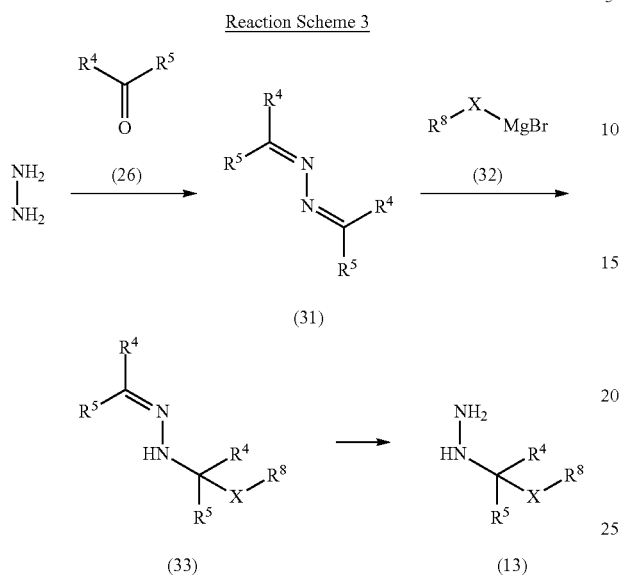

Hydrazine and a carbonyl compound represented by the formula (26) are reacted, if necessary by using a solvent inert to the reaction, and the resulting hydrazine compound represented by the formula (31) is reacted with a Grignard reagent represented by the formula (32) to obtain a hydrazine compound represented by the formula (33).

The resulting hydrazine compound represented by the formula (33) is reacted in the presence of an acid, if necessary by using a solvent inert to the reaction to obtain a hydrazine compound represented by the formula (13).

Some of the compounds represented by the formula (26) used herein are known compounds, and some of them are commercially available. The rest of them can be readily synthesized by ordinary methods for synthesis of carbonyl compounds disclosed in the literature.

Some of the compounds represented by the formula (32) used herein are known compounds, and some of them are commercially available. The rest of them can be readily synthesized by ordinary methods for synthesis of Grignard reagents disclosed in the literature.

In each of these reactions, the reaction mixture is worked up by ordinary operations to obtain each intermediate used as a starting compound.

Each intermediate produced in these processes can be used for the reaction in the next step without isolation or purification.

As specific compounds of the present invention, for example, those shown in Tables 2 to 15 may be mentioned. However, the compounds merely exemplify the present invention, and the present invention is by no means restricted thereto.

In the Tables, Et denotes ethyl group, and similarly, n-Pr and Pr-n denote normal propyl group, i-Pr and Pr—I denote isopropyl group, c-Pr and Pr-c denote cyclopropyl group, n-Bu and Bu-n denote normal butyl group, s-Bu and Bu-s denote secondary butyl group, i-Bu and Bu—I denote isobutyl group, t-Bu and Bu-t denote t-butyl group, c-Bu and Bu-c denote cyclobutyl group, n-Pen and Pen-n denote normal pentyl group, c-Pen and Pen-c denote cyclopentyl group, n-Hex and Hex-n denote normal hexyl group, c-Hex and Hex-c denote cyclohexyl group, and Ph denotes phenyl group.

The aromatic heterocyclic rings represented by A001 to A044 in the Talbes have the following structures, respectively.

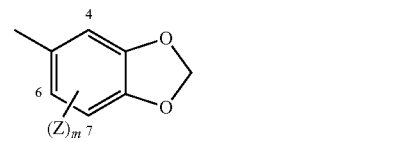
A041

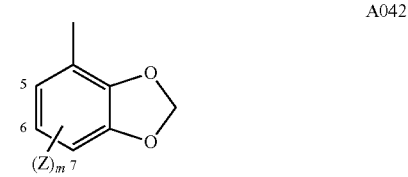
A042

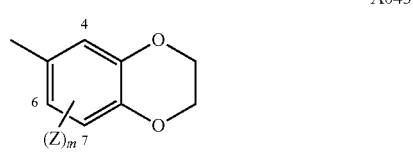
A043

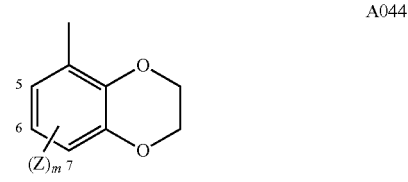
A044

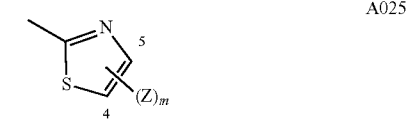
A025

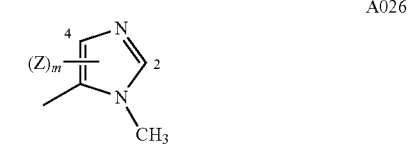
A026

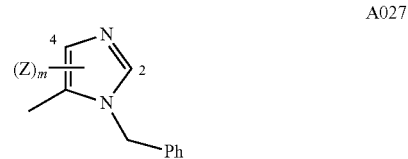
A027

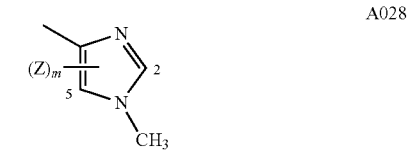
A028

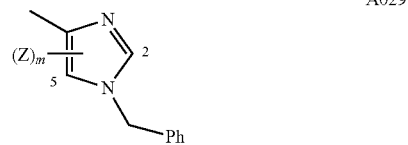
A029

US 8,658,686 B2
-continued
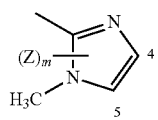 A030
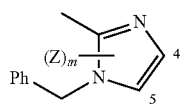 A031
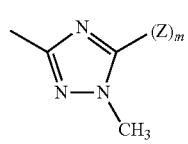 A032
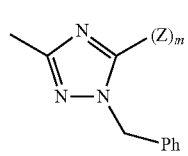 A033
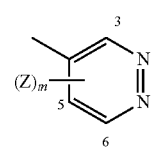 A034
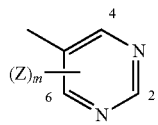 A035
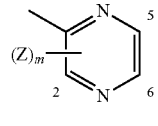 A036
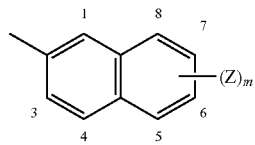 A037
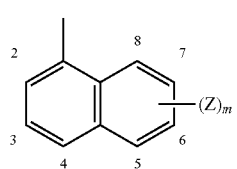 A038
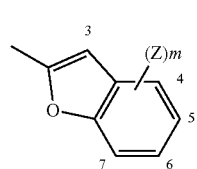 A039
-continued
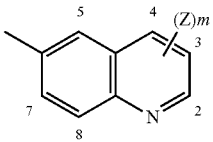 A040
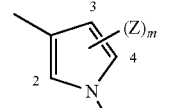 A017
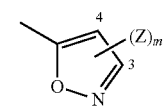 A018
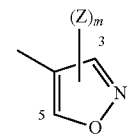 A019
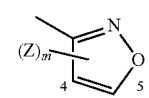 A020
The aliphatic heterocyclic rings represented by A051 to A068 in the Talbes have the following structures, respectively.
 A051
 A052
 A053
 A054
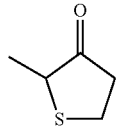 A055
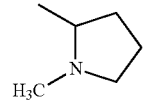 A056

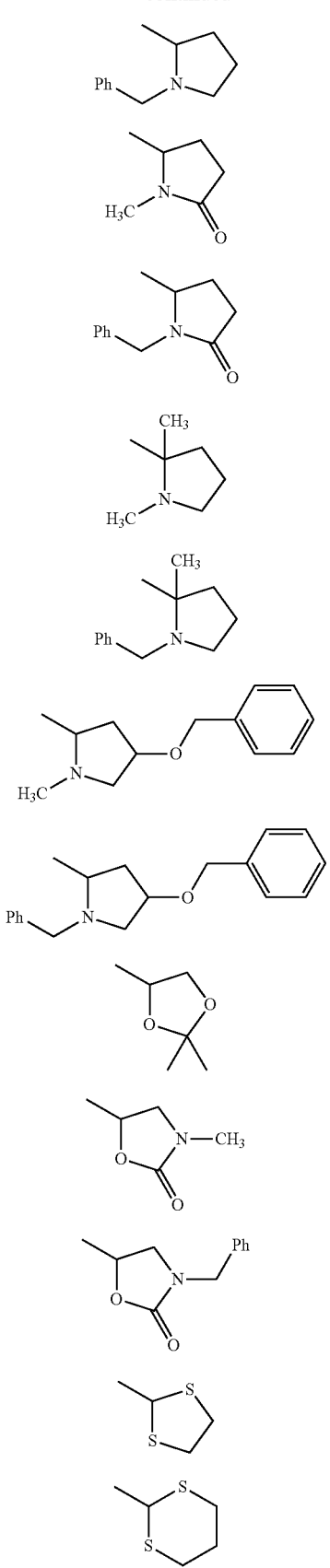
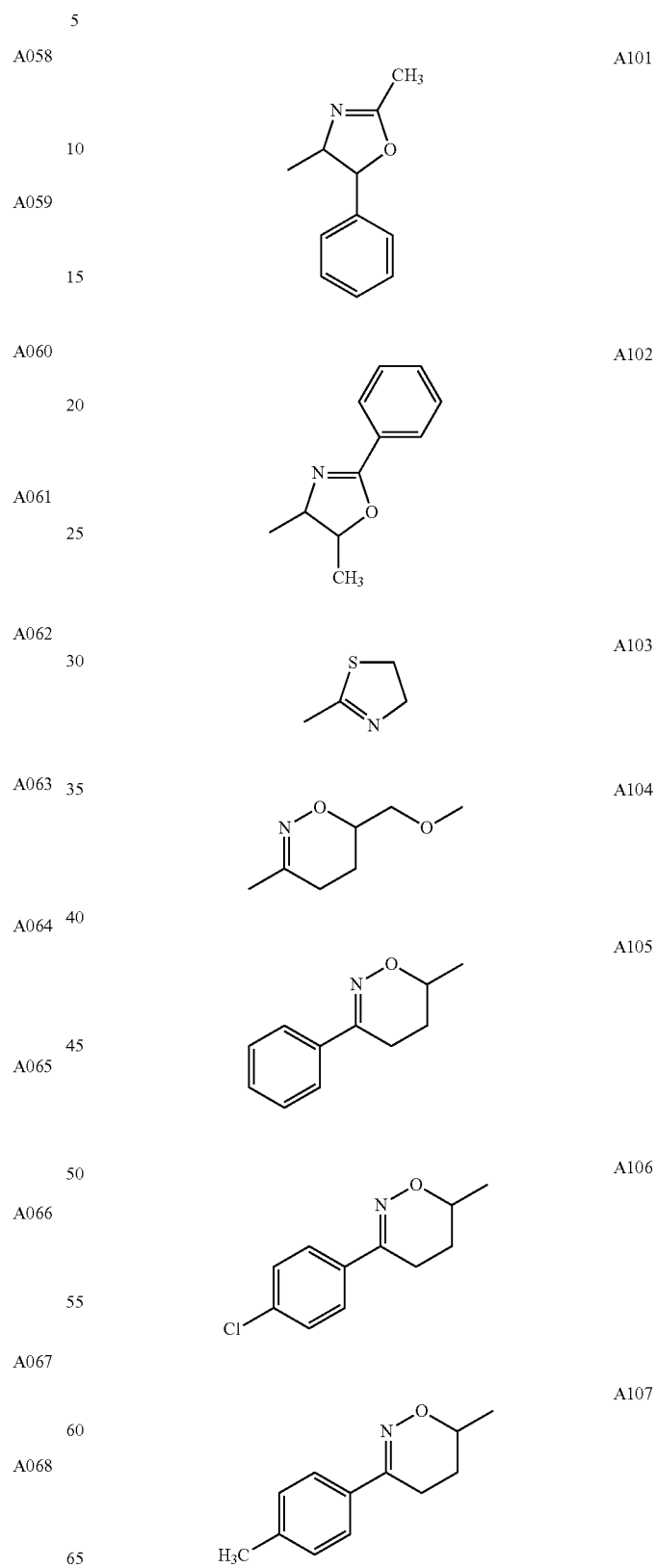
The partially saturated heterocyclic rings represented by A101 to A107 in the Talbes have the following structures, respectively.

TABLE 2
The locants for the substituents $R^{21}$ and $R^{81}$ in the Table correspond to the positions indicated in the following structural formulae.
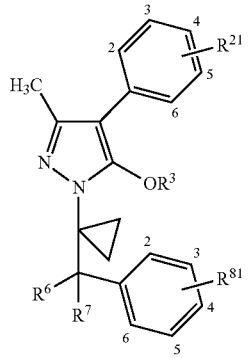
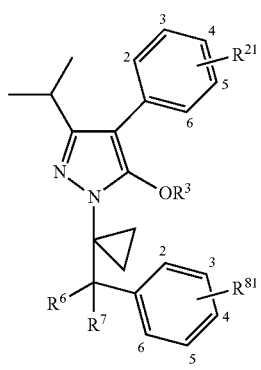
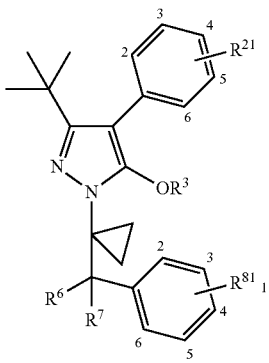
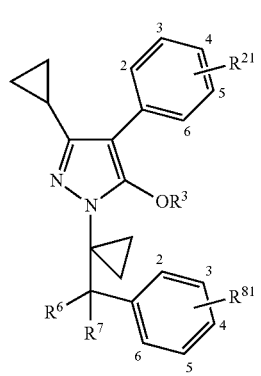
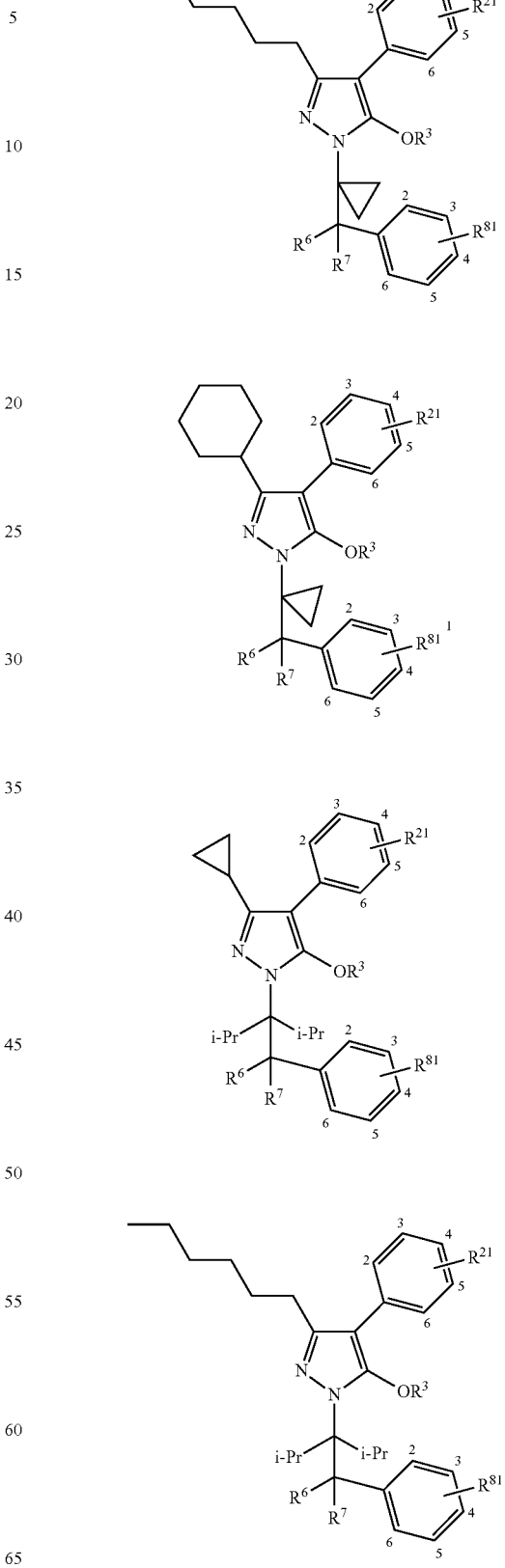

TABLE 2-continued

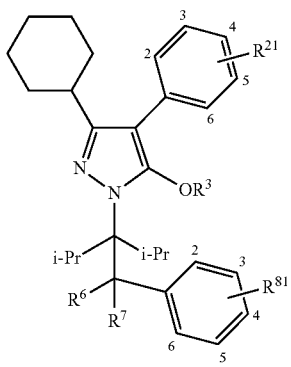

| R²¹ | R⁸¹ | R³ | R⁶ | R⁷ |
|---|---|---|---|---|
| H | H | H | H | H |
| H | 4-F | H | H | H |
| H | 2-Cl | H | H | H |
| H | 3-Cl | H | H | H |
| H | 4-Cl | H | H | H |
| H | 4-Cl | CH₃ | H | H |
| H | 4-Cl | CH₂Ph | H | H |
| H | 4-Cl | C(O)Ph | H | H |
| H | 4-Cl | C(O)OEt | H | H |
| H | 4-Cl | H | H | CH₃ |
| H | 4-Cl | CH₃ | H | CH₃ |
| H | 4-Cl | H | CH₃ | CH₃ |
| H | 4-Br | H | H | H |
| H | 4-I | H | H | H |
| H | 2,4-Cl₂ | H | H | H |
| H | 3,4-Cl₂ | H | H | H |
| H | 4-NO₂ | H | H | H |
| H | 4-CN | H | H | H |
| H | 2-CH₃ | H | H | H |
| H | 3-CH₃ | H | H | H |
| H | 4-CH₃ | H | H | H |
| H | 4-CH₃ | CH₃ | H | H |
| H | 4-CH₃ | CH₂Ph | H | H |
| H | 4-CH₃ | C(O)Ph | H | H |
| H | 4-CH₃ | C(O)OEt | H | H |
| H | 4-CH₃ | H | H | CH₃ |
| H | 4-CH₃ | CH₃ | H | CH₃ |
| H | 4-CH₃ | H | CH₃ | CH₃ |
| H | 4-Et | H | H | H |
| H | 4-n-Pr | H | H | H |
| H | 4-c-Pr | H | H | H |
| H | 4-i-Pr | H | H | H |
| H | 4-n-Bu | H | H | H |
| H | 4-c-Bu | H | H | H |
| H | 4-i-Bu | H | H | H |
| H | 4-t-Bu | H | H | H |
| H | 4-t-Bu | CH₃ | H | H |
| H | 4-t-Bu | CH₂Ph | H | H |
| H | 4-t-Bu | C(O)Ph | H | H |
| H | 4-t-Bu | C(O)OEt | H | H |
| H | 4-t-Bu | H | H | CH₃ |
| H | 4-t-Bu | CH₃ | H | CH₃ |
| H | 4-t-Bu | H | CH₃ | CH₃ |
| H | 4-n-Pen | H | H | H |
| H | 4-c-Pen | H | H | H |
| H | 4-n-Hex | H | H | H |
| H | 4-n-Hex | CH₃ | H | H |
| H | 4-n-Hex | CH₂Ph | H | H |
| H | 4-n-Hex | C(O)Ph | H | H |
| H | 4-n-Hex | C(O)OEt | H | H |
| H | 4-n-Hex | H | H | CH₃ |
| H | 4-n-Hex | CH₃ | H | CH₃ |
| H | 4-n-Hex | H | CH₃ | CH₃ |
| H | 4-c-Hex | H | H | H |
| H | 4-n-C₇H₁₅ | H | H | H |
| H | 4-n-C₈H₁₇ | H | H | H |
| H | 4-n-C₉H₁₉ | H | H | H |
| H | 4-n-C₁₀H₂₁ | H | H | H |
| H | 2,4-(CH₃) | H | H | H |
| H | 3,4-(CH₃)₂ | H | H | H |
| H | 4-CF₃ | H | H | H |
| H | 4-OH | H | H | H |
| H | 2-OCH₃ | H | H | H |
| H | 3-OCH₃ | H | H | H |
| H | 4-OCH₃ | H | H | H |
| H | 4-O-n-Hex | H | H | H |
| H | 4-O-c-Hex | H | H | H |
| H | 2,4-(OCH₃)₂ | H | H | H |
| H | 3,4-(OCH₃)₂ | H | H | H |
| H | 4-OCH₂OCH₃ | H | H | H |
| H | 4-OC₂H₄OEt | H | H | H |
| H | 4-OCF₃ | H | H | H |
| H | 4-OPh | H | H | H |
| H | 4-OCH₂Ph | H | H | H |
| H | 4-C(CH₃)=NCH₃ | H | H | H |
| H | 4-C(CH₃)=NPh | H | H | H |
| H | 4-C(Ph)=NCH₃ | H | H | H |
| H | 4-C(Ph)=NPh | H | H | H |
| H | 4-C(CH₃)=NOCH₃ | H | H | H |
| H | 4-C(CH₃)=NOPh | H | H | H |
| H | 4-C(Ph)=NOCH₃ | H | H | H |
| H | 4-C(Ph)=NOPh | H | H | H |
| H | 4-C(O)CH₃ | H | H | H |
| H | 4-C(O)CF₃ | H | H | H |
| H | 4-C(O)Ph | H | H | H |
| H | 4-C(O)OCH₃ | H | H | H |
| H | 2-C(O)OEt | H | H | H |
| H | 3-C(O)OEt | H | H | H |
| H | 4-C(O)OEt | H | H | H |
| H | 4-C(O)OPh | H | H | H |
| H | 4-C(O)OCH₂Ph | H | H | H |
| H | 4-C(O)OCH(CH₃)Ph | H | H | H |
| H | 4-C(O)OC₂H₄Ph | H | H | H |
| H | 4-SCH₃ | H | H | H |
| H | 4-S(O)CH₃ | H | H | H |
| H | 4-S(O)₂CH₃ | H | H | H |
| H | 4-SPh | H | H | H |
| H | 4-S(O)Ph | H | H | H |
| H | 4-S(O)₂Ph | H | H | H |
| H | 4-OS(O)₂CH₃ | H | H | H |
| H | 4-OS(O)₂Ph | H | H | H |
| H | 4-N(CH₃)₂ | H | H | H |
| H | 4-N(CH₂Ph)₂ | H | H | H |
| H | 4-N(CH₃)(CH₂Ph) | H | H | H |
| H | 4-NHCH₃ | H | H | H |
| H | 4-NH(CH₂Ph) | H | H | H |
| H | 4-C(O)N(CH₃)₂ | H | H | H |
| H | 4-C(O)N(CH₂Ph)₂ | H | H | H |
| H | 4-C(O)N(CH₃)(CH₂Ph) | H | H | H |
| H | 4-C(O)NHCH₃ | H | H | H |
| H | 4-C(O)NH(CH₂Ph) | H | H | H |
| H | 4-C(O)NH(CH(CH₃)Ph) | H | H | H |
| H | 4-C(O)NH(C₂H₄Ph) | H | H | H |
| H | 4-C(S)NH₂ | H | H | H |
| H | 4-S(O)₂N(CH₃)₂ | H | H | H |
| H | 4-S(O)₂N(CH₂Ph)₂ | H | H | H |
| H | 4-S(O)₂N(CH₃)(CH₂Ph) | H | H | H |
| H | 4-S(O)₂NHCH₃ | H | H | H |
| H | 4-S(O)₂NHPh | H | H | H |
| H | 4-S(O)₂NH(CH₂Ph) | H | H | H |
| H | 4-S(O)₂NH{CH(CH₃)Ph} | H | H | H |
| H | 4-S(O)₂NH(C₂H₄Ph) | H | H | H |
| H | 4-Ph | H | H | H |
| H | 4-Ph | CH₃ | H | H |
| H | 4-Ph | CH₂Ph | H | H |
| H | 4-Ph | C(O)Ph | H | H |
| H | 4-Ph | C(O)OEt | H | H |
| H | 4-Ph | H | H | CH₃ |
| H | 4-Ph | CH₃ | H | CH₃ |
| H | 4-Ph | H | CH₃ | CH₃ |
| 4-F | H | H | H | H |
| 4-F | 4-Cl | H | H | H |
| 4-F | 4-Br | H | H | H |
| 4-F | 4-CH₃ | H | H | H |
| 4-F | 4-t-Bu | H | H | H |
| 4-F | 4-n-Hex | H | H | H |
| 4-F | 4-Ph | H | H | H |
| 2-Cl | H | H | H | H |
| 2-Cl | 4-Cl | H | H | H |

TABLE 2-continued

| | | | | |
|---|---|---|---|---|
| 2-Cl | 4-Br | H | H | H |
| 2-Cl | 4-CH₃ | H | H | H |
| 2-Cl | 4-t-Bu | H | H | H |
| 2-Cl | 4-n-Hex | H | H | H |
| 2-Cl | 4-Ph | H | H | H |
| 3-Cl | H | H | H | H |
| 3-Cl | 4-Cl | H | H | H |
| 3-Cl | 4-Br | H | H | H |
| 3-Cl | 4-CH₃ | H | H | H |
| 3-Cl | 4-t-Bu | H | H | H |
| 3-Cl | 4-n-Hex | H | H | H |
| 3-Cl | 4-Ph | H | H | H |
| 4-Cl | H | H | H | H |
| 4-Cl | 4-Cl | H | H | H |
| 4-Cl | 4-Br | H | H | H |
| 4-Cl | 4-CH₃ | H | H | H |
| 4-Cl | 4-t-Bu | H | H | H |
| 4-Cl | 4-t-Bu | CH₃ | H | H |
| 4-Cl | 4-n-Hex | H | H | H |
| 4-Cl | 4-n-Hex | CH₃ | H | H |
| 4-Cl | 4-n-Hex | H | H | CH₃ |
| 4-Cl | 4-n-Hex | H | CH₃ | CH₃ |
| 4-Cl | 4-Ph | H | H | H |
| 4-Cl | 4-Ph | CH₃ | H | H |
| 4-Br | H | H | H | H |
| 4-Br | 4-Cl | H | H | H |
| 4-Br | 4-Br | H | H | H |
| 4-Br | 4-CH₃ | H | H | H |
| 4-Br | 4-t-Bu | H | H | H |
| 4-Br | 4-n-Hex | H | H | H |
| 4-Br | 4-Ph | H | H | H |
| 3,4-Cl₂ | H | H | H | H |
| 3,4-Cl₂ | 4-Cl | H | H | H |
| 3,4-Cl₂ | 4-Br | H | H | H |
| 3,4-Cl₂ | 4-CH₃ | H | H | H |
| 3,4-Cl₂ | 4-t-Bu | H | H | H |
| 3,4-Cl₂ | 4-n-Hex | H | H | H |
| 3,4-Cl₂ | 4-Ph | H | H | H |
| 4-NO₂ | H | H | H | H |
| 4-NO₂ | 4-Cl | H | H | H |
| 4-NO₂ | 4-Br | H | H | H |
| 4-NO₂ | 4-CH₃ | H | H | H |
| 4-NO₂ | 4-t-Bu | H | H | H |
| 4-NO₂ | 4-n-Hex | H | H | H |
| 4-NO₂ | 4-Ph | H | H | H |
| 4-CN | H | H | H | H |
| 4-CN | 4-Cl | H | H | H |
| 4-CN | 4-Br | H | H | H |
| 4-CN | 4-CH₃ | H | H | H |
| 4-CN | 4-t-Bu | H | H | H |
| 4-CN | 4-n-Hex | H | H | H |
| 4-CN | 4-Ph | H | H | H |
| 2-CH₃ | H | H | H | H |
| 2-CH₃ | 4-Cl | H | H | H |
| 2-CH₃ | 4-Br | H | H | H |
| 2-CH₃ | 4-CH₃ | H | H | H |
| 2-CH₃ | 4-t-Bu | H | H | H |
| 2-CH₃ | 4-n-Hex | H | H | H |
| 2-CH₃ | 4-Ph | H | H | H |
| 3-CH₃ | H | H | H | H |
| 3-CH₃ | 4-Cl | H | H | H |
| 3-CH₃ | 4-Br | H | H | H |
| 3-CH₃ | 4-CH₃ | H | H | H |
| 3-CH₃ | 4-t-Bu | H | H | H |
| 3-CH₃ | 4-n-Hex | H | H | H |
| 3-CH₃ | 4-Ph | H | H | H |
| 4-CH₃ | H | H | H | H |
| 4-CH₃ | 4-Cl | H | H | H |
| 4-CH₃ | 4-Br | H | H | H |
| 4-CH₃ | 4-CH₃ | H | H | H |
| 4-CH₃ | 4-t-Bu | H | H | H |
| 4-CH₃ | 4-t-Bu | CH₃ | H | H |
| 4-CH₃ | 4-n-Hex | H | H | H |
| 4-CH₃ | 4-n-Hex | CH₃ | H | H |
| 4-CH₃ | 4-n-Hex | H | H | CH₃ |
| 4-CH₃ | 4-n-Hex | H | CH₃ | CH₃ |
| 4-CH₃ | 4-Ph | H | H | H |
| 4-CH₃ | 4-Ph | CH₃ | H | H |
| 4-c-Pr | H | H | H | H |
| 4-c-Pr | 4-Cl | H | H | H |
| 4-c-Pr | 4-Br | H | H | H |
| 4-c-Pr | 4-CH₃ | H | H | H |
| 4-c-Pr | 4-t-Bu | H | H | H |
| 4-c-Pr | 4-n-Hex | H | H | H |
| 4-c-Pr | 4-Ph | H | H | H |
| 4-i-Pr | H | H | H | H |
| 4-i-Pr | 4-Cl | H | H | H |
| 4-i-Pr | 4-Br | H | H | H |
| 4-i-Pr | 4-CH₃ | H | H | H |
| 4-i-Pr | 4-t-Bu | H | H | H |
| 4-i-Pr | 4-n-Hex | H | H | H |
| 4-i-Pr | 4-Ph | H | H | H |
| 4-t-Bu | H | H | H | H |
| 4-t-Bu | 4-Cl | H | H | H |
| 4-t-Bu | 4-Br | H | H | H |
| 4-t-Bu | 4-CH₃ | H | H | H |
| 4-t-Bu | 4-t-Bu | H | H | H |
| 4-t-Bu | 4-t-Bu | CH₃ | H | H |
| 4-t-Bu | 4-n-Hex | H | H | H |
| 4-t-Bu | 4-n-Hex | CH₃ | H | H |
| 4-t-Bu | 4-n-Hex | H | H | CH₃ |
| 4-t-Bu | 4-n-Hex | H | CH₃ | CH₃ |
| 4-t-Bu | 4-Ph | H | H | H |
| 4-t-Bu | 4-Ph | CH₃ | H | H |
| 4-n-Hex | H | H | H | H |
| 4-n-Hex | H | CH₃ | H | H |
| 4-n-Hex | H | CH₂Ph | H | H |
| 4-n-Hex | H | C(O)Ph | H | H |
| 4-n-Hex | H | C(O)OEt | H | H |
| 4-n-Hex | H | H | H | CH₃ |
| 4-n-Hex | H | CH₃ | H | CH₃ |
| 4-n-Hex | H | H | CH₃ | CH₃ |
| 4-n-Hex | 4-F | H | H | H |
| 4-n-Hex | 2-Cl | H | H | H |
| 4-n-Hex | 3-Cl | H | H | H |
| 4-n-Hex | 4-Cl | H | H | H |
| 4-n-Hex | 4-Cl | CH₃ | H | H |
| 4-n-Hex | 4-Cl | CH₂Ph | H | H |
| 4-n-Hex | 4-Cl | C(O)Ph | H | H |
| 4-n-Hex | 4-Cl | C(O)OEt | H | H |
| 4-n-Hex | 4-Cl | H | H | CH₃ |
| 4-n-Hex | 4-Cl | CH₃ | H | CH₃ |
| 4-n-Hex | 4-Cl | H | CH₃ | CH₃ |
| 4-n-Hex | 4-Br | H | H | H |
| 4-n-Hex | 4-I | H | H | H |
| 4-n-Hex | 2,4-Cl₂ | H | H | H |
| 4-n-Hex | 3,4-Cl₂ | H | H | H |
| 4-n-Hex | 4-NO₂ | H | H | H |
| 4-n-Hex | 4-CN | H | H | H |
| 4-n-Hex | 2-CH₃ | H | H | H |
| 4-n-Hex | 3-CH₃ | H | H | H |
| 4-n-Hex | 4-CH₃ | H | H | H |
| 4-n-Hex | 4-CH₃ | CH₃ | H | H |
| 4-n-Hex | 4-CH₃ | CH₂Ph | H | H |
| 4-n-Hex | 4-CH₃ | C(O)Ph | H | H |
| 4-n-Hex | 4-CH₃ | C(O)OEt | H | H |
| 4-n-Hex | 4-CH₃ | H | H | CH₃ |
| 4-n-Hex | 4-CH₃ | CH₃ | H | CH₃ |
| 4-n-Hex | 4-CH₃ | H | CH₃ | CH₃ |
| 4-n-Hex | 4-Et | H | H | H |
| 4-n-Hex | 4-n-Pr | H | H | H |
| 4-n-Hex | 4-c-Pr | H | H | H |
| 4-n-Hex | 4-i-Pr | H | H | H |
| 4-n-Hex | 4-n-Bu | H | H | H |
| 4-n-Hex | 4-c-Bu | H | H | H |
| 4-n-Hex | 4-i-Bu | H | H | H |
| 4-n-Hex | 4-t-Bu | H | H | H |
| 4-n-Hex | 4-t-Bu | CH₃ | H | H |
| 4-n-Hex | 4-t-Bu | CH₂Ph | H | H |
| 4-n-Hex | 4-t-Bu | C(O)Ph | H | H |
| 4-n-Hex | 4-t-Bu | C(O)0Et | H | H |
| 4-n-Hex | 4-t-Bu | H | H | CH₃ |
| 4-n-Hex | 4-t-Bu | CH₃ | H | CH₃ |
| 4-n-Hex | 4-t-Bu | H | CH₃ | CH₃ |
| 4-n-Hex | 4-n-Pen | H | H | H |
| 4-n-Hex | 4-c-Pen | H | H | H |
| 4-n-Hex | 4-n-Hex | H | H | H |
| 4-n-Hex | 4-n-Hex | CH₃ | H | H |
| 4-n-Hex | 4-n-Hex | CH₂Ph | H | H |
| 4-n-Hex | 4-n-Hex | C(O)Ph | H | H |

TABLE 2-continued

| | | | | |
|---|---|---|---|---|
| 4-n-Hex | 4-n-Hex | C(O)OEt | H | H |
| 4-n-Hex | 4-n-Hex | H | H | CH$_3$ |
| 4-n-Hex | 4-n-Hex | CH$_3$ | H | CH$_3$ |
| 4-n-Hex | 4-n-Hex | H | CH$_3$ | CH$_3$ |
| 4-n-Hex | 4-c-Hex | H | H | H |
| 4-n-Hex | 4-n-C$_7$H$_{15}$ | H | H | H |
| 4-n-Hex | 4-n-C$_8$H$_{17}$ | H | H | H |
| 4-n-Hex | 4-n-C$_9$H$_{19}$ | H | H | H |
| 4-n-Hex | 4-n-C$_{10}$H$_{21}$ | H | H | H |
| 4-n-Hex | 2,4-(CH$_3$) | H | H | H |
| 4-n-Hex | 3,4-(CH$_3$)$_2$ | H | H | H |
| 4-n-Hex | 4-CF$_3$ | H | H | H |
| 4-n-Hex | 4-OH | H | H | H |
| 4-n-Hex | 2-OCH$_3$ | H | H | H |
| 4-n-Hex | 3-OCH$_3$ | H | H | H |
| 4-n-Hex | 4-OCH$_3$ | H | H | H |
| 4-n-Hex | 4-O-n-Hex | H | H | H |
| 4-n-Hex | 4-O-c-Hex | H | H | H |
| 4-n-Hex | 2,4-(OCH$_3$)$_2$ | H | H | H |
| 4-n-Hex | 3,4-(OCH$_3$)$_2$ | H | H | H |
| 4-n-Hex | 4-OCH$_2$OCH$_3$ | H | H | H |
| 4-n-Hex | 4-OC$_2$H$_4$OEt | H | H | H |
| 4-n-Hex | 4-OCF$_3$ | H | H | H |
| 4-n-Hex | 4-OPh | H | H | H |
| 4-n-Hex | 4-OCH$_2$Ph | H | H | H |
| 4-n-Hex | 4-C(CH$_3$)=NCH$_3$ | H | H | H |
| 4-n-Hex | 4-C(CH$_3$)=NPh | H | H | H |
| 4-n-Hex | 4-C(Ph)=NCH$_3$ | H | H | H |
| 4-n-Hex | 4-C(Ph)=NPh | H | H | H |
| 4-n-Hex | 4-C(CH$_3$)=NOCH$_3$ | H | H | H |
| 4-n-Hex | 4-C(CH$_3$)=NOPh | H | H | H |
| 4-n-Hex | 4-C(Ph)=NOCH$_3$ | H | H | H |
| 4-n-Hex | 4-C(Ph)=NOPh | H | H | H |
| 4-n-Hex | 4-C(O)CH$_3$ | H | H | H |
| 4-n-Hex | 4-C(O)CF$_3$ | H | H | H |
| 4-n-Hex | 4-C(O)Ph | H | H | H |
| 4-n-Hex | 4-C(O)OCH$_3$ | H | H | H |
| 4-n-Hex | 2-C(O)OEt | H | H | H |
| 4-n-Hex | 3-C(O)OEt | H | H | H |
| 4-n-Hex | 4-C(O)OEt | H | H | H |
| 4-n-Hex | 4-C(O)OPh | H | H | H |
| 4-n-Hex | 4-C(O)OCH$_2$Ph | H | H | H |
| 4-n-Hex | 4-C(O)OCH(CH$_3$)Ph | H | H | H |
| 4-n-Hex | 4-C(O)OC$_2$H$_4$Ph | H | H | H |
| 4-n-Hex | 4-SCH$_3$ | H | H | H |
| 4-n-Hex | 4-S(O)CH$_3$ | H | H | H |
| 4-n-Hex | 4-S(O)$_2$CH$_3$ | H | H | H |
| 4-n-Hex | 4-SPh | H | H | H |
| 4-n-Hex | 4-S(O)Ph | H | H | H |
| 4-n-Hex | 4-S(O)$_2$Ph | H | H | H |
| 4-n-Hex | 4-OS(O)$_2$CH$_3$ | H | H | H |
| 4-n-Hex | 4-OS(O)$_2$Ph | H | H | H |
| 4-n-Hex | 4-N(CH$_3$)$_2$ | H | H | H |
| 4-n-Hex | 4-N(CH$_2$Ph)$_2$ | H | H | H |
| 4-n-Hex | 4-N(CH$_3$)(CH$_2$Ph) | H | H | H |
| 4-n-Hex | 4-NHCH$_3$ | H | H | H |
| 4-n-Hex | 4-NH(CH$_2$Ph) | H | H | H |
| 4-n-Hex | 4-C(O)N(CH$_3$)$_2$ | H | H | H |
| 4-n-Hex | 4-C(O)N(CH$_2$Ph)$_2$ | H | H | H |
| 4-n-Hex | 4-C(O)N(CH$_3$)(CH$_2$Ph) | H | H | H |
| 4-n-Hex | 4-C(O)NHCH$_3$ | H | H | H |
| 4-n-Hex | 4-C(O)NH(CH$_2$Ph) | H | H | H |
| 4-n-Hex | 4-C(O)NH{CH(CH$_3$)Ph} | H | H | H |
| 4-n-Hex | 4-C(O)NH(C$_2$H$_4$Ph) | H | H | H |
| 4-n-Hex | 4-C(S)NH$_2$ | H | H | H |
| 4-n-Hex | 4-S(O)$_2$N(CH$_3$)$_2$ | H | H | H |
| 4-n-Hex | 4-S(O)$_2$N(CH$_2$Ph)$_2$ | H | H | H |
| 4-n-Hex | 4-S(O)$_2$N(CH$_3$)(CH$_2$Ph) | H | H | H |
| 4-n-Hex | 4-S(O)$_2$NHCH$_3$ | H | H | H |
| 4-n-Hex | 4-S(O)$_2$NHPh | H | H | H |
| 4-n-Hex | 4-S(O)$_2$NH(CH$_2$Ph) | H | H | H |
| 4-n-Hex | 4-S(O)$_2$NH{CH(CH$_3$)Ph} | H | H | H |
| 4-n-Hex | 4-S(O)$_2$NH(C$_2$H$_4$Ph) | H | H | H |
| 4-n-Hex | 4-Ph | H | H | H |
| 4-n-Hex | 4-Ph | CH$_3$ | H | H |
| 4-n-Hex | 4-Ph | CH$_2$Ph | H | H |
| 4-n-Hex | 4-Ph | C(O)Ph | H | H |
| 4-n-Hex | 4-Ph | C(O)OEt | H | H |
| 4-n-Hex | 4-Ph | H | H | CH$_3$ |
| 4-n-Hex | 4-Ph | CH$_3$ | H | CH$_3$ |
| 4-n-Hex | 4-Ph | H | CH$_3$ | CH$_3$ |
| 4-c-Hex | H | H | H | H |
| 4-c-Hex | 4-Cl | H | H | H |
| 4-c-Hex | 4-Br | H | H | H |
| 4-c-Hex | 4-CH$_3$ | H | H | H |
| 4-c-Hex | 4-t-Bu | H | H | H |
| 4-c-Hex | 4-t-Bu | CH$_3$ | H | H |
| 4-c-Hex | 4-n-Hex | H | H | H |
| 4-c-Hex | 4-n-Hex | CH$_3$ | H | H |
| 4-c-Hex | 4-n-Hex | H | H | CH$_3$ |
| 4-c-Hex | 4-n-Hex | H | CH$_3$ | CH$_3$ |
| 4-c-Hex | 4-Ph | H | H | H |
| 4-c-Hex | 4-Ph | CH$_3$ | H | H |
| 3,4-(CH$_3$)$_2$ | H | H | H | H |
| 3,4-(CH$_3$)$_2$ | 4-Cl | H | H | H |
| 3,4-(CH$_3$)$_2$ | 4-Br | H | H | H |
| 3,4-(CH$_3$)$_2$ | 4-CH$_3$ | H | H | H |
| 3,4-(CH$_3$)$_2$ | 4-t-Bu | H | H | H |
| 3,4-(CH$_3$)$_2$ | 4-n-Hex | H | H | H |
| 3,4-(CH$_3$)$_2$ | 4-Ph | H | H | H |
| 2,4-(t-Bu)$_2$ | H | H | H | H |
| 2,4-(t-Bu)$_2$ | 4-Cl | H | H | H |
| 2,4-(t-Bu)$_2$ | 4-Br | H | H | H |
| 2,4-(t-Bu)$_2$ | 4-CH$_3$ | H | H | H |
| 2,4-(t-Bu)$_2$ | 4-t-Bu | H | H | H |
| 2,4-(t-Bu)$_2$ | 4-n-Hex | H | H | H |
| 2,4-(t-Bu)$_2$ | 4-Ph | H | H | H |
| 4-CF$_3$ | H | H | H | H |
| 4-CF$_3$ | 4-Cl | H | H | H |
| 4-CF$_3$ | 4-Br | H | H | H |
| 4-CF$_3$ | 4-CH$_3$ | H | H | H |
| 4-CF$_3$ | 4-t-Bu | H | H | H |
| 4-CF$_3$ | 4-n-Hex | H | H | H |
| 4-CF$_3$ | 4-Ph | H | H | H |
| 4-OH | H | H | H | H |
| 4-OH | 4-Cl | H | H | H |
| 4-OH | 4-Br | H | H | H |
| 4-OH | 4-CH$_3$ | H | H | H |
| 4-OH | 4-t-Bu | H | H | H |
| 4-OH | 4-n-Hex | H | H | H |
| 4-OH | 4-Ph | H | H | H |
| 4-OCH$_3$ | H | H | H | H |
| 4-OCH$_3$ | 4-Cl | H | H | H |
| 4-OCH$_3$ | 4-Br | H | H | H |
| 4-OCH$_3$ | 4-CH$_3$ | H | H | H |
| 4-OCH$_3$ | 4-t-Bu | H | H | H |
| 4-OCH$_3$ | 4-n-Hex | H | H | H |
| 4-OCH$_3$ | 4-Ph | H | H | H |
| 4-O-i-Pr | H | H | H | H |
| 4-O-i-Pr | 4-Cl | H | H | H |
| 4-O-i-Pr | 4-Br | H | H | H |
| 4-O-i-Pr | 4-CH$_3$ | H | H | H |
| 4-O-i-Pr | 4-t-Bu | H | H | H |
| 4-O-i-Pr | 4-n-Hex | H | H | H |
| 4-O-i-Pr | 4-Ph | H | H | H |
| 4-O-n-Hex | H | H | H | H |
| 4-O-n-Hex | 4-Cl | H | H | H |
| 4-O-n-Hex | 4-Br | H | H | H |
| 4-O-n-Hex | 4-CH$_3$ | H | H | H |
| 4-O-n-Hex | 4-t-Bu | H | H | H |
| 4-O-n-Hex | 4-n-Hex | H | H | H |
| 4-O-n-Hex | 4-Ph | H | H | H |
| 3,4-(OCH$_3$)$_2$ | H | H | H | H |
| 3,4-(OCH$_3$)$_2$ | 4-Cl | H | H | H |
| 3,4-(OCH$_3$)$_2$ | 4-Br | H | H | H |
| 3,4-(OCH$_3$)$_2$ | 4-CH$_3$ | H | H | H |
| 3,4-(OCH$_3$)$_2$ | 4-t-Bu | H | H | H |
| 3,4-(OCH$_3$)$_2$ | 4-n-Hex | H | H | H |
| 3,4-(OCH$_3$)$_2$ | 4-Ph | H | H | H |
| 4-OC$_2$H$_4$OEt | H | H | H | H |
| 4-OC$_2$H$_4$OEt | 4-Cl | H | H | H |
| 4-OC$_2$H$_4$OEt | 4-Br | H | H | H |
| 4-OC$_2$H$_4$OEt | 4-CH$_3$ | H | H | H |
| 4-OC$_2$H$_4$OEt | 4-t-Bu | H | H | H |
| 4-OC$_2$H$_4$OEt | 4-n-Hex | H | H | H |
| 4-OC$_2$H$_4$OEt | 4-Ph | H | H | H |
| 4-OPh | H | H | H | H |
| 4-OPh | 4-Cl | H | H | H |
| 4-OPh | 4-Br | H | H | H |
| 4-OPh | 4-CH$_3$ | H | H | H |

TABLE 2-continued

| | | | | |
|---|---|---|---|---|
| 4-OPh | 4-t-Bu | H | H | H |
| 4-OPh | 4-n-Hex | H | H | H |
| 4-OPh | 4-Ph | H | H | H |
| 4-OCH$_2$Ph | H | H | H | H |
| 4-OCH$_2$Ph | 4-Cl | H | H | H |
| 4-OCH$_2$Ph | 4-Br | H | H | H |
| 4-OCH$_2$Ph | 4-CH$_3$ | H | H | H |
| 4-OCH$_2$Ph | 4-t-Bu | H | H | H |
| 4-OCH$_2$Ph | 4-n-Hex | H | H | H |
| 4-OCH$_2$Ph | 4-Ph | H | H | H |
| 4-Ph | H | H | H | H |
| 4-Ph | 4-Cl | H | H | H |
| 4-Ph | 4-Br | H | H | H |
| 4-Ph | 4-CH$_3$ | H | H | H |
| 4-Ph | 4-t-Bu | H | H | H |
| 4-Ph | 4-t-Bu | CH$_3$ | H | H |
| 4-Ph | 4-n-Hex | H | H | H |
| 4-Ph | 4-n-Hex | CH$_3$ | H | H |
| 4-Ph | 4-n-Hex | H | H | CH$_3$ |
| 4-Ph | 4-n-Hex | H | CH$_3$ | CH$_3$ |
| 4-Ph | 4-Ph | H | H | H |
| 4-Ph | 4-Ph | CH$_3$ | H | H |

TABLE 3

The locants for the substituent R$^{81}$ in the Table correspond to the positions indicated in the following structural formulae.

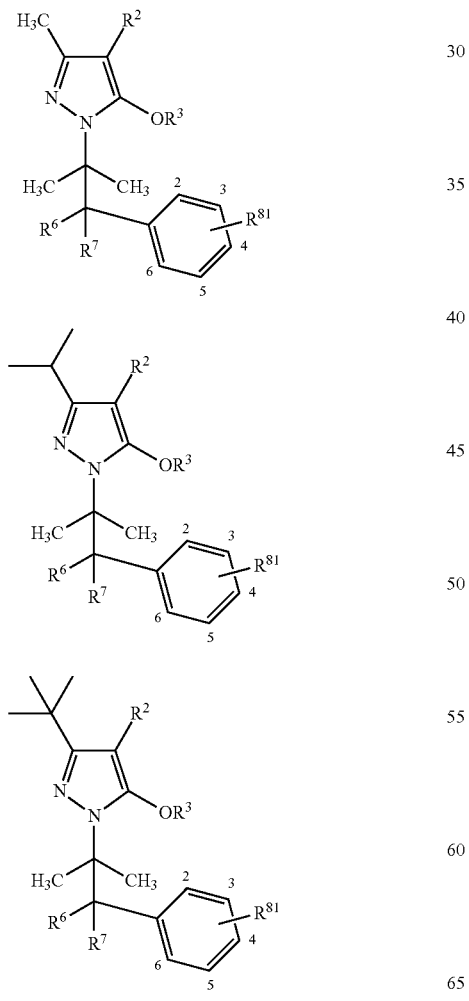

TABLE 3-continued

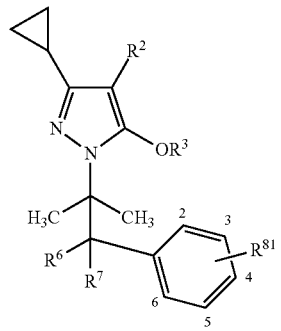

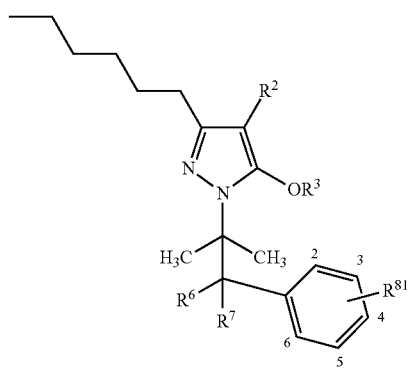

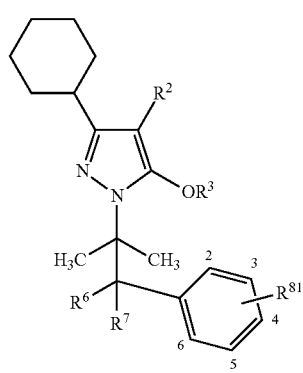

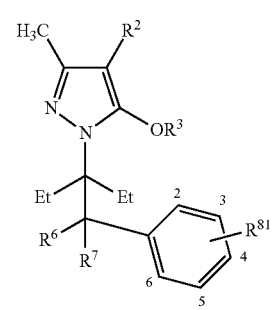

TABLE 3-continued
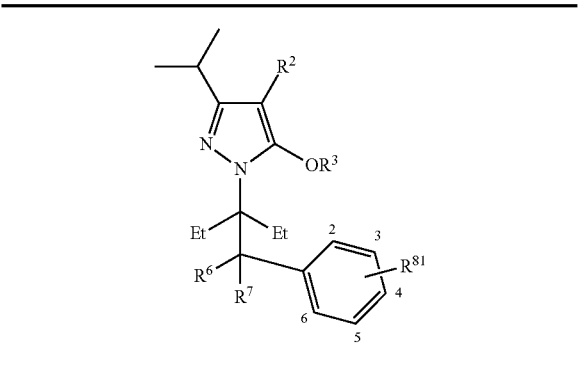
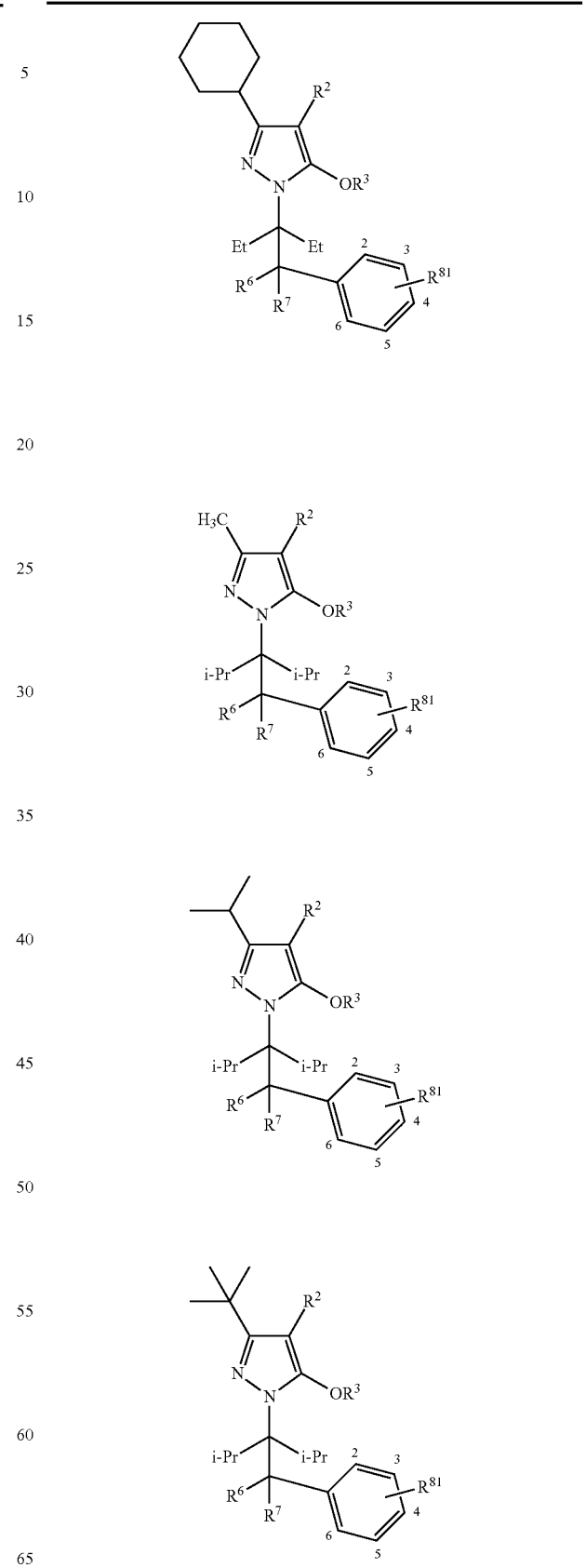

TABLE 3-continued
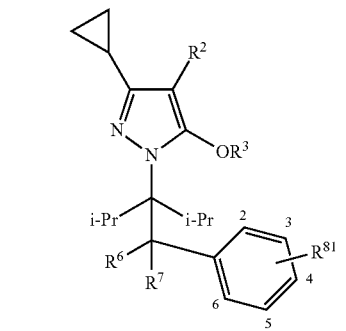
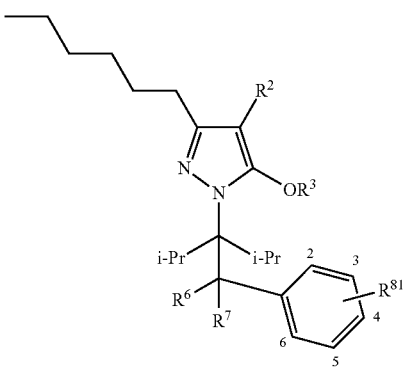
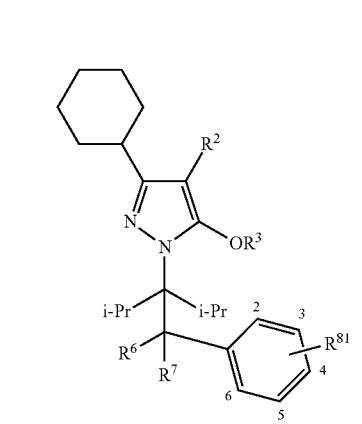
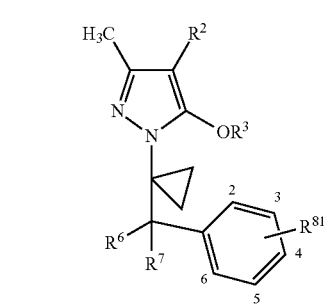
TABLE 3-continued
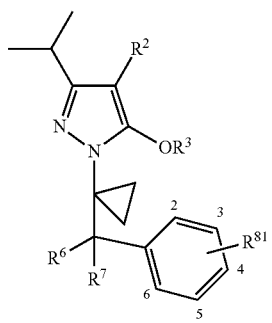
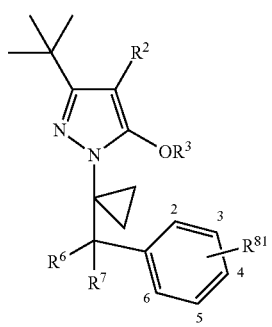
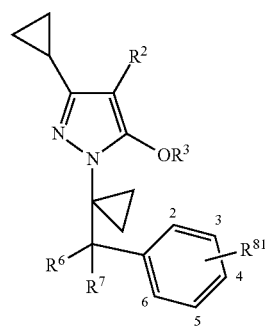
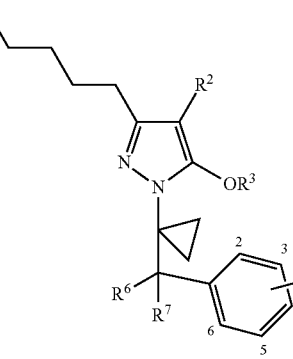

TABLE 3-continued

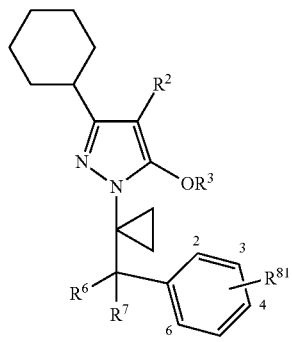

| R² | (Z)m | R⁸¹ | R³ | R⁶ | R⁷ |
|---|---|---|---|---|---|
| H | — | H | H | H | H |
| H | — | 4-CH₃ | H | H | H |
| F | — | H | H | H | H |
| CH₃ | — | H | H | H | H |
| Et | — | H | H | H | H |
| n-Pr | — | H | H | H | H |
| c-Pr | — | H | H | H | H |
| i-Pr | — | H | H | H | H |
| n-Bu | — | H | H | H | H |
| c-Bu | — | H | H | H | H |
| i-Bu | — | H | H | H | H |
| t-Bu | — | H | H | H | H |
| n-Pen | — | H | H | H | H |
| c-Pen | — | H | H | H | H |
| n-Hex | — | H | H | H | H |
| c-Hex | — | H | H | H | H |
| n-C₇H₁₅ | — | H | H | H | H |
| n-C₈H₁₇ | — | H | H | H | H |
| n-C₉H₁₉ | — | H | H | H | H |
| n-C₁₀H₂ | — | H | H | H | H |
| CF₃ | — | H | H | H | H |
| C(Ph)=NCH₃ | — | H | H | H | H |
| C(CH₃)=NPh | — | H | H | H | H |
| C(Ph)=NOCH₃ | — | H | H | H | H |
| C(O)CH₃ | — | H | H | H | H |
| C(O)Et | — | H | H | H | H |
| C(O)CF₃ | — | H | H | H | H |
| C(O)Ph | — | H | H | H | H |
| C(O)Ph | — | 4-Cl | H | H | H |
| C(O)Ph | — | 4-Cl | H | H | CH₃ |
| C(O)Ph | — | 4-CH₃ | H | H | H |
| C(O)Ph | — | 4-CH₃ | CH₃ | H | H |
| C(O)Ph | — | 4-CH₃ | CH₂Ph | H | H |
| C(O)Ph | — | 4-CH₃ | C(O)Ph | H | H |
| C(O)Ph | — | 4-CH₃ | C(O)OEt | H | H |
| C(O)Ph | — | 4-CH₃ | H | H | CH₃ |
| C(O)Ph | — | 4-CH₃ | H | CH₃ | CH₃ |
| C(O)Ph | — | 4-t-Bu | H | H | H |
| C(O)Ph | — | 4-t-Bu | H | H | CH₃ |
| C(O)Ph | — | 4-n-hex | H | H | H |
| C(O)Ph | — | 4-n-hex | H | H | CH₃ |
| C(O)Ph | — | 4-OCH₃ | H | H | H |
| C(O)Ph | — | 4-OCH₃ | H | H | CH₃ |
| C(O)Ph | — | 4-Ph | H | H | H |
| C(O)Ph | — | 4-Ph | H | H | CH₃ |
| C(O)CH₂Ph | — | H | H | H | H |
| C(O)CH(CH₃)Ph | — | H | H | H | H |
| C(O)C₂H₄Ph | — | H | H | H | H |
| C(O)OCH₃ | — | H | H | H | H |
| C(O)OEt | — | H | H | H | H |
| C(O)OEt | — | 4-Cl | H | H | H |
| C(O)OEt | — | 4-Cl | H | H | CH₃ |
| C(O)OEt | — | 4-CH, | H | H | H |
| C(O)OEt | — | 4-CH₃ | CH₃ | H | H |
| C(O)OEt | — | 4-CH₃ | CH₂Ph | H | H |
| C(O)OEt | — | 4-CH₃ | C(O)Ph | H | H |
| C(O)OEt | — | 4-CH₃ | C(O)OEt | H | H |
| C(O)OEt | — | 4-CH₃ | H | H | CH₃ |
| C(O)OEt | — | 4-CH₃ | H | CH₃ | CH₃ |
| C(O)OEt | — | 4-t-Bu | H | H | H |
| C(O)OEt | — | 4-t-Bu | H | H | CH₃ |
| C(O)OEt | — | 4-n-hex | H | H | H |
| C(O)OEt | — | 4-n-hex | H | H | CH₃ |
| C(O)OEt | — | 4-OCH₃ | H | H | H |
| C(O)OEt | — | 4-OCH₃ | H | H | CH₃ |
| C(O)OEt | — | 4-Ph | H | H | H |
| C(O)OEt | — | 4-Ph | H | H | CH₃ |
| C(O)OPh | — | H | H | H | H |
| C(O)OCH₂Ph | — | H | H | H | H |
| C(O)OCH(CH₃)Ph | — | H | H | H | H |
| C(O)OC₂H₄Ph | — | H | H | H | H |
| C(O)N(CH₃)2 | — | H | H | H | H |
| C(O)NHCH₃ | — | H | H | H | H |
| C(O)NH(CH₂Ph) | — | H | H | H | H |
| CH₂Ph | — | H | H | H | H |
| CH₂(4-Cl-Ph) | — | H | H | H | H |
| A001 | H | H | H | H | H |
| A001 | 3-n-Bu | H | H | H | H |
| A002 | H | H | H | H | H |
| A002 | 2-Cl | H | H | H | H |
| A003 | H | H | H | H | H |
| A004 | H | H | H | H | H |
| A005 | H | H | H | H | H |
| A005 | H | 4-Cl | H | H | H |
| A005 | H | 4-Cl | H | H | CH₃ |
| A005 | H | 4-CH₃ | H | H | H |
| A005 | H | 4-CH₃ | CH₃ | H | H |
| A005 | H | 4-CH₃ | CH₂Ph | H | H |
| A005 | H | 4-CH₃ | C(O)Ph | H | H |
| A005 | H | 4-CH₃ | C(O)OEt | H | H |
| A005 | H | 4-CH₃ | H | H | CH₃ |
| A005 | H | 4-CH₃ | H | CH₃ | CH₃ |
| A005 | H | 4-t-Bu | H | H | H |
| A005 | H | 4-t-Bu | H | H | CH₃ |
| A005 | H | 4-n-hex | H | H | H |
| A005 | H | 4-n-hex | H | H | CH₃ |
| A005 | H | 4-OCH₃ | H | H | H |
| A005 | H | 4-OCH₃ | H | H | CH₃ |
| A005 | H | 4-Ph | H | H | H |
| A005 | H | 4-Ph | H | H | CH₃ |
| A005 | 2,5-(CH₃)₂ | H | H | H | H |
| A005 | 2,5-Cl₂ | H | H | H | H |
| A005 | 2-Br | H | H | H | H |
| A006 | H | H | H | H | H |
| A006 | H | 4-Cl | H | H | H |
| A006 | H | 4-Cl | H | H | CH₃ |
| A006 | H | 4-CH₃ | H | H | H |
| A006 | H | 4-CH₃ | CH₃ | H | H |
| A006 | H | 4-CH₃ | CH₂Ph | H | H |
| A006 | H | 4-CH₃ | C(O)Ph | H | H |
| A006 | H | 4-CH₃ | C(O)OEt | H | H |
| A006 | H | 4-CH₃ | H | H | CH₃ |
| A006 | H | 4-CH₃ | H | CH3 | CH₃ |
| A006 | H | 4-t-Bu | H | H | H |
| A006 | H | 4-t-Bu | H | H | CH₃ |
| A006 | H | 4-n-hex | H | H | H |
| A006 | H | 4-n-hex | H | H | CH₃ |
| A006 | H | 4-OCH₃ | H | H | H |
| A006 | H | 4-OCH₃ | H | H | CH₃ |
| A006 | H | 4-Ph | H | H | H |
| A006 | H | 4-Ph | H | H | CH₃ |
| A006 | 3-CH₃ | H | H | H | H |
| A006 | 5-CH₃ | H | H | H | H |
| A006 | 3-Cl | H | H | H | H |
| A006 | 5-Et | H | H | H | H |
| A006 | 5-Cl | H | H | H | H |
| A006 | 5-Br | H | H | H | H |
| A006 | 3-Br | H | H | H | H |
| A006 | 4-Br | H | H | H | H |
| A006 | 5-NO₂ | H | H | H | H |
| A007 | H | H | H | H | H |
| A007 | 5-CH₃ | H | H | H | H |
| A007 | 3-CH₃ | H | H | H | H |
| A007 | 5-Br | H | H | H | H |
| A007 | 5-NO₂ | H | H | H | H |
| A007 | 5-Ph | H | H | H | H |
| A008 | 5-CH₃ | H | H | H | H |
| A009 | 5-CH₃ | H | H | H | H |
| A010 | 3,5-(CH₃)₂ | H | H | H | H |
| A010 | 3,5-Cl₂ | H | H | H | H |

TABLE 3-continued

| | | | | |
|---|---|---|---|---|
| A011 | 3,5-(CH$_3$)$_2$ | H | H | H | H |
| A011 | 3,5-Cl$_2$ | H | H | H | H |
| A012 | 3-CH$_3$ | H | H | H | H |
| A012 | 3-CH$_3$ | H | H | H | H |
| A012 | 3-Cl | H | H | H | H |
| A013 | 3-CH$_3$ | H | H | H | H |
| A013 | 3-CH$_3$ | H | H | H | H |
| A013 | 3-Cl | H | H | H | H |
| A014 | H | H | H | H | H |
| A014 | H | 4-Cl | H | H | H |
| A014 | H | 4-Cl | H | H | CH$_3$ |
| A014 | H | 4-CH$_3$ | H | H | H |
| A014 | H | 4-CH$_3$ | CH$_3$ | H | H |
| A014 | H | 4-CH$_3$ | CH$_2$Ph | H | H |
| A014 | H | 4-CH$_3$ | C(O)Ph | H | H |
| A014 | H | 4-CH$_3$ | C(O)OEt | H | H |
| A014 | H | 4-CH$_3$ | H | H | CH$_3$ |
| A014 | H | 4-CH$_3$ | H | CH$_3$ | CH$_3$ |
| A014 | H | 4-t-Bu | H | H | H |
| A014 | H | 4-t-Bu | H | H | CH$_3$ |
| A014 | H | 4-n-hex | H | H | H |
| A014 | H | 4-n-hex | H | H | CH$_3$ |
| A014 | H | 4-OCH$_3$ | H | H | H |
| A014 | H | 4-OCH$_3$ | H | H | CH$_3$ |
| A014 | H | 4-Ph | H | H | H |
| A014 | H | 4-Ph | H | H | CH$_3$ |
| A015 | H | H | H | H | H |
| A016 | 2,4-(CH$_3$)$_2$ | H | H | H | H |
| A016 | 2,4-(CH$_3$)$_2$ | 4-Cl | H | H | H |
| A016 | 2,4-(CH$_3$)$_2$ | 4-Cl | H | H | CH$_3$ |
| A016 | 2,4-(CH$_3$)$_2$ | 4-CH$_3$ | H | H | H |
| A016 | 2,4-(CH$_3$)$_2$ | 4-CH$_3$ | CH$_3$ | H | H |
| A016 | 2,4-(CH$_3$)$_2$ | 4-CH$_3$ | CH$_2$Ph | H | H |
| A016 | 2,4-(CH$_3$)$_2$ | 4-CH$_3$ | C(O)Ph | H | H |
| A016 | 2,4-(CH$_3$)$_2$ | 4-CH$_3$ | C(O)OEt | H | H |
| A016 | 2,4-(CH$_3$)$_2$ | 4-CH$_3$ | H | H | CH$_3$ |
| A016 | 2,4-(CH$_3$)$_2$ | 4-CH$_3$ | H | CH$_3$ | CH$_3$ |
| A016 | 2,4-(CH$_3$)$_2$ | 4-t-Bu | H | H | H |
| A016 | 2,4-(CH$_3$)$_2$ | 4-t-Bu | H | H | CH$_3$ |
| A016 | 2,4-(CH$_3$)$_2$ | 4-n-hex | H | H | H |
| A016 | 2,4-(CH$_3$)$_2$ | 4-n-hex | H | H | CH$_3$ |
| A016 | 2,4-(CH$_3$)$_2$ | 4-OCH$_3$ | H | H | H |
| A016 | 2,4-(CH$_3$)$_2$ | 4-OCH$_3$ | H | H | CH$_3$ |
| A016 | 2,4-(CH$_3$)$_2$ | 4-Ph | H | H | H |
| A016 | 2,4-(CH$_3$)$_2$ | 4-Ph | H | H | CH$_3$ |
| A017 | 2,4-(CH$_3$)$_2$ | H | H | H | H |
| A018 | H | H | H | H | H |
| A018 | 3-CH$_3$ | H | H | H | H |
| A019 | 3-Ph, 5-CH$_3$ | H | H | H | H |
| A019 | 3,5-(CH$_3$)$_2$ | H | H | H | H |
| A020 | 5-CH$_3$ | H | H | H | H |
| A021 | 4-CH$_3$ | H | H | H | H |
| A022 | H | H | H | H | H |
| A023 | 2,4-(CH$_3$)$_2$ | H | H | H | H |
| A024 | 2-(4-pyridil) | H | H | H | H |
| A025 | H | H | H | H | H |
| A026 | H | H | H | H | H |
| A026 | 4-CH$_3$ | H | H | H | H |
| A027 | H | H | H | H | H |
| A027 | 4-CH$_3$ | H | H | H | H |
| A028 | H | H | H | H | H |
| A029 | H | H | H | H | H |
| A030 | H | H | H | H | H |
| A031 | H | H | H | H | H |
| A032 | H | H | H | H | H |
| A033 | H | H | H | H | H |
| A034 | H | H | H | H | H |
| A034 | 3,6-Cl$_2$ | H | H | H | H |
| A035 | H | H | H | H | H |
| A036 | H | H | H | H | H |
| A036 | H | 4-Cl | H | H | H |
| A036 | H | 4-Cl | H | H | CH$_3$ |
| A036 | H | 4-CH$_3$ | H | H | H |
| A036 | H | 4-CH$_3$ | CH$_3$ | H | H |
| A036 | H | 4-CH$_3$ | CH$_2$Ph | H | H |
| A036 | H | 4-CH$_3$ | C(O)Ph | H | H |
| A036 | H | 4-CH$_3$ | C(O)OEt | H | H |
| A036 | H | 4-CH$_3$ | H | H | CH$_3$ |
| A036 | H | 4-CH$_3$ | H | CH$_3$ | CH$_3$ |
| A036 | H | 4-t-Bu | H | H | H |
| A036 | H | 4-t-Bu | H | H | CH$_3$ |
| A036 | H | 4-n-hex | H | H | H |
| A036 | H | 4-n-hex | H | H | CH$_3$ |
| A036 | H | 4-OCH$_3$ | H | H | H |
| A036 | H | 4-OCH$_3$ | H | H | CH$_3$ |
| A036 | H | 4-Ph | H | H | H |
| A036 | H | 4-Ph | H | H | CH$_3$ |
| A037 | H | H | H | H | H |
| A037 | H | 4-Cl | H | H | CH$_3$ |
| A037 | H | 4-CH$_3$ | H | H | H |
| A037 | H | 4-CH$_3$ | CH$_3$ | H | H |
| A037 | H | 4-CH$_3$ | CH$_2$Ph | H | H |
| A037 | H | 4-CH$_3$ | C(O)Ph | H | H |
| A037 | H | 4-CH$_3$ | C(O)OEt | H | H |
| A037 | H | 4-CH$_3$ | H | H | CH$_3$ |
| A037 | H | 4-CH$_3$ | H | CH$_3$ | CH$_3$ |
| A037 | H | 4-t-Bu | H | H | H |
| A037 | H | 4-t-Bu | H | H | CH$_3$ |
| A037 | H | 4-n-hex | H | H | H |
| A037 | H | 4-n-hex | H | H | CH$_3$ |
| A037 | H | 4-OCH$_3$ | H | H | H |
| A037 | H | 4-OCH$_3$ | H | H | CH$_3$ |
| A037 | H | 4-Ph | H | H | H |
| A037 | H | 4-Ph | H | H | CH$_3$ |
| A037 | 6-OCH$_3$ | H | H | H | H |
| A037 | 6-Br | H | H | H | H |
| A038 | H | H | H | H | H |
| A038 | H | 4-Cl | H | H | H |
| A038 | H | 4-Cl | H | H | CH$_3$ |
| A038 | H | 4-CH$_3$ | H | H | H |
| A038 | H | 4-CH$_3$ | CH$_3$ | H | H |
| A038 | H | 4-CH$_3$ | CH$_2$Ph | H | H |
| A038 | H | 4-CH$_3$ | C(O)Ph | H | H |
| A038 | H | 4-CH$_3$ | C(O)OEt | H | H |
| A038 | H | 4-CH$_3$ | H | H | CH$_3$ |
| A038 | H | 4-CH$_3$ | H | CH$_3$ | CH$_3$ |
| A038 | H | 4-t-Bu | H | H | H |
| A038 | H | 4-t-Bu | H | H | CH$_3$ |
| A038 | H | 4-n-hex | H | H | H |
| A038 | H | 4-n-hex | H | H | CH$_3$ |
| A038 | H | 4-OCH$_3$ | H | H | H |
| A038 | H | 4-OCH$_3$ | H | H | CH$_3$ |
| A038 | H | 4-Ph | H | H | H |
| A038 | H | 4-Ph | H | H | CH$_3$ |
| A038 | 2-OCH$_3$ | H | H | H | H |
| A038 | 4-OCH$_3$ | H | H | H | H |
| A038 | 4-F | H | H | H | H |
| A039 | H | H | H | H | H |
| A039 | 3-CH$_3$ | H | H | H | H |
| A039 | 7-OCH$_3$ | H | H | H | H |
| A040 | H | H | H | H | H |
| A041 | H | H | H | H | H |
| A041 | H | 4-Cl | H | H | H |
| A041 | H | 4-Cl | H | H | CH$_3$ |
| A041 | H | 4-CH$_3$ | H | H | H |
| A041 | H | 4-CH$_3$ | CH$_3$ | H | H |
| A041 | H | 4-CH$_3$ | CH$_2$Ph | H | H |
| A041 | H | 4-CH$_3$ | C(O)Ph | H | H |
| A041 | H | 4-CH$_3$ | C(O)OEt | H | H |
| A041 | H | 4-CH$_3$ | H | H | CH$_3$ |
| A041 | H | 4-CH$_3$ | H | CH$_3$ | CH$_3$ |
| A041 | H | 4-t-Bu | H | H | H |
| A041 | H | 4-t-Bu | H | H | CH$_3$ |
| A041 | H | 4-n-hex | H | H | H |
| A041 | H | 4-n-hex | H | H | CH$_3$ |
| A041 | H | 4-OCH$_3$ | H | H | H |
| A041 | H | 4-OCH$_3$ | H | H | CH$_3$ |
| A041 | H | 4-Ph | H | H | H |
| A041 | H | 4-Ph | H | H | CH$_3$ |
| A041 | 6-NO$_2$ | H | H | H | H |
| A041 | 6-Br | H | H | H | H |
| A042 | H | H | H | H | H |
| A042 | H | 4-Cl | H | H | H |
| A042 | H | 4-Cl | H | H | CH$_3$ |
| A042 | H | 4-CH$_3$ | H | H | H |
| A042 | H | 4-CH$_3$ | CH$_3$ | H | H |
| A042 | H | 4-CH$_3$ | CH$_2$Ph | H | H |
| A042 | H | 4-CH$_3$ | C(O)Ph | H | H |
| A042 | H | 4-CH$_3$ | C(O)OEt | H | H |

TABLE 3-continued

| A042 | H | 4-CH₃ | H | H | CH₃ |
| --- | --- | --- | --- | --- | --- |
| A042 | H | 4-CH₃ | H | CH₃ | CH₃ |
| A042 | H | 4-t-Bu | H | H | H |
| A042 | H | 4-t-Bu | H | H | CH₃ |
| A042 | H | 4-n-hex | H | H | H |
| A042 | H | 4-n-hex | H | H | CH₃ |
| A042 | H | 4-OCH₃ | H | H | H |
| A042 | H | 4-OCH₃ | H | H | CH₃ |
| A042 | H | 4-Ph | H | H | H |
| A042 | H | 4-Ph | H | H | CH₃ |
| A042 | 5-Br | H | H | H | H |
| A043 | H | H | H | H | H |
| A044 | H | H | H | H | H |
| A051 | — | H | H | H | H |
| A052 | — | H | H | H | H |
| A053 | — | H | H | H | H |
| A054 | — | H | H | H | H |
| A055 | — | H | H | H | H |
| A056 | — | H | H | H | H |
| A057 | — | H | H | H | H |
| A058 | — | H | H | H | H |
| A059 | — | H | H | H | H |
| A060 | — | H | H | H | H |
| A061 | — | H | H | H | H |
| A062 | — | H | H | H | H |
| A063 | — | H | H | H | H |
| A064 | — | H | H | H | H |
| A065 | — | H | H | H | H |
| A066 | — | H | H | H | H |
| A067 | — | H | H | H | H |
| A068 | — | H | H | H | H |
| A101 | — | H | H | H | H |
| A102 | — | H | H | H | H |
| A103 | — | H | H | H | H |
| A104 | — | H | H | H | H |
| A105 | — | H | H | H | H |
| A106 | — | H | H | H | H |
| A107 | — | H | H | H | H |

TABLE 4

The locants for the substituent $R^{21}$ herein correspond to the positions indicated in the following structural formulae, and the expression — indicates unsubstituted.

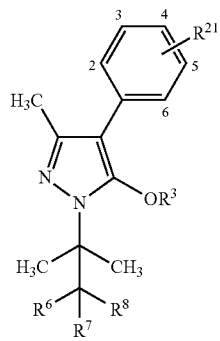

TABLE 4-continued

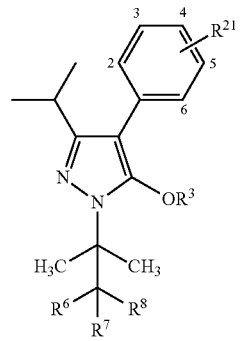

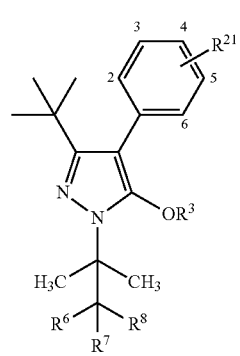

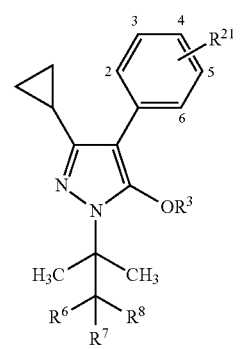

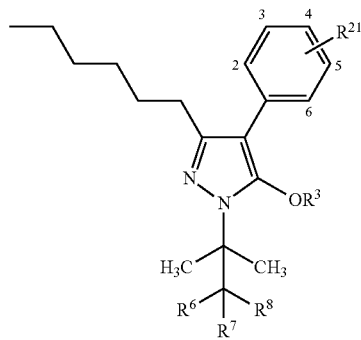

TABLE 4-continued
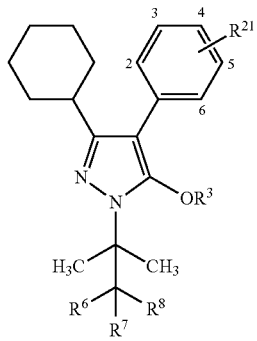
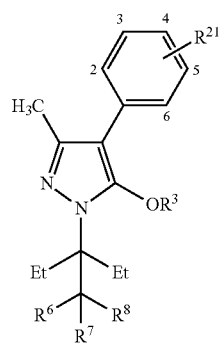
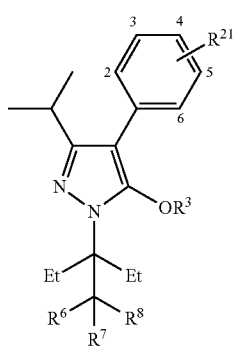
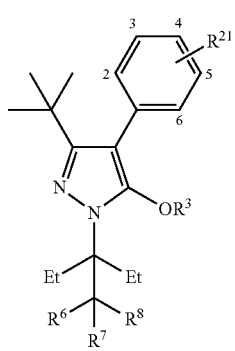
TABLE 4-continued
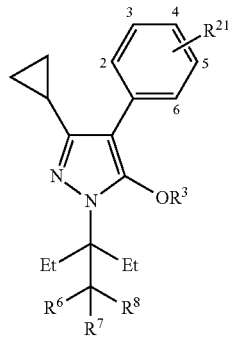
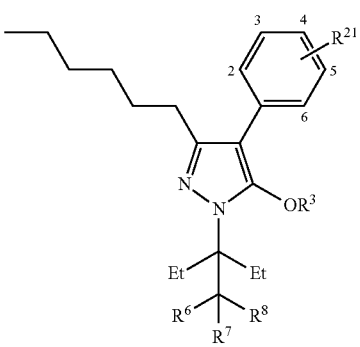
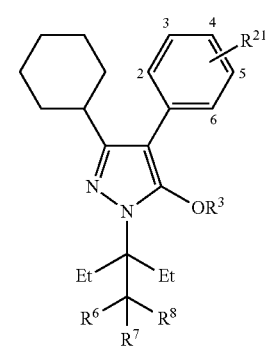
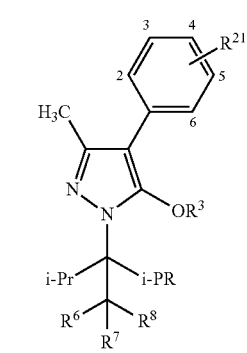

TABLE 4-continued

TABLE 4-continued

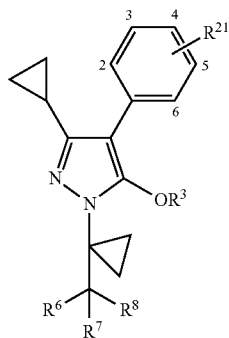

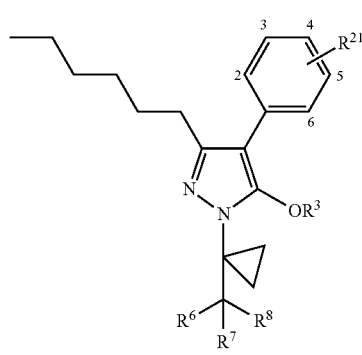

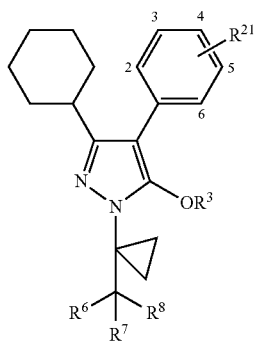

| R21 | R8 | (Z)m | R3 | R6 | R7 |
|---|---|---|---|---|---|
| H | c-Pr | — | H | H | H |
| 4-Cl | c-Pr | — | H | H | H |
| 4-Cl | c-Pr | — | H | H | CH3 |
| 4-CH3 | c-Pr | — | H | H | H |
| 4-CH3 | c-Pr | — | CH3 | H | H |
| 4-CH3 | c-Pr | — | CH2Ph | H | H |
| 4-CH3 | c-Pr | — | C(O)Ph | H | H |
| 4-CH3 | c-Pr | — | C(O)OEt | H | H |
| 4-CH3 | c-Pr | — | H | H | CH3 |
| 4-CH3 | c-Pr | — | H | CH, | CH3 |
| 4-t-Bu | c-Pr | — | H | H | H |
| 4-t-Bu | c-Pr | — | H | H | CH3 |
| 4-n-hex | c-Pr | — | H | H | H |
| 4-n-hex | c-Pr | — | CH3 | H | H |
| 4-n-hex | c-Pr | — | CH2Ph | H | H |
| 4-n-hex | c-Pr | — | C(O)Ph | H | H |
| 4-n-hex | c-Pr | — | C(O)OEt | H | H |
| 4-n-hex | c-Pr | — | H | H | CH3 |
| 4-n-hex | c-Pr | — | H | CH3 | CH3 |
| 4-OCH3 | c-Pr | — | H | H | H |
| 4-OCH3 | c-Pr | — | H | H | CH3 |
| 4-Ph | c-Pr | — | H | H | H |
| 4-Ph | c-Pr | — | H | H | CH3 |
| H | c-Bu | — | H | H | H |
| H | c-Pen | — | H | H | H |
| H | c-Hex | — | H | H | H |
| 4-Cl | c-Hex | — | H | H | H |
| 4-Cl | c-Hex | — | H | H | CH3 |
| 4-CH3 | c-Hex | — | H | H | H |
| 4-CH3 | c-Hex | — | CH3 | H | H |
| 4-CH3 | c-Hex | — | CH2Ph | H | H |
| 4-CH3 | c-Hex | — | C(O)Ph | H | H |
| 4-CH3 | c-Hex | — | C(O)OEt | H | H |
| 4-CH3 | c-Hex | — | H | H | CH3 |
| 4-CH3 | c-Hex | — | H | CH3 | CH3 |
| 4-t-Bu | c-Hex | — | H | H | H |
| 4-t-Bu | c-Hex | — | H | H | CH3 |
| 4-n-hex | c-Hex | — | H | H | H |
| 4-n-hex | c-Hex | — | CH3 | H | H |
| 4-n-hex | c-Hex | — | CH2Ph | H | H |
| 4-n-hex | c-Hex | — | C(O)Ph | H | H |
| 4-n-hex | c-Hex | — | C(O)OEt | H | H |
| 4-n-hex | c-Hex | — | H | H | CH3 |
| 4-n-hex | c-Hex | — | H | CH3 | CH3 |
| 4-OCH3 | c-Hex | — | H | H | H |
| 4-OCH3 | c-Hex | — | H | H | CH3 |
| 4-Ph | c-Hex | — | H | H | H |
| 4-Ph | c-Hex | — | H | H | CH3 |
| H | c-C7H15 | — | H | H | H |
| H | c-C8H17 | — | H | H | H |
| H | bicyclo[2.2.1]heptan-2-yl | — | H | H | H |
| H | 1-adamantyl | — | H | H | H |
| H | 2-adamantyl | — | H | H | H |
| H | A001 | H | H | H | H |
| H | A001 | 3-n-Bu | H | H | H |
| H | A002 | H | H | H | H |
| H | A002 | 2-Cl | H | H | H |
| H | A003 | H | H | H | H |
| H | A004 | H | H | H | H |
| H | A005 | H | H | H | H |
| 4-Cl | A005 | H | H | H | H |
| 4-Cl | A005 | H | H | H | CH3 |
| 4-CH3 | A005 | H | H | H | H |
| 4-CH3 | A005 | H | CH3 | H | H |
| 4-CH3 | A005 | H | CH2Ph | H | H |
| 4-CH3 | A005 | H | C(O)Ph | H | H |
| 4-CH3 | A005 | H | C(O)OEt | H | H |
| 4-CH3 | A005 | H | H | H | CH3 |
| 4-CH3 | A005 | H | H | CH3 | CH3 |
| 4-t-Bu | A005 | H | H | H | H |
| 4-t-Bu | A005 | H | H | H | CH3 |
| 4-n-hex | A005 | H | H | H | H |
| 4-n-hex | A005 | H | CH3 | H | H |
| 4-n-hex | A005 | H | CH2Ph | H | H |
| 4-n-hex | A005 | H | C(O)Ph | H | H |
| 4-n-hex | A005 | H | C(O)OEt | H | H |
| 4-n-hex | A005 | H | H | H | CH3 |
| 4-n-hex | A005 | H | H | CH3 | CH3 |
| 4-OCH3 | A005 | H | H | H | H |
| 4-OCH3 | A005 | H | H | H | CH3 |
| 4-Ph | A005 | H | H | H | H |
| 4-Ph | A005 | H | H | H | CH3 |
| H | A005 | 2,5-(CH3)2 | H | H | H |
| H | A005 | 2,5-Cl2 | H | H | H |
| H | A005 | 2-Br | H | H | H |
| H | A006 | H | H | H | H |
| 4-Cl | A006 | H | H | H | H |
| 4-Cl | A006 | H | H | H | CH3 |
| 4-CH3 | A006 | H | H | H | H |
| 4-CH3 | A006 | H | CH3 | H | H |
| 4-CH3 | A006 | H | CH2Ph | H | H |
| 4-CH3 | A006 | H | C(O)Ph | H | H |
| 4-CH3 | A006 | H | C(O)OEt | H | H |
| 4-CH3 | A006 | H | H | H | CH3 |
| 4-CH3 | A006 | H | H | CH3 | CH3 |
| 4-t-Bu | A006 | H | H | H | H |
| 4-t-Bu | A006 | H | H | H | CH3 |
| 4-n-hex | A006 | H | H | H | H |
| 4-n-hex | A006 | H | CH3 | H | H |
| 4-n-hex | A006 | H | CH2Ph | H | H |
| 4-n-hex | A006 | H | C(O)Ph | H | H |
| 4-n-hex | A006 | H | C(O)OEt | H | H |
| 4-n-hex | A006 | H | H | H | CH3 |
| 4-n-hex | A006 | H | H | CH3 | CH3 |
| 4-OCH3 | A006 | H | H | H | H |
| 4-OCH3 | A006 | H | H | H | CH3 |

TABLE 4-continued

| | | | | | |
|---|---|---|---|---|---|
| 4-Ph | A006 | H | H | H | H |
| 4-Ph | A006 | H | H | H | CH₃ |
| H | A006 | 3-CH₃ | H | H | H |
| H | A006 | 5-CH₃ | H | H | H |
| H | A006 | 3-Cl | H | H | H |
| H | A006 | 5-Et | H | H | H |
| H | A006 | 5-Cl | H | H | H |
| H | A006 | 5-Br | H | H | H |
| H | A006 | 3-Br | H | H | H |
| H | A006 | 4-Br | H | H | H |
| H | A006 | 5-NO₂ | H | H | H |
| H | A007 | H | H | H | H |
| H | A007 | 5-CH₃ | H | H | H |
| H | A007 | 3-CH₃ | H | H | H |
| H | A007 | 5-Br | H | H | H |
| H | A007 | 5-NO₂ | H | H | H |
| H | A007 | 5-Ph | H | H | H |
| H | A008 | 5-CH₃ | H | H | H |
| H | A009 | 5-CH₃ | H | H | H |
| H | A010 | 3,5-(CH₃)₂ | H | H | H |
| H | A010 | 3,5-Cl₂ | H | H | H |
| H | A011 | 3,5-(CH₃)₂ | H | H | H |
| H | A011 | 3,5-Cl₂ | H | H | H |
| H | A012 | 3-CH₃ | H | H | H |
| H | A012 | 3-Me | H | H | H |
| H | A012 | 3-Cl | H | H | H |
| H | A013 | 3-CH₃ | H | H | H |
| H | A013 | 3-Me | H | H | H |
| H | A013 | 3-Cl | H | H | H |
| H | A014 | H | H | H | H |
| 4-Cl | A014 | H | H | H | H |
| 4-Cl | A014 | H | H | H | CH₃ |
| 4-CH₃ | A014 | H | H | H | H |
| 4-CH₃ | A014 | H | CH₃ | H | H |
| 4-CH₃ | A014 | H | CH₂Ph | H | H |
| 4-CH₃ | A014 | H | C(O)Ph | H | H |
| 4-CH₃ | A014 | H | C(O)OEt | H | H |
| 4-CH₃ | A014 | H | H | H | CH₃ |
| 4-CH₃ | A014 | H | H | CH₃ | CH₃ |
| 4-t-Bu | A014 | H | H | H | H |
| 4-t-Bu | A014 | H | H | H | CH₃ |
| 4-n-hex | A014 | H | H | H | H |
| 4-n-hex | A014 | H | H | H | CH₃ |
| 4-OCH₃ | A014 | H | H | H | H |
| 4-OCH₃ | A014 | H | H | H | CH₃ |
| 4-Ph | A014 | H | H | H | H |
| 4-Ph | A014 | H | H | H | CH₃ |
| H | A015 | H | H | H | H |
| H | A016 | 2,4-(CH₃)₂ | H | H | H |
| 4-Cl | A016 | 2,4-(CH₃)₂ | H | H | H |
| 4-Cl | A016 | 2,4-(CH₃)₂ | H | H | CH₃ |
| 4-CH₃ | A016 | 2,4-(CH₃)₂ | H | H | H |
| 4-CH₃ | A016 | 2,4-(CH₃)₂ | CH₃ | H | H |
| 4-CH₃ | A016 | 2,4-(CH₃)₂ | CH₂Ph | H | H |
| 4-CH₃ | A016 | 2,4-(CH₃)₂ | C(O)Ph | H | H |
| 4-CH₃ | A016 | 2,4-(CH₃)₂ | C(O)OEt | H | H |
| 4-CH₃ | A016 | 2,4-(CH₃)₂ | H | H | CH₃ |
| 4-CH₃ | A016 | 2,4-(CH₃)₂ | H | CH₃ | CH₃ |
| 4-t-Bu | A016 | 2,4-(CH₃)₂ | H | H | H |
| 4-t-Bu | A016 | 2,4-(CH₃)₂ | H | H | CH₃ |
| 4-n-hex | A016 | 2,4-(CH₃)₂ | H | H | H |
| 4-n-hex | A016 | 2,4-(CH₃)₂ | H | H | CH₃ |
| 4-OCH₃ | A016 | 2,4-(CH₃)₂ | H | H | H |
| 4-OCH₃ | A016 | 2,4-(CH₃)₂ | H | H | CH₃ |
| 4-Ph | A016 | 2,4-(CH₃)₂ | H | H | H |
| 4-Ph | A016 | 2,4-(CH₃)₂ | H | H | CH₃ |
| H | A017 | 2,4-(CH₃)₂ | H | H | H |
| H | A018 | H | H | H | H |
| H | A018 | 3-CH₃ | H | H | H |
| H | A019 | 3-Ph, 5-CH₃ | H | H | H |
| H | A019 | 3,5-(CH₃)₂ | H | H | H |
| H | A020 | 5-CH₃ | H | H | H |
| H | A021 | 4-CH₃ | H | H | H |
| H | A022 | H | H | H | H |
| H | A023 | 2,4-(CH₃)₂ | H | H | H |
| H | A024 | 2-(4-pyridil) | H | H | H |
| H | A025 | H | H | H | H |
| H | A026 | H | H | H | H |
| H | A026 | 4-CH₃ | H | H | H |
| H | A027 | H | H | H | H |
| H | A027 | 4-CH₃ | H | H | H |
| H | A028 | H | H | H | H |
| H | A029 | H | H | H | H |
| H | A030 | H | H | H | H |
| H | A031 | H | H | H | H |
| H | A032 | H | H | H | H |
| H | A033 | H | H | H | H |
| H | A034 | H | H | H | H |
| H | A034 | 3,6-Cl₂ | H | H | H |
| H | A035 | H | H | H | H |
| H | A036 | H | H | H | H |
| H | A037 | H | H | H | H |
| 4-Cl | A037 | H | H | H | H |
| 4-Cl | A037 | H | H | H | CH₃ |
| 4-CH₃ | A037 | H | H | H | H |
| 4-CH₃ | A037 | H | CH₃ | H | H |
| 4-CH₃ | A037 | H | CH₂Ph | H | H |
| 4-CH₃ | A037 | H | C(O)Ph | H | H |
| 4-CH₃ | A037 | H | C(O)OEt | H | H |
| 4-CH₃ | A037 | H | H | H | CH₃ |
| 4-CH₃ | A037 | H | H | CH₃ | CH₃ |
| 4-t-Bu | A037 | H | H | H | H |
| 4-t-Bu | A037 | H | H | H | CH₃ |
| 4-n-hex | A037 | H | H | H | H |
| 4-n-hex | A037 | H | CH₃ | H | H |
| 4-n-hex | A037 | H | CH₂Ph | H | H |
| 4-n-hex | A037 | H | C(O)Ph | H | H |
| 4-n-hex | A037 | H | C(O)OEt | H | H |
| 4-n-hex | A037 | H | H | H | CH₃ |
| 4-n-hex | A037 | H | H | CH₃ | CH₃ |
| 4-OCH₃ | A037 | H | H | H | H |
| 4-OCH₃ | A037 | H | H | H | CH₃ |
| 4-Ph | A037 | H | H | H | H |
| 4-Ph | A037 | H | H | H | CH₃ |
| H | A037 | 6-OCH₃ | H | H | H |
| H | A037 | 6-Br | H | H | H |
| H | A038 | H | H | H | H |
| 4-Cl | A038 | H | H | H | H |
| 4-Cl | A038 | H | H | H | CH₃ |
| 4-CH₃ | A038 | H | H | H | H |
| 4-CH₃ | A038 | H | CH₃ | H | H |
| 4-CH₃ | A038 | H | CH₂Ph | H | H |
| 4-CH₃ | A038 | H | C(O)Ph | H | H |
| 4-CH₃ | A038 | H | C(O)OEt | H | H |
| 4-CH₃ | A038 | H | H | H | CH₃ |
| 4-CH₃ | A038 | H | H | CH₃ | CH₃ |
| 4-t-Bu | A038 | H | H | H | H |
| 4-t-Bu | A038 | H | H | H | CH₃ |
| 4-n-hex | A038 | H | H | H | H |
| 4-n-hex | A038 | H | CH₃ | H | H |
| 4-n-hex | A038 | H | CH₂Ph | H | H |
| 4-n-hex | A038 | H | C(O)Ph | H | H |
| 4-n-hex | A038 | H | C(O)OEt | H | H |
| 4-n-hex | A038 | H | H | H | CH₃ |
| 4-n-hex | A038 | H | H | CH₃ | CH₃ |
| 4-OCH₃ | A038 | H | H | H | H |
| 4-OCH₃ | A038 | H | H | H | CH₃ |
| 4-Ph | A038 | H | H | H | H |
| 4-Ph | A038 | H | H | H | CH₃ |
| H | A038 | 2-OCH₃ | H | H | H |
| H | A038 | 4-OCH₃ | H | H | H |
| H | A038 | 4-F | H | H | H |
| H | A039 | H | H | H | H |
| H | A039 | 3-CH₃ | H | H | H |
| H | A039 | 7-OCH₃ | H | H | H |
| H | A040 | H | H | H | H |
| H | A041 | H | H | H | H |
| 4-Cl | A041 | H | H | H | H |
| 4-Cl | A041 | H | H | H | CH₃ |
| 4-CH₃ | A041 | H | H | H | H |
| 4-CH₃ | A041 | H | CH₃ | H | H |
| 4-CH₃ | A041 | H | CH₂Ph | H | H |
| 4-CH₃ | A041 | H | C(O)Ph | H | H |
| 4-CH₃ | A041 | H | C(O)OEt | H | H |
| 4-CH₃ | A041 | H | H | H | CH₃ |
| 4-CH₃ | A041 | H | H | CH₃ | CH₃ |
| 4-t-Bu | A041 | H | H | H | H |
| 4-t-Bu | A041 | H | H | H | CH₃ |
| 4-n-hex | A041 | H | H | H | H |
| 4-n-hex | A041 | H | H | H | CH₃ |

TABLE 4-continued

| | | | | | |
|---|---|---|---|---|---|
| 4-OCH₃ | A041 | H | H | H | H |
| 4-OCH₃ | A041 | H | H | H | CH₃ |
| 4-Ph | A041 | H | H | H | H |
| 4-Ph | A041 | H | H | H | CH₃ |
| H | A041 | 6-NO₂ | H | H | H |
| H | A041 | 6-Br | H | H | H |
| H | A042 | H | H | H | H |
| 4-Cl | A042 | H | H | H | H |
| 4-Cl | A042 | H | H | H | CH₃ |
| 4-CH₃ | A042 | H | H | H | H |
| 4-CH₃ | A042 | H | CH₃ | H | H |
| 4-CH₃ | A042 | H | CH₂Ph | H | H |
| 4-CH₃ | A042 | H | C(O)Ph | H | H |
| 4-CH₃ | A042 | H | C(O)OEt | H | H |
| 4-CH₃ | A042 | H | H | H | CH₃ |
| 4-CH₃ | A042 | H | H | CH₃ | CH₃ |
| 4-t-Bu | A042 | H | H | H | H |
| 4-t-Bu | A042 | H | H | H | CH₃ |
| 4-n-hex | A042 | H | H | H | H |
| 4-n-hex | A042 | H | H | H | CH₃ |
| 4-OCH₃ | A042 | H | H | H | H |
| 4-OCH₃ | A042 | H | H | H | CH₃ |
| 4-Ph | A042 | H | H | H | H |
| 4-Ph | A042 | H | H | H | CH₃ |
| H | A042 | 5-Br | H | H | H |
| H | A043 | H | H | H | H |
| 4-Cl | A043 | H | H | H | H |
| 4-Cl | A043 | H | H | H | CH₃ |
| 4-CH₃ | A043 | H | H | H | H |
| 4-CH₃ | A043 | H | CH₃ | H | H |
| 4-CH₃ | A043 | H | CH₂Ph | H | H |
| 4-CH₃ | A043 | H | C(O)Ph | H | H |
| 4-CH₃ | A043 | H | C(O)OEt | H | H |
| 4-CH₃ | A043 | H | H | H | CH₃ |
| 4-CH₃ | A043 | H | H | CH₃ | CH₃ |
| 4-t-Bu | A043 | H | H | H | H |
| 4-t-Bu | A043 | H | H | H | CH₃ |
| 4-n-hex | A043 | H | H | H | H |
| 4-n-hex | A043 | H | H | H | CH₃ |
| 4-OCH₃ | A043 | H | H | H | H |
| 4-OCH₃ | A043 | H | H | H | CH₃ |
| 4-Ph | A043 | H | H | H | H |
| 4-Ph | A043 | H | H | H | CH₃ |
| H | A044 | H | H | H | H |
| 4-Cl | A044 | H | H | H | H |
| 4-Cl | A044 | H | H | H | CH₃ |
| 4-CH₃ | A044 | H | H | H | H |
| 4-CH₃ | A044 | H | CH₃ | H | H |
| 4-CH₃ | A044 | H | CH₂Ph | H | H |
| 4-CH₃ | A044 | H | C(O)Ph | H | H |
| 4-CH₃ | A044 | H | C(O)OEt | H | H |
| 4-CH₃ | A044 | H | H | H | CH₃ |
| 4-CH₃ | A044 | H | H | CH₃ | CH₃ |
| 4-t-Bu | A044 | H | H | H | H |
| 4-t-Bu | A044 | H | H | H | CH₃ |
| 4-n-hex | A044 | H | H | H | H |
| 4-n-hex | A044 | H | H | H | CH₃ |
| 4-OCH₃ | A044 | H | H | H | H |
| 4-OCH₃ | A044 | H | H | H | CH₃ |
| 4-Ph | A044 | H | H | H | H |
| 4-Ph | A044 | H | H | H | CH₃ |
| H | A051 | — | H | H | H |
| H | A052 | — | H | H | H |
| H | A053 | — | H | H | H |
| H | A054 | — | H | H | H |
| H | A055 | — | H | H | H |
| H | A056 | — | H | H | H |
| H | A057 | — | H | H | H |
| H | A058 | — | H | H | H |
| H | A059 | — | H | H | H |
| H | A060 | — | H | H | H |
| H | A061 | — | H | H | H |
| H | A062 | — | H | H | H |
| H | A063 | — | H | H | H |
| H | A064 | — | H | H | H |
| H | A065 | — | H | H | H |
| H | A066 | — | H | H | H |
| H | A067 | — | H | H | H |
| H | A068 | — | H | H | H |
| H | A101 | — | H | H | H |
| H | A102 | — | H | H | H |
| H | A103 | — | H | H | H |
| H | A104 | — | H | H | H |
| H | A105 | — | H | H | H |
| H | A106 | — | H | H | H |
| H | A107 | — | H | H | H |

TABLE 5

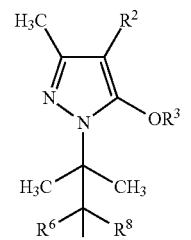

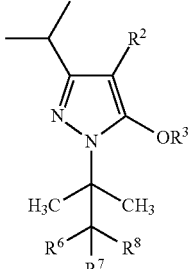

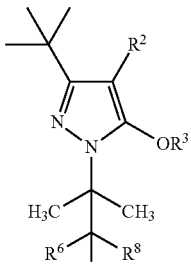

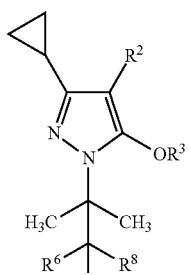

TABLE 5-continued
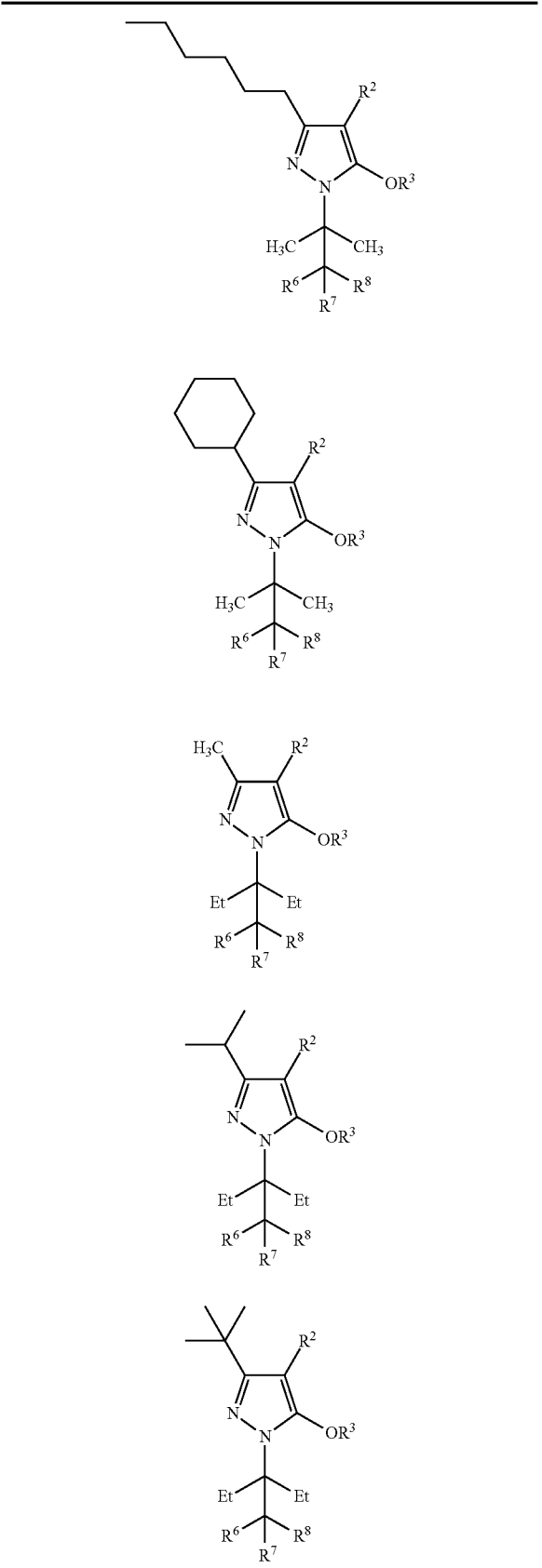
TABLE 5-continued
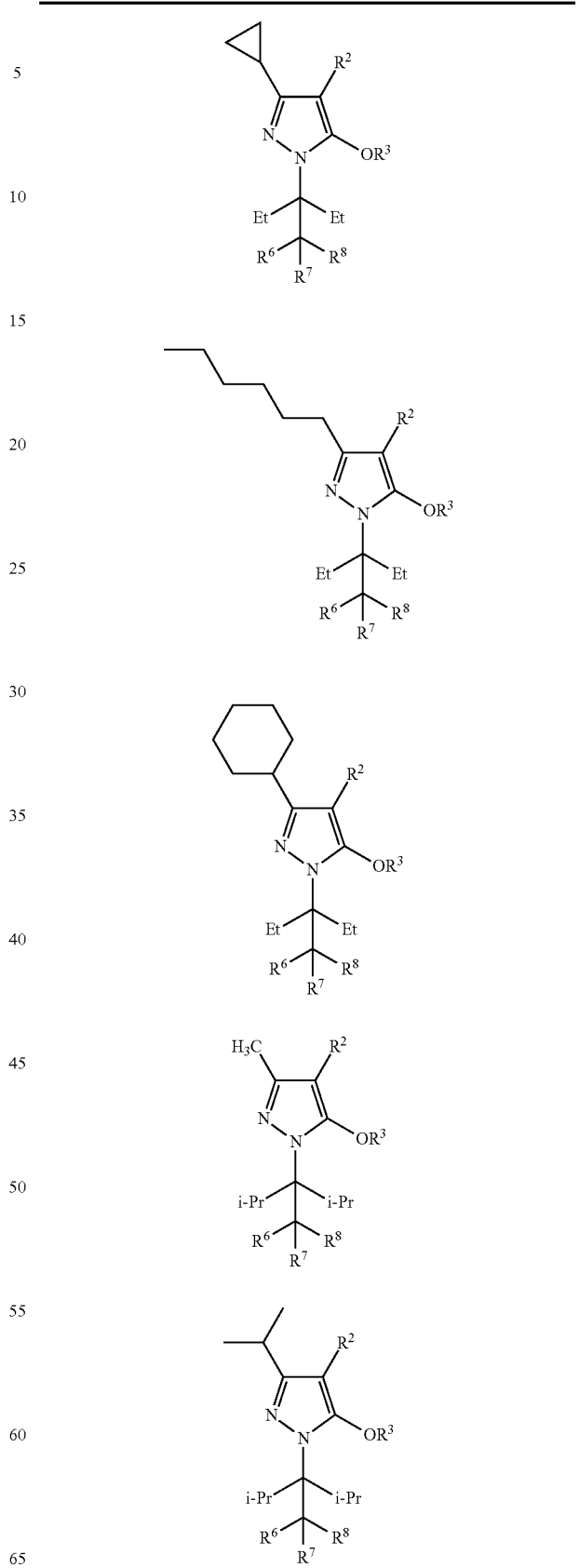

TABLE 5-continued
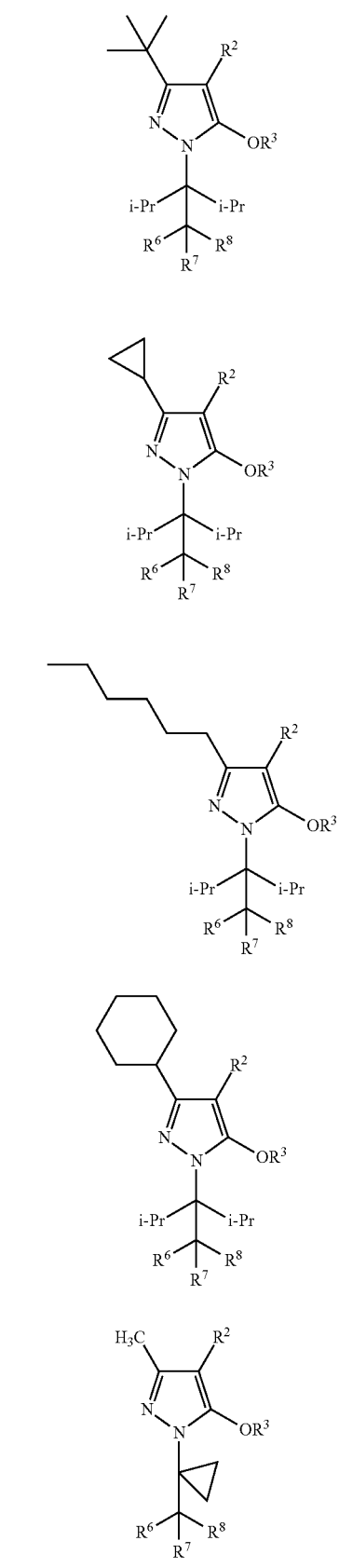
TABLE 5-continued
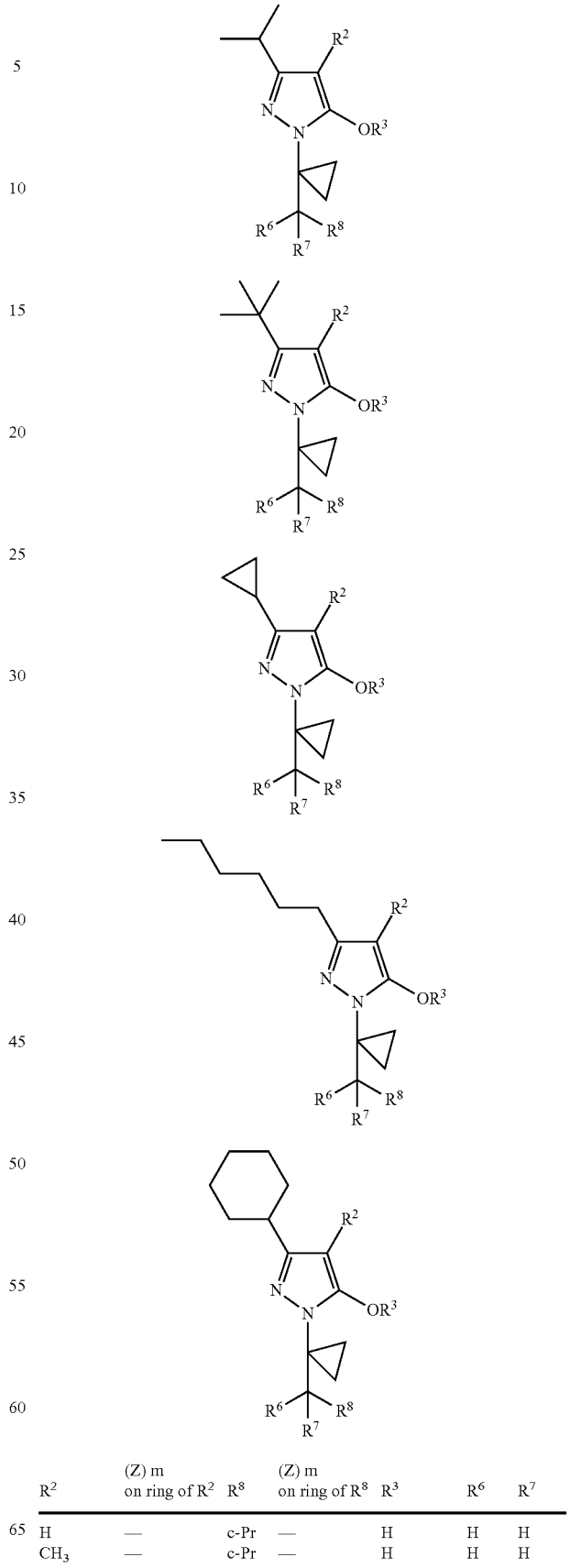
| R² | (Z) m on ring of R² | R⁸ | (Z) m on ring of R⁸ | R³ | R⁶ | R⁷ |
|---|---|---|---|---|---|---|
| H | — | c-Pr | — | H | H | H |
| CH₃ | — | c-Pr | — | H | H | H |

TABLE 5-continued

| | | | | | | |
|---|---|---|---|---|---|---|
| H | — | c-Bu | — | H | H | H |
| CH₃ | — | c-Bu | — | H | H | H |
| H | — | c-Pen | — | H | H | H |
| CH₃ | — | c-Pen | — | H | H | H |
| H | — | c-Hex | — | H | H | H |
| CH₃ | — | c-Hex | — | H | H | H |
| CH₃ | — | c-Hex | — | CH₃ | H | H |
| CH₃ | — | c-Hex | — | CH₂Ph | H | H |
| CH₃ | — | c-Hex | — | C(O)Ph | H | H |
| CH₃ | — | c-Hex | — | C(O)OEt | H | H |
| CH₃ | — | c-Hex | — | H | H | CH₃ |
| CH₃ | — | c-Hex | — | H | CH₃ | CH₃ |
| C(O)CH₃ | — | c-Pr | — | H | H | H |
| C(O)CH₃ | — | c-Hex | — | H | H | H |
| C(O)CH₃ | — | c-Hex | — | CH₃ | H | H |
| C(O)CH₃ | — | c-Hex | — | CH₂Ph | H | H |
| C(O)CH₃ | — | c-Hex | — | C(O)Ph | H | H |
| C(O)CH₃ | — | c-Hex | — | C(O)OEt | H | H |
| C(O)CH₃ | — | c-Hex | — | H | H | CH₃ |
| C(O)CH₃ | — | c-Hex | — | H | CH₃ | CH₃ |
| C(O)Ph | — | c-Pr | — | H | H | H |
| C(O)Ph | — | c-Hex | — | H | H | H |
| C(O)Ph | — | c-Hex | — | CH₃ | H | H |
| C(O)Ph | — | c-Hex | — | CH₂Ph | H | H |
| C(O)Ph | — | c-Hex | — | C(O)Ph | H | H |
| C(O)Ph | — | c-Hex | — | C(O)OEt | H | H |
| C(O)Ph | — | c-Hex | — | H | H | CH₃ |
| C(O)Ph | — | c-Hex | — | H | CH₃ | CH₃ |
| A005 | H | A005 | H | H | H | H |
| A005 | H | A006 | H | H | H | H |
| A005 | H | A014 | H | H | H | H |
| A005 | H | A016 | 2,4-(CH₃)₂ | H | H | H |
| A005 | H | A037 | H | H | H | H |
| A005 | H | A038 | H | H | H | H |
| A005 | H | A041 | H | H | H | H |
| A005 | H | A042 | H | H | H | H |
| A005 | H | A043 | H | H | H | H |
| A005 | H | A044 | H | H | H | H |
| A006 | H | A005 | H | H | H | H |
| A006 | H | A006 | H | H | H | H |
| A006 | H | A006 | H | CH₃ | H | H |
| A006 | H | A006 | H | CH₂Ph | H | H |
| A006 | H | A006 | H | C(O)Ph | H | H |
| A006 | H | A006 | H | H | H | CH₃ |
| A006 | H | A006 | H | H | CH₃ | CH₃ |
| A006 | H | A014 | H | H | H | H |
| A006 | H | A016 | 2,4-(CH₃)₂ | CH | H | H |
| A006 | H | A037 | H | H | H | H |
| A006 | H | A037 | H | CH₃ | H | H |
| A006 | H | A037 | H | CH₂Ph | H | H |
| A006 | H | A037 | H | C(O)Ph | H | H |
| A006 | H | A037 | H | H | H | CH₃ |
| A006 | H | A037 | H | H | CH₃ | CH₃ |
| A006 | H | A038 | H | H | H | H |
| A006 | H | A038 | H | CH₃ | H | H |
| A006 | H | A038 | H | CH₂Ph | H | H |
| A006 | H | A038 | H | C(O)Ph | H | H |
| A006 | H | A038 | H | H | H | CH₃ |
| A006 | H | A038 | H | H | CH₃ | CH₃ |
| A006 | H | A041 | H | H | H | H |
| A006 | H | A041 | H | CH₃ | H | H |
| A006 | H | A041 | H | CH₂Ph | H | H |
| A006 | H | A041 | H | C(O)Ph | H | H |
| A006 | H | A041 | H | H | H | CH₃ |
| A006 | H | A041 | H | H | CH₃ | CH₃ |
| A006 | H | A042 | H | H | H | H |
| A006 | H | A042 | H | CH₃ | H | H |
| A006 | H | A042 | H | CH₂Ph | H | H |
| A006 | H | A042 | H | C(O)Ph | H | H |
| A006 | H | A042 | H | H | H | CH₃ |
| A006 | H | A042 | H | H | CH₃ | CH₃ |
| A006 | H | A043 | H | H | H | H |
| A006 | H | A044 | H | H | H | H |
| A014 | H | A005 | H | H | H | H |
| A014 | H | A006 | H | H | H | H |
| A014 | H | A014 | H | H | H | H |
| A014 | H | A016 | 2,4-(CH₃)₂ | H | H | H |
| A014 | H | A037 | H | H | H | H |
| A014 | H | A038 | H | H | H | H |
| A014 | H | A041 | H | H | H | H |
| A014 | H | A042 | H | H | H | H |
| A014 | H | A043 | H | H | H | H |
| A014 | H | A044 | H | H | H | H |
| A016 | 2,4-(CH₃)₂ | A005 | H | H | H | H |
| A016 | 2,4-(CH₃)₂ | A006 | H | H | H | H |
| A016 | 2,4-(CH₃)₂ | A014 | H | H | H | H |
| A016 | 2,4-(CH₃)₂ | A016 | 2,4-(CH₃)₂ | H | H | H |
| A016 | 2,4-(CH₃)₂ | A037 | H | H | H | H |
| A016 | 2,4-(CH₃)₂ | A038 | H | H | H | H |
| A016 | 2,4-(CH₃)₂ | A041 | H | H | H | H |
| A016 | 2,4-(CH₃)₂ | A042 | H | H | H | H |
| A016 | 2,4-(CH₃)₂ | A043 | H | H | H | H |
| A016 | 2,4-(CH₃)₂ | A044 | H | H | H | H |
| A036 | H | A005 | H | H | H | H |
| A036 | H | A006 | H | H | H | H |
| A036 | H | A014 | H | H | H | H |
| A036 | H | A016 | 2,4-(CH₃)₂ | H | H | H |
| A036 | H | A037 | H | H | H | H |
| A036 | H | A038 | H | H | H | H |
| A036 | H | A041 | H | H | H | H |
| A036 | H | A042 | H | H | H | H |
| A036 | H | A043 | H | H | H | H |
| A036 | H | A044 | H | H | H | H |
| A037 | H | A005 | H | H | H | H |
| A037 | H | A006 | H | H | H | H |
| A037 | H | A006 | H | CH₃ | H | H |
| A037 | H | A006 | H | CH₂Ph | H | H |
| A037 | H | A006 | H | C(O)Ph | H | H |
| A037 | H | A006 | H | H | H | CH₃ |
| A037 | H | A006 | H | H | CH₃ | CH₃ |
| A037 | H | A014 | H | H | H | H |
| A037 | H | A016 | 2,4-(CH₃)₂ | H | H | H |
| A037 | H | A037 | H | H | H | H |
| A037 | H | A037 | H | CH₃ | H | H |
| A037 | H | A037 | H | CH₂Ph | H | H |
| A037 | H | A037 | H | C(O)Ph | H | H |
| A037 | H | A037 | H | H | H | CH₃ |
| A037 | H | A037 | H | H | CH₃ | CH₃ |
| A037 | H | A038 | H | H | H | H |
| A037 | H | A038 | H | CH₃ | H | H |
| A037 | H | A038 | H | CH₂Ph | H | H |
| A037 | H | A038 | H | C(O)Ph | H | H |
| A037 | H | A038 | H | H | H | CH₃ |
| A037 | H | A038 | H | H | CH₃ | CH₃ |
| A037 | H | A041 | H | H | H | H |
| A037 | H | A041 | H | CH₃ | H | H |
| A037 | H | A041 | H | CH₂Ph | H | H |
| A037 | H | A041 | H | C(O)Ph | H | H |
| A037 | H | A041 | H | H | H | CH₃ |
| A037 | H | A041 | H | H | CH₃ | CH₃ |
| A037 | H | A042 | H | H | H | H |
| A037 | H | A042 | H | CH₃ | H | H |
| A037 | H | A042 | H | CH₂Ph | H | H |
| A037 | H | A042 | H | C(O)Ph | H | H |
| A037 | H | A042 | H | H | H | CH₃ |
| A037 | H | A042 | H | H | CH₃ | CH₃ |
| A037 | H | A043 | H | H | H | H |
| A037 | H | A044 | H | H | H | H |
| A038 | H | A005 | H | H | H | H |
| A038 | H | A006 | H | H | H | H |
| A038 | H | A006 | H | CH₃ | H | H |
| A038 | H | A006 | H | CH₂Ph | H | H |
| A038 | H | A006 | H | C(O)Ph | H | H |
| A038 | H | A006 | H | H | H | CH₃ |
| A038 | H | A006 | H | H | CH₃ | CH₃ |
| A038 | H | A014 | H | H | H | H |
| A038 | H | A016 | 2,4-(CH₃)₂ | H | H | H |
| A038 | H | A037 | H | H | H | H |
| A038 | H | A037 | H | CH₃ | H | H |
| A038 | H | A037 | H | CH₂Ph | H | H |
| A038 | H | A037 | H | C(O)Ph | H | H |
| A038 | H | A037 | H | H | H | CH₃ |
| A038 | H | A037 | H | H | CH₃ | CH₃ |
| A038 | H | A038 | H | H | H | H |
| A038 | H | A038 | H | CH₃ | H | H |
| A038 | H | A038 | H | CH₂Ph | H | H |
| A038 | H | A038 | H | C(O)Ph | H | H |
| A038 | H | A038 | H | H | H | CH₃ |
| A038 | H | A038 | H | H | CH₃ | CH₃ |
| A038 | H | A041 | H | H | H | H |

TABLE 5-continued

| | | | | | | |
|---|---|---|---|---|---|---|
| A038 | H | A041 | H | CH$_3$ | H | H |
| A038 | H | A041 | H | CH$_2$Ph | H | H |
| A038 | H | A041 | H | C(O)Ph | H | H |
| A038 | H | A041 | H | H | H | CH$_3$ |
| A038 | H | A041 | H | H | CH$_3$ | CH$_3$ |
| A038 | H | A042 | H | H | H | H |
| A038 | H | A042 | H | CH$_3$ | H | H |
| A038 | H | A042 | H | CH$_2$Ph | H | H |
| A038 | H | A042 | H | C(O)Ph | H | H |
| A038 | H | A042 | H | H | H | CH$_3$ |
| A038 | H | A042 | H | H | CH$_3$ | CH$_3$ |
| A038 | H | A043 | H | H | H | H |
| A038 | H | A044 | H | H | H | H |
| A041 | H | A005 | H | H | H | H |
| A041 | H | A006 | H | H | H | H |
| A041 | H | A006 | H | CH$_3$ | H | H |
| A041 | H | A006 | H | CH$_2$Ph | H | H |
| A041 | H | A006 | H | C(O)Ph | H | H |
| A041 | H | A006 | H | H | H | CH$_3$ |
| A041 | H | A006 | H | H | CH$_3$ | CH$_3$ |
| A041 | H | A014 | H | H | H | H |
| A041 | H | A016 | 2,4-(CH$_3$)$_2$ | H | H | H |
| A041 | H | A037 | H | H | H | H |
| A041 | H | A037 | H | CH$_3$ | H | H |
| A041 | H | A037 | H | CH$_2$Ph | H | H |
| A041 | H | A037 | H | C(O)Ph | H | H |
| A041 | H | A037 | H | H | H | CH$_3$ |
| A041 | H | A037 | H | H | CH$_3$ | CH$_3$ |
| A041 | H | A038 | H | H | H | H |
| A041 | H | A038 | H | CH$_3$ | H | H |
| A041 | H | A038 | H | CH$_2$Ph | H | H |
| A041 | H | A038 | H | C(O)Ph | H | H |
| A041 | H | A038 | H | H | H | CH$_3$ |
| A041 | H | A038 | H | H | CH$_3$ | CH$_3$ |
| A041 | H | A041 | H | H | H | H |
| A041 | H | A041 | H | CH$_3$ | H | H |
| A041 | H | A041 | H | CH$_2$Ph | H | H |
| A041 | H | A041 | H | C(O)Ph | H | H |
| A041 | H | A041 | H | H | H | CH$_3$ |
| A041 | H | A041 | H | H | CH$_3$ | CH$_3$ |
| A041 | H | A042 | H | H | H | H |
| A041 | H | A042 | H | CH$_3$ | H | H |
| A041 | H | A042 | H | CH$_2$Ph | H | H |
| A041 | H | A042 | H | C(O)Ph | H | H |
| A041 | H | A042 | H | H | H | CH$_3$ |
| A041 | H | A042 | H | H | CH$_3$ | CH$_3$ |
| A041 | H | A043 | H | H | H | H |
| A041 | H | A044 | H | H | H | H |
| A042 | H | A005 | H | H | H | H |
| A042 | H | A006 | H | H | H | H |
| A042 | H | A006 | H | CH$_3$ | H | H |
| A042 | H | A006 | H | CH$_2$Ph | H | H |
| A042 | H | A006 | H | C(O)Ph | H | H |
| A042 | H | A006 | H | H | H | CH$_3$ |
| A042 | H | A006 | H | H | CH$_3$ | CH$_3$ |
| A042 | H | A014 | H | H | H | H |
| A042 | H | A016 | 2,4-(CH$_3$)$_2$ | H | H | H |
| A042 | H | A037 | H | H | H | H |
| A042 | H | A037 | H | CH$_3$ | H | H |
| A042 | H | A037 | H | CH$_2$Ph | H | H |
| A042 | H | A037 | H | C(O)Ph | H | H |
| A042 | H | A037 | H | H | H | CH$_3$ |
| A042 | H | A037 | H | H | CH$_3$ | CH$_3$ |
| A042 | H | A038 | H | H | H | H |
| A042 | H | A038 | H | CH$_3$ | H | H |
| A042 | H | A038 | H | CH$_2$Ph | H | H |
| A042 | H | A038 | H | C(O)Ph | H | H |
| A042 | H | A038 | H | H | H | CH$_3$ |
| A042 | H | A038 | H | H | CH$_3$ | CH$_3$ |
| A042 | H | A041 | H | H | H | H |
| A042 | H | A041 | H | CH$_3$ | H | H |
| A042 | H | A041 | H | CH$_2$Ph | H | H |
| A042 | H | A041 | H | C(O)Ph | H | H |
| A042 | H | A041 | H | H | H | CH$_3$ |
| A042 | H | A041 | H | H | CH$_3$ | CH$_3$ |
| A042 | H | A042 | H | H | H | H |
| A042 | H | A042 | H | CH$_3$ | H | H |
| A042 | H | A042 | H | CH$_2$Ph | H | H |
| A042 | H | A042 | H | C(O)Ph | H | H |
| A042 | H | A042 | H | H | H | CH$_3$ |
| A042 | H | A042 | H | H | CH$_3$ | CH$_3$ |
| A042 | H | A043 | H | H | H | H |
| A042 | H | A044 | H | H | H | H |

The expression — indicates unsubstituted.

TABLE 6

The locants for the substituents $R^{11}$, $R^{21}$ and $R^{81}$ in the Table correspond to the positions indicated in the following structural formulae.

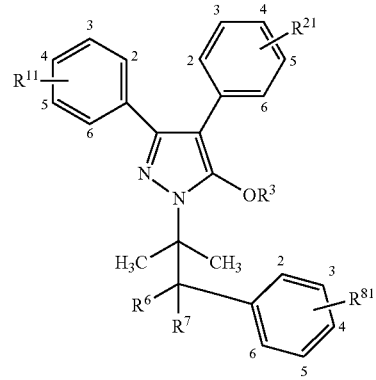

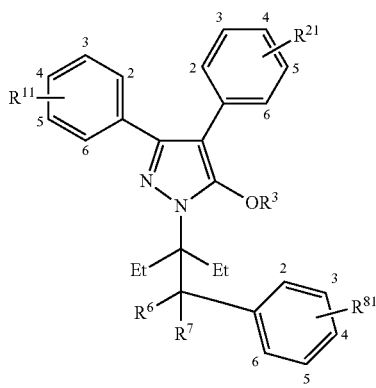

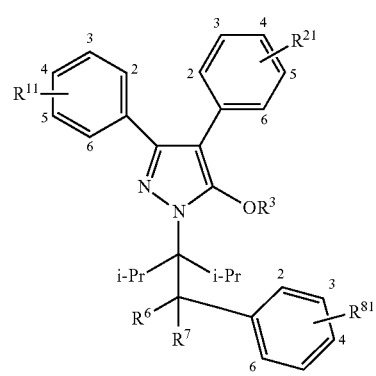

TABLE 6-continued

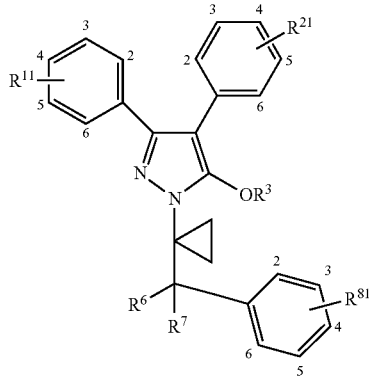

| R11 | R21 | R81 | R3 | R6 | R7 |
|---|---|---|---|---|---|
| H | H | H | H | H | H |
| H | 4-CH$_3$ | H | H | H | H |
| H | 4-t-Bu | H | H | H | H |
| H | 4-t-Bu | 4-CH$_3$ | H | H | H |
| H | 4-t-Bu | H | CH$_3$ | H | H |
| H | 4-t-Bu | 4-CH$_3$ | CH$_3$ | H | H |
| H | 4-n-Hex | H | H | H | H |
| H | 4-n-Hex | 4-Cl | H | H | H |
| H | 4-n-Hex | 4-Br | H | H | H |
| H | 4-n-Hex | 4-CH$_3$ | H | H | H |
| H | 4-n-Hex | H | CH$_3$ | H | H |
| H | 4-n-Hex | 4-CH$_3$ | CH$_3$ | H | H |
| H | 4-n-Hex | H | CH$_2$Ph | H | H |
| H | 4-n-Hex | H | C(O)OEt | H | H |
| H | 4-n-Hex | H | C(O)Ph | H | H |
| H | 4-n-Hex | H | H | H | CH$_3$ |
| H | 4-n-Hex | H | H | CH$_3$ | CH$_3$ |
| H | 4-Ph | H | H | H | H |
| H | 4-Ph | 4-CH$_3$ | H | H | H |
| H | 4-Ph | H | CH$_3$ | H | H |
| H | 4-Ph | 4-CH$_3$ | CH$_3$ | H | H |
| 4-F | H | H | H | H | H |
| 2-Cl | H | H | H | H | H |
| 3-Cl | H | H | H | H | H |
| 4-Cl | H | H | H | H | H |
| 4-Cl | 4-t-Bu | H | H | H | H |
| 4-Cl | 4-t-Bu | 4-CH$_3$ | H | H | H |
| 4-Cl | 4-n-Hex | H | H | H | H |
| 4-Cl | 4-n-Hex | 4-Cl | H | H | H |
| 4-Cl | 4-n-Hex | 4-Br | H | H | H |
| 4-Cl | 4-n-Hex | 4-CH$_3$ | H | H | H |
| 4-Cl | 4-Ph | H | H | H | H |
| 4-Cl | 4-Ph | 4-CH$_3$ | H | H | H |
| 4-Br | H | H | H | H | H |
| 3,4-Cl$_2$ | H | H | H | H | H |
| 4-NO$_3$ | H | H | H | H | H |
| 4-CN | H | H | H | H | H |
| 2-CH$_3$ | H | H | H | H | H |
| 3-CH$_3$ | H | H | H | H | H |
| 4-CH$_3$ | H | H | H | H | H |
| 4-CH$_3$ | 4-t-Bu | H | H | H | H |
| 4-CH$_3$ | 4-t-Bu | 4-CH$_3$ | H | H | H |
| 4-CH$_3$ | 4-n-Hex | H | H | H | H |
| 4-CH$_3$ | 4-n-Hex | 4-Cl | H | H | H |
| 4-CH$_3$ | 4-n-Hex | 4-Br | H | H | H |
| 4-CH$_3$ | 4-n-Hex | 4-CH$_3$ | H | H | H |
| 4-CH$_3$ | 4-Ph | H | H | H | H |
| 4-CH$_3$ | 4-Ph | 4-CH$_3$ | H | H | H |
| 3,4-(CH$_3$)$_2$ | H | H | H | H | H |
| 4-OCH$_3$ | H | H | H | H | H |
| 4-OCH$_3$ | 4-t-Bu | H | H | H | H |
| 4-OCH$_3$ | 4-n-Hex | H | H | H | H |
| 4-OCH$_3$ | 4-n-Hex | 4-Cl | H | H | H |
| 4-OCH$_3$ | 4-n-Hex | 4-Br | H | H | H |
| 4-OCH$_3$ | 4-n-Hex | 4-CH$_3$ | H | H | H |
| 4-OCH$_3$ | 4-Ph | H | H | H | H |
| 3,4-(OCH$_3$) | H | H | H | H | H |
| 4-Ph | H | H | H | H | H |

TABLE 7

The locants for the substituent R$^{81}$ in the Table correspond to the positions indicated in the following structural formulae.

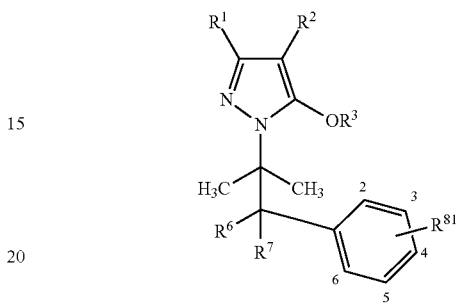

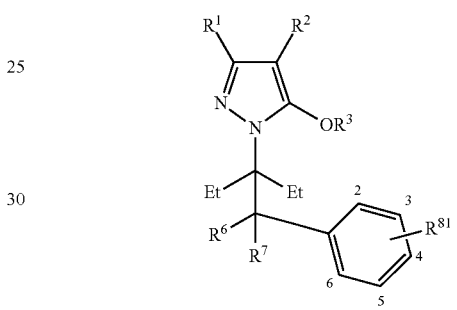

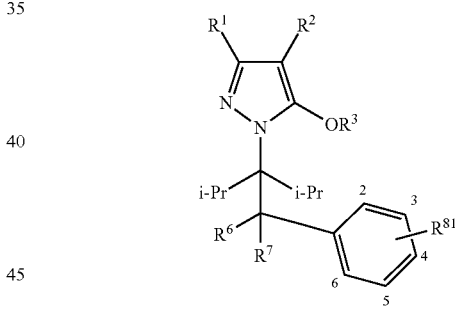

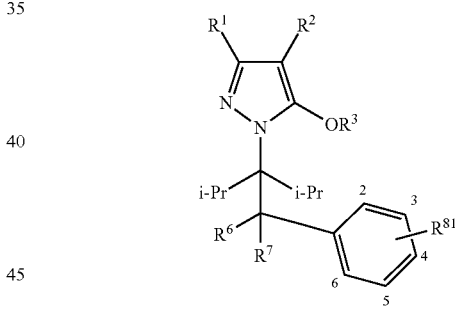

| R$^1$ | R$^2$ | (Z)m | R$^{81}$ | R$^3$ | R$^6$ | R$^7$ |
|---|---|---|---|---|---|---|
| H | H | — | H | H | H | H |
| Et | H | — | H | H | H | H |
| n-Pr | H | — | H | H | H | H |
| n-Bu | H | — | H | H | H | H |
| c-Bu | H | — | H | H | H | H |
| n-Pen | H | — | H | H | H | H |
| c-Pen | H | — | H | H | H | H |

TABLE 7-continued

| | | | | | | |
|---|---|---|---|---|---|---|
| CF₃ | H | — | H | H | H | H |
| CF₃ | H | — | 4-CH₃ | H | H | H |
| CF₃ | H | — | 4-CH₃ | CH₃ | H | H |
| CF₃ | A005 | — | H | H | H | H |
| CF₃ | A006 | — | H | H | H | H |
| CF₃ | A014 | — | H | H | H | H |
| CF₃ | A016 | 2,4-(CH₃)₂ | H | H | H | H |
| CF₃ | A036 | H | H | H | H | H |
| CF₃ | A037 | — | H | H | H | H |
| CF₃ | A038 | — | H | H | H | H |
| CF₃ | A041 | — | H | H | H | H |
| CF₃ | A042 | — | H | H | H | H |
| CN | H | — | H | H | H | H |
| C(O)OEt | H | — | H | H | H | H |
| Ph | H | — | H | H | H | H |
| (4-CH₃)Ph | H | — | H | H | H | H |
| (4-i-Pr)Ph | H | — | H | H | H | H |
| (4-OCH₃)Ph | H | — | H | H | H | H |
| (4-OCH₃)Ph | H | — | 4-CH₃ | H | H | H |

TABLE 8

The locants for the substituents $R^{21}$ and $R^{81}$ in the Table correspond to the positions indicated in the following structural formulae, and the expression — indicates unsubstituted.

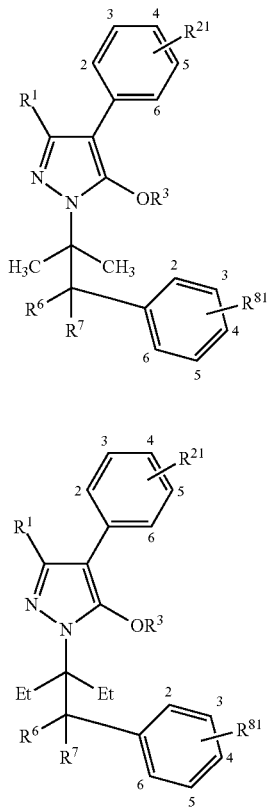

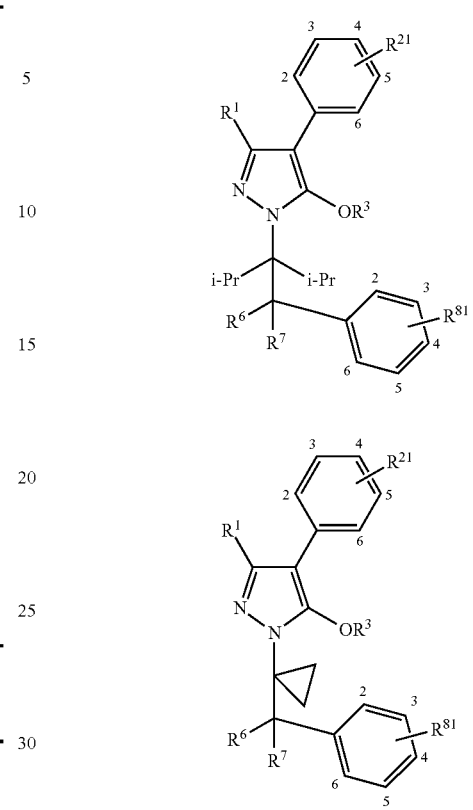

| R¹ | (Z)m | R²¹ | R⁸¹ | R³ | R⁶ | R⁷ |
|---|---|---|---|---|---|---|
| H | — | H | H | H | H | H |
| Et | — | H | H | H | H | H |
| n-Pr | — | H | H | H | H | H |
| n-Bu | — | H | H | H | H | H |
| CF₃ | — | H | H | H | H | H |
| CF₃ | — | 4-CH₃ | H | H | H | H |
| CF₃ | — | 4-CH₃ | 4-CH₃ | H | H | H |
| CF₃ | — | 4-CH₃ | 4-CH₃ | CH₃ | H | H |
| CF₃ | — | 4-CH₃ | H | H | H | CH₃ |
| CF₃ | — | 4-t-Bu | H | H | H | H |
| CF₃ | — | 4-n-Hex | H | H | H | H |
| CF₃ | — | 4-n-Hex | 4-CH₃ | H | H | H |
| CF₃ | — | 4-n-Hex | 4-CH₃ | CH₃ | H | H |
| CF₃ | — | 4-n-Hex | 4-CH₃ | H | H | CH₃ |
| CF₃ | — | 4-n-Hex | 4-CH₃ | H | CH₃ | CH₃ |
| CF₃ | — | 4-Ph | H | H | H | H |
| CO₂Et | — | H | H | H | H | H |
| A001 | H | H | H | H | H | H |
| A002 | H | H | H | H | H | H |
| A003 | H | H | H | H | H | H |
| A005 | H | H | H | H | H | H |
| A005 | 2,5-(CH₃)₂ | H | H | H | H | H |
| A005 | 2,5-Cl₂ | H | H | H | H | H |
| A005 | 2-Br | H | H | H | H | H |
| A006 | H | H | H | H | H | H |
| A006 | 3-CH₃ | H | H | H | H | H |
| A006 | 5-CH₃ | H | H | H | H | H |
| A006 | 3-Cl | H | H | H | H | H |
| A006 | 5-Et | H | H | H | H | H |
| A006 | 5-Cl | H | H | H | H | H |
| A006 | 5-Br | H | H | H | H | H |
| A006 | 3-Br | H | H | H | H | H |
| A006 | 4-Br | H | H | H | H | H |
| A006 | 5-NO₂ | H | H | H | H | H |
| A007 | H | H | H | H | H | H |
| A007 | 5-CH₃ | H | H | H | H | H |
| A007 | 3-CH₃ | H | H | H | H | H |
| A007 | 5-Br | H | H | H | H | H |
| A007 | 5-NO₂ | H | H | H | H | H |
| A007 | 5-Ph | H | H | H | H | H |

TABLE 8-continued

| | | | | | | |
|---|---|---|---|---|---|---|
| A008 | 5-CH$_3$ | H | H | H | H | H |
| A009 | 5-CH$_3$ | H | H | H | H | H |
| A010 | 3,5-(CH$_3$)$_2$ | H | H | H | H | H |
| A010 | 3,5-Cl$_2$ | H | H | H | H | H |
| A011 | 3,5-(CH$_3$)$_2$ | H | H | H | H | H |
| A011 | 3,5-Cl$_2$ | H | H | H | H | H |
| A012 | 3-CH$_3$ | H | H | H | H | H |
| A012 | 3-CH$_3$ | H | H | H | H | H |
| A012 | 3-Cl | H | H | H | H | H |
| A013 | 3-CH$_3$ | H | H | H | H | H |
| A013 | 3-CH$_3$ | H | H | H | H | H |
| A013 | 3-Cl | H | H | H | H | H |
| A014 | H | H | H | H | H | H |
| A015 | H | H | H | H | H | H |
| A016 | 2,4-(CH$_3$)$_2$ | H | H | H | H | H |
| A017 | 2,4-(CH$_3$)$_2$ | H | H | H | H | H |
| A034 | H | H | H | H | H | H |
| A034 | 3,6-Cl$_2$ | H | H | H | H | H |
| A035 | H | H | H | H | H | H |
| A036 | H | H | H | H | H | H |
| A037 | H | H | H | H | H | H |
| A037 | 6-OCH$_3$ | H | H | H | H | H |
| A037 | 6-Br | H | H | H | H | H |
| A038 | H | H | H | H | H | H |
| A038 | 2-OCH$_3$ | H | H | H | H | H |
| A038 | 4-OCH$_3$ | H | H | H | H | H |
| A038 | 4-F | H | H | H | H | H |

TABLE 9

The locants for the substituent R$^{21}$ and R$^{81}$ in the Table correspond to the positions indicated in the following structural formulae.

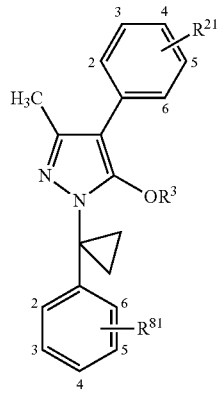

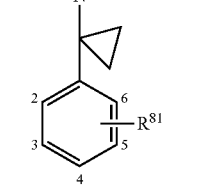

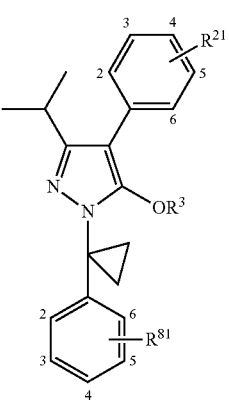

TABLE 9-continued

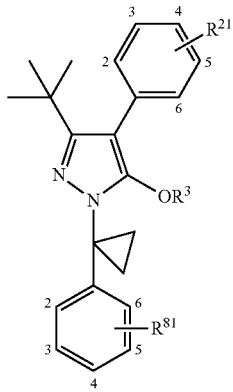

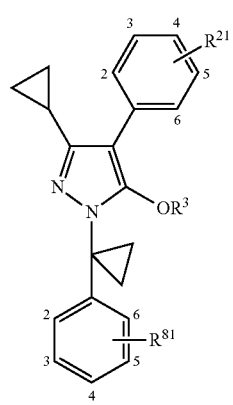

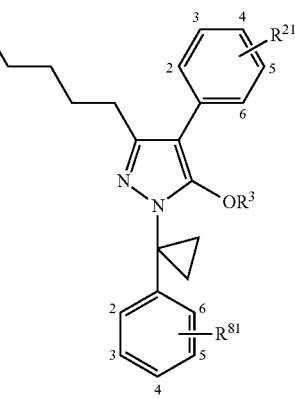

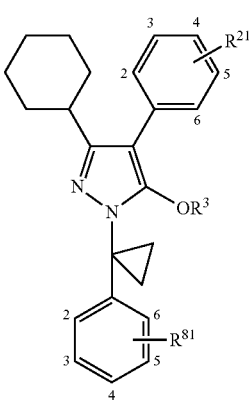

TABLE 9-continued

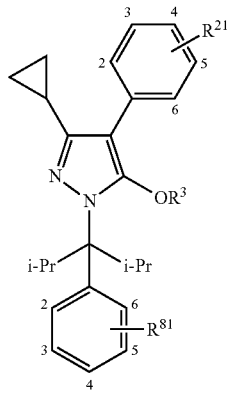

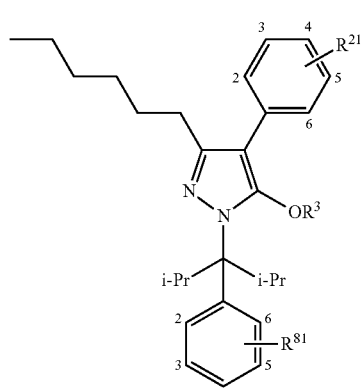

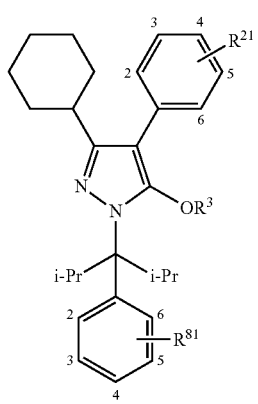

| R²¹ | R⁸¹ | R³ |
|---|---|---|
| H | H | H |
| H | 4-F | H |
| H | 2-Cl | H |
| H | 3-Cl | H |
| H | 4-Cl | H |
| H | 4-Cl | CH₃ |
| H | 4-Cl | CH₂Ph |
| H | 4-Cl | C(O)Ph |
| H | 4-Cl | C(O)OEt |
| H | 4-Br | H |
| H | 4-I | H |
| H | 2,4-Cl₂ | H |
| H | 3,4-Cl₂ | H |
| H | 4-NO₂ | H |
| H | 4-CN | H |
| H | 2-CH₃ | H |
| H | 3-CH₃ | H |
| H | 4-CH₃ | H |
| H | 4-CH₃ | CH₃ |
| H | 4-CH₃ | CH₂Ph |
| H | 4-CH₃ | C(O)Ph |
| H | 4-CH₃ | C(O)OEt |
| H | 4-Et | H |
| H | 4-n-Pr | H |
| H | 4-c-Pr | H |
| H | 4-i-Pr | H |
| H | 4-n-Bu | H |
| H | 4-c-Bu | H |
| H | 4-i-Bu | H |
| H | 4-t-Bu | H |
| H | 4-t-Bu | CH₃ |
| H | 4-t-Bu | CH₂Ph |
| H | 4-t-Bu | C(O)Ph |
| H | 4-t-Bu | C(O)OEt |
| H | 4-n-Pen | H |
| H | 4-c-Pen | H |
| H | 4-n-Hex | H |
| H | 4-n-Hex | CH₃ |
| H | 4-n-Hex | CH₂Ph |
| H | 4-n-Hex | C(O)Ph |
| H | 4-n-Hex | C(O)OEt |
| H | 4-c-Hex | H |
| H | 4-n-C₇H₁₅ | H |
| H | 4-n-C₈H₁₇ | H |
| H | 4-n-C₉H₁₉ | H |
| H | 4-n-C₁₀H₂₁ | H |
| H | 2,4-(CH₃) | H |
| H | 3,4-(CH₃)₂ | H |
| H | 4-CF₃ | H |
| H | 4-OH | H |
| H | 2-OCH₃ | H |
| H | 3-OCH₃ | H |
| H | 4-OCH₃ | H |
| H | 4-O-n-Hex | H |
| H | 4-O-c-Hex | H |
| H | 2,4-(OCH₃)₂ | H |
| H | 3,4-(OCH₃)₂ | H |
| H | 4-OCH₂OCH₃ | H |
| H | 4-OC₂H₄OEt | H |
| H | 4-OCF₃ | H |
| H | 4-OPh | H |
| H | 4-OCH₂Ph | H |
| H | 4-C(CH₃)=NCH₃ | H |
| H | 4-C(CH₃)=NPh | H |
| H | 4-C(Ph)=NCH₃ | H |
| H | 4-C(Ph)=NPh | H |
| H | 4-C(CH₃)=NOCH₃ | H |
| H | 4-C(CH₃)=NOPh | H |
| H | 4-C(Ph)=NOCH₃ | H |
| H | 4-C(Ph)=NOPh | H |
| H | 4-C(O)CH₃ | H |
| H | 4-C(O)CF₃ | H |
| H | 4-C(O)Ph | H |
| H | 4-C(O)OCH₃ | H |
| H | 2-C(O)OEt | H |
| H | 3-C(O)OEt | H |
| H | 4-C(O)OEt | H |
| H | 4-C(O)OPh | H |
| H | 4-C(O)OCH₂Ph | H |
| H | 4-C(O)OCH(CH₃)Ph | H |
| H | 4-C(O)OC₂H₄Ph | H |
| H | 4-SCH₃ | H |
| H | 4-S(O)CH₃ | H |
| H | 4-S(O)₂CH₃ | H |
| H | 4-SPh | H |
| H | 4-S(O)Ph | H |
| H | 4-S(O)₂Ph | H |
| H | 4-OS(O)₂CH₃ | H |
| H | 4-OS(O)₂Ph | H |
| H | 4-N(CH₃)₂ | H |
| H | 4-N(CH₂Ph)₂ | H |
| H | 4-N(CH₃)(CH₂Ph) | H |
| H | 4-NHCH₃ | H |
| H | 4-NH(CH₂Ph) | H |
| H | 4-C(O)N(CH₃)₂ | H |
| H | 4-C(O)N(CH₂Ph)₂ | H |
| H | 4-C(O)N(CH₃)(CH₃Ph) | H |
| H | 4-C(O)NHCH₃ | H |

TABLE 9-continued

| | | |
|---|---|---|
| H | 4-C(O)NH(CH₂Ph) | H |
| H | 4-C(O)NH(CH(CH₃)Ph) | H |
| H | 4-C(O)NH(C₂H₄Ph) | H |
| H | 4-C(S)NH₂ | H |
| H | 4-S(O)₂N(CH₃)₂ | H |
| H | 4-S(O)₂N(CH₂Ph)₂ | H |
| H | 4-S(O)₂N(CH₃)(CH₂Ph) | H |
| H | 4-S(O)₂NHCH₃ | H |
| H | 4-S(O)₂NHPh | H |
| H | 4-S(O)₂NH(CH₂Ph) | H |
| H | 4-S(O)₂NH{CH(CH₃)Ph} | H |
| H | 4-S(O)₂NH(C₂H₄Ph) | H |
| H | 4-Ph | H |
| H | 4-Ph | CH₃ |
| H | 4-Ph | CH₂Ph |
| H | 4-Ph | C(O)Ph |
| H | 4-Ph | C(O)OEt |
| 4-F | H | H |
| 4-F | 4-Cl | H |
| 4-F | 4-Br | H |
| 4-F | 4-CH₃ | H |
| 4-F | 4-t-Bu | H |
| 4-F | 4-n-Hex | H |
| 4-F | 4-Ph | H |
| 2-Cl | H | H |
| 2-Cl | 4-Cl | H |
| 2-Cl | 4-Br | H |
| 2-Cl | 4-CH₃ | H |
| 2-Cl | 4-t-Bu | H |
| 2-Cl | 4-n-Hex | H |
| 2-Cl | 4-Ph | H |
| 3-Cl | H | H |
| 3-Cl | 4-Cl | H |
| 3-Cl | 4-Br | H |
| 3-Cl | 4-CH₃ | H |
| 3-Cl | 4-t-Bu | H |
| 3-Cl | 4-n-Hex | H |
| 3-Cl | 4-Ph | H |
| 4-Cl | H | H |
| 4-Cl | 4-Cl | H |
| 4-Cl | 4-Br | H |
| 4-Cl | 4-CH₃ | H |
| 4-Cl | 4-t-Bu | H |
| 4-Cl | 4-t-Bu | CH₃ |
| 4-Cl | 4-n-Hex | H |
| 4-Cl | 4-n-Hex | CH₃ |
| 4-Cl | 4-Ph | H |
| 4-Cl | 4-Ph | CH₃ |
| 4-Br | H | H |
| 4-Br | 4-Cl | H |
| 4-Br | 4-Br | H |
| 4-Br | 4-CH₃ | H |
| 4-Br | 4-t-Bu | H |
| 4-Br | 4-n-Hex | H |
| 4-Br | 4-Ph | H |
| 3,4-Cl₂ | H | H |
| 3,4-Cl₂ | 4-Cl | H |
| 3,4-Cl₂ | 4-Br | H |
| 3,4-Cl₂ | 4-CH₃ | H |
| 3,4-Cl₂ | 4-t-Bu | H |
| 3,4-Cl₂ | 4-n-Hex | H |
| 3,4-Cl₂ | 4-Ph | H |
| 4-NO₂ | H | H |
| 4-NO₂ | 4-Cl | H |
| 4-NO₂ | 4-Br | H |
| 4-NO₂ | 4-CH₃ | H |
| 4-NO₂ | 4-t-Bu | H |
| 4-NO₂ | 4-n-Hex | H |
| 4-NO₂ | 4-Ph | H |
| 4-CN | H | H |
| 4-CN | 4-Cl | H |
| 4-CN | 4-Br | H |
| 4-CN | 4-CH₃ | H |
| 4-CN | 4-t-Bu | H |
| 4-CN | 4-n-Hex | H |
| 4-CN | 4-Ph | H |
| 2-CH₃ | H | H |
| 2-CH₃ | 4-Cl | H |
| 2-CH₃ | 4-Br | H |
| 2-CH₃ | 4-CH₃ | H |
| 2-CH₃ | 4-t-Bu | H |
| 2-CH₃ | 4-n-Hex | H |
| 2-CH₃ | 4-Ph | H |
| 3-CH₃ | H | H |
| 3-CH₃ | 4-Cl | H |
| 3-CH₃ | 4-Br | H |
| 3-CH₃ | 4-CH₃ | H |
| 3-CH₃ | 4-t-Bu | H |
| 3-CH₃ | 4-n-Hex | H |
| 3-CH₃ | 4-Ph | H |
| 4-CH₃ | H | H |
| 4-CH₃ | 4-Cl | H |
| 4-CH₃ | 4-Br | H |
| 4-CH₃ | 4-CH₃ | H |
| 4-CH₃ | 4-t-Bu | H |
| 4-CH₃ | 4-t-Bu | CH₃ |
| 4-CH₃ | 4-n-Hex | H |
| 4-CH₃ | 4-n-Hex | CH₃ |
| 4-CH₃ | 4-Ph | H |
| 4-CH₃ | 4-Ph | CH₃ |
| 4-c-Pr | H | H |
| 4-c-Pr | 4-Cl | H |
| 4-c-Pr | 4-Br | H |
| 4-c-Pr | 4-CH₃ | H |
| 4-c-Pr | 4-t-Bu | H |
| 4-c-Pr | 4-n-Hex | H |
| 4-c-Pr | 4-Ph | H |
| 4-i-Pr | H | H |
| 4-i-Pr | 4-Cl | H |
| 4-i-Pr | 4-Br | H |
| 4-i-Pr | 4-CH₃ | H |
| 4-i-Pr | 4-t-Bu | H |
| 4-i-Pr | 4-n-Hex | H |
| 4-i-Pr | 4-Ph | H |
| 4-t-Bu | H | H |
| 4-t-Bu | 4-Cl | H |
| 4-t-Bu | 4-Br | H |
| 4-t-Bu | 4-CH₃ | H |
| 4-t-Bu | 4-t-Bu | H |
| 4-t-Bu | 4-t-Bu | CH₃ |
| 4-t-Bu | 4-n-Hex | H |
| 4-t-Bu | 4-n-Hex | CH₃ |
| 4-t-Bu | 4-Ph | H |
| 4-t-Bu | 4-Ph | CH₃ |
| 4-n-Hex | H | H |
| 4-n-Hex | H | CH₃ |
| 4-n-Hex | H | CH₂Ph |
| 4-n-Hex | H | C(O)Ph |
| 4-n-Hex | H | C(O)OEt |
| 4-n-Hex | 4-F | H |
| 4-n-Hex | 2-Cl | H |
| 4-n-Hex | 3-Cl | H |
| 4-n-Hex | 4-Cl | H |
| 4-n-Hex | 4-Cl | CH₃ |
| 4-n-Hex | 4-Cl | CH₂Ph |
| 4-n-Hex | 4-Cl | C(O)Ph |
| 4-n-Hex | 4-Cl | C(O)OEt |
| 4-n-Hex | 4-Br | H |
| 4-n-Hex | 4-I | H |
| 4-n-Hex | 2,4-Cl₂ | H |
| 4-n-Hex | 3,4-Cl₂ | H |
| 4-n-Hex | 4-NO₂ | H |
| 4-n-Hex | 4-CN | H |
| 4-n-Hex | 2-CH₃ | H |
| 4-n-Hex | 3-CH₃ | H |
| 4-n-Hex | 4-CH₃ | H |
| 4-n-Hex | 4-CH₃ | CH₃ |
| 4-n-Hex | 4-CH₃ | CH₂Ph |
| 4-n-Hex | 4-CH₃ | C(O)Ph |
| 4-n-Hex | 4-CH₃ | C(O)OEt |
| 4-n-Hex | 4-Et | H |
| 4-n-Hex | 4-n-Pr | H |
| 4-n-Hex | 4-c-Pr | H |
| 4-n-Hex | 4-i-Pr | H |
| 4-n-Hex | 4-n-Bu | H |
| 4-n-Hex | 4-c-Bu | H |
| 4-n-Hex | 4-i-Bu | H |
| 4-n-Hex | 4-t-Bu | H |
| 4-n-Hex | 4-t-Bu | CH₃ |
| 4-n-Hex | 4-t-Bu | CH₂Ph |

TABLE 9-continued

| | | |
|---|---|---|
| 4-n-Hex | 4-t-Bu | C(O)Ph |
| 4-n-Hex | 4-t-Bu | C(O)OEt |
| 4-n-Hex | 4-n-Pen | H |
| 4-n-Hex | 4-c-Pen | H |
| 4-n-Hex | 4-n-Hex | H |
| 4-n-Hex | 4-n-Hex | $CH_3$ |
| 4-n-Hex | 4-n-Hex | $CH_2Ph$ |
| 4-n-Hex | 4-n-Hex | C(O)Ph |
| 4-n-Hex | 4-n-Hex | C(O)OEt |
| 4-n-Hex | 4-c-Hex | H |
| 4-n-Hex | 4-n-$C_7H_{15}$ | H |
| 4-n-Hex | 4-n-$C_8H_{17}$ | H |
| 4-n-Hex | 4-n-$C_9H_{19}$ | H |
| 4-n-Hex | 4-n-$C_{10}H_{21}$ | H |
| 4-n-Hex | 2,4-$(CH_3)$ | H |
| 4-n-Hex | 3,4-$(CH_3)_2$ | H |
| 4-n-Hex | 4-$CF_3$ | H |
| 4-n-Hex | 4-OH | H |
| 4-n-Hex | 2-$OCH_3$ | H |
| 4-n-Hex | 3-$OCH_3$ | H |
| 4-n-Hex | 4-$OCH_3$ | H |
| 4-n-Hex | 4-O-n-Hex | H |
| 4-n-Hex | 4-O-c-Hex | H |
| 4-n-Hex | 2,4-$(OCH_3)_2$ | H |
| 4-n-Hex | 3,4-$(OCH_3)_2$ | H |
| 4-n-Hex | 4-$OCH_2OCH_3$ | H |
| 4-n-Hex | 4-$OC_2H_4OEt$ | H |
| 4-n-Hex | 4-$OCF_3$ | H |
| 4-n-Hex | 4-OPh | H |
| 4-n-Hex | 4-$OCH_2Ph$ | H |
| 4-n-Hex | 4-C($CH_3$)=$NCH_3$ | H |
| 4-n-Hex | 4-C($CH_3$)=NPh | H |
| 4-n-Hex | 4-C(Ph)=$NCH_3$ | H |
| 4-n-Hex | 4-C(Ph)=NPh | H |
| 4-n-Hex | 4-C($CH_3$)=$NOCH_3$ | H |
| 4-n-Hex | 4-C($CH_3$)=NOPh | H |
| 4-n-Hex | 4-C(Ph)=$NOCH_3$ | H |
| 4-n-Hex | 4-C(Ph)=NOPh | H |
| 4-n-Hex | 4-C(O)$CH_3$ | H |
| 4-n-Hex | 4-C(O)$CF_3$ | H |
| 4-n-Hex | 4-C(O)Ph | H |
| 4-n-Hex | 4-C(O)$OCH_3$ | H |
| 4-n-Hex | 2-C(O)OEt | H |
| 4-n-Hex | 3-C(O)OEt | H |
| 4-n-Hex | 4-C(O)OEt | H |
| 4-n-Hex | 4-C(O)OPh | H |
| 4-n-Hex | 4-C(O)$OCH_2Ph$ | H |
| 4-n-Hex | 4-C(O)OCH($CH_3$)Ph | H |
| 4-n-Hex | 4-C(O)$OC_2H_4Ph$ | H |
| 4-n-Hex | 4-$SCH_3$ | H |
| 4-n-Hex | 4-S(O)$CH_3$ | H |
| 4-n-Hex | 4-S(O)$_2CH_3$ | H |
| 4-n-Hex | 4-SPh | H |
| 4-n-Hex | 4-S(O)Ph | H |
| 4-n-Hex | 4-S(O)$_2$Ph | H |
| 4-n-Hex | 4-OS(O)$_2CH_3$ | H |
| 4-n-Hex | 4-OS(O)$_2$Ph | H |
| 4-n-Hex | 4-N$(CH_3)_2$ | H |
| 4-n-Hex | 4-N$(CH_2Ph)_2$ | H |
| 4-n-Hex | 4-N$(CH_3)$($CH_2Ph$) | H |
| 4-n-Hex | 4-$NHCH_3$ | H |
| 4-n-Hex | 4-NH($CH_2Ph$) | H |
| 4-n-Hex | 4-C(O)N$(CH_3)_2$ | H |
| 4-n-Hex | 4-C(O)N$(CH_2Ph)_2$ | H |
| 4-n-Hex | 4-C(O)N$(CH_3)$($CH_2Ph$) | H |
| 4-n-Hex | 4-C(O)$NHCH_3$ | H |
| 4-n-Hex | 4-C(O)NH($CH_2Ph$) | H |
| 4-n-Hex | 4-C(O)NH{CH($CH_3$)Ph} | H |
| 4-n-Hex | 4-C(O)NH($C_2H_4Ph$) | H |
| 4-n-Hex | 4-C(S)$NH_2$ | H |
| 4-n-Hex | 4-S(O)$_2$N$(CH_3)_2$ | H |
| 4-n-Hex | 4-S(O)$_2$N$(CH_2Ph)_2$ | H |
| 4-n-Hex | 4-S(O)$_2$N$(CH_3)$($CH_2Ph$) | H |
| 4-n-Hex | 4-S(O)$_2NHCH_3$ | H |
| 4-n-Hex | 4-S(O)$_2$NHPh | H |
| 4-n-Hex | 4-S(O)$_2$NH($CH_2Ph$) | H |
| 4-n-Hex | 4-S(O)$_2$NH{CH($CH_3$)Ph} | H |
| 4-n-Hex | 4-S(O)$_2$NH($C_2H_4Ph$) | H |
| 4-n-Hex | 4-Ph | H |
| 4-n-Hex | 4-Ph | $CH_3$ |
| 4-n-Hex | 4-Ph | $CH_2Ph$ |
| 4-n-Hex | 4-Ph | C(O)Ph |
| 4-n-Hex | 4-Ph | C(O)OEt |
| 4-c-Hex | H | H |
| 4-c-Hex | 4-Cl | H |
| 4-c-Hex | 4-Br | H |
| 4-c-Hex | 4-$CH_3$ | H |
| 4-c-Hex | 4-t-Bu | H |
| 4-c-Hex | 4-t-Bu | $CH_3$ |
| 4-c-Hex | 4-n-Hex | H |
| 4-c-Hex | 4-n-Hex | $CH_3$ |
| 4-c-Hex | 4-Ph | H |
| 4-c-Hex | 4-Ph | $CH_3$ |
| 3,4-$(CH_3)_2$ | H | H |
| 3,4-$(CH_3)_2$ | 4-Cl | H |
| 3,4-$(CH_3)_2$ | 4-Br | H |
| 3,4-$(CH_3)_2$ | 4-$CH_3$ | H |
| 3,4-$(CH_3)_2$ | 4-t-Bu | H |
| 3,4-$(CH_3)_2$ | 4-n-Hex | H |
| 3,4-$(CH_3)_2$ | 4-Ph | H |
| 2,4-(t-Bu)$_2$ | H | H |
| 2,4-(t-Bu)$_2$ | 4-Cl | H |
| 2,4-(t-Bu)$_2$ | 4-Br | H |
| 2,4-(t-Bu)$_2$ | 4-$CH_3$ | H |
| 2,4-(t-Bu)$_2$ | 4-t-Bu | H |
| 2,4-(t-Bu)$_2$ | 4-n-Hex | H |
| 2,4-(t-Bu)$_2$ | 4-Ph | H |
| 4-$CF_3$ | H | H |
| 4-$CF_3$ | 4-Cl | H |
| 4-$CF_3$ | 4-Br | H |
| 4-$CF_3$ | 4-$CH_3$ | H |
| 4-$CF_3$ | 4-t-Bu | H |
| 4-$CF_3$ | 4-n-Hex | H |
| 4-$CF_3$ | 4-Ph | H |
| 4-OH | H | H |
| 4-OH | 4-Cl | H |
| 4-OH | 4-Br | H |
| 4-OH | 4-$CH_3$ | H |
| 4-OH | 4-t-Bu | H |
| 4-OH | 4-n-Hex | H |
| 4-OH | 4-Ph | H |
| 4-$OCH_3$ | H | H |
| 4-$OCH_3$ | 4-Cl | H |
| 4-$OCH_3$ | 4-Br | H |
| 4-$OCH_3$ | 4-$CH_3$ | H |
| 4-$OCH_3$ | 4-t-Bu | H |
| 4-$OCH_3$ | 4-n-Hex | H |
| 4-$OCH_3$ | 4-Ph | H |
| 4-O-i-Pr | H | H |
| 4-O-i-Pr | 4-Cl | H |
| 4-O-i-Pr | 4-Br | H |
| 4-O-i-Pr | 4-$CH_3$ | H |
| 4-O-i-Pr | 4-t-Bu | H |
| 4-O-i-Pr | 4-n-Hex | H |
| 4-O-i-Pr | 4-Ph | H |
| 4-O-n-Hex | H | H |
| 4-O-n-Hex | 4-Cl | H |
| 4-O-n-Hex | 4-Br | H |
| 4-O-n-Hex | 4-$CH_3$ | H |
| 4-O-n-Hex | 4-t-Bu | H |
| 4-O-n-Hex | 4-n-Hex | H |
| 4-O-n-Hex | 4-Ph | H |
| 3,4-$(OCH_3)_2$ | H | H |
| 3,4-$(OCH_3)_2$ | 4-Cl | H |
| 3,4-$(OCH_3)_2$ | 4-Br | H |
| 3,4-$(OCH_3)_2$ | 4-$CH_3$ | H |
| 3,4-$(OCH_3)_2$ | 4-t-Bu | H |
| 3,4-$(OCH_3)_2$ | 4-n-Hex | H |
| 3,4-$(OCH_3)_2$ | 4-Ph | H |
| 4-$OC_2H_4OEt$ | H | H |
| 4-$OC_2H_4OEt$ | 4-Cl | H |
| 4-$OC_2H_4OEt$ | 4-Br | H |
| 4-$OC_2H_4OEt$ | 4-$CH_3$ | H |
| 4-$OC_2H_4OEt$ | 4-t-Bu | H |
| 4-$OC_2H_4OEt$ | 4-n-Hex | H |
| 4-$OC_2H_4OEt$ | 4-Ph | H |
| 4-OPh | H | H |
| 4-OPh | 4-Cl | H |
| 4-OPh | 4-Br | H |
| 4-OPh | 4-$CH_3$ | H |

TABLE 9-continued

| | | |
|---|---|---|
| 4-OPh | 4-t-Bu | H |
| 4-OPh | 4-n-Hex | H |
| 4-OPh | 4-Ph | H |
| 4-OCH$_2$Ph | H | H |
| 4-OCH$_2$Ph | 4-Cl | H |
| 4-OCH$_2$Ph | 4-Br | H |
| 4-OCH$_2$Ph | 4-CH$_3$ | H |
| 4-OCH$_2$Ph | 4-t-Bu | H |
| 4-OCH$_2$Ph | 4-n-Hex | H |
| 4-OCH$_2$Ph | 4-Ph | H |
| 4-Ph | H | H |
| 4-Ph | 4-Cl | H |
| 4-Ph | 4-Br | H |
| 4-Ph | 4-CH$_3$ | H |
| 4-Ph | 4-t-Bu | H |
| 4-Ph | 4-t-Bu | CH$_3$ |
| 4-Ph | 4-n-Hex | H |
| 4-Ph | 4-n-Hex | CH$_3$ |
| 4-Ph | 4-Ph | H |
| 4-Ph | 4-Ph | CH$_3$ |

TABLE 10

The locants for the substituent R$^{81}$ in the Table correspond to the positions indicated in the following structural formulae, and the expression — indicates unsubstituted.

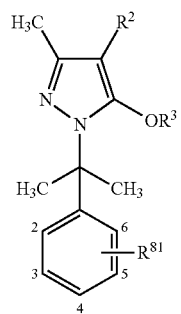

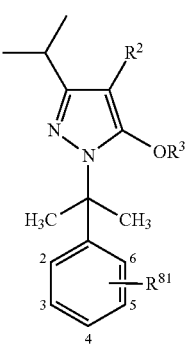

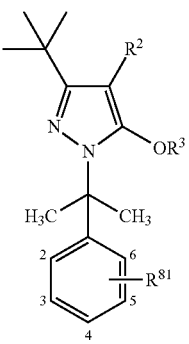

TABLE 10-continued

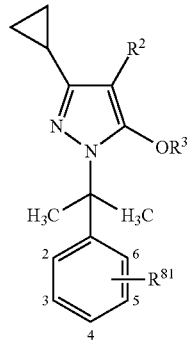

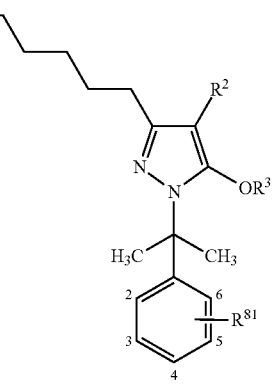

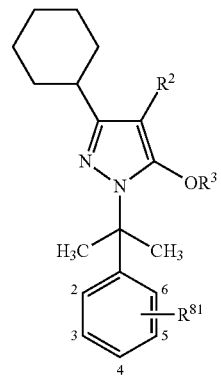

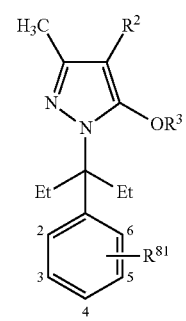

TABLE 10-continued
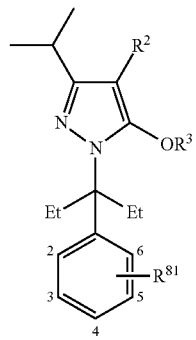
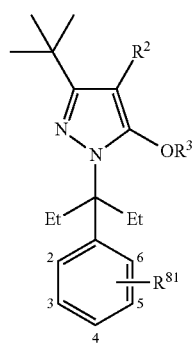
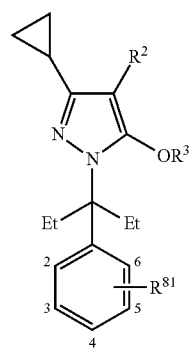
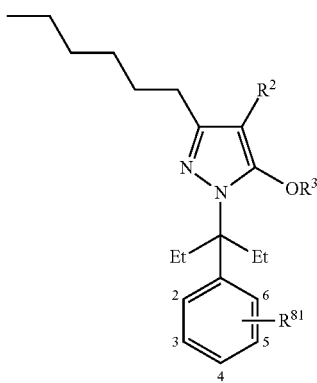
TABLE 10-continued
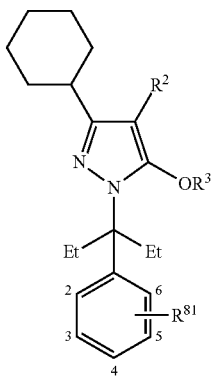
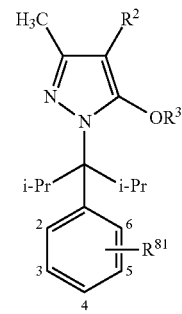
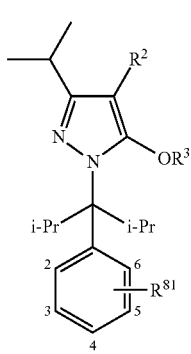
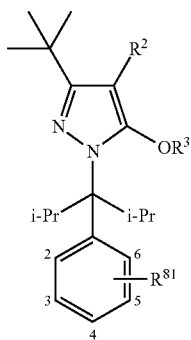

TABLE 10-continued
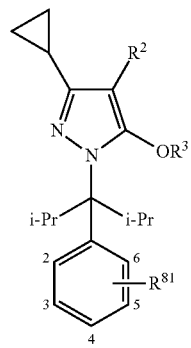
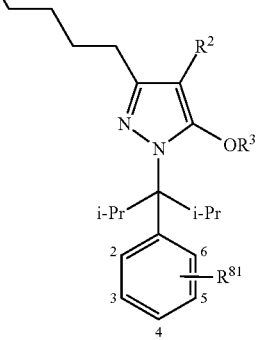
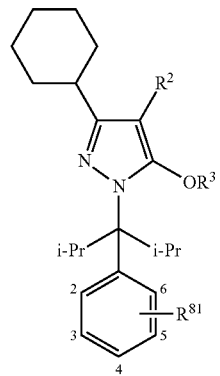
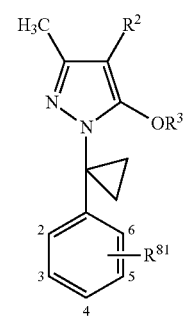
TABLE 10-continued
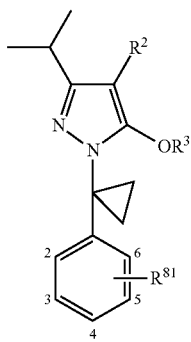
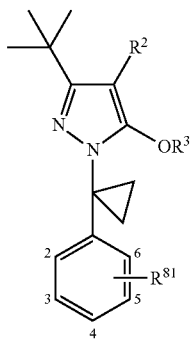
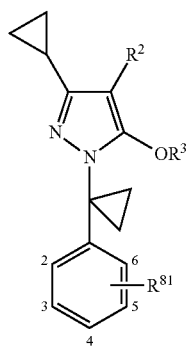
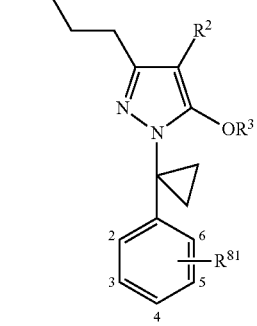

TABLE 10-continued

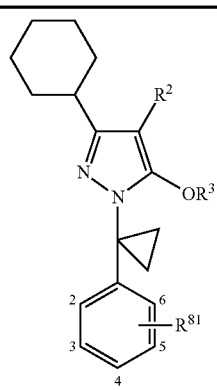

| $R^2$ | (Z)m | $R^{81}$ | $R^3$ |
|---|---|---|---|
| H | — | H | H |
| H | — | 4-CH₃ | H |
| F | — | H | H |
| CH₃ | — | H | H |
| Et | — | H | H |
| n-Pr | — | H | H |
| c-Pr | — | H | H |
| i-Pr | — | H | H |
| n-Bu | — | H | H |
| c-Bu | — | H | H |
| i-Bu | — | H | H |
| t-Bu | — | H | H |
| n-Pen | — | H | H |
| c-Pen | — | H | H |
| n-Hex | — | H | H |
| c-Hex | — | H | H |
| n-C₇H₁₅ | — | H | H |
| n-C₈H₁₇ | — | H | H |
| n-C₉H₁₉ | — | H | H |
| n-C₁₀H₂ | — | H | H |
| CF₃ | — | H | H |
| C(Ph)=NCH₃ | — | H | H |
| C(CH₃)=NPh | — | H | H |
| C(Ph)=NOCH₃ | — | H | H |
| C(O)CH₃ | — | H | H |
| C(O)Et | — | H | H |
| C(O)CF₃ | — | H | H |
| C(O)Ph | — | H | H |
| C(O)Ph | — | 4-Cl | H |
| C(O)Ph | — | 4-CH₃ | H |
| C(O)Ph | — | 4-CH₃ | CH₃ |
| C(O)Ph | — | 4-CH₃ | CH₂Ph |
| C(O)Ph | — | 4-CH₃ | C(O)Ph |
| C(O)Ph | — | 4-CH₃ | C(O)OEt |
| C(O)Ph | — | 4-t-Bu | H |
| C(O)Ph | — | 4-n-hex | H |
| C(O)Ph | — | 4-OCH₃ | H |
| C(O)Ph | — | 4-Ph | H |
| C(O)CH₂Ph | — | H | H |
| C(O)CH(CH₃)Ph | — | H | H |
| C(O)C₂H₄Ph | — | H | H |
| C(O)OCH₃ | — | H | H |
| C(O)OEt | — | H | H |
| C(O)OEt | — | 4-Cl | H |
| C(O)OEt | — | 4-CH₃ | H |
| C(O)OEt | — | 4-CH₃ | CH₃ |
| C(O)OEt | — | 4-CH₃ | CH₂Ph |
| C(O)OEt | — | 4-CH₃ | C(O)Ph |
| C(O)OEt | — | 4-CH₃ | C(O)OEt |
| C(O)OEt | — | 4-t-Bu | H |
| C(O)OEt | — | 4-n-hex | H |
| C(O)OEt | — | 4-OCH₃ | H |
| C(O)OEt | — | 4-Ph | H |
| C(O)OPh | — | H | H |
| C(O)OCH₂Ph | — | H | H |
| C(O)OCH(CH3)Ph | — | H | H |
| C(O)OC₂H₄Ph | — | H | H |
| C(O)N(CH₃)₂ | — | H | H |
| C(O)NHCH₃ | — | H | H |
| C(O)NH(CH₂Ph) | — | H | H |
| CH₂Ph | — | H | H |
| CH₂(4-Cl-Ph) | — | H | H |
| A001 | H | H | H |
| A001 | 3-n-Bu | H | H |
| A002 | H | H | H |
| A002 | 2-Cl | H | H |
| A003 | H | H | H |
| A004 | H | H | H |
| A005 | H | H | H |
| A005 | H | 4-Cl | H |
| A005 | H | 4-CH₃ | H |
| A005 | H | 4-CH₃ | CH₃ |
| A005 | H | 4-CH₃ | CH₂Ph |
| A005 | H | 4-CH₃ | C(O)Ph |
| A005 | H | 4-CH₃ | C(O)OEt |
| A005 | H | 4-t-Bu | H |
| A005 | H | 4-n-hex | H |
| A005 | H | 4-OCH₃ | H |
| A005 | H | 4-Ph | H |
| A005 | 2,5-(CH₃)₂ | H | H |
| A005 | 2,5-Cl₂ | H | H |
| A005 | 2-Br | H | H |
| A006 | H | H | H |
| A006 | H | 4-Cl | H |
| A006 | H | 4-CH₃ | H |
| A006 | H | 4-CH₃ | CH₃ |
| A006 | H | 4-CH₃ | CH₂Ph |
| A006 | H | 4-CH₃ | C(O)Ph |
| A006 | H | 4-CH₃ | C(O)OEt |
| A006 | H | 4-t-Bu | H |
| A006 | H | 4-n-hex | H |
| A006 | H | 4-OCH₃ | H |
| A006 | H | 4-Ph | H |
| A006 | 3-CH₃ | H | H |
| A006 | 5-CH₃ | H | H |
| A006 | 3-Cl | H | H |
| A006 | 5-Et | H | H |
| A006 | 5-Cl | H | H |
| A006 | 5-Br | H | H |
| A006 | 3-Br | H | H |
| A006 | 4-Br | H | H |
| A006 | 5-NO₂ | H | H |
| A007 | H | H | H |
| A007 | 5-CH₃ | H | H |
| A007 | 3-CH₃ | H | H |
| A007 | 5-Br | H | H |
| A007 | 5-NO₂ | H | H |
| A007 | 5-Ph | H | H |
| A008 | 5-CH₃ | H | H |
| A009 | 5-CH₃ | H | H |
| A010 | 3,5-(CH₃)₂ | H | H |
| A010 | 3,5-Cl₂ | H | H |
| A011 | 3,5-(CH₃)₂ | H | H |
| A011 | 3,5-Cl₂ | H | H |
| A012 | 3-CH₃ | H | H |
| A012 | 3-CH₃ | H | H |
| A012 | 3-Cl | H | H |
| A013 | 3-CH₃ | H | H |
| A013 | 3-CH₃ | H | H |
| A013 | 3-Cl | H | H |
| A014 | H | H | H |
| A014 | H | 4-Cl | H |
| A014 | H | 4-CH₃ | H |
| A014 | H | 4-CH₃ | CH₃ |
| A014 | H | 4-CH₃ | CH₂Ph |
| A014 | H | 4-CH₃ | C(O)Ph |
| A014 | H | 4-CH₃ | C(O)OEt |
| A014 | H | 4-t-Bu | H |
| A014 | H | 4-n-hex | H |
| A014 | H | 4-OCH₃ | H |
| A014 | H | 4-Ph | H |
| A015 | H | H | H |
| A016 | 2,4-(CH₃)₂ | H | H |
| A016 | 2,4-(CH₃)₂ | 4-Cl | H |
| A016 | 2,4-(CH₃)₂ | 4-CH₃ | H |
| A016 | 2,4-(CH₃)₂ | 4-CH₃ | CH₃ |
| A016 | 2,4-(CH₃)₂ | 4-CH₃ | CH₂Ph |
| A016 | 2,4-(CH₃)₂ | 4-CH₃ | C(O)Ph |
| A016 | 2,4-(CH₃)₂ | 4-CH₃ | C(O)OEt |

TABLE 10-continued

| | | | |
|---|---|---|---|
| A016 | 2,4-(CH$_3$)$_2$ | 4-t-Bu | H |
| A016 | 2,4-(CH$_3$)$_2$ | 4-n-hex | H |
| A016 | 2,4-(CH$_3$)$_2$ | 4-OCH$_3$ | H |
| A016 | 2,4-(CH$_3$)$_2$ | 4-Ph | H |
| A017 | 2,4-(CH$_3$)$_2$ | H | H |
| A018 | H | H | H |
| A018 | 3-CH$_3$ | H | H |
| A019 | 3-Ph, 5-CH$_3$ | H | H |
| A019 | 3,5-(CH$_3$)$_2$ | H | H |
| A020 | 5-CH$_3$ | H | H |
| A021 | 4-CH$_3$ | H | H |
| A022 | H | H | H |
| A023 | 2,4-(CH$_3$)$_2$ | H | H |
| A024 | 2-(4-pyridil) | H | H |
| A025 | H | H | H |
| A026 | H | H | H |
| A026 | 4-CH$_3$ | H | H |
| A027 | H | H | H |
| A027 | 4-CH$_3$ | H | H |
| A028 | H | H | H |
| A029 | H | H | H |
| A030 | H | H | H |
| A031 | H | H | H |
| A032 | H | H | H |
| A033 | H | H | H |
| A034 | H | H | H |
| A034 | 3,6-Cl$_2$ | H | H |
| A035 | H | H | H |
| A036 | H | H | H |
| A036 | H | 4-Cl | H |
| A036 | H | 4-CH$_3$ | H |
| A036 | H | 4-CH$_3$ | CH$_3$ |
| A036 | H | 4-CH$_3$ | CH$_2$Ph |
| A036 | H | 4-CH$_3$ | C(O)Ph |
| A036 | H | 4-CH$_3$ | C(O)OEt |
| A036 | H | 4-t-Bu | H |
| A036 | H | 4-n-hex | H |
| A036 | H | 4-OCH$_3$ | H |
| A036 | H | 4-Ph | H |
| A037 | H | H | H |
| A037 | H | 4-Cl | H |
| A037 | H | 4-CH$_3$ | H |
| A037 | H | 4-CH$_3$ | CH$_3$ |
| A037 | H | 4-CH$_3$ | CH$_2$Ph |
| A037 | H | 4-CH$_3$ | C(O)Ph |
| A037 | H | 4-CH$_3$ | C(O)OEt |
| A037 | H | 4-t-Bu | H |
| A037 | H | 4-n-hex | H |
| A037 | H | 4-OCH$_3$ | H |
| A037 | H | 4-Ph | H |
| A037 | 6-OCH$_3$ | H | H |
| A037 | 6-Br | H | H |
| A038 | H | H | H |
| A038 | H | 4-Cl | H |
| A038 | H | 4-CH$_3$ | H |
| A038 | H | 4-CH$_3$ | CH$_3$ |
| A038 | H | 4-CH$_3$ | CH$_2$Ph |
| A038 | H | 4-CH$_3$ | C(O)Ph |
| A038 | H | 4-CH$_3$ | C(O)OEt |
| A038 | H | 4-t-Bu | H |
| A038 | H | 4-n-hex | H |
| A038 | H | 4-OCH$_3$ | H |
| A038 | H | 4-Ph | H |
| A038 | 2-OCH$_3$ | H | H |
| A038 | 4-OCH$_3$ | H | H |
| A038 | 4-F | H | H |
| A039 | H | H | H |
| A039 | 3-CH$_3$ | H | H |
| A039 | 7-OCH$_3$ | H | H |
| A040 | H | H | H |
| A041 | H | H | H |
| A041 | H | 4-Cl | H |
| A041 | H | 4-CH$_3$ | H |
| A041 | H | 4-CH$_3$ | CH$_3$ |
| A041 | H | 4-CH$_3$ | CH$_2$Ph |
| A041 | H | 4-CH$_3$ | C(O)Ph |
| A041 | H | 4-CH$_3$ | C(O)OEt |
| A041 | H | 4-t-Bu | H |
| A041 | H | 4-n-hex | H |
| A041 | H | 4-OCH$_3$ | H |

TABLE 10-continued

| | | | |
|---|---|---|---|
| A041 | H | 4-Ph | H |
| A041 | 6-NO$_2$ | H | H |
| A041 | 6-Br | H | H |
| A042 | H | H | H |
| A042 | H | 4-Cl | H |
| A042 | H | 4-CH$_3$ | H |
| A042 | H | 4-CH$_3$ | CH$_3$ |
| A042 | H | 4-CH$_3$ | CH$_2$Ph |
| A042 | H | 4-CH$_3$ | C(O)Ph |
| A042 | H | 4-CH$_3$ | C(O)OEt |
| A042 | H | 4-t-Bu | H |
| A042 | H | 4-n-hex | H |
| A042 | H | 4-OCH$_3$ | H |
| A042 | H | 4-Ph | H |
| A042 | 5-Br | H | H |
| A043 | H | H | H |
| A044 | H | H | H |
| A051 | — | H | H |
| A052 | — | H | H |
| A053 | — | H | H |
| A054 | — | H | H |
| A055 | — | H | H |
| A056 | — | H | H |
| A057 | — | H | H |
| A058 | — | H | H |
| A059 | — | H | H |
| A060 | — | H | H |
| A061 | — | H | H |
| A062 | — | H | H |
| A063 | — | H | H |
| A064 | — | H | H |
| A065 | — | H | H |
| A066 | — | H | H |
| A067 | — | H | H |
| A068 | — | H | H |
| A101 | — | H | H |
| A102 | — | H | H |
| A103 | — | H | H |
| A104 | — | H | H |
| A105 | — | H | H |
| A106 | — | H | H |
| A107 | — | H | H |

TABLE 11

The locants for the substituent R$^{21}$ in the Table correspond to the positions indicated in the following structural formulae, and the expression — indicates unsubstituted.

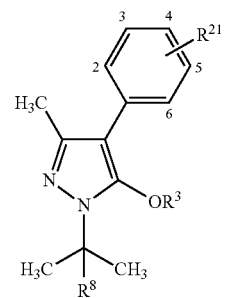

TABLE 11-continued
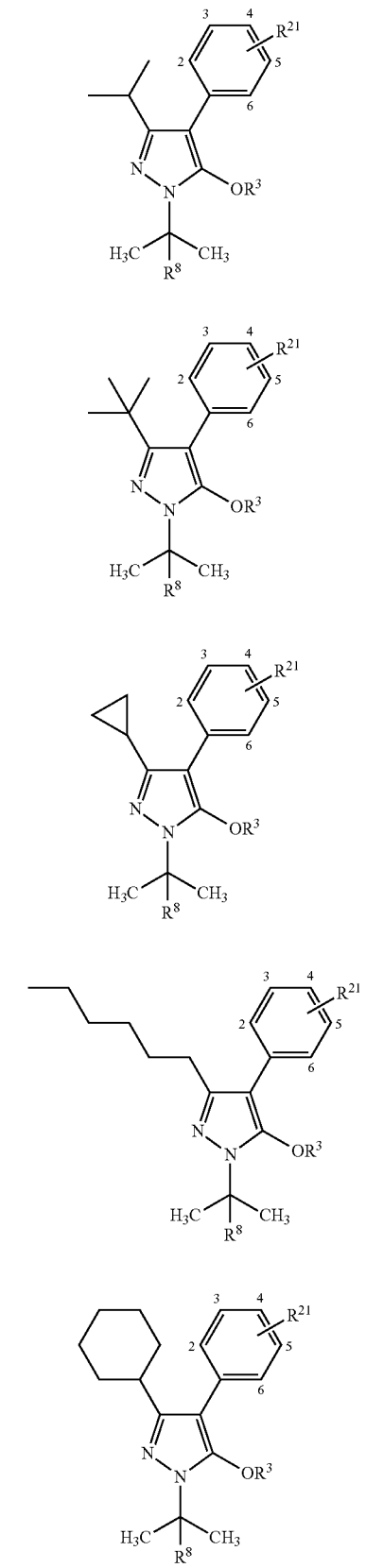
TABLE 11-continued
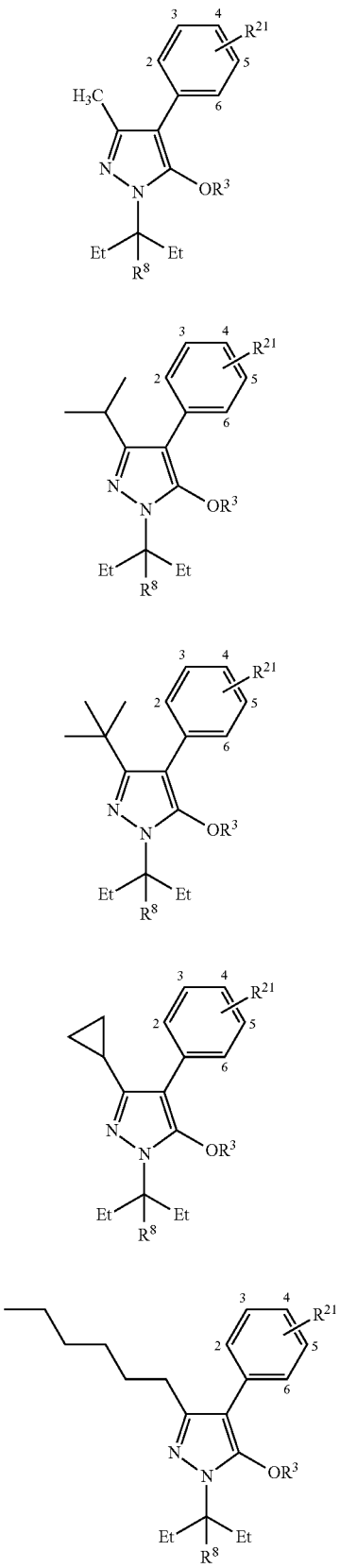

TABLE 11-continued
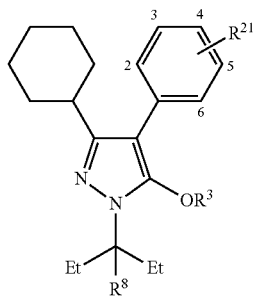
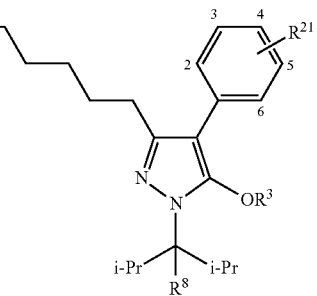
TABLE 11-continued
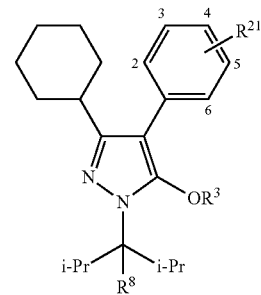
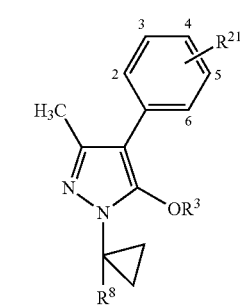
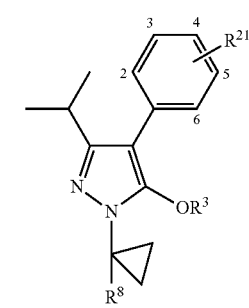
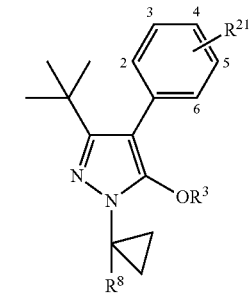

TABLE 11-continued

[Structure 1: Pyrazole with cyclopropyl at 3-position, phenyl (with R21) at 4-position, OR3 at 5-position, R8-substituted cyclopropyl on N1]

[Structure 2: Pyrazole with n-pentyl at 3-position, phenyl (with R21) at 4-position, OR3 at 5-position, R8-substituted cyclopropyl on N1]

[Structure 3: Pyrazole with cyclohexyl at 3-position, phenyl (with R21) at 4-position, OR3 at 5-position, R8-substituted cyclopropyl on N1]

| R21 | R8 | (Z)m | R3 |
|---|---|---|---|
| H | c-Pr | — | H |
| 4-Cl | c-Pr | — | H |
| 4-CH3 | c-Pr | — | H |
| 4-CH3 | c-Pr | — | CH3 |
| 4-CH3 | c-Pr | — | CH2Ph |
| 4-CH3 | c-Pr | — | C(O)Ph |
| 4-CH3 | c-Pr | — | C(O)OEt |
| 4-t-Bu | c-Pr | — | H |
| 4-n-hex | c-Pr | — | H |
| 4-n-hex | c-Pr | — | CH3 |
| 4-n-hex | c-Pr | — | CH2Ph |
| 4-n-hex | c-Pr | — | C(O)Ph |
| 4-n-hex | c-Pr | — | C(O)OEt |
| 4-OCH3 | c-Pr | — | H |
| 4-Ph | c-Pr | — | H |
| H | c-Bu | — | H |
| H | c-Pen | — | H |
| H | c-Hex | — | H |
| 4-Cl | c-Hex | — | H |
| 4-CH3 | c-Hex | — | H |
| 4-CH3 | c-Hex | — | CH3 |
| 4-CH3 | c-Hex | — | CH2Ph |
| 4-CH3 | c-Hex | — | C(O)Ph |
| 4-CH3 | c-Hex | — | C(O)OEt |
| 4-t-Bu | c-Hex | — | H |
| 4-n-hex | c-Hex | — | H |
| 4-n-hex | c-Hex | — | CH3 |
| 4-n-hex | c-Hex | — | CH2Ph |
| 4-n-hex | c-Hex | — | C(O)Ph |
| 4-n-hex | c-Hex | — | C(O)OEt |
| 4-OCH3 | c-Hex | — | H |
| 4-Ph | c-Hex | — | H |
| H | c-C7H15 | — | H |
| H | c-C8H17 | — | H |
| H | bicyclo[2.2.1]heptan-2-yl | — | H |
| H | 1-adamantyl | — | H |
| H | 2-adamantyl | — | H |
| H | A001 | H | H |
| H | A001 | 3-n-Bu | H |
| H | A002 | H | H |
| H | A002 | 2-Cl | H |
| H | A003 | H | H |
| H | A004 | H | H |
| H | A005 | H | H |
| 4-Cl | A005 | H | H |
| 4-CH3 | A005 | H | H |
| 4-CH3 | A005 | H | CH3 |
| 4-CH3 | A005 | H | CH2Ph |
| 4-CH3 | A005 | H | C(O)Ph |
| 4-CH3 | A005 | H | C(O)OEt |
| 4-t-Bu | A005 | H | H |
| 4-n-hex | A005 | H | H |
| 4-n-hex | A005 | H | CH3 |
| 4-n-hex | A005 | H | CH2Ph |
| 4-n-hex | A005 | H | C(O)Ph |
| 4-n-hex | A005 | H | C(O)OEt |
| 4-OCH3 | A005 | H | H |
| 4-Ph | A005 | H | H |
| H | A005 | 2,5-(CH3)2 | H |
| H | A005 | 2,5-Cl2 | H |
| H | A005 | 2-Br | H |
| H | A006 | H | H |
| 4-Cl | A006 | H | H |
| 4-CH3 | A006 | H | H |
| 4-CH3 | A006 | H | CH3 |
| 4-CH3 | A006 | H | CH2Ph |
| 4-CH3 | A006 | H | C(O)Ph |
| 4-CH3 | A006 | H | C(O)OEt |
| 4-t-Bu | A006 | H | H |
| 4-n-hex | A006 | H | H |
| 4-n-hex | A006 | H | CH3 |
| 4-n-hex | A006 | H | CH2Ph |
| 4-n-hex | A006 | H | C(O)Ph |
| 4-n-hex | A006 | H | C(O)OEt |
| 4-OCH3 | A006 | H | H |
| 4-Ph | A006 | H | H |
| H | A006 | 3-CH3 | H |
| H | A006 | 5-CH3 | H |
| H | A006 | 3-Cl | H |
| H | A006 | 5-Et | H |
| H | A006 | 5-Cl | H |
| H | A006 | 5-Br | H |
| H | A006 | 3-Br | H |
| H | A006 | 4-Br | H |
| H | A006 | 5-NO2 | H |
| H | A007 | H | H |
| H | A007 | 5-CH3 | H |
| H | A007 | 3-CH3 | H |
| H | A007 | 5-Br | H |
| H | A007 | 5-NO2 | H |
| H | A007 | 5-Ph | H |
| H | A008 | 5-CH3 | H |
| H | A009 | 5-CH3 | H |
| H | A010 | 3,5-(CH3)2 | H |
| H | A010 | 3,5-Cl2 | H |
| H | A011 | 3,5-(CH3)2 | H |
| H | A011 | 3,5-Cl2 | H |
| H | A012 | 3-CH3 | H |
| H | A012 | 3-Me | H |
| H | A012 | 3-Cl | H |
| H | A013 | 3-CH3 | H |
| H | A013 | 3-Me | H |
| H | A013 | 3-Cl | H |
| H | A014 | H | H |
| 4-Cl | A014 | H | H |
| 4-CH3 | A014 | H | H |
| 4-CH3 | A014 | H | CH3 |
| 4-CH3 | A014 | H | CH2Ph |
| 4-CH3 | A014 | H | C(O)Ph |
| 4-CH3 | A014 | H | C(O)OEt |
| 4-t-Bu | A014 | H | H |
| 4-n-hex | A014 | H | H |

TABLE 11-continued

| | | | |
|---|---|---|---|
| 4-OCH$_3$ | A014 | H | H |
| 4-Ph | A014 | H | H |
| H | A015 | H | H |
| H | A016 | 2,4-(CH$_3$)$_2$ | H |
| 4-Cl | A016 | 2,4-(CH$_3$)$_2$ | H |
| 4-CH$_3$ | A016 | 2,4-(CH$_3$)$_2$ | H |
| 4-CH$_3$ | A016 | 2,4-(CH$_3$)$_2$ | CH$_3$ |
| 4-CH$_3$ | A016 | 2,4-(CH$_3$)$_2$ | CH$_2$Ph |
| 4-CH$_3$ | A016 | 2,4-(CH$_3$)$_2$ | C(O)Ph |
| 4-CH$_3$ | A016 | 2,4-(CH$_3$)$_2$ | C(O)OEt |
| 4-t-Bu | A016 | 2,4-(CH$_3$)$_2$ | H |
| 4-n-hex | A016 | 2,4-(CH$_3$)$_2$ | H |
| 4-OCH$_3$ | A016 | 2,4-(CH$_3$)$_2$ | H |
| 4-Ph | A016 | 2,4-(CH$_3$)$_2$ | H |
| H | A017 | 2,4-(CH$_3$)$_2$ | H |
| H | A018 | H | H |
| H | A018 | 3-CH$_3$ | H |
| H | A019 | 3-Ph, 5-CH$_3$ | H |
| H | A019 | 3,5-(CH$_3$)$_2$ | H |
| H | A020 | 5-CH$_3$ | H |
| H | A021 | 4-CH$_3$ | H |
| H | A022 | H | H |
| H | A023 | 2,4-(CH$_3$)$_2$ | H |
| H | A024 | 2-(4-pyridil) | H |
| H | A025 | H | H |
| H | A026 | H | H |
| H | A026 | 4-CH$_3$ | H |
| H | A027 | H | H |
| H | A027 | 4-CH$_3$ | H |
| H | A028 | H | H |
| H | A029 | H | H |
| H | A030 | H | H |
| H | A031 | H | H |
| H | A032 | H | H |
| H | A033 | H | H |
| H | A034 | H | H |
| H | A034 | 3,6-Cl$_2$ | H |
| H | A035 | H | H |
| H | A036 | H | H |
| H | A037 | H | H |
| 4-Cl | A037 | H | H |
| 4-CH$_3$ | A037 | H | H |
| 4-CH$_3$ | A037 | H | CH$_3$ |
| 4-CH$_3$ | A037 | H | CH$_2$Ph |
| 4-CH$_3$ | A037 | H | C(O)Ph |
| 4-CH$_3$ | A037 | H | C(O)OEt |
| 4-t-Bu | A037 | H | H |
| 4-n-hex | A037 | H | H |
| 4-n-hex | A037 | H | CH$_3$ |
| 4-n-hex | A037 | H | CH$_2$Ph |
| 4-n-hex | A037 | H | C(O)Ph |
| 4-n-hex | A037 | H | C(O)OEt |
| 4-OCH$_3$ | A037 | H | H |
| 4-Ph | A037 | H | H |
| H | A037 | 6-OCH$_3$ | H |
| H | A037 | 6-Br | H |
| H | A038 | H | H |
| 4-Cl | A038 | H | H |
| 4-CH$_3$ | A038 | H | H |
| 4-CH$_3$ | A038 | H | CH$_3$ |
| 4-CH$_3$ | A038 | H | CH$_2$Ph |
| 4-CH$_3$ | A038 | H | C(O)Ph |
| 4-CH$_3$ | A038 | H | C(O)OEt |
| 4-t-Bu | A038 | H | H |
| 4-n-hex | A038 | H | H |
| 4-n-hex | A038 | H | CH$_3$ |
| 4-n-hex | A038 | H | CH$_2$Ph |
| 4-n-hex | A038 | H | C(O)Ph |
| 4-n-hex | A038 | H | C(O)OEt |
| 4-OCH$_3$ | A038 | H | H |
| 4-Ph | A038 | H | H |
| H | A038 | 2-OCH$_3$ | H |
| H | A038 | 4-OCH$_3$ | H |
| H | A038 | 4-F | H |
| H | A039 | H | H |
| H | A039 | 3-CH$_3$ | H |
| H | A039 | 7-OCH$_3$ | H |
| H | A040 | H | H |
| H | A041 | H | H |
| 4-Cl | A041 | H | H |
| 4-CH$_3$ | A041 | H | H |
| 4-CH$_3$ | A041 | H | CH$_3$ |
| 4-CH$_3$ | A041 | H | CH$_2$Ph |
| 4-CH$_3$ | A041 | H | C(O)Ph |
| 4-CH$_3$ | A041 | H | C(O)OEt |
| 4-t-Bu | A041 | H | H |
| 4-n-hex | A041 | H | H |
| 4-OCH$_3$ | A041 | H | H |
| 4-Ph | A041 | H | H |
| H | A041 | 6-NO$_2$ | H |
| H | A041 | 6-Br | H |
| H | A042 | H | H |
| 4-Cl | A042 | H | H |
| 4-CH$_3$ | A042 | H | H |
| 4-CH$_3$ | A042 | H | CH$_3$ |
| 4-CH$_3$ | A042 | H | CH$_2$Ph |
| 4-CH$_3$ | A042 | H | C(O)Ph |
| 4-CH$_3$ | A042 | H | C(O)OEt |
| 4-t-Bu | A042 | H | H |
| 4-n-hex | A042 | H | H |
| 4-OCH$_3$ | A042 | H | H |
| 4-Ph | A042 | H | H |
| H | A042 | 5-Br | H |
| H | A043 | H | H |
| 4-Cl | A043 | H | H |
| 4-CH$_3$ | A043 | H | H |
| 4-CH$_3$ | A043 | H | CH$_3$ |
| 4-CH$_3$ | A043 | H | CH$_2$Ph |
| 4-CH$_3$ | A043 | H | C(O)Ph |
| 4-CH$_3$ | A043 | H | C(O)OEt |
| 4-t-Bu | A043 | H | H |
| 4-n-hex | A043 | H | H |
| 4-OCH$_3$ | A043 | H | H |
| 4-Ph | A043 | H | H |
| H | A044 | H | H |
| 4-Cl | A044 | H | H |
| 4-CH$_3$ | A044 | H | H |
| 4-CH$_3$ | A044 | H | CH$_3$ |
| 4-CH$_3$ | A044 | H | CH$_2$Ph |
| 4-CH$_3$ | A044 | H | C(O)Ph |
| 4-CH$_3$ | A044 | H | C(O)OEt |
| 4-t-Bu | A044 | H | H |
| 4-n-hex | A044 | H | H |
| 4-OCH$_3$ | A044 | H | H |
| 4-Ph | A044 | H | H |
| H | A051 | — | H |
| H | A052 | — | H |
| H | A053 | — | H |
| H | A054 | — | H |
| H | A055 | — | H |
| H | A056 | — | H |
| H | A057 | — | H |
| H | A058 | — | H |
| H | A059 | — | H |
| H | A060 | — | H |
| H | A061 | — | H |
| H | A062 | — | H |
| H | A063 | — | H |
| H | A064 | — | H |
| H | A065 | — | H |
| H | A066 | — | H |
| H | A067 | — | H |
| H | A068 | — | H |
| H | A101 | — | H |
| H | A102 | — | H |
| H | A103 | — | H |
| H | A104 | — | H |
| H | A105 | — | H |
| H | A106 | — | H |
| H | A107 | — | H |

TABLE 12
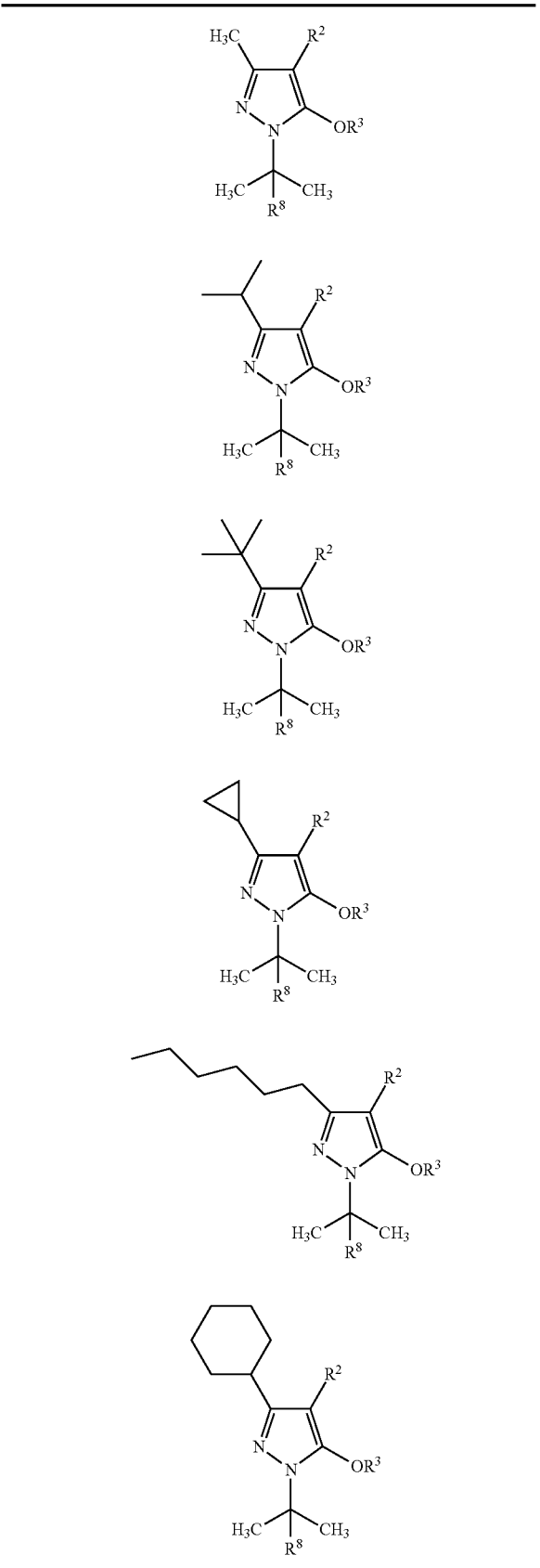
TABLE 12-continued
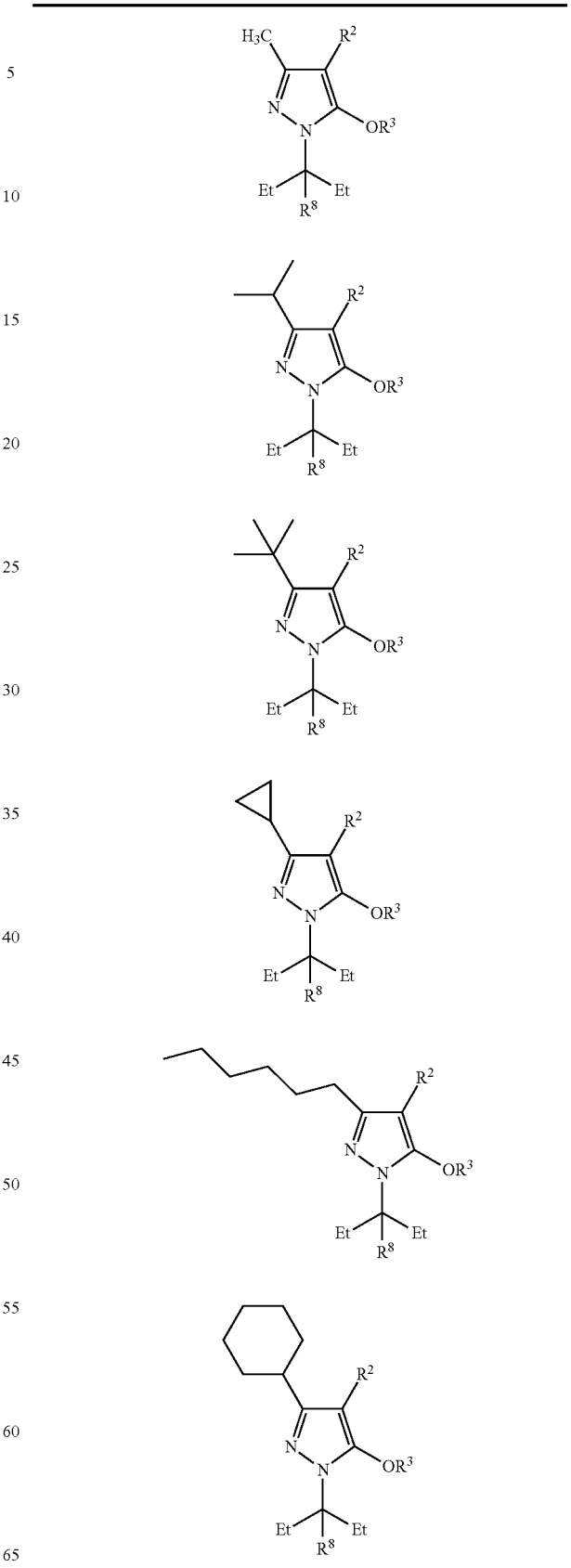

TABLE 12-continued
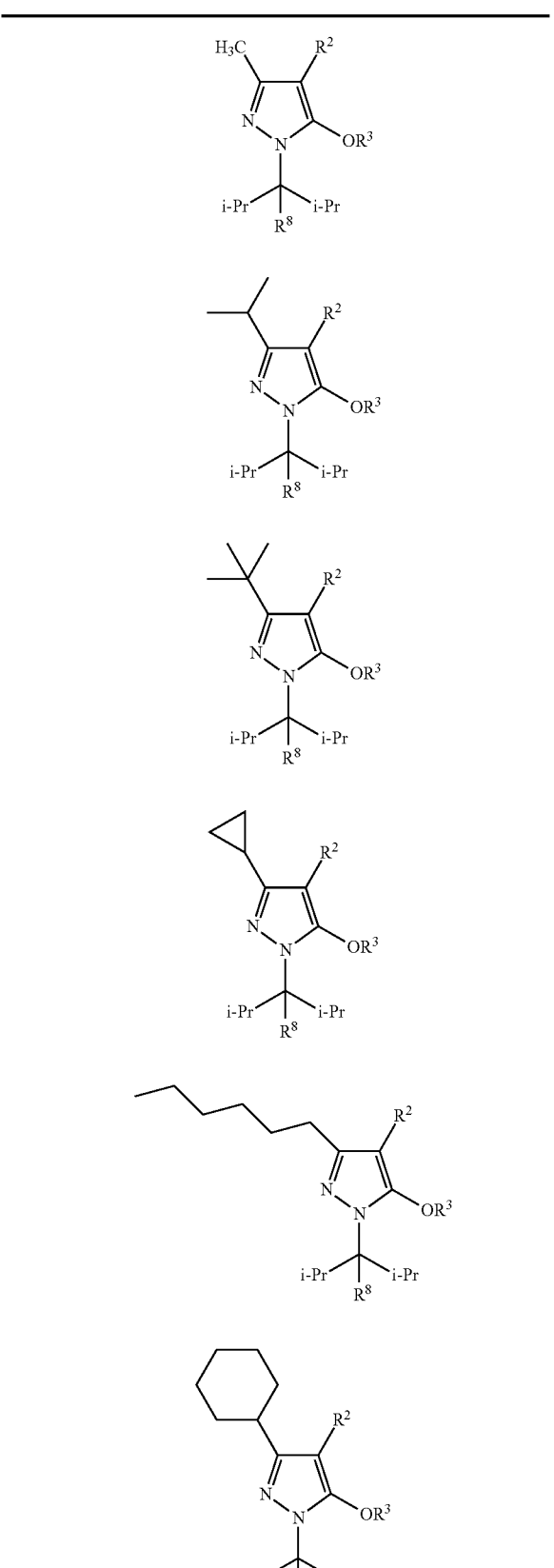
TABLE 12-continued
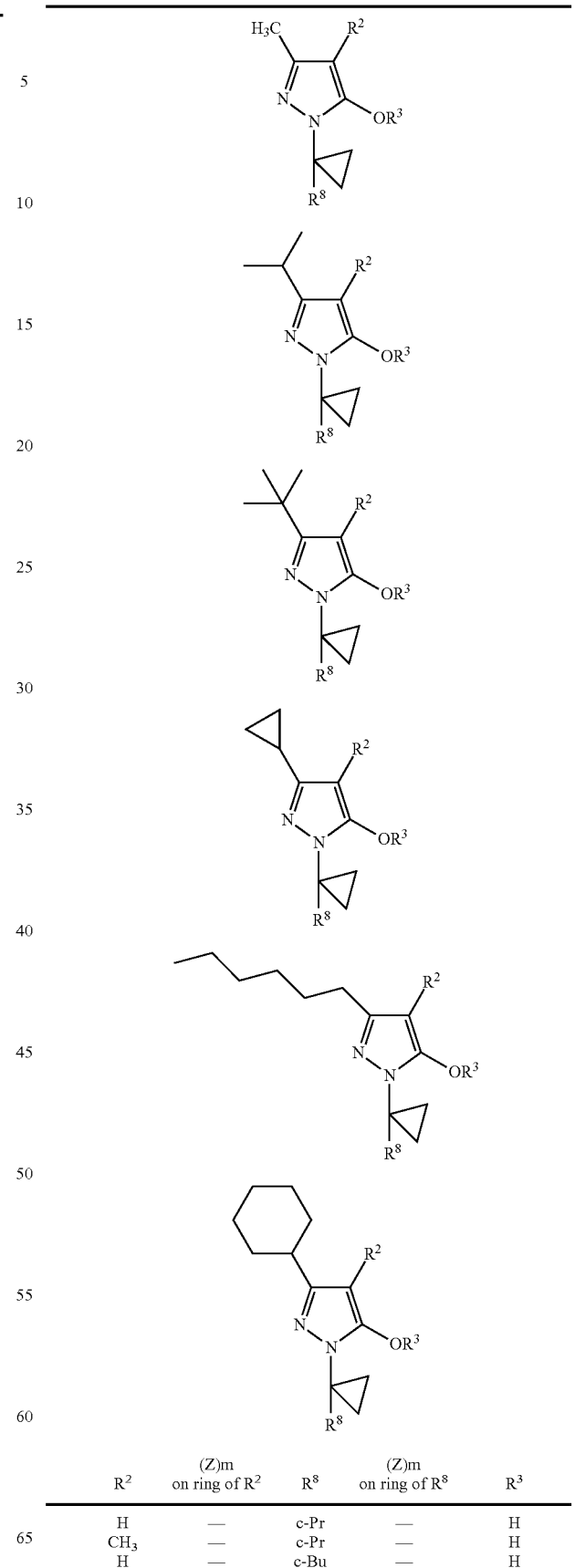
| R² | (Z)m on ring of R² | R⁸ | (Z)m on ring of R⁸ | R³ |
|---|---|---|---|---|
| H | — | c-Pr | — | H |
| CH₃ | — | c-Pr | — | H |
| H | — | c-Bu | — | H |

TABLE 12-continued

| | | | | |
|---|---|---|---|---|
| CH₃ | — | c-Bu | — | H |
| H | — | c-Pen | — | H |
| CH₃ | — | c-Pen | — | H |
| H | — | c-Hex | — | H |
| CH₃ | — | c-Hex | — | H |
| CH₃ | — | c-Hex | — | CH₃ |
| CH₃ | — | c-Hex | — | CH₂Ph |
| CH₃ | — | c-Hex | — | C(O)Ph |
| CH₃ | — | c-Hex | — | C(O)OEt |
| C(O)CH₃ | — | c-Pr | — | H |
| C(O)CH₃ | — | c-Hex | — | H |
| C(O)CH₃ | — | c-Hex | — | CH₃ |
| C(O)CH₃ | — | c-Hex | — | CH₂Ph |
| C(O)CH₃ | — | c-Hex | — | C(O)Ph |
| C(O)CH₃ | — | c-Hex | — | C(O)OEt |
| C(O)Ph | — | c-Pr | — | H |
| C(O)Ph | — | c-Hex | — | H |
| C(O)Ph | — | c-Hex | — | CH₃ |
| C(O)Ph | — | c-Hex | — | CH₂Ph |
| C(O)Ph | — | c-Hex | — | C(O)Ph |
| C(O)Ph | — | c-Hex | — | C(O)OEt |
| A005 | H | A005 | H | H |
| A005 | H | A006 | H | H |
| A005 | H | A014 | H | H |
| A005 | H | A016 | 2,4-(CH₃)₂ | H |
| A005 | H | A037 | H | H |
| A005 | H | A038 | H | H |
| A005 | H | A041 | H | H |
| A005 | H | A042 | H | H |
| A005 | H | A043 | H | H |
| A005 | H | A044 | H | H |
| A006 | H | A005 | H | H |
| A006 | H | A006 | H | H |
| A006 | H | A006 | H | CH₃ |
| A006 | H | A006 | H | CH₂Ph |
| A006 | H | A006 | H | C(O)Ph |
| A006 | H | A014 | H | H |
| A006 | H | A016 | 2,4-(CH₃)₂ | CH |
| A006 | H | A037 | H | H |
| A006 | H | A037 | H | CH₃ |
| A006 | H | A037 | H | CH₂Ph |
| A006 | H | A037 | H | C(O)Ph |
| A006 | H | A038 | H | H |
| A006 | H | A038 | H | CH₃ |
| A006 | H | A038 | H | CH₂Ph |
| A006 | H | A038 | H | C(O)Ph |
| A006 | H | A041 | H | H |
| A006 | H | A041 | H | CH₃ |
| A006 | H | A041 | H | CH₂Ph |
| A006 | H | A041 | H | C(O)Ph |
| A006 | H | A042 | H | H |
| A006 | H | A042 | H | CH₃ |
| A006 | H | A042 | H | CH₂Ph |
| A006 | H | A042 | H | C(O)Ph |
| A006 | H | A043 | H | H |
| A006 | H | A044 | H | H |
| A014 | H | A005 | H | H |
| A014 | H | A006 | H | H |
| A014 | H | A014 | H | H |
| A014 | H | A016 | 2,4-(CH₃)₂ | H |
| A014 | H | A037 | H | H |
| A014 | H | A038 | H | H |
| A014 | H | A041 | H | H |
| A014 | H | A042 | H | H |
| A014 | H | A043 | H | H |
| A014 | H | A044 | H | H |
| A016 | 2,4-(CH₃)₂ | A005 | H | H |
| A016 | 2,4-(CH₃)₂ | A006 | H | H |
| A016 | 2,4-(CH₃)₂ | A014 | H | H |
| A016 | 2,4-(CH₃)₂ | A016 | 2,4-(CH₃)₂ | H |
| A016 | 2,4-(CH₃)₂ | A037 | H | H |
| A016 | 2,4-(CH₃)₂ | A038 | H | H |
| A016 | 2,4-(CH₃)₂ | A041 | H | H |
| A016 | 2,4-(CH₃)₂ | A042 | H | H |
| A016 | 2,4-(CH₃)₂ | A043 | H | H |
| A016 | 2,4-(CH₃)₂ | A044 | H | H |
| A036 | H | A005 | H | H |
| A036 | H | A006 | H | H |
| A036 | H | A014 | H | H |
| A036 | H | A016 | 2,4-(CH₃)₂ | H |
| A036 | H | A037 | H | H |
| A036 | H | A038 | H | H |
| A036 | H | A041 | H | H |
| A036 | H | A042 | H | H |
| A036 | H | A043 | H | H |
| A036 | H | A044 | H | H |
| A037 | H | A005 | H | H |
| A037 | H | A006 | H | H |
| A037 | H | A006 | H | CH₃ |
| A037 | H | A006 | H | CH₂Ph |
| A037 | H | A006 | H | C(O)Ph |
| A037 | H | A014 | H | H |
| A037 | H | A016 | 2,4-(CH₃)₂ | H |
| A037 | H | A037 | H | H |
| A037 | H | A037 | H | CH₃ |
| A037 | H | A037 | H | CH₂Ph |
| A037 | H | A037 | H | C(O)Ph |
| A037 | H | A038 | H | H |
| A037 | H | A038 | H | CH₃ |
| A037 | H | A038 | H | CH₂Ph |
| A037 | H | A038 | H | C(O)Ph |
| A037 | H | A041 | H | H |
| A037 | H | A041 | H | CH₃ |
| A037 | H | A041 | H | 1CH₂Ph |
| A037 | H | A041 | H | C(O)Ph |
| A037 | H | A042 | H | H |
| A037 | H | A042 | H | CH₃ |
| A037 | H | A042 | H | CH₂Ph |
| A037 | H | A042 | H | C(O)Ph |
| A037 | H | A043 | H | H |
| A037 | H | A044 | H | H |
| A038 | H | A005 | H | H |
| A038 | H | A006 | H | H |
| A038 | H | A006 | H | CH₃ |
| A038 | H | A006 | H | CH₂Ph |
| A038 | H | A006 | H | C(O)Ph |
| A038 | H | A014 | H | H |
| A038 | H | A016 | 2,4-(CH₃)₂ | H |
| A038 | H | A037 | H | H |
| A038 | H | A037 | H | CH₃ |
| A038 | H | A037 | H | CH₂Ph |
| A038 | H | A037 | H | C(O)Ph |
| A038 | H | A038 | H | H |
| A038 | H | A038 | H | CH₃ |
| A038 | H | A038 | H | CH₂Ph |
| A038 | H | A038 | H | C(O)Ph |
| A038 | H | A041 | H | H |
| A038 | H | A041 | H | CH₃ |
| A038 | H | A041 | H | CH₂Ph |
| A038 | H | A041 | H | C(O)Ph |
| A038 | H | A042 | H | H |
| A038 | H | A042 | H | CH₃ |
| A038 | H | A042 | H | CH₂Ph |
| A038 | H | A042 | H | C(O)Ph |
| A038 | H | A043 | H | H |
| A038 | H | A044 | H | H |
| A041 | H | A005 | H | H |
| A041 | H | A006 | H | H |
| A041 | H | A006 | H | CH₃ |
| A041 | H | A006 | H | CH₂Ph |
| A041 | H | A006 | H | C(O)Ph |
| A041 | H | A014 | H | H |
| A041 | H | A016 | 2,4-(CH₃)₂ | H |
| A041 | H | A037 | H | H |
| A041 | H | A037 | H | CH₃ |
| A041 | H | A037 | H | CH₂Ph |
| A041 | H | A037 | H | C(O)Ph |
| A041 | H | A038 | H | H |
| A041 | H | A038 | H | CH₃ |
| A041 | H | A038 | H | CH₂Ph |
| A041 | H | A038 | H | C(O)Ph |
| A041 | H | A041 | H | H |
| A041 | H | A041 | H | CH₃ |
| A041 | H | A041 | H | CH₂Ph |
| A041 | H | A041 | H | C(O)Ph |
| A041 | H | A042 | H | H |
| A041 | H | A042 | H | CH₃ |
| A041 | H | A042 | H | CH₂Ph |
| A041 | H | A042 | H | C(O)Ph |
| A041 | H | A043 | H | H |

TABLE 12-continued

| | | | | |
|---|---|---|---|---|
| A041 | H | A044 | H | H |
| A042 | H | A005 | H | H |
| A042 | H | A006 | H | H |
| A042 | H | A006 | H | CH₃ |
| A042 | H | A006 | H | CH₂Ph |
| A042 | H | A006 | H | C(O)Ph |
| A042 | H | A014 | H | H |
| A042 | H | A016 | 2,4-(CH₃)₂ | H |
| A042 | H | A037 | H | H |
| A042 | H | A037 | H | CH₃ |
| A042 | H | A037 | H | CH₂Ph |
| A042 | H | A037 | H | C(O)Ph |
| A042 | H | A038 | H | H |
| A042 | H | A038 | H | CH₃ |
| A042 | H | A038 | H | CH₂Ph |
| A042 | H | A038 | H | C(O)Ph |
| A042 | H | A041 | H | H |
| A042 | H | A041 | H | CH₃ |
| A042 | H | A041 | H | CH₂Ph |
| A042 | H | A041 | H | C(O)Ph |
| A042 | H | A042 | H | H |
| A042 | H | A042 | H | CH₃ |
| A042 | H | A042 | H | CH₂Ph |
| A042 | H | A042 | H | C(O)Ph |
| A042 | H | A043 | H | H |
| A042 | H | A044 | H | H |

The expression — indicates unsubstituted.

TABLE 13

The locants for the substituents $R^{11}$, $R^{21}$ and $R^{81}$ in the Table correspond to the positions indicated in the following structural formulae, and the expression — indicates unsubstituted.

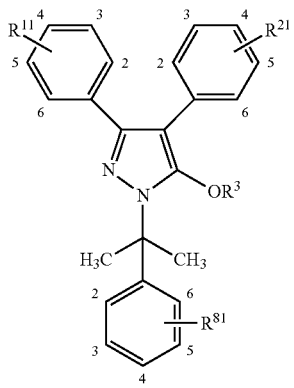

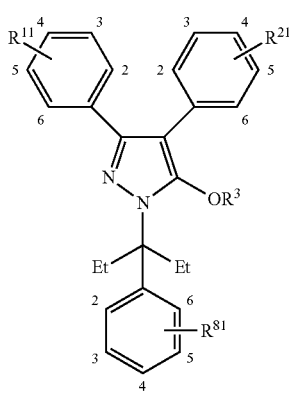

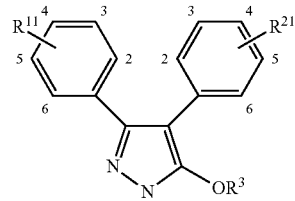

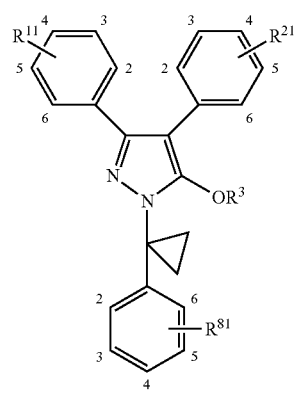

| $R^{11}$ | $R^{21}$ | $R^{81}$ | $R^3$ |
|---|---|---|---|
| H | H | H | H |
| H | 4-CH₃ | H | H |
| H | 4-t-Bu | H | H |
| H | 4-t-Bu | 4-CH₃ | H |
| H | 4-t-Bu | H | CH₃ |
| H | 4-t-Bu | 4-CH₃ | CH₃ |
| H | 4-n-Hex | H | H |
| H | 4-n-Hex | 4-Cl | H |
| H | 4-n-Hex | 4-Br | H |
| H | 4-n-Hex | 4-CH₃ | H |
| H | 4-n-Hex | H | CH₃ |
| H | 4-n-Hex | 4-CH₃ | CH₃ |
| H | 4-n-Hex | H | CH₂Ph |
| H | 4-n-Hex | H | C(O)OEt |
| H | 4-n-Hex | H | C(O)Ph |
| H | 4-Ph | H | H |
| H | 4-Ph | 4-CH₃ | H |
| H | 4-Ph | H | CH₃ |
| H | 4-Ph | 4-CH₃ | CH₃ |
| 4-F | H | H | H |
| 2-Cl | H | H | H |
| 3-Cl | H | H | H |
| 4-Cl | H | H | H |
| 4-Cl | 4-t-Bu | H | H |
| 4-Cl | 4-t-Bu | 4-CH₃ | H |
| 4-Cl | 4-n-Hex | H | H |
| 4-Cl | 4-n-Hex | 4-Cl | H |
| 4-Cl | 4-n-Hex | 4-Br | H |
| 4-Cl | 4-n-Hex | 4-CH₃ | H |
| 4-Cl | 4-Ph | H | H |
| 4-Cl | 4-Ph | 4-CH₃ | H |
| 4-Br | H | H | H |
| 3,4-Cl₂ | H | H | H |
| 4-NO₂ | H | H | H |
| 4-CN | H | H | H |
| 2-CH₃ | H | H | H |
| 3-CH₃ | H | H | H |
| 4-CH₃ | H | H | H |
| 4-CH₃ | 4-t-Bu | H | H |
| 4-CH₃ | 4-t-Bu | 4-CH₃ | H |

TABLE 13-continued

| | | | |
|---|---|---|---|
| 4-CH₃ | 4-n-Hex | H | H |
| 4-CH₃ | 4-n-Hex | 4-Cl | H |
| 4-CH₃ | 4-n-Hex | 4-Br | H |
| 4-CH₃ | 4-n-Hex | 4-CH₃ | H |
| 4-CH₃ | 4-Ph | H | H |
| 4-CH₃ | 4-Ph | 4-CH₃ | H |
| 3,4-(CH₃)₂ | H | H | H |
| 4-OCH₃ | H | H | H |
| 4-OCH₃ | 4-t-Bu | H | H |
| 4-OCH₃ | 4-n-Hex | H | H |
| 4-OCH₃ | 4-n-Hex | 4-Cl | H |
| 4-OCH₃ | 4-n-Hex | 4-Br | H |
| 4-OCH₃ | 4-n-Hex | 4-CH₃ | H |
| 4-OCH₃ | 4-Ph | H | H |
| 3,4-(OCH₃) | H | H | H |
| 4-Ph | H | H | H |

TABLE 14

The locants for the substituent $R^{81}$ herein correspond to the positions indicated in the following structural formulae, and the expression — indicates unsubstituted.

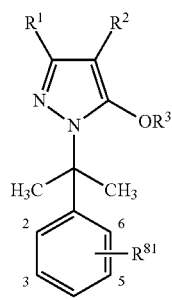

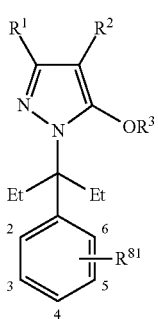

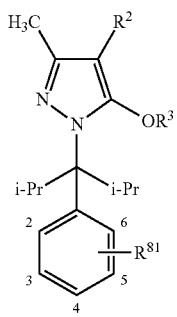

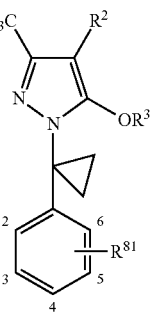

| $R^1$ | $R^2$ | (Z)m | $R^{81}$ | $R^3$ |
|---|---|---|---|---|
| H | H | — | H | H |
| Et | H | — | H | H |
| n-Pr | H | — | H | H |
| n-Bu | H | — | H | H |
| c-Bu | H | — | H | H |
| n-Pen | H | — | H | H |
| c-Pen | H | — | H | H |
| CF₃ | H | — | H | H |
| CF₃ | H | — | 4-CH₃ | H |
| CF₃ | H | — | 4-CH₃ | CH₃ |
| CF₃ | A005 | — | H | H |
| CF₃ | A006 | — | H | H |
| CF₃ | A014 | — | H | H |
| CF₃ | A016 | 2,4-(CH₃)₂ | H | H |
| CF₃ | A036 | H | H | H |
| CF₃ | A037 | — | H | H |
| CF₃ | A038 | — | H | H |
| CF₃ | A041 | — | H | H |
| CF₃ | A042 | — | H | H |
| CN | H | — | H | H |
| C(O)OEt | H | — | H | H |
| Ph | H | — | H | H |
| (4-CH₃)Ph | H | — | H | H |
| (4-i-Pr)Ph | H | — | H | H |
| (4-OCH₃)Ph | H | — | H | H |
| (4-OCH₃)Ph | H | — | 4-CH₃ | H |

TABLE 15

The locants for the substituents $R^{21}$ and $R^{81}$ in the Table correspond to the positions indicated in the following structural formulae, and the expression — indicates unsubstituted.

TABLE 15-continued

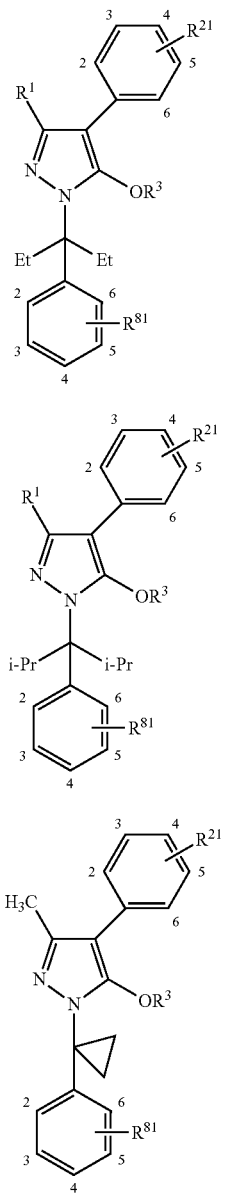

| R¹ | (Z)m | R²¹ | R⁸¹ | R³ |
|---|---|---|---|---|
| H | — | H | H | H |
| Et | — | H | H | H |
| n-Pr | — | H | H | H |
| n-Bu | — | H | H | H |
| $CF_3$ | — | H | H | H |
| $CF_3$ | — | 4-$CH_3$ | H | H |
| $CF_3$ | — | 4-$CH_3$ | 4-$CH_3$ | H |
| $CF_3$ | — | 4-$CH_3$ | 4-$CH_3$ | $CH_3$ |
| $CF_3$ | — | 4-t-Bu | H | H |
| $CF_3$ | — | 4-n-Hex | 4-$CH_3$ | H |
| $CF_3$ | — | 4-n-Hex | 4-$CH_3$ | $CH_3$ |
| $CF_3$ | — | 4-Ph | H | H |
| $CO_2Et$ | — | H | H | H |
| A001 | H | H | H | H |
| A002 | H | H | H | H |
| A003 | H | H | H | H |
| A005 | H | H | H | H |
| A005 | 2,5-$(CH_3)_2$ | H | H | H |
| A005 | 2,5-$Cl_2$ | H | H | H |
| A005 | 2-Br | H | H | H |
| A006 | H | H | H | H |
| A006 | 3-$CH_3$ | H | H | H |
| A006 | 5-$CH_3$ | H | H | H |
| A006 | 3-Cl | H | H | H |
| A006 | 5-Et | H | H | H |
| A006 | 5-Cl | H | H | H |
| A006 | 5-Br | H | H | H |
| A006 | 3-Br | H | H | H |
| A006 | 4-Br | H | H | H |
| A006 | 5-$NO_2$ | H | H | H |
| A007 | H | H | H | H |
| A007 | 5-$CH_3$ | H | H | H |
| A007 | 3-$CH_3$ | H | H | H |
| A007 | 5-Br | H | H | H |
| A007 | 5-$NO_2$ | H | H | H |
| A007 | 5-Ph | H | H | H |
| A008 | 5-$CH_3$ | H | H | H |
| A009 | 5-$CH_3$ | H | H | H |
| A010 | 3,5-$(CH_3)_2$ | H | H | H |
| A010 | 3,5-$Cl_2$ | H | H | H |
| A011 | 3,5-$(CH_3)_2$ | H | H | H |
| A011 | 3,5-$Cl_2$ | H | H | H |
| A012 | 3-$CH_3$ | H | H | H |
| A012 | 3-$CH_3$ | H | H | H |
| A012 | 3-Cl | H | H | H |
| A013 | 3-$CH_3$ | H | H | H |
| A013 | 3-$CH_3$ | H | H | H |
| A013 | 3-Cl | H | H | H |
| A014 | H | H | H | H |
| A015 | H | H | H | H |
| A016 | 2,4-$(CH_3)_2$ | H | H | H |
| A017 | 2,4-$(CH_3)_2$ | H | H | H |
| A034 | H | H | H | H |
| A034 | 3,6-$Cl_2$ | H | H | H |
| A035 | H | H | H | H |
| A036 | H | H | H | H |
| A037 | H | H | H | H |
| A037 | 6-$OCH_3$ | H | H | H |
| A037 | 6-Br | H | H | H |
| A038 | H | H | H | H |
| A038 | 2-$OCH_2$ | H | H | H |
| A038 | 4-$OCH_3$ | H | H | H |
| A038 | 4-F | H | H | H |

EXAMPLES

Now, the present invention will be described in further detail with reference to Synthetic Examples and Assay Examples of the compounds of the present invention.

However, it should be understood that the present invention is by no means restricted by these specific Examples.

The compounds obtained in the Synthetic Examples were identified by proton nuclear magnetic resonance ($^1$H NMR) by chemical shifts relative to tetramethylsilane ($Me_4Si$) as the standard.

SYNTHETIC EXAMPLES

Synthetic Example 1

Synthesis of 4-(4-hexylphenyl)-3-isopropyl-1-(2-methyl-1-p-tolylpropan-2-yl)-1H-pyrazol-5-ol (Compound No. 3-07 of the Present Invention)

Step 1

Synthesis of Triphenyl(t-butoxycarbonylimino)phosphorane 25 g (0.19 mol) of t-butylcarbazate was dissolved in 80 mL of acetic acid and 160 mL of water, and 15 g (0.22 mol) of sodium nitrite was added in small portions under cooling with ice. The reaction solution was stirred for 30 minutes under cooling with ice and extracted with 250 ml of diisopropyl ether. The organic layer was washed with 200 mL of saturated aqueous sodium hydrogen carbonate twice and with 100 mL of saturated aqueous sodium chloride once successively, dried over anhydrous sodium sulfate and filtered to give a solution of t-butyl carbonazidate in diethyl ether To the solution of t-butyl carbonazidate in diethyl ether, 49.6 g (0.189 mol) of triphenylphosphine was added in small portions under cooling with ice, and the reaction solution was stirred at room temperature for 1 hour, and the precipitated solid was collected by filtration, washed with 200 mL of hexane and dried under reduced pressure to give 67 g of the desired product as white crystals.

Step 2

Synthesis of t-Butyl 3-(trichloromethyl)-1,2-oxaziridine-2-carboxylate 20.0 g (53.0 mol) of triphenyl(t-butoxycarbonylimino) phosphorane was suspended in 80 mL of toluene, mixed with 8.84 g (60.0 mmol) of anhydrous chloral and heated at 120° C. for 4 hours under reflux. After cooling to room temperature, 300 mL of hexane was added, and the resulting white solid was separated by filtration. The filtrate was concentrated under reduced pressure. The resulting brown liquid was dissolved in 200 mL of chloroform, and simultaneous addition of 3.74 g (50.0 mmol) of potassium carbonate in 20 mL of ice-cold water and 4.94 g (15 mmol) of OXONE (2 $KHSC_5.KHSC_4.K_2SC_4$, supplied from Du Pont) in 40 mL of ice-cold water and 1 hour of stirring under cooling with ice were repeated three times. After removal of the aqueous layer, simultaneous addition of aqueous potassium carbonate and aqueous OXONE (2 $KHSC_5.KHSC_4.K_2SC_4$, supplied from Du Pont) and 1 hour of stirring under cooling with ice were repeated three times, similarly. After removal of the aqueous layer, simultaneous addition of aqueous potassium carbonate and aqueous OXONE and 1 hour of stirring under cooling with ice were repeated three times, similarly. After removal of the aqueous layer, 11.2 g (150 mmol) of potassium carbonate in 60 mL of ice-cold water and 14.8 g (45 mmol) of OXONE in 120 mL of ice-cold water were added simultaneously, and the reaction solution was stirred for 1 hour of stirring under cooling with ice. After removal of the aqueous layer, aqueous potassium carbonate and aqueous OXONE were simultaneously added, the reaction solution was stirred for 1 hour of stirring under cooling with ice, similarly. After removal of the aqueous layer, aqueous potassium carbonate and aqueous OXONE were simultaneously added, the reaction solution was stirred for 1 hour of stirring under cooling with ice, similarly. After removal of the aqueous layer, the chloroform layer was dried over anhydrous sodium sulfate and filtered, and the filtrate was concentrated under reduced pressure. The resulting residue was purified by silica gel column chromatography using hexane-ethyl acetate {100:0 (volume ratio, hereinafter the same applies) to 80:20} as the eluent to give 10.3 g of the desired product as a pale yellow oil.

Step 3

Synthesis of 2-chloro-N-(2-methyl-1-p-tolylpropan-2-yl)acetamide 8.21 g (50 mmol) of 2-methyl-1-p-tolylpropan-2-ol and 12.0 mL of acetic acid were dissolved in 11.3 g (0.15 mol) of chloroacetonitrile, mixed with 12.0 mL (0.15 mol) of sulfuric acid under cooling with ice and stirred at room temperature for 5 hours. The reaction solution was poured into 200 mL of ice-cold water and extracted with diisopropyl ether. The organic layer was washed with saturated aqueous sodium hydrogen carbonate and saturated aqueous sodium chloride successively, dried over anhydrous sodium sulfate and filtered, and the filtrate was concentrated under reduced pressure to give 10.8 g of the desired product as white crystals.

$^1$H NMR (CDCl$_3$, Me$_4$Si, 300 MHz) δ7.11 (d, J=7.7 Hz, 2H), 7.03 (d, J=8.3 Hz, 2H), 6.24 (br, 1H), 3.94 (s, 2H), 2.98 (s, 2H). 2.33 (s, 3H), 1.37 (s, 6H)zz

Step 4

Synthesis of 2-methyl-1-p-tolylpropan-2-amine 6.24 g (26.0 mmol) of 2-chloro-N-(2-methyl-1-p-tolylpropan-2-yl)acetamide and 1.98 g (26.0 mmol) of thiourea were dissolved in 50 mL of ethanol, and 10.2 mL of acetic acid was added dropwise at room temperature. After 3 hours of stirring at 85° C. the resulting white suspension was allowed to cool and diluted with 300 mL of water. The reaction solution was basified with 20 wt % aqueous sodium hydroxide and extracted with hexane, and the extract was washed with saturated aqueous sodium chloride. The organic layer was concentrated under reduced pressure to give 4.04 g of the desired product as a yellow green liquid.

$^1$H NMR (CDCl$_3$, Me$_4$Si, 300 MHz) δ7.02-7.13 (m, 4H), 2.61 (s, 2H), 2.33 (s, 3H). 1.18 (br, 2H), 1.16 (s, 6H)

Step 5

Synthesis of t-butyl 2-(2-methyl-1-p-tolylpropan-2-yl)hydrazinecarboxylate 2.40 g (14.7 mmol) of separately prepared 2-methyl-1-p-tolylpropan-2-amine was dissolved in 20 mL of methylene chloride, and 2.60 g (10.0 mmol) of separately prepared t-butyl 3-(trichloromethyl)-1,2-oxaziridine-2-carboxylate in 10 mL of methylene chloride was added under cooling with ice. The reaction slution was stirred under cooling with ice for 30 minutes and at room temperature for 1 hour, and the methylene chloride was removed under reduced pressure. The resulting residue was purified by silica gel column chromatography using hexane-ethyl acetate (100:0 to 0:100) as the eluent to give 1.61 g of the desired product as colorless crystals.

Step 6

Synthesis of 2-(4-hexylphenyl)-1-morpholinoethanethione 5.0 g (25 mmol) of 1-(4-hexylphenyl)ethanone was dissolved in 2.13 g (24.5 mmol) of morpholine and heated with 1.33 g (41.6 mmol) of sulfur at 115° C. for 5 hours under reflux. After completion of the reaction, the reaction solution was cooled to room temperature and mixed with methanol, and the reaction product precipitated as crystals were collected by filtration, washed and dried to give 4.50 g of the desired product as pale yellow crystals.

$^1$H NMR (CDCl$_3$, Me$_4$Si, 300 MHz) δ7.11~7.26 (m, 4H), 4.3~4.5 (m, 4H), 3.6~3.9 (m, 4H) 3.35~3.48 (m, 2H), 2.55~2.60 (m, 2H), 1.51-1.70 (m, 2H), 1.23-1.42 (m, 6H), 0.82-1.01 (m, 3H)

Step 7

Synthesis of 2-(4-hexylphenyl)acetic acid 12.0 g (39.3 mmol) of 1-(4-hexylphenyl)ethanone was dissolved in 23.6 g (393 mmol) of glacial acetic acid, mixed with 4.95 g (275 mmol) of water and 5.79 g (58.9 mmol) of sulfuric acid and heated at 150° C. for 6.5 hours under reflux. After completion of the reaction, the reaction solution was diluted with 400 mL of water and extracted with ethyl acetate. The resulting organic layer was dried over anhydrous magnesium sulfate and filtered, and the filtrate was concentrated under reduced pressure. The resulting residue was purified by silica gel column chromatography using ethyl acetate:hexane (1:20 to 1:4) as the eluent to give 5.74 g of the desired product as white crystals.

$^1$H NMR (CDCl$_3$, Me$_4$Si, 300 MHz) δ7.08~7.21 (m, 4H), 3.61 (s, 2H), 2.55~2.61 (m, 2H), 1.51~1.67 (m, 2H), 1.20~1.41 (m, 6H), 0.86~0.90 (m, 3H)

Step 8

Synthesis of ethyl 2-(4-hexylphenyl)acetate 5.5 g (25 mmol) of 2-(4-hexylphenyl)acetic acid was dissolved in 11 mL of ethanol and mixed with 1.1 g (11.2 mmol) of sulfuric acid and stirred at 60° C. for 1 hour. The reaction was quenched with cold saturated aqueous sodium carbonate (100 ml), and the reaction solution was extracted with ethyl acetate. The organic layer was dried over anhydrous magnesium sulfate and filtered, and the filtrate was concentrated under reduced pressure to give 5.68 g of the desired product as a pale yellow oil.

$^1$H NMR (CDCl$_3$, Me$_4$Si, 300 MHz) δ7.06~7.22 (m, 4H), 4.14 (q, J=7.2 Hz, 2H), 3.57 (s, 2H), 2.58 (t, J=7.8 Hz, 2H), 1.50~1.65 (m, 2H), 1.1~1.4 (m, 6H), 1.25 (t, J=7.2 Hz, 3H), 0.82~0.92 (m, 3H)

Step 9

Synthesis of ethyl 2-(4-hexylphenyl)-4-methyl-3-oxopentanoate 6.0 g (24 mmol) of ethyl 2-(4-hexylphenyl)acetate was dissolved in 130 mL of dry tetrahydrofuran under a nitrogen atmosphere and cooled to −60° C. After addition of 31.8 mL (36.2 mmol) of 1.14 M solution of lithiumdiisopropylamine in hexane/tetrahydrofuran, the solution was warmed to 0° C. and stirred for 1 hours. The reactuion solution was cooled to −60° C. again and stirred with 3.6 g (34 mmol) of isobutyryl chloride at −60° C. to room temperature for 15 hours. The reaction was quenched with saturated aqueous sodium hydrogen carbonate (150 ml), and the reaction solution was extracted with ethyl acetate. The organic layer was dried over anhydrous magnesium sulfate and filtered, and the filtrate was concentrated under reduced pressure. The resulting residue was purified by silica gel column chromatography using ethyl acetate:hexane (0:100 to 1:9) as the eluent to give 5.39 g of the desired product as a pale yellw oil.

$^1$H NMR (CDCl$_3$, Me$_4$Si, 300 MHz) δ7.11~7.33 (m, 4H), 4.84 (s, 1H), 4.19 (d, J=7.1 Hz, 2H), 2.67~2.81 (m, 1H), 2.59 (t, J=7.8 Hz, 2H), 1.50~1.71 (m, 2H), 1.22~1.42 (m, 6H), 1.27 (d, J=7.1 Hz, 3H), 1.12 (d, J=6.8 Hz, 3H), 1.01 (d, J=6.8 Hz, 3H), 0.81~0.95 (m, 3H)

Step 10

Synthesis of 4-(4-hexylphenyl)-3-isopropyl-1-(2-methyl-1-p-tolylpropan-2-yl)-1H-pyrazol-5-ol (Compound No. 3-07 of the Present Invention)

200 mg (0.72 mmol) of t-butyl 2-(2-phenylpropan-2-yl)hydrazinecarboxylate was dissolved in 3 mL of methylene chloride and stirred with 251 mg (1.3 mmol) of paratoluenesulfonic acid monohydrate at room temperature for 23 hours. The reaction solution was basified with saturated aqueous sodium hydrogen carbonate (50 ml) and separated, and the organic layer was dried over anhydrous sodium sulfate and filtered. The filtrate was concentrated under reduced pressure. The resulting residue was dissolved in 0.80 mL of toluene and 35 μL of acetic acid and stirred with 226 mg (0.71 mmol) of separately preprared ethyl 2-(4-hexylphenyl)-4-methyl-3-oxopentanoate at 90° C. for 8 hours. The reaction solution was cooled to room temperature, diluted with ethyl acetate, washed with saturated aqueous sodium hydrogen carbonate, dried over anhydrous sodium sulfate and filtered, and the filtrate was concentrated under reduced pressure. The resulting residue was purified by intermediate pressure silica gel column chromatography using hexane-ethyl acetate (1:20 to 1:3) as the eluent to give 130 mg of the desired product as a pale yellow solid.

$^1$H NMR (CDCl$_3$, Me$_4$Si, 300 MHz) δ7.18~7.42 (m, 4H), 7.00 (s, 4H), 3.21 (s, 2H), 3.16 (sep, J=7.2 Hz, 1H), 2.61 (t, J=7.5 Hz, 2H), 2.29 (s, 3H), 1.62 (s, 6H), 1.54~1.58 (m, 2H), 1.26~1.36 (m, 6H), 1.07 (d, J=7.2 Hz, 6H), 0.87~0.92 (m, 3H)

Synthetic Example 2

Synthesis of 1-(2-methyl-1-phenylpropan-2-yl)-3-phenyl-1H-pyrazol-5(4H)-one (Compound No. 3-16 of the Present Invention)

Step 1

Synthesis of 1-(2-methyl-1-phenylpropan-2-yl)-2-(propan-2-ylidene)hydrazine

Acetone azine (1.50 g, 13.4 mmol) was dissolved in 10 mL of diethyl ether, mixed with 32 mL (19.2 mmol) of 0.6 M benzylmagnesium bromide in tetrahydrofuran and stirred at 45° C. for 24 hours. The reaction was quenched with saturated aqueous ammonium chloride (100 ml), and the reaction solution was extracted with ethyl acetate. The resulting organic layer was dried over anhydrous magnesium sulfate and filtered, and the filtrate was concentrated under reduced pressure. The resulting residue was purified by silica gel column chromatography using hexane-ethyl acetate (9:1 to 6:1) as the eluent to give 710 mg of the desired product as a pale yellow oil.

$^1$H NMR (CDCl$_3$, Me$_4$Si, 300 MHz) δ7.03~7.28 (m, 5H), 4.2~4.4 (m, 1H), 2.78 (s, 2H), 1.99 (s, 3H), 1.62 (s, 3H), 1.18 (s, 6H)

Step 2

Synthesis of 1-(2-methyl-1-phenylpropan-2-yl)-3-phenyl-1H-pyrazol-5(4H)-one (Compound No. 3-16 of the Present Invention)

500 mg (2.45 mmol) of 1-(2-methyl-1-phenylpropan-2-yl)-2-(propan-2-ylidene)hydrazine was dissolved in 3.0 mL of glacial acetic acid, mixed with 429 mg (2.23 mmol) of ethyl 3-oxo-3-phenylpropanoate and stirred at 100° C. for 4 hours. The reaction solution was cooled to room temperature, diluted with ethyl acetate, neutralized with saturated aqueous sodium hydrogen carbonate (100 ml) and extracted with ethyl acetate. The resulting organic layer was dried over anhydrous sodium sulfate and filtered, and the filtrate was concentrated under reduced pressure. The resulting residue was purified by silica gel column chromatography using hexane-ethyl acetate (100:1 to 9:1) as the eluent to give 330 mg of the desired product as a pale orange solid.

$^1$H NMR (CDCl$_3$, Me$_4$Si, 300 MHz) δ7.12~7.62 (m, 10H), 3.59 (s, 2H), 3.19 (s, 2H), 1.59 (s, 6H)

Synthetic Example 3

Synthesis of 3-(2-methyl-1-phenylpropan-2-yl)-1-(2-phenylpropan-2-yl)-1H-pyrazol-5(4H)-one (Compound No. 3-04 of the Present Invention)

Step 1

Synthesis of 2,2-dimethyl-3-phenylpropanoic acid

Hexamethyldisilazane (34 g, 0.21 mol) was dissolved in tetrahydrofuran (280 mL), and 1.67M n-butyllithium in hexane (127 mL, 0.21 mol) was added dropwise at −78° C. The reaction solution was warmed to 0° C. over 1 hour and then cooled to −78° C. again. Benzyl isobutyrate (25 g, 0.14 mol) in tetrahydrofuran (70 mL) was added dropwise, and the reaction solution was stirred at −78° C. for 1 hour. Chlorotrimethylsilane (36 mL, 0.12 mol) was further added dropwise at the same temperature, and the reaction solution was stirred for 1 hour, then warmed to room temperature and stirred for 19 hours. After completion of the reaction, the solvent was partially removed from the reaction solution under reduced pressure, and the resulting white suspension was diluted with hexane (200 mL) and filtered through Celite under a nitrogen atmosphere to remove the white solid from the reaction solution. The filtrate was distiled under reduced pressure, and the resulting pale yellow oil was heated at 100° C. for 2 hours to give a brown oil. The brown oil was mixed with 10 mL of 1 M hydrochloric acid and stirred at 60° C. for 4 hours, neutralized with saturated aqueous sodium hydrogen carbonate and extracted with ethyl acetate (100 mL×2) and chloroform (100 mL×2). The resulting organic layer was concentrated, and the resulting residue was purified by intermediate pressure silica gel column chromatography (silica gel 80 g, ethyl acetate 100%) to give 8.41 g of the desired product as white crystals.

$^1$H NMR (CDCl$_3$, Me$_4$Si, 300 MHz) δ7.20-7.30 (m, 3H), 7.16 (d, J=7.1 Hz, 2H), 2.89 (s, 2H), 1.21 (s, 6H)

Step 2

Synthesis of 2,2-dimethyl-3-phenylpropanoyl chloride

To 2,2-dimethyl-3-phenylpropanoic acid (4.0 g, 0.023 mol) thionyl chloride (2.97 g, 0.025 mol) was added in small portions at room temperature, and the resulting solution was stirred at 70° C. for 3 hours, then at room temperature for another 15 hours. The reaction solution was fractionally distilled (113-115° C., 5 mmHg) to give 2.89 g of the desired product as a colorless liquid.

$^1$H NMR (CDCl$_3$, Me$_4$Si, 300 MHz) δ7.20-7.30 (m, 3H), 7.18 (d, J=7.1 Hz, 2H), 2.97 (s, 2H), 1.28 (s, 6H)

Step 3

Synthesis of ethyl 4,4-dimethyl-3-oxo-5-phenylpentanoate

Ethyl 3-oxobutanoate (1.09 g, 8.3 mmol) in methylene chloride (16 mL) was mixed with anhydrous magnesium chloride (158 mg, 1.66 mmol), and the reaction solution was cooled to 0° C., mixed with pyridine (1.34 mL, 16.6 mmol), stirred for 30 minutes, then mixed with 2,2-dimethyl-3-phenylpropanoyl chloride (1.64 g, 8.3 mmol) and stirred for another 30 minutes at the same temperature. The reaction solution was warmed to room temperature and stirred for 20 hours. The methylene chloride was distilled off under reduced pressure, and the residue was with ethanol (2 mL) and at room temperature for 2 days and with toluene (2 mL) at 60° C. for 5 hours. After completion of the reaction, the reaction solution was washed with saturated aqueous sodium hydrogen carbonate and extracted with ethyl acetate (50 mL×2). The solvent was removed from the resulting organic layer under reduced pressure, and the resulting brown oil was purified by intermediate pressure silica gel column chromatography (silica gel 12 g, ethyl acetate:hexane=1:19 to 1:9) to give 370 mg of the desired product as a light brown oil.

$^1$H NMR (CDCl$_3$, Me$_4$Si, 300 MHz) δ7.18-7.32 (m, 3H), 7.10 (d, J=7.1 Hz, 2H), 4.18 (q, J=7.1 Hz, 3H), 3.46 (s, 2H), 2.83 (s, 2H), 1.29 (t, J=7.1 Hz, 3H), 1.15 (s, 6H)

Step 4

Synthesis of 3-(2-methyl-1-phenylpropan-2-yl)-1-(2-phenylpropan-2-yl)-1H-pyrazol-5(4H)-one (Compound No. 3-04 of the Present Invention)

tert-Butyl 2-(2-phenylpropan-2-yl)hydrazinecarboxylate (250 mg, 1.00 mmol) was dissolved in methylene chloride (2 mL), mixed with p-toluenesulfonic acid monohydrate (0.40 g, 2.1 mmol) and stirred at room temperature for 16 hours. After the stirring, the reaction solution was washed with saturated aqueous sodium hydrogen carbonate to terminate the reaction and then separated. The organic layer was washed with saturated aqueous sodium chloride, dried over anhydrous sodium sulfate and filtered, and the filtrate was concentrated under reduced pressure. The resulting residue was dissolved in toluene (3.0 mL) and acetic acid (70 μL), and mixed with ethyl 4,4-dimethyl-3-oxo-5-phenylpentanoate (248 mg, 1.00 mmol) and stirred at 90° C. for 3 hours. After completion of the reaction, the reaction solution was cooled to room temperature and mixed with ethyl acetate. The resulting organic layer was washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel 12 g, ethyl acetate: hexane=1:9 to 3:7) to give 42 mg of the desired product as a brown oil.

$^1$H NMR (CDCl$_3$, Me$_4$Si, 300 MHz) δ7.15-7.34 (m, 8H), 6.98-7.10 (m, 2H), 3.08 (s, 2H), 2.79 (s, 2H)., 1.84 (s, 6H), 1.18 (s, 6H)

Synthetic Example 4

Synthesis of 5-methoxy-3-phenyl-1-(2-phenylpropan-2-yl)-1H-pyrazole (Compound No. 3-13 of the Present Invention) and 5-methoxy-4-methyl-3-phenyl-1-(2-phenylpropan-2-yl)-1H-pyrazole (Compound No. 3-14 of the Present Invention)

3-Phenyl-1-(2-phenylpropan-2-yl)-1H-pyrazol-5-ol (83 mg, 0.30 mmol) was dissolved in N,N-dimethylformamide (3.0 mL), and 55 wt % sodium hydride (suspended in mineral oil) (26 mg, 0.60 mmol) was added at room temperature. After 1 hour of stirring at room temperature, methyl iodide (18 μL, 0.30 mmol) was added dropwise, and the reaction solution was stirred at the same temperature for 18 hours. The reaction was quenched with water, and the reaction solution was extracted with ethyl acetate (10 mL×2). The organic layer was washed with saturated aqueous sodium chloride (10 mL) and dried over anhydrous sodium sulfate and concentrated under reduced pressure. The resulting residue was purified by intermediate pressure silica gel column chromatography (silica gel 12 g, hexane 100%) to give 35 mg of 5-methoxy-3-phenyl-1-(2-phenylpropan-2-yl)-1H-pyrazole as a colorless solid and 10 mg of 5-methoxy-4-methyl-3-phenyl-1-(2-phenylpropan-2-yl)-1H-pyrazole as a colorless oil, respectively.

5-methoxy-3-phenyl-1-(2-phenylpropan-2-yl)-1H-pyrazole $^1$H NMR (CDCl$_3$, Me$_4$Si, 300 MHz) δ7.83 (d, J=7.4 Hz, 2H), 7.38 (t, J=7.4 Hz, 2H), 7.15-7.33 (m, 4H), 7.08 (d, J=7.1 Hz, 2H), 5.91 (s, 1H), 3.60 (s, 3H), 1.98 (s, 6H) 5-methoxy-4-methyl-3-phenyl-1-(2-phenylpropan-2-yl)-1H-pyrazole $^1$H NMR (CDCl$_3$, Me$_4$Si, 300 MHz)67.73 (d, J=7.4 Hz, 2H), 7.41 (t, J=7.4 Hz, 2H), 7.16-7.36 (m, 4H), 3.16 (s, 3H), 2.10 (s, 3H), 1.98 (s, 6H)

Synthetic Example 5

Synthesis of 1-(1-(4-bromophenyl)-2-methylpropan-2-yl)-3-isopropyl-1H-pyrazol-5(4H)-one (Compound No. 3-12 of the Present Invention)

To 1-(2,2-dimethyl-1,1-diphenylpropyl)-2-(propan-2-ylidene)hydrazine (147 mg, 0.500 mmol) in tetrahydrofuran (5 mL), 1.61 M n-butyllithium in hexane (0.37 mL, 0.60 mmol) was added dropwise at −78° C., and after 1 hour of stirring at the same temperature, p-bromobenzyl bromide (125 mg, 0.50 mmol) was added dropwise. The reaction solution was stirred at the same temperature for 1 hour, warmed to room temperature and stirred at room temperature for 18 hours. The reaction solution was quenched with saturated aqueous sodium hydrogen carbonate and extracted with ethyl acetate (10 mL×3). The resulting organic layer was concentrated under reduced pressure, and the resulting residue was dissolved in 2 mL of ethanol, mixed with trifluoroacetic acid (1 mL) and stirred at room temperature for 24 hours. After the stirring, the reaction solution was mixed with concentrated hydrochloric acid (3 mL) and stirred at 80° C. for 5 hours. After the stirring, the reaction solution was neutralized with saturated aqueous sodium hydrogen carbonate and extracted with methylene chloride. The resulting organic layer was washed with saturated aqueous sodium chloride, dried over anhydrous sodium sulfate and filtered, and the filtrate was concentrated under reduced pressure. The resulting residue was dissolved in toluene (3.0 mL) and acetic acid (70 μL), mixed with methyl isobutyrylacetic acid (72 mg, 0.50 mmol) and stirred at 90° C. for 3 hours. The reaction solution was allowed to cool to room temperature, diluted with ethyl acetate and washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel12 g, ethyl acetate:hexane=1:9 to 3:7) to give 15 mg of the desired product as a brown oil.

$^1$H NMR (CDCl$_3$, Me$_4$Si, 300 MHz) δ7.35 (d, J=8.6 Hz, 2H), 6.98 (d, J=8.6 Hz, 2H), 3.14 (s, 2H), 3.06 (s, 2H), 2.59 (sep, J=6.8 Hz, 1H), 1.50 (s, 6H), 1.10 (d, J=7.1 Hz, 6H)

Synthetic Example 6

Synthesis of ethyl 5-hydroxy-3-isopropyl-1-(2-phenylpropan-2-yl)-1H-pyrazole-4-carboxylate (Compound No. 4-27 of the Present Invention)

3-Isopropyl-1-(2-phenylpropan-2-yl)-1H-pyrazol-5(4H)-one (1.22 g, 5.00 mmol) and calcium hydroxide (435 mg, 7.50 mmol) were suspended in dioxane (20 mL), heated to 45° C. and stirred for 1 hour. After the stirring, the reaction solution was allowed to cool to room temperature, and after dropwise addition of ethyl chloroformate (597 mg, 5.50 mmol), stirred at 90° C. for 6 hours. After completion of the reaction, the resulting light brown suspension was poured into ice-cold 3 M hydrochloric acid and extracted with chloroform (20 mL×5). The resulting organic layer was washed with 0.06 M hydrochloric acid (50 mL×2), dried over anhydrous sodium sulfate and filtered, and the filtrate was concentrated under reduced pressure. The resulting residue was purified by intermediate pressure silica gel column chromatography (silica gel 40 g, ethyl acetate:hexane=1:19 to 1:9) to give 650 mg of the desired product as a yellow oil.

$^1$H NMR (CDCl$_3$, Me$_4$Si, 300 MHz) δ9.71 (s, 1H), 7.13-7.33 (m, 3H)., 7.05-7.12 (m, 2H), 4.31 (q, J=7.1 Hz, 2H), 3.23 (sep, J=6.9 Hz, 1H), 1.94 (s, 6H), 1.36 (t, 7.3 Hz, 3H), 1.30 (d, J=6.8 Hz, 6H)

Synthetic Example 7

Synthesis of methyl 2-(5-oxo-1-(2-phenylpropan-2-yl)-4,5-dihydro-1H-pyrazol-3-yl)acetate (Compound No. 4-01 of the Present Invention)

tert-Butyl 2-(2-phenylpropan-2-yl)hydrazinecarboxylate (250 mg, 1.00 mmol) was dissolved in methylene chloride (2 mL), mixed with p-toluenesulfonic acid monohydrate (0.40 g, 2.1 mmol) and stirred at room temperature for 18 hours. The reaction solution was basified with saturated aqueous sodium hydrogen carbonate and separated. The organic layer was washed with saturated aqueous sodium chloride, dried over anhydrous sodium sulfate and filtered, and the filtrate was concentrated under reduced pressure. The resulting residue was dissolved in toluene (2.0 mL) and acetic acid (70 μL), mixed with dimethyl 1,3-acetonedicarboxylate (174 mg, 1.00 mmol) and stirred at 90° C. for 3 hours and at 105° C. for 3 hours. After completion of the reaction, the reaction solution was allowed to cool to room temperature and diluted with ethyl acetate. The organic layer was washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel12 g, ethyl acetate:hexane=1:9 to 3:7) to give 96.3 mg of the desired product as a white solid.

$^1$H NMR (CDCl$_3$, Me$_4$Si, 300 MHz) δ7.18-7.34 (m, 5H), 3.75 (s, 3H), 3.48 (s, 2H), 3.41 (s, 2H), 1.87 (s, 6H)

Synthetic Example 8

Synthesis of 4-bromo-3-isopropyl-1-(2-methyl-1-phenylpropan-2-yl)-1H-pyrazol-5(4H)-one (Compound No. 3-47 of the Present Invention)

3-Isopropyl-1-(2-methyl-1-phenylpropan-2-yl)-1H-pyrazol-5(4H)-one (1.2 g, 4.6 mmol) was dissolved in N,N-dimethylformamide (35 mL), mixed with N,N-bromosuccinimide (908 mg, 5.10 mmol) and stirred at room temperature for 30 minutes. The reaction solution was extracted with ethyl acetate. The organic layer was dried over anhydrous magnesium sulfate and filtered, and the filtrate was concentrated under reduced pressure. The resulting residue was purified by suspending in hexane to give 1.26 g of the desired product as a pale blue solid.

$^1$H NMR (CDCl$_3$, Me$_4$Si, 300 MHz) δ7.06-7.29 (m, 5H), 4.64 (s, 1H), 3.12 (d, J=13.4 Hz, 1H), 3.03 (d, J=13.4 Hz, 1H), 2.73-2.88 (m, 1H), 1.53 (s, 3H), 1.52 (s, 3H), 1.16 (d, J=6.9 Hz, 3H), 1.13 (d, J=7.2 Hz, 3H)

Synthetic Example 9

Synthesis of methyl 4-(5-hydroxy-3-isopropyl-1-(2-methyl-1-phenylpropan-2-yl)-1H-pyrazol-4-yl)benzoate (Compound No. 4-23 of the Present Invention)

4-Bromo-3-isopropyl-1-(2-methyl-1-phenylpropan-2-yl)-1H-pyrazol-5-yl benzoate (360 mg, 0.82 mmol) in 1,2-dimethoxyethane (4.8 ml) was mixed with 4-(methoxycarbonyl)phenylboronic acid (164 mg, 0.911 mmol), tetrakis(triphenylphosphine)palladium (80 mg, 0.07 mmol) and 2 M aqueous sodium carbonate (3.6 ml) and stirred at 86° C. for 16 hours under a nitrogen atmosphere. After completion of the reaction, the 1,2-dimethoxyethane was distilled off under reduced pressure, and the reaction solution was extracted with dichloromethane. The organic layer was dried over anhydrous magnesium sulfate and filtered, and the filtrate was purified by intermediate pressure silica gel column chromatography (silica gel 12 g, ethyl acetate:hexane=1:20 to 1:4) to give 100 mg of the desired product as a pale yellow solid mixture of tautomers.

$^1$H NMR (CDCl$_3$, Me$_4$Si, 300 MHz) δ8.0-8.1 (m, 2H), 7.6-7.7 (m, 2H), 7.15-7.3 (m, 3H), 7.05-7.15 (m, 2H), 6.37 (br, 1H), 3.92 (s, 3H), 3.27 (s, 2H), 3.12-3.19 (m, 1H), 1.65 (s, 6H), 1.08 (d, J=7.2 Hz, 6H)

$^1$H NMR (CDCl$_3$, Me$_4$Si, 300 MHz) δ8.0-8.1 (m, 2H), 7.6-7.7 (m, 2H), 7.15-7.3 (m, 3H), 7.05-7.15 (m, 2H), 4.2-4.3 (m, 1H), 3.92 (s, 3H), 3.1-3.2 (m, 2H), 2.35-2.5 (m, 1H), 1.65 (s, 6H), 0.95-1.05 (m, 6H)

Synthetic Example 10

Synthesis of (5-hydroxy-3-isopropyl-1-(2-methyl-1-phenylpropan-2-yl)-1H-pyrazol-4-yl)(phenyl)methanone (Compound No. 4-71 of the Present Invention)

Step 1

Synthesis of 4-bromo-3-isopropyl-1-(2-methyl-1-phenylpropan-2-yl)-1H-pyrazol-5-yl benzoate 4-Bromo-3-isopropyl-1-(2-methyl-1-phenylpropan-2-yl)-1H-pyrazol-5(4H)-one (3.00 g, 8.90 mmol) was dissolved in 39 mL of tetrahydrofuran and cooled with ice to 0° C., and after dropwise addition of 1.80 g (17.8 mmol) of triethylamine and 1.38 g (9.82 mmol) of benzoyl chloride, stirred at room temperature for 3 hours under a nitrogen atmosphere. The reaction was quenched with distilled water, and the reaction solution was extracted with ethyl acetate. The organic layer was dried over anhydrous sodium sulfate and filtered, and the filtrate was concentrated under reduced pressure. The resulting residue was purified by silica gel column chromatography (silica gel 12 g, ethyl acetate:hexane=1:20) to give 3.34 g of the desired product as a yellow oil.

$^1$H NMR (CDCl$_3$, Me$_4$Si, 300 MHz) δ7.98-8.05 (m, 2H), 7.62-7.70 (m, 1H), 7.44-7.56 (m, 2H), 7.18-7.26 (m, 3H), 6.78-6.88 (m, 2H), 3.07 (s, 2H), 2.92-3.06 (m, 1H), 1.56 (s, 6H), 1.29 (d, J=6.9 Hz, 6H)

Step 2

Synthesis of (5-hydroxy-3-isopropyl-1-(2-methyl-1-phenylpropan-2-yl)-1H-pyrazol-4-yl)(phenyl)methanone (Compound No 4-71 of the Present Invention)

1.60 g (3.63 mmol) of 4-bromo-3-isopropyl-1-(2-methyl-1-phenylpropan-2-yl)-1H-pyrazol-5-yl benzoate was dissolved in 16 mL of tetrahydrofuran and cooled with a coolant (acetone/dry ice) to −60° C., and after dropwise addition of 2.60 ml (4.24 mmol) of 1.63 M n-butyllithium in n-hexane, stirred at 72° C. for 4 hours under a nitrogen atmoephere. The reaction was quenched with distilled water, and the reaction solution was extracted with ethyl acetate. The organic layer was dried over anhydrous magnesium sulfate and filtered, and the filtrate was concentrated under reduced pressure. The resulting residue was purified by silica gel column chromatography (silica gel 12 g, ethyl acetate:hexane=1:20) to give 520 mg of the desired product as a yellow oil.

$^1$H NMR (CDCl$_3$, Me$_4$Si, 300 MHz) δ7.15-7.63 (m, 8H), 6.90-6.98 (m, 2H), 3.17 (s, 2H), 2.60-2.74 (m, 1H), 1.64 (s, 6H), 0.96 (d, J=6.9 Hz, 6H)

Synthetic Example 11

4-(4-Hexylphenyl)-5-hydroxy-1-(2-methyl-1-(p-tolyl)propan-2-yl)-1H-pyrazole-3-carbonitrile (Compound No. 4-86 of the Present Invention)

Step 1

Synthesis of ethyl 4-(4-hexylphenyl)-5-(methoxymethoxy)-1-(2-methyl-1-(p-tolyl)propan-2-yl)-1H-pyrazole-3-carboxylate 152 mg (0.329 mol) of ethyl 4-(4-hexylphenyl)-5-hydroxy-1-(2-methyl-1-(p-tolyl)propan-2-yl)-1H-pyrazole-3-carboxylate was dissolved in 1.6 mL of N,N-dimethylformamide, mixed with 26 mg (0.65 mmol) of 60 wt % sodium hydride (suspended in mineral oil) and 0.050 mL (0.66 mmol) of chloromethyl methyl ether under cooling with ice successively and stirred at room temperature for 3 hours. After completion of the reaction, the reaction mixture was diluted with diethyl ether and washed with 1 M hydrochloric acid, with saturated aqueous sodium hydrogen carbonateand with saturated aqueous sodium chloride successively. The organic layer was dried over anhydrous sodium sulfate and filtered, and the filtrate was concentrated under reduced pressure to give the desired product (crude yield 174 mg).

Step 2

Synthesis of 4-(4-hexylphenyl)-5-(methoxymethoxy)-1-(2-methyl-1-(p-tolyl)propan-2-yl)-1H-pyrazole-3-carboxylic acid Ethyl 4-(4-hexylphenyl)-5-(methoxymethoxy)-1-(2-methyl-1-(p-tolyl)propan-2-yl)-1H-pyrazole-3-carboxylate (138 mg) was dissolved in 2 mL of tetrahydrofuran and 0.7 mL of methanol, mixed with 0.27 mL (1.4 mmol) of 5 M aqueous sodium hydroxide and stirred at room temperature for 20 hours. After completion of the reaction, the reaction mixture was diluted with methylene chloride and washed with saturated aqueous ammonium chloride. The organic layer was dried over anhydrous sodium sulfate and filtered, and the filtrate was concentrated under reduced pressure to give the desired product (crude yield 142 mg).

Step 3

Synthesis of 4-(4-hexylphenyl)-5-(methoxymethoxy)-1-(2-methyl-1-(p-tolyl)propan-2-yl-1H-pyrazole-3-carboxamide 4-(4-Hexylphenyl)-5-(methoxymethoxy)-1-(2-methyl-1-(p-tolyl)propan-2-yl)-1H-pyrazole-3-carboxylic acid (142 mg) was dissolved in 1.4 mL of ethanol and mixed with 125 mg (0.407 mmol) of (4.6-dimethoxy-1,3,5-triazin-2-yl)-4-methylmorphlinium chloride with a 90% purity. The reaction solution was stirred at room temperature for 30 minutes and stirred with 0.54 mL (1.1 mmol) of 2 M ammonia in ethanol for 1.5 hours. After completion of the reaction, the solvent was distilled off under reduced pressure, and ethyl acetate was added. The organic layer was washed with saturated aqueous sodium hydrogen carbonate and with saturated aqueous sodium chloride successively, dried over anhydrous sodium sulfate and filtered, and the filtrate was concentrated under reduced pressure to give Compound 5 (crude yield 171 mg) as a white amorphous substance.

Step 4

Synthesis of 4-(4-hexylphenyl)-5-(methoxymethoxy)-1-(2-methyl-1-(p-tolyl)propan-2-yl)-1H-pyrazole-3-carbonitrile 171 mg of 4-(4-hexylphenyl)-5-(methoxymethoxy)-1-(2-methyl-1-(p-tolyl)propan-2-yl)-1H-pyrazole-3-carboxamide was dissolved in 2 mL of methylene chloride and mixed with 0.3 mL (2 mmol) of triethylamine. The reaction solution was cooled to 0° C. in an ice bath, and after dropwise addition of 0.080 mL (0.72 mmol) of trichloroacetyl chloride at room temperature for 1.5 hours. After completion of the reaction, the reaction mixture was mixed with methylene chloride and washed with saturated aqueous sodium hydrogen carbonate and with saturated aqueous sodium chloride successively. The organic layer was dried over anhydrous sodium sulfate and filtered, and the filtrate was concentrated under reduced pressure to give the desired product (crude yield 266 mg).

Step 5

Synthesis of 4-(4-hexylphenyl)-5-hydroxy-1-(2-methyl-1-(p-tolyl)propan-2-yl)-1H-pyrazole-3-carbonitrile (Compound No. 4-86 of the Present Invention)

266 mg of 4-(4-hexylphenyl)-5-(methoxymethoxy)-1-(2-methyl-1-(p-tolyl)propan-2-yl)-1H-pyrazole-3-carbonitrile was dissolved in 4 mL of tetrahydrofuran and 0.8 mL of methanol, mixed with 4 M hydrochloric acid in dioxane (0.70 mL, 2.8 mmol) and stirred at room temperature for 14 hours. After completion of the reaction, the solvent was partly distilled off under reduced pressure, and the crystals precipitated in the reaction mixture were separated by filtration and washed with isopropyl ether. The filtrate was combined with the isopropyl ether washing and concentrated under reduced pressure, and the resulting residue was purified by intermediate pressure silica gel column chromatography (silica gel 10 g, ethyl acetate:hexane=0:100 to 20:80) to give 88.1 mg of the desired product as a white solid.

m.p. 140-142° C.

Synthetice Example 12

1-(5-Hydroxy-3-isopropyl-1-(2-methyl-1-phenylpropan-2-yl)-1H-pyrazol-4-yl)ethanone O-methyl oxime (Compound No. 4-89 of the Present Invention)

150 mg (0.50 mmol) of 1-(5-hydroxy-3-isopropyl-1-(2-methyl-1-phenylpropan-2-yl)-1H-pyrazol-4-yl)ethanone, 209 mg (2.50 mmol) of methoxyamine hydrochloride and 286 mg (3.49 mmol) of sodium acetate were mixed with 1.3 ml of distilled water and 1.3 ml of ethanol and stirred at room temperature for 16 hours. After completion of the reaction, the reaction solution was extracted with ethyl acetate. The organic layer was dried over anhydrous magnesium sulfate and filtered, and the filtrate was concentrated under reduced pressure. The resulting residue was purified by silica gel column chromatography (silica gel 4 g, ethyl acetate:hexane=1:99) to give 70 mg of the desired product as an orange oil.

$^1$H NMR (CDCl$_3$, Me$_4$Si, 300 MHz) δ7.12-7.22 (m, 3H), 6.84-6.95 (m, 2H), 3.87 (s, 3H), 3.16 (s, 2H), 2.98-3.12 (m, 1H), 2.25 (s, 3H), 1.57 (s, 6H), 1.21 (d, J=6.8 Hz, 6H)

Synthetic Example 13

4-(4-Hexylphenyl)-1-(2-methyl-1-(p-tolyl)propan-2-yl)-1H-pyrazol-5-ol (Compound No. 4-90 of the Present Invention)

Step 1

Synthesis of ethyl 3-(dimethylamino)-2-(4-hexylphenyl)acrylate 0.50 g (2.0 mmol) of ethyl 2-(4-hexylphenyl)acetate was dissolved in 7 mL of N,N-dimethylformamide, mixed with 0.31 mL (2.3 mmol) of N,N-dimethylformamide dimethyl acetal and stirred at 60° C. for 18 hours. After the stirring, the reaction mixture was further mixed with 0.65 mL (4.9 mmol) of N,N-dimethylformamide dimethyl acetal and stirred at 60° C. for 24 hours. After completion of the reaction, the reaction mixture was diluted with diethyl ether and washed with saturated aqueous sodium hydrogen carbonate and with saturated aqueous sodium chloride successively. The organic layer was dried over anhydrous sodium sulfate and filtered, and the filtrate was concentrated under reduced pressure to give the desired product as a brown liquid.

Step 2

Synthesis of 4-(4-hexylphenyl)-1-(2-methyl-1-(p-tolyl)propan-2-yl)-1H-pyrazol-5-ol (Compound No. 4-90 of the Present Invention)

Ethyl 3-(dimethylamino)-2-(4-hexylphenyl)acrylate and 0.50 g (1.8 mmol) of tert-butyl 2-(2-methyl-1-(p-tolyl)propan-2-yl)hydrazinecarboxylate were dissolved in 2 mL of acetic acid and stirred at 90° C. for 24 hours. After the stirring, the reaction mixture was mixed with 0.5 mL of acetic acid and stirred for 48 hours. After completion of the reaction, the reaction mixture was cooled to room temperature, diluted with diethyl ether and washed with distilled water, with saturated aqueous sodium hydrogen carbonate and with saturated aqueous sodium chloride successively. The organic layer was dried over anhydrous sodium sulfate and filtered, and the filtrate was concentrated under reduced pressure. The resulting residue was purified by intermediate pressure silica gel column chromatography (silica gel 30 g, ethyl acetate:hexane=0:100 to 35:65). The resulting solid was washed with isopropyl ether to give 164 mg of the desired product as a white solid.

m.p. 149-151° C.

Synthetic Example 14

Synthesis of tert-butyl 2-(2-methyl-1-(4-(trifluoromethyl)phenyl)propan-2-yl)hydrazinecarboxylate Step 1

Synthesis of 1-(2-azido-2-methylpropyl)-4-(trifluoromethyl)benzene 25 g (0.12 mol) of 4-trifluoromethylphenyl acetate was mixed with 300 mL of ethanol and concentrated sulfuric acid (95%, 5 mL) and stirred at 40° C. for 16 hours. After completion of the reaction, ethanol was distilled off under reduced pressure, and the reaction solution was diluted wiht ethyl acetate and washed with distilled water, with saturated aqueous sodium hydrogen carbonate and with saturated aqueous sodium chloride successively. The organic layer was dried over anhydrous sodium sulfate and filtered, and the filtrate was concentrated under reduced pressure to give 27.9 g of crude ethyl 2-(4-(trifluoromethyl)phenyl)acetate.

27.9 g of ethyl 2-(4-(trifluoromethyl)phenyl)acetate was dissolved in 150 mL of dry tetrahydrofuran, and 280 mL (0.28 mol) of 0.99 M methylmagnesium bromide in tetrahydrofuran was added dropwise under cooling with ice under a nitrogen atmosphere. The reaction mixture was stirred at room temperature for 2 hours, and after the stirring, the reaction was quenched with distilled water. The organic layer was washed with 1 M hydrochloric acid, with saturated aqueous sodium hydrogen carbonate and with saturated aqueous sodium chloride successively, dried over anhydrous sodium sulfate and filtered, and the filtrate was concentrated under reduced pressure to give 26.3 g of crude 2-methyl-1-(4-(trifluoromethyl)phenyl)propan-2-ol.

26.3 g of 2-methyl-1-(4-(trifluoromethyl)phenyl)propan-2-ol was dissolved in 400 mL of methylene chloride, and 25 mL (0.19 mol) of trimethylsilyl azide and 24 mL (0.19 mol) of boron trifluoride diethyl ether complex were added dropwise under cooling with ice. The reaction mixture was stirred at room temperature for 20 hours. After completion of the reaction, the reaction mixture was washed with saturated aqueous sodium hydrogen carbonate and with saturated aqueous sodium chloride successively, dried over anhydrous sodium sulfate and filtered, and the filtrate was concentrated under reduced pressure to give 25.4 g of the desired product.

Step 2

Synthesis of 2-methyl-1-(4-(trifluoromethyl)phenyl)propan-2-amine 25.4 g of 1-(2-azido-2-methylpropyl)-4-(trifluoromethyl)benzene was dissolved in 210 mL of ethyl acetate and mixed with 0.84 g of 20 wt % palladium hydroxide carbon. The atmosphere in the reaction vessel was replaced with hydrogen gas, and the reaction solution was stirred at room temperature for 18 hours. After completion of the reaction, the palladium hydroxide carbon was filtered off, and the filtrate was mixed with 3 M hydrochloric acid and separated. The aqueous layer was basified with 5 M sodium hydroxide and extracted with methylene chloride. The organic layer was concentrated under reduced pressure to give 4.27 g of the desired product as a brown liquid.

$^1$H NMR (CDCl$_3$, Me$_4$Si, 300 MHz) δ7.56 (d, J=8.3 Hz, 2H), 7.31 (d, J=8.1 Hz, 2H), 2.72 (s, 2H), 1.2-1.5 (m, 2H), 1.32 (s, 6H)

Step 3

Synthesis of tert-butyl 2-(2-methyl-1-(4-(trifluoromethyl)phenyl)propan-2-yl)hydrazinecarboxylate 4.2 g of 2-methyl-1-(4-(trifluoromethyl)phenyl)propan-2-amine was dissolved in 30 mL of methylene chloride and mixed with 5.6 g (21 mmol) of separately prepared t-butyl 3-(trichloromethyl)-1,2-oxaziridine-2-carboxylate under cooling with ice. The reaction solution was stirred at room temperature for 30 minutes, washed with 10% aqueous citric acid, with saturated aqueous sodium hydrogen carbonate and with saturated aqueous sodium chloride successively and dried over anhydrous sodium sulfate, and methylene chloride was removed under reduced pressure. The resulting residue was purified by intermediate pressure silica gel column chromatography (silica gel 100 g, ethyl acetate:hexane) to give 1.38 g of the desired product as a white solid.

$^1$H NMR (CDCl$_3$, Me$_4$Si, 300 MHz) δ7.54 (d, J=8.3 Hz, 2H), 7.30 (d, J=8.2 Hz, 2H), 5.8-6.0 (m, 1H), 2.74 (s, 2H), 1.46 (s, 9H), 1.4-1.5 (m, 1H), 1.03 (s, 6H)

Synthetic Example 15

Synthesis of tert-butyl 2-(1-benzylcyclopropyl)hydrazinecarboxylate

Step 1

Synthesis of 1-benzylcyclopropanamine 4.5 g (38 mmol) of phenylacetonitrile was dissolved in 50 mL of tetrahydrofuran, mixed with 12.4 mL (41.9 mmol) of tetraisopropyl propylorthotitanate and 78 mL (76 mmol) of 0.98M ethylmagnesium bromide in tetrahydrofuran and stirred at room temperature for 1 hour. After the stirring, 9.6 mL (78 mmol) of boron trifluoride ethyl ether complex was added, and the reaction solution was stirred at room temperature for another 1 hour. After completion of the reaction, 2 M aqueous sodium hydroxide was added, and the reaction solution was extracted with diethyl ether. After addition of 3 M hydrochloric acid, the organic layer was separated. The resulting aqueous layer was basified with 5 M aqueous sodium hydroxide and extracted with methylene chloride. The solvent was removed from the organic layer under reduced pressure to give 3.28 g of the desired product.

$^1$H NMR (CDCl$_3$, Me$_4$Si, 300 MHz) δ7.2-7.4 (m, 5H), 2.75 (s, 2H), 1.4-1.6 (m, 2H), 0.6-0.7 (m, 4H)

Step 2

Synthesis of tert-butyl 2-(1-benzylcyclopropyl)hydrazinecarboxylate 10.6 g (72.0 mmol) of 1-benzylcyclopropanamine was dissolved in 90 mL of methylene chloride, mixed with 14.3 g (54.5 mmol) of separately prepared t-butyl 3-(trichloromethyl)-1,2-oxaziridine-2-carboxylate under cooling with ice, and stirred at room temperature for 30 minutes. After completion of the reaction, methylene chloride was distilled off under reduced pressure, and the resulting residue was purified by silica gel column chromatography (silica gel 350 g, ethyl acetate:hexane=1:20) to give 4.6 g of the desired product as a brown solid.

$^1$H NMR (CDCl$_3$, Me$_4$Si, 300 MHz) δ7.2-7.4 (m, 5H), 5.8-6.0 (m, 1H), 3.9-4.2 (m, 1H), 2.87 (s, 2H), 1.45 (s, 9H), 0.75-0.85 (m, 2H), 0.5-0.55 (m, 2H)

Synthetic Example 16

Synthesis of tert-butyl 2-(3-benzylpentan-3-yl)hydrazinecarboxylate

Step 1

Synthesis of 3-benzylpentan-3-amine 3.0 g (26 mmol) of phenylacetonitrile was dissolved in 50 mL of tetrahydrofuran and mixed with 8.3 mL (28 mmol) fo titanium isopropoxide, and 115 mL (104 mmol) of 0.90 Methylmagnesium bromide in tetrahydrofuran was added dropwise under a nitrogen atmosphere. After 1 hour of stirring, the reaction was quenched by adding water dropwise under cooling with ice. The reaction mixture was diluted with ethyl acetate and separated. After addition of 1 M hydrochloric acid, the organic layer was separated. The aqueous layer was basified with 5 M aqueous sodium hydroxide and extracted with methylene chloride. The methylene chloride layer was concentrated under reduced pressure to give the desired product (crude yield 2.68 g).

$^1$H NMR (CDCl$_3$, Me$_4$Si, 300 MHz) δ7.1-7.5 (m, 5H), 2.64 (s, 2H), 1.2-1.5 (m, 6H), 0.91 (t, J=7.5 Hz, 6H)

Step 2

Synthesis of tert-butyl 2-(3-benzylpentan-3-yl)hydrazinecarboxylate 2.68 g of 3-benzylpentan-3-amine was dissolved in 20 mL of methylene chloride, mixed with 4.8 g (18 mmol) of separately prepared t-butyl 3-(trichloromethyl)-1,2-oxaziridine-2-carboxylate under cooling with ice and stirred at room temperature for 30 mitues, and the reaction solution was washed with 10% aquoeous citric acid, with saturated aqueous sodium hydrogen carbonate and with saturated aqueous sodium chloride successively and dried over anhydrous sodium sulfate, and methylene chloride was removed under reduced pressure. The resulting residue was purified by intermediate pressure silica gel column chromatography (silica gel 30 g, ethyl acetate:hexane=0:100 to 20:80) to give 1.62 g of the desired product as a light brown solid.

$^1$H NMR (CDCl$_3$, Me$_4$Si, 300 MHz) δ7.1-7.4 (m, 5H), 5.5-5.7 (br, 1H), 3.6-3.8 (Br, 1H), 2.66 (s, 2H), 1.55 (s, 9H), 1.3-1.5 (m, 4H), 0.93 (t, J=7.5 Hz, 6H)

Synthetic Example 17

Synthesis of ethyl 2-(furan-2-yl)-4-methyl-3-oxopentanoate

Step 1

Synthesis of 2-(furan-2-yl)acetic acid 25 g (0.25 mmol) of furfuryl alcohol was dissloved in 250 mL of tetrahydrofuran, mixed with 8.7 mL of phosphorus tribromide under cooling with ice and stirred at the same temperature for 90 minutes. After completion of the reaction, the reaction solution was diluted with diethyl ether and washed with distilled water, and the organic layer was washed with saturated aqueous sodium hydrogen carbonate and with saturated aqueous sodium chloride successively, dried over anhydrous magnesium sulfate and filtered. The filtrate was concentrated under reduced pressure to give crude 2-(bromomethyl)furan.

2-(Bromomethyl)furan was dissolved in 125 mL of N,N-dimethylformaide, mixed with 13.7 g (0.280 mmol) of sodium cyanide and stirred at room temperature for 11 hours. After the stirring, the reaction solution was mixed with 100 mL of N,N-dimethylformamide and 13.7 g (0.280 mmol) of sodium cyanide and stirred for another 8 hours. After completion of the reaction, the reaction solution was diluted with diethyl ether and washed with distilled water. The organic layer was washed with saturated aqueous sodium hydrogen carbonate and with saturated aqueous sodium chloride, dried over anhydrous sodium sulfate and filtered, and the filtrate was concentrated under reduced pressure to give crude 2-(furan-2-yl)acetonitrile.

2-(Furan-2-yl)acetonitrile was suspended in 300 mL of distilled water, mixed with 50 g (0.89 mmol) of potassium hydroxide and heated for 4 hours under reflux. After completion of the reaction, the reaction solution was diluted with diethyl ether and separated. The resulting aqueous layer was acidified with concentrated hydrochloric acid and extracted with ethyl acetate. The organic layer was washed with saturated aqueous sodium chloride, dried over anhydrous magnesium sulfate and filterd, and the filtrate was concentrated under reduced pressure to give 25.2 g of the desired product.

Step 2

Synthesis of ethyl 2-(furan-2-yl)acetate 24.8 g of 2-(furan-2-yl)acetic acid was dissolved in 590 mL of N,N-dimethylformamide and mixed with 32.6 g (0.236 mol) of potassium carbonate and 6.42 g (19.7 mmol) cesium carbonate successively. The reaction mixture was further mixed with 19 mL (0.24 mol) of iodoethane under cooling with ice and stirred at room temperature for 14 hours. After completion of the reaction, the reaction mixture was diluted with distilled water and extracted with ethyl acetate. The organic layer was washed with saturated aqueous sodium chloride, dried over anhydrous sodium sulfate and filtered, and the filtrate was concentrated under reduced pressure to give 17.0 g of the desired product as a brown liquid.

Step 3

Synthesis of ethyl 2-(furan-2-yl)-4-methyl-3-oxopentanoate

To 60 mL of tetrahydrofuran and 9.3 mL (66 mmol) of diisopropylamine, 38 mL (60 mmol) of 1.57 M n-butyllithium in n-hexane was added dropwise under a nitrogen atmosphere under cooling with ice, and the reaction mixture was warmed to room temperature and stirred for 30 minutes. After the stirring, the reaction mixture was cooled to −78° C., and after dropwise addition of 4.62 g (30.0 mmol) of ethyl 2-(furan-2-yl)acetate, stirred at the same temperature for 1 hour. After the stirring, 3.8 mL (36 mmol) of isobutyryl chloride was added at −78° C., and the reaction mixture was gradually warmed and then stirred at room temperature for 15 hours. After completion of the reaction, the reaction mixture was diluted with saturated aqueous ammonium chloride under cooling with ice and extracted with ethyl acetate. The organic layer was washed with saturated aqueous sodium hydrogen carbonate and with saturated aqueous sodium chloride successively, dried over anhydrous magnesium sulfate and filtered, and the filtrate was concentrated under reduced pressure. The resulting residue was purified by intermediate pressure silica gel column chromatography (silica gel 30 g, ethyl acetate:hexane=1:10) to give 22 g of the desired product as an orange liquid.

$^1$H NMR (CDCl$_3$, Me$_4$Si, 300 MHz) δ13.5 (s, 1H), 7.4-7.5 (m, 1H), 6.35-6.45 (m, 1H), 6.1-6.2 (m, 1H), 4.19 (q, J=7.1 Hz, 2H), 2.4-2.6 (m, 1H), 1.22 (t, J=7.1 Hz, 3H), 1.11 (d, J=6.9 Hz, 6H)

Synthetic Example 18

Synthesis of O-hexylhydroxylamine

Step 1

Synthesis of 2-(hexyloxy)isoindoline-1,3-dione 3.0 g (18 mmol) of N-hydroxysuccinimide was dissolved in 30 mL of N,N-dimethylformamide, mixed with 0.81 g (20 mmol) of 60 wt % sodium hydride (dispersed in mineral oil) under cooling with ice and stirred at room temperature for 30 minutes. After the stirring, 2.8 mL (20 mmol) of bromohexane and 35 mg (0.23 mmol) of sodium iodide were added dropwise successively under cooling with ice, and the reaction mixture was stirred at 70° C. for 20 hours. After completion of the reaction, the reaction mixture was poured into ice-cold water, and the solid precipitated in the reaction mixture was collected by filtration and dried to give 5.82 g of the desired product as a white solid.

Step 2

Synthesis of O-hexylhydroxylamine 5.82 g of 2-(hexyloxy)isoindoline-1,3-dione was dissolved in 95 mL of methanol, mixed with 3.0 mL (62 mmol) of hydrazine monohydrate and stirred at 65° C. for 30 minutes. After completion of the reaction, the solid precipitated in the reaction mixture was collected by filtration and washed with methylene chloride. The filtrate was combined with the methylene chloride washings and concentrated under reduced pressure and distilled by simple distillation (column top 110° C.) to give a mixture of the desired product and hydrazine. The mixture was diluted with diethyl ether, washed with distilled water, dried over anhydrous sodium sulfate and filtered, and the filtrate was concentrated under reduced pressure to give 0.76 g of the desired product as a colorless liquid.

$^1$H NMR (CDCl$_3$, Me$_4$Si, 300 MHz) δ5.84 (s, 2H), 3.49 (t, J=6.6 Hz, 3H), 1.4-1.6 (m, 2H), 1.2-1.4 (m, 6H), 0.86 (t, J=6.6 Hz, 3H)

The compounds of the present invention other than those mentioned above can be obtained in accordance with the previously mentioned processes and the Examples. Compounds obtained in the same manners as in Synthetic Examples 1 and 2 are listed in Tables 16 to 20 together with those obtained in the Examples. However, the present invention is not restricted thereto.

In the Tables, Et denotes ethyl group, and similarly, n-Pr and Pr-n denote normal propyl group, i-Pr and Pr—I denote isopropyl group, c-Pr and Pr-c denote cyclopropyl group, n-Bu and Bu-n denote normal butyl group, s-Bu and Bu-s denote secondary butyl group, i-Bu and Bu—I denote isobutyl group, t-Bu and Bu-t denote t-butyl group, c-Bu and Bu-c denote cyclobutyl group, n-Pen and Pen-n denote normal pentyl group, c-Pen and Pen-c denote cyclopentyl group, n-Hex and Hex-n denote normal hexyl group, c-Hex and Hex-c denote cyclohexyl group, and Ph denotes phenyl group.

In Table 16, Table 17, Table 18, Table 19 and Table 20, "No." means the numbers by which compounds of the present invention are designated.

TABLE 16

| No. | R$^1$ | R$^2$ | R$^3$ | R$^{81}$ |
|---|---|---|---|---|
| 1-01 | CH$_3$ | H | H | H |
| 1-02 | CH$_3$ | CH$_3$ | H | H |
| 1-03 | CH$_3$ | n-Hex | H | H |
| 1-04 | CH$_3$ | PhCH$_2$ | H | H |
| 1-06 | Ph | Ph | H | H |
| 1-07 | n-Pr | Ph | H | H |
| 1-11 | CH$_3$ | Ph | H | H |
| 3-01 | 4-(OCH$_3$)Ph | H | H | H |
| 3-02 | i-Pr | H | H | H |
| 3-03 | Ph | H | H | H |
| 3-04 | 1,1-(CH$_3$)$_2$-2-Ph—Et | H | H | H |
| 3-08 | i-Pr | (4-n-Hex)Ph | H | H |
| 3-13 | Ph | H | CH$_3$ | H |
| 3-14 | Ph | CH$_3$ | CH$_3$ | H |
| 3-27 | c-Pr | (4-n-Hex)Ph | H | H |
| 3-28 | i-Pr | (4-n-Hex)Ph | H | 4-Cl |
| 3-29 | c-Pr | (4-n-Hex)Ph | H | 4-Cl |
| 3-30 | (4-Ph)Ph | (4-n-Hex)Ph | H | 4-Cl |
| 3-31 | (4-Ph)Ph | n-Hex | H | 4-Cl |
| 3-32 | (4-t-Bu)Ph | (4-n-Hex)Ph | H | 4-Cl |
| 4-01 | CH$_2$C(O)OCH$_3$ | H | H | H |
| 4-12 | i-Pr | n-Pr | H | H |
| 4-13 | (4-Ph)Ph | (4-n-Hex)Ph | H | H |
| 4-14 | (4-Ph)Ph | n-Hex | H | H |
| 4-15 | (4-t-Bu)Ph | (4-n-Hex)Ph | H | H |
| 4-16 | (4-t-Bu)Ph | n-Hex | H | H |
| 4-17 | (4-t-Bu)Ph | n-Hex | H | 4-Cl |
| 4-27 | i-Pr | C(O)OEt | H | H |

TABLE 17

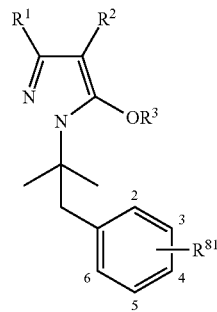

| No. | R¹ | R² | R³ | R⁸¹ |
|---|---|---|---|---|
| 1-12 | CH₃ | Ph | H | H |
| 2-01 | CH₃ | H | H | H |
| 2-02 | CH₃ | CH₃ | H | H |
| 2-03 | CH₃ | n-Hex | H | H |
| 2-04 | CH₃ | PhCH₂ | H | H |
| 2-05 | CF₃ | Ph | H | H |
| 2-06 | Ph | Ph | H | H |
| 2-07 | n-Pr | Ph | H | H |
| 2-09 | i-Pr | Ph | H | H |
| 2-10 | c-Pr | Ph | H | H |
| 2-12 | n-Bu | Ph | H | H |
| 2-14 | (4-CH₃)Ph | Ph | H | H |
| 2-15 | (4-Cl)Ph | Ph | H | H |
| 2-16 | (3,4-(OCH₃)₂)Ph | Ph | H | H |
| 2-18 | pyridin-2-yl | Ph | H | H |
| 2-19 | CH₃ | (4-CH₃)Ph | H | H |
| 2-20 | CH₃ | (2-CH₃)Ph | H | H |
| 2-21 | CH₃ | {3,4-(CH₃)₂}Ph | H | H |
| 2-22 | CH₃ | (4-Ph)Ph | H | H |
| 2-23 | CH₃ | (4-t-Bu)Ph | H | H |
| 2-24 | CH₃ | naphthalen-1-yl | H | H |
| 2-25 | CH₃ | (4-n-Hex)Ph | H | H |
| 2-28 | CH₃ | (4-OCH₃)Ph | H | H |
| 2-29 | CH₃ | benzo[d][1,3]dioxol-5-yl | H | H |
| 2-30 | CH₃ | {4-O(CH₂)₂OEt}Ph | H | H |
| 2-31 | CH₃ | (4-Cl)Ph | H | H |
| 2-32 | CH₃ | (3,4-Cl₂)Ph | H | H |
| 2-33 | CH₃ | thiophen-2-yl | H | H |
| 2-34 | i-Pr | (4-CH₃)Ph | H | H |
| 2-35 | i-Pr | (2-CH₃)Ph | H | H |
| 2-36 | i-Pr | {3,4-(CH₃)₂}Ph | H | H |
| 2-37 | i-Pr | (4-Ph)Ph | H | H |
| 2-38 | i-Pr | (4-t-Bu)Ph | H | H |
| 2-39 | i-Pr | naphthalen-1-yl | H | H |
| 2-40 | i-Pr | (4-n-Hex)Ph | H | H |
| 2-43 | i-Pr | (4-OCH₃)Ph | H | H |
| 2-44 | i-Pr | benzo[d][1,3]dioxol-5-yl | H | H |
| 2-45 | i-Pr | {4-O(CH₂)₂OEt}Ph | H | H |
| 2-46 | i-Pr | (4-Cl)Ph | H | H |
| 2-47 | i-Pr | (3,4-Cl₂)Ph | H | H |
| 2-48 | i-Pr | thiophen-2-yl | H | H |
| 2-49 | CH₃ | (4-CF₃)Ph | H | H |
| 2-50 | i-Pr | (4-CF₃)Ph | H | H |
| 3-05 | i-Pr | H | H | 4-CH₃ |
| 3-06 | (4-OCH₃)Ph | H | H | 4-CH₃ |
| 3-07 | i-Pr | (4-n-Hex)Ph | H | 4-CH₃ |
| 3-09 | CF₃ | H | H | 4-CH₃ |
| 3-10 | 1,1-(CH₃)₂-2-Ph—Et | H | H | 4-CH₃ |
| 3-11 | Ph | H | H | 4-CH₃ |
| 3-12 | i-Pr | H | H | 4-Br |
| 3-16 | Ph | H | H | H |
| 3-17 | i-Pr | H | H | H |
| 3-18 | i-Pr | (4-n-Hex)Ph | H | 2-CH₃ |
| 3-19 | i-Pr | H | H | 3-CH₃ |
| 3-20 | i-Pr | (4-n-Hex)Ph | H | 3-CH₃ |
| 3-21 | i-Pr | (4-n-Hex)Ph | PhC(O) | 3-CH₃ |
| 3-22 | i-Pr | H | H | 4-t-Bu |
| 3-23 | i-Pr | (4-n-Hex)Ph | PhC(O) | 4-t-Bu |
| 3-33 | i-Pr | (4-n-Hex)Ph | H | 4-Cl |
| 3-34 | c-Pr | (4-n-Hex)Ph | H | 4-Cl |
| 3-35 | i-Pr | n-Pr | H | 4-Cl |
| 3-36 | (4-Ph)Ph | (4-n-Hex)Ph | H | 4-Cl |
| 3-37 | (4-t-Bu)Ph | (4-n-Hex)Ph | H | 4-Cl |
| 3-38 | i-Pr | (4-n-Hex)Ph | H | 4-OCH₃ |
| 3-39 | c-Pr | (4-n-Hex)Ph | H | 4-OCH₃ |
| 3-40 | (4-Ph)Ph | (4-n-Hex)Ph | H | 4-OCH₃ |
| 3-41 | (4-t-Bu)Ph | (4-n-Hex)Ph | H | 4-OCH₃ |
| 3-43 | i-Pr | H | PhC(O) | 4-t-Bu |
| 3-44 | i-Pr | n-Pr | H | H |
| 3-45 | (4-t-Bu)Ph | n-Hex | H | H |
| 3-46 | i-Pr | Br | H | 3-CH₃ |
| 3-47 | i-Pr | Br | H | H |
| 3-48 | i-Pr | (4-n-Hex)Ph | H | 4-n-Hex |
| 3-49 | i-Pr | H | PhC(O) | H |
| 4-03 | i-Pr | (4-n-Hex)Ph | CH₃ | 4-n-Hex |
| 4-18 | (4-Ph)Ph | n-Hex | H | 4-Cl |
| 4-19 | (4-t-Bu)Ph | n-Hex | H | 4-Cl |
| 4-20 | (4-Ph)Ph | n-Hex | H | 4-OCH₃ |
| 4-21 | (4-t-Bu)Ph | n-Hex | H | 4-OCH₃ |
| 4-22 | i-Pr | n-Pr | H | 4-OCH₃ |
| 4-23 | i-Pr | (4-C(O)OMe)Ph | CH₃ | H |
| 4-56 | i-Pr | (4-n-C₈H₁₇)Ph | H | 4-CH₃ |
| 4-57 | i-Pr | (4-c-Hex)Ph | H | 4-CH₃ |
| 4-58 | i-Pr | furan-2-yl | H | 4-CH₃ |
| 4-59 | n-Hex | (4-n-Hex)Ph | H | 4-CH₃ |
| 4-60 | c-Hex | (4-n-Hex)Ph | H | 4-CH₃ |
| 4-61 | furan-2-yl | (4-n-Hex)Ph | H | 4-CH₃ |
| 4-62 | i-Pr | (4-n-Hex)Ph | H | C(O)OEt |
| 4-71 | i-Pr | C(O)Ph | H | H |
| 4-72 | (2,4-F₂)Ph | (4-n-Hex)Ph | H | 4-CH₃ |
| 4-73 | C(O)OEt | (4-n-Hex)Ph | H | 4-CH₃ |
| 4-74 | i-Pr | (4-n-Hex)Ph | H | 4-CF₃ |
| 4-75 | (2,4-F₂)Ph | (4-n-Hex)Ph | H | 4-CF₃ |
| 4-76 | C(O)OEt | (4-n-Hex)Ph | H | 4-CF₃ |
| 4-83 | i-Pr | (4-n-Hex)Ph | H | 2,4-F₂ |
| 4-84 | (2,4-F₂)Ph | (4-n-Hex)Ph | H | 2,4-F₂ |
| 4-85 | C(O)OEt | (4-n-Hex)Ph | H | 2,4-F₂ |
| 4-86 | CN | (4-n-Hex)Ph | H | 4-CH₃ |
| 4-88 | i-Pr | C(O)CH₃ | H | H |
| 4-89 | i-Pr | C(NOCH₃)CH₃ | H | H |
| 4-90 | H | (4-n-Hex)Ph | H | 4-CH₃ |
| 4-91 | i-Pr | C(NO-n-Hex)CH₃ | H | H |

TABLE 18

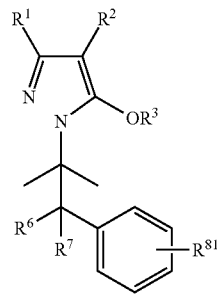

| No. | $R^1$ | $R^2$ | $R^3$ | $R^6$ | $R^7$ | $R^{81}$ |
|---|---|---|---|---|---|---|
| 3-24 | i-Pr | H | H | $CH_3$ | H | H |
| 3-25 | i-Pr | (4-n-Hex)Ph | H | $CH_3$ | H | H |

TABLE 19

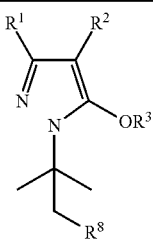

| No. | $R^1$ | $R^2$ | $R^3$ | $R^8$ |
|---|---|---|---|---|
| 4-28 | i-Pr | (4-n-Hex)Ph | H | naphthalen-1-yl |
| 4-29 | i-Pr | (4-n-$C_8H_{17}$)Ph | H | naphthalen-1-yl |
| 4-30 | i-Pr | (4-c-Hex)Ph | H | naphthalen-1-yl |
| 4-31 | i-Pr | furan-2-yl | H | naphthalen-1-yl |
| 4-32 | n-Hex | (4-n-Hex)Ph | H | naphthalen-1-yl |
| 4-33 | c-Hex | (4-n-Hex)Ph | H | naphthalen-1-yl |
| 4-34 | furan-2-yl | (4-n-Hex)Ph | H | naphthalen-1-yl |
| 4-35 | i-Pr | (4-n-Hex)Ph | H | thiophen-2-yl |
| 4-36 | i-Pr | (4-n-$C_8H_{17}$)Ph | H | thiophen-2-yl |
| 4-37 | i-Pr | (4-c-Hex)Ph | H | thiophen-2-yl |
| 4-38 | i-Pr | furan-2-yl | H | thiophen-2-yl |
| 4-39 | n-Hex | (4-n-Hex)Ph | H | thiophen-2-yl |
| 4-40 | c-Hex | (4-n-Hex)Ph | H | thiophen-2-yl |
| 4-41 | furan-2-yl | (4-n-Hex)Ph | H | thiophen-2-yl |
| 4-42 | i-Pr | (4-n-Hex)Ph | H | 1-adamantyl |
| 4-43 | i-Pr | (4-n-$C_8H_{17}$)Ph | H | 1-adamantyl |
| 4-44 | i-Pr | (4-c-Hex)Ph | H | 1-adamantyl |
| 4-45 | i-Pr | furan-2-yl | H | 1-adamantyl |
| 4-46 | n-Hex | (4-n-Hex)Ph | H | 1-adamantyl |
| 4-47 | c-Hex | (4-n-Hex)Ph | H | 1-adamantyl |
| 4-48 | furan-2-yl | (4-n-Hex)Ph | H | 1-adamantyl |
| 4-80 | i-Pr | (4-n-Hex)Ph | H | 2,3-dihydro-1H-inden-5-yl |
| 4-81 | (2,4-$F_2$)Ph | (4-n-Hex)Ph | H | 2,3-dihydro-1H-inden-5-yl |
| 4-82 | C(O)OEt | (4-n-Hex)Ph | H | 2,3-dihydro-1H-inden-5-yl |

TABLE 20

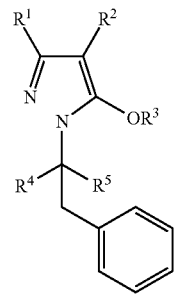

| No. | $R^1$ | $R^2$ | $R^3$ | $R^4$ | $R^5$ |
|---|---|---|---|---|---|
| 4-49 | i-Pr | (4-n-Hex)Ph | H | | —$CH_2CH_2$— |
| 4-50 | i-Pr | (4-n-Oct)Ph | H | | —$CH_2CH_2$— |
| 4-51 | i-Pr | (4-c-Hex)Ph | H | | —$CH_2CH_2$— |
| 4-52 | i-Pr | furan-2-yl | H | | —$CH_2CH_2$— |
| 4-53 | n-Hex | (4-n-Hex)Ph | H | | —$CH_2CH_2$— |
| 4-54 | c-Hex | (4-n-Hex)Ph | H | | —$CH_2CH_2$— |
| 4-55 | furan-2-yl | (4-n-Hex)Ph | H | | —$CH_2CH_2$— |
| 4-87 | i-Pr | (4-n-Hex)Ph | H | $C_2H_5$ | $C_2H_5$ |

Next, the physical properties such as proton nuclear magnetic resonance (1H NMR) chemical shifts or melting points of the compounds listed in Tables 16 to 20 are shown in Table 21.

As compounds having a hydrogen atom as $R^3$ are known to have a tautomeric structure P-1, P-2 or P-3 depending on the $^1$H NMR measuring conditions, for these compounds, the $^1$H NMR measuring conditions, the structures of the tautomers and the mixing ratio of the tautomers, in the case of tautomeric mixtures, are shown in Table 21 as well as the physical properties.

$^1$H NMR was measured by using tetramethylsilane ($Me_4Si$) as the standard under the following conditions (i)~(iii).

(i); solvent $CDCl_3$, 300 MHz.
(ii); solvent DMSO-$d_6$, 300 MHz.
(iii); solvent DMSO-$d_6$, 400 MHz.

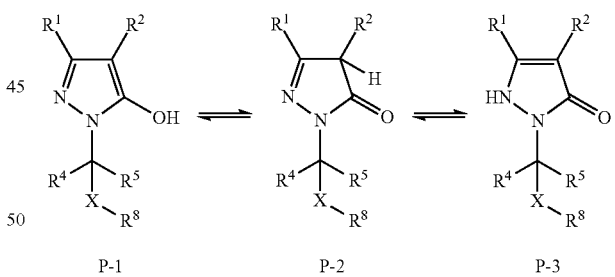

TABLE 21

| No. | measuring conditions | tautomers | mixing ratio | $^1$H NMR chemical shift or melting point |
|---|---|---|---|---|
| 1-01 | (i) | P-2 | | δ 7.2-7.4 (m, 5H), 3.22 (s, 2H), 2.07 (s, 3H), 1.87 (s, 6H) |
| 1-02 | (i) | P-2 | | δ 7.2-7.4 (m, 5H), 3.00 (q, J = 8.0 Hz, 1H), 2.03 (s, 3H), 1.91 (s, 6H), 1.30 (d, J = 7.7 Hz, 3H) |
| 1-03 | (ii) | mixture of P-1 & P-3 | 6:4 | δ 9.33 (s, 1H), 6.8-7.5 (m, 5H), 2.1-2.3 (m, 2H), 2.03 (s, 3H), 1.80 (s, 6H), 1.1-1.4 (m, 8H), 0.8-0.9 (m, 3H) |
| | | | | δ 9.4-9.5 (br, 1H), 6.8-7.5 (m, 5H), 2.1-2.3 (m, 2H), 2.03 (s, 3H), 1.74 (s, 6H), 1.1-1.4 (m, 8H), 0.8-0.9 (m, 3H) |
| 1-04 | (i) | P-2 | | δ 6.8-7.4 (m, 10H), 2.9-3.7 (m, 3H), 1.4-2.2 (m, 9H) |
| 1-06 | (ii) | P-1 | | δ 9.89 (s, 1H), 7.0-7.5 (m, 15H), 1.96 (s, 6H) |

TABLE 21-continued

| No. | measuring conditions | tautomers | mixing ratio | $^1$H NMR chemical shift or melting point |
|---|---|---|---|---|
| 1-07 | (ii) | mixture of P-1 and P-3 | 7:3 | δ 9.66 (s, 1H), 6.9-7.6 (m, 10H), 2.5-2.6 (m, 2H), 1.8-2.0 (m, 6H), 1.4-1.7 (m, 2H), 0.8-1.0 (m, 3H) |
|  |  |  |  | δ 10.27 (s, 1H), 6.9-7.6 (m, 10H), 2.6-2.7 (m, 2H), 1.8-2.0 (m, 6H), 1.4-1.7 (m, 2H), 0.8-1.0 (m, 3H) |
| 1-11 |  |  |  | m.p. 224~225° C. |
| 1-12 |  |  |  | m.p. 188~189° C. |
| 2-01 | (i) | P-2 |  | δ 7.1-7.3 (m, 5H), 3.17 (s, 2H), 3.11 (s, 2H), 2.01 (s, 3H), 1.50 (s, 6H) |
| 2-02 | (i) | P-2 |  | δ 7.0-7.3 (m, 5H), 2.8-3.3 (m, 3H), 1.2-2.1 (m, 12H) |
| 2-03 | (i) | P-2 |  | δ 7.0-7.3 (m, 5H), 3.19 (d, J = 13.2 Hz, 1H), 3.06 (d, J = 13.2 Hz, 1H), 2.97 (t, J = 5.7 Hz, 1H), 1.98 (s, 3H), 1.49 (s, 6H), 0.8-1.4 (m, 13H) |
| 2-04 | (iii) | mixture of P-1 and P-3 | 5:5 | δ 10.04 (s, 1H), 7.0-7.4 (m, 8H), 6.8-6.9 (m, 2H), 3.67 (s, 2H), 3.15 (s, 2H), 1.77 (s, 3H), 1.48 (s, 6H) |
|  |  |  |  | δ 9.43 (s, 1H), 7.0-7.4 (m, 8H), 6.8-6.9 (m, 2H), 3.46 (s, 2H), 3.21 (s, 2H), 1.90 (s, 3H),, 1.40 (s, 6H) |
| 2-05 | (ii) | P-1 |  | δ 10.96 (s, 1H), 7.3-7.6 (m, 5H), 7.1-7.3 (m, 3H), 6.9-7.0 (m, 2H), 3.23 (s, 2H), 1.59 (s, 6H) |
| 2-06 | (ii) | P-1 |  | δ 10.14 (s, 1H), 7.1-7.5 (m, 13H), 6.9-7.1 (m, 2H), 3.24 (s, 2H), 1.61 (s, 6H) |
| 2-07 | (ii) | mixture of P-1 and P-3 | 5:5 | δ 9.89 (s, 1H), 6.8-7.6 (m, 10H), 3.26 (s, 2H), 2.3-2.5 (m, 2H), 1.52 (s, 6H), 1.3-1.5 (m, 2H), 0.7-0.9 (m, 3H) |
|  |  |  |  | δ 9.84 (s, 1H), 6.8-7.6 (m, 10H), 3.17 (s, 2H), 2.3-2.5 (m, 2H), 1.49 (s, 6H), 1.3-1.5 (m, 2H), 0.7-0.9 (m, 3H) |
| 2-09 | (ii) | mixture of P-1 and P-3 | 7:3 | δ 9.79 (s, 1H), 7.3-7.5 (m, 4H), 7.1-7.3 (m, 4H), 6.8-6.9 (m, 2H), 3.14 (s, 2H), 2.87 (sep, J = 6.9 Hz, 1H), 1.53 (s, 6H), 1.02 (d, J = 6.8 Hz, 6H) |
|  |  |  |  | δ 9.39 (s, 1H), 7.3-7.5 (m, 4H), 7.1-7.3 (m, 4H), 7.0-7.1 (m, 2H), 3.20 (s, 2H), 2.8-3.1 (m, 1H), 1.53 (s, 6H), 1.06 (d, J = 7.1 Hz, 6H) |
| 2-10 | (ii) | mixture of P-1 and P-3 | 7:3 | δ 9.95 (s, 1H), 7.51 (d, J = 6.9 Hz, 2H), 7.3-7.5 (m, 3H), 7.1-7.3 (m, 3H), 6.8-6.9 (m, 2H), 3.14 (s, 2H), 1.6-1.8 (m, 1H), 1.49 (s, 6H), 0.6-0.7 (m, 4H) |
|  |  |  |  | δ 9.19 (s, 1H), 7.75 (d, J = 7.4 Hz, 2H), 7.3-7.5 (m, 3H), 7.1-7.3 (m, 3H), 7.0-7.1 (m, 2H), 3.21 (s, 2H), 1.8-2.0 (m, 1H), 1.46 (s, 6H) 0.8-0.9 (m, 4H) |
| 2-12 | (ii) | mixture of P-1 and P-3 | 5:5 | δ 9.90 (s, 1H), 6.8-7.6 (m, 10H), 3.25 (s, 2H), 2.42 (t, J = 7.6 Hz, 2H), 1.52 (s, 6H),, 1.1-1.5 (m, 4H), 0.7-0.9 (m, 3H) |
|  |  |  |  | δ 9.84 (s, 1H), 6.8-7.6 (m, 10H), 3.17 (s, 2H), 2.42 (t, J = 7.6 Hz, 2H), 1.49 (s, 6H), 1.1-1.5 (m, 4H), 0.7-0.9 (m, 3H) |
| 2-14 | (ii) | P-1 |  | δ 9.9-10.2 (br, 1H), 6.9-7.4 (m, 14H), 3.24 (s, 2H), 2.24 (s, 3H), 1.59 (s, 6H) |
| 2-15 | (ii) | P-1 |  | δ 10.25 (s, 1H), 7.1-7.5 (m, 12H), 6.9-7.1 (m, 2H), 3.24 (s, 2H), 1.60 (s, 6H) |
| 2-16 | (ii) | P-1 |  | δ 10.11 (s, 1H), 6.6-7.4 (m, 13H), 3.71 (s, 3H), 3.48 (s, 3H), 3.24 (s, 2H), 1.59 (s, 6H) |
| 2-18 | (ii) | P-1 |  | δ 10.22 (s, 1H), 8.36 (d, J = 4.7 Hz, 1H), 7.69 (t, J = 7.8 Hz, 1H), 7.42 (d, J = 8.0 Hz, 1H), 7.1-7.4 (m, 9H), 6.99 (d, J = 7.7 Hz, 2H) 3.27 (s, 2H), 1.61 (s, 6H) |
| 2-19 | (ii) | mixture of P-1 and P-3 | 5:5 | δ 9.97 (s, 1H), 6.9-7.6 (m, 9H), 3.19 (s, 2H), 2.31 (s, 3H), 2.04 (s, 3H), 1.46 (s, 6H) |
|  |  |  |  | δ 9.89 (s, 1H), 6.9-7.6 (m, 9H), 3.28 (s, 2H), 2.31 (s, 3H), 2.15 (s, 3H), 1.46 (s, 6H) |
| 2-20 | (ii) | mixture of P-1 and P-3 | 6:4 | δ 9.97 (s, 1H), 7.1-7.3 (m, 7H), 6.9-7.0 (m, 2H), 3.0-3.4 (m, 2H), 2.19 (s, 3H),, 1.79 (s, 3H), 1.51 (s, 6H) |
|  |  |  |  | δ 9.83 (s, 1H), 7.1-7.3 (m, 7H), 6.9-7.0 (m, 2H), 3.0-3.4 (m, 2H), 2.26 (s, 3H), 1.89 (s, 3H), 1.45 (s, 6H) |
| 2-21 | (ii) | mixture of P-1 and P-3 | 5:5 | δ 9.84 (s, 1H), 7.41 (s, 1H), 7.0-7.3 (m, 6H), 6.95 (d, J = 7.1 Hz, 2H), 3.28 (s, 2H), 2.24 (s, 3H), 2.22 (s, 3H), 2.15 (s, 3H), 1.44 (s, 6H) |
|  |  |  |  | δ 9.94 (s, 1H), 7.41 (s, 1H), 7.0-7.3 (m, 6H), 6.95 (d, J = 7.1 Hz, 2H), 3.18 (s, 2H), 2.24 (s, 3H), 2.22 (s, 3H), 2.03 (s, 3H), 1.50 (s, 6H), |
| 2-22 | (ii) | mixture of P-1 and P-3 | 6:4 | δ 10.08 (s, 1H), 6.9-7.8 (m, 14H), 3.31 (s, 2H), 2.24 (s, 3H), 1.48 (s, 6H) |
|  |  |  |  | δ 10.15 (s, 1H), 6.9-7.8 (m, 14H), 3.21 (s, 2H), 2.11 (s, 3H), 1.53 (s, 6H) |
| 2-23 | (ii) | mixture of P-1 and P-3 | 6:4 | δ 9.88 (s, 1H), 6.9-7.6 (m, 9H), 3.28 (s, 2H), 2.16 (s, 3H), 1.45 (s, 6H), 1.30 (s, 18H) |
|  |  |  |  | δ 9.97 (s, 1H), 6.9-7.6 (m, 9H), 3.18 (s, 2H), 2.05 (s, 3H), 1.50 (s, 6H), 1.30 (s, 18H) |
| 2-24 | (ii) | mixture of P-1 and P-3 | 7:3 | δ 10.00 (s, 1H), 6.9-8.0 (m, 12H), 3.29 (d, J = 14.0 Hz, 1H), 3.13 (d, J = 12.7 Hz, 1H), 1.77 (s, 3H), 1.58 (s, 6H) |
|  |  |  |  | δ 10.06 (s, 1H), 6.9-8.0 (m, 12H), 3.1-3.4 (m, 2H), 1.90 (s, 3H), 1.52 (s, 6H) |
| 2-25 | (ii) | mixture of P-1 and P-3 | 6:4 | δ 9.88 (s, 1H), 6.9-7.7 (m, 9H), 3.29 (s, 2H), 3.57 (t, J = 7.5 Hz, 2H), 2.16 (s, 3H), 1.4-1.7 (m, 8H), 1.30 (s, 6H), 0.8-1.0 (m, 3H) |
|  |  |  |  | δ 9.96 (s, 1H), 6.9-7.7 (m, 9H), 3.18 (s, 2H), 3.57 (t, J = 7.5 Hz, 2H), 2.04 (s, 3H), 1.4-1.7 (m, 8H), 1.30 (s, 6H), 0.8-1.0 (m, 3H) |
| 2-28 | (ii) | mixture of P-1 and P-3 | 5:5 | δ 9.90 (s, 1H), 6.9-7.6 (m, 9H), 3.76 (s, 3H), 3.19 (s, 2H), 2.03 (s, 3H), 1.45 (s, 6H) |
|  |  |  |  | δ 9.80 (s, 1H), 6.9-7.6 (m, 9H), 3.76 (s, 3H), 3.28 (s, 2H), 2.13 (s, 3H), 1.45 (s, 6H) |
| 2-29 | (ii) | mixture of P-1 and P-3 | 5:5 | δ 9.94 (s, 1H), 6.8-7.4 (m, 8H), 6.00 (s, 2H), 3.27 (s, 2H), 2.15 (s, 3H), 2.04 (s, 3H), 1.44 (s, 6H) |
|  |  |  |  | δ 9.89 (s, 1H), 6.8-7.4 (m, 8H), 6.01 (s, 2H), 3.17 (s, 2H), 2.02 (s, 3H), 2.04 (s, 3H), 1.49 (s, 6H) |
| 2-30 | (ii) | mixture of P-1 and P-3 | 6:4 | δ 9.80 (s, 1H), 7.52 (d, J = 8.5 Hz, 2H) 7.1-7.4 (m, 5H), 6.9-7.1 (m, 2H), 4.0-4.2 (m, 2H), 3.6-3.8 (m, 2H), 3.51 (q, J = 7.0 Hz, 2H), 3.29 (s, 2H), 2.14 (s, 3H), 1.44 (s, 6H), 1.14 (t, J = 7.0 Hz, 6H) |

TABLE 21-continued

| No. | measuring conditions | tautomers | mixing ratio | ¹H NMR chemical shift or melting point |
|---|---|---|---|---|
| | | | | δ 9.90 (s, 1H), 7.52 (d, J = 8.5 Hz, 2H) 7.1-7.4 (m, 5H), 6.9-7.1 (m, 2H), 4.0-4.2 (m, 2H), 3.6-3.8 (m, 2H), 3.51 (q, J = 7.0 Hz, 2H), 3.19 (s, 2H), 2.02 (s, 3H), 1.50 (s, 6H), 1.14 (t, J = 7.0 Hz, 3H) |
| 2-31 | (ii) | mixture of P-1 and P-3 | 7:3 | δ 10.16 (s, 1H), 6.9-7.8 (m, 9H), 3.29 (s, 2H), 2.19 (s, 3H), 1.46 (s, 6H) |
| | | | | δ 10.16 (s, 1H), 6.9-7.8 (m, 9H), 3.18 (s, 2H), 2.06 (s, 3H), 1.51 (s, 6H) |
| 2-32 | (ii) | mixture of P-1 and P-3 | 7:3 | δ 10.4-10.5 (m, 1H), 6.8-8.2 (m, 8H), 3.1-3.4 (m, 2H), 2.1-2.4 (m, 3H), 1.48 (s, 6H) |
| | | | | δ 10.3-10.4 (m, 1H), 6.8-8.2 (m, 8H), 3.1-3.4 (m, 2H), 2.0-2.2 (m, 3H), 1.48 (s, 6H) |
| 2-33 | (ii) | mixture of P-1 and P-3 | 8:2 | δ 10.3 (s, 1H), 6.9-7.5 (m, 8H), 3.28 (s, 2H), 2.26 (s, 3H), 1.45 (s, 6H) |
| | | | | δ 10.2 (s, 1H), 6.9-7.5 (m, 8H), 3.18 (s, 2H), 2.12 (s, 3H), 1.50 (s, 6H) |
| 2-34 | (ii) | mixture of P-1 and P-3 | 8:2 | δ 9.73 (s, 1H), 7.1-7.4 (m, 7H), 6.8-6.9 (m, 2H), 3.13 (s, 2H), 2.84 (sep, J = 7.1 Hz, 1H), 2.31 (s, 3H), 1.52 (s, 6H), 1.01 (d, J = 6.9 Hz, 6H) |
| | | | | δ 9.31 (s, 1H), 7.1-7.4 (m, 7H), 7.0-7.1 (m, 2H), 3.20 (s, 2H), 2.9-3.1 (m, 1H), 2.31 (s, 3H), 1.52 (s, 6H), 1.05 (d, J = 6.9 Hz, 6H) |
| 2-35 | (ii) | mixture of P-1 and P-3 | 8:2 | δ 9.76 (s, 1H), 7.1-7.3 (m, 7H), 6.8-6.9 (m, 2H), 3.21 (d, J = 12.7 Hz, 1H), 3.06 (d, J = 13.2 Hz, 1H), 2.4-2.6 (m, 1H), 2.18 (s, 3H), 1.51 (s, 6H), 0.95 (d, J = 6.9 Hz, 3H) |
| | | | | δ 9.41 (s, 1H), 7.1-7.3 (m, 7H), 7.0-7.1 (m, 2H), 3.1-3.4 (m, 2H), 2.4-2.6 (m, 1H), 2.22 (s, 3H), 1.55 (s, 6H), 0.86 (d, J = 6.9 Hz, 3H) |
| 2-36 | (ii) | mixture of P-1 and P-3 | 7:3 | δ 9.70 (s, 1H), 6.8-7.3 (m, 8H), 3.14 (s, 2H), 2.85 (sep, J = 7.7 Hz, 1H), 2.23 (s, 3H), 2.22 (s, 3H), 1.52 (s, 6H), 1.01 (d, J = 6.9 Hz, 6H) |
| | | | | δ 9.28 (s, 1H), 6.8-7.3 (m, 8H), 3.20 (s, 2H), 2.9-3.1 (m, 1H), 2.24 (s, 3H), 2.22 (s, 3H), 1.51 (s, 6H), 1.05 (d, J = 7.1 Hz, 6H) |
| 2-37 | (ii) | mixture of P-1 and P-3 | 7:3 | δ 9.91 (s, 1H), 6.8-7.8 (m, 14H), 3.16 (s, 2H), 2.93 (sep, J = 6.9 Hz, 1H), 1.54 (s, 6H), 1.06 (d, J = 6.9 Hz, 6H) |
| | | | | δ 9.48 (s, 1H), 6.8-7.8 (m, 14H), 3.22 (s, 2H), 3.0-3.1 (m, 1H), 1.54 (s, 6H), 1.10 (d, J = 7.1 Hz, 6H) |
| 2-38 | (ii) | mixture of P-1 and P-3 | 8:2 | δ 9.7-9.8 (m, 1H), 7.1-7.5 (m, 7H), 6.8-6.9 (m, 2H), 3.13 (s, 2H), 2.8-2.9 (m, 1H), 1.52 (s, 6H), 1.31 (s, 9H), 1.03 (d, J = 6.6 Hz, 6H) |
| | | | | δ 9.3-9.4 (m, 1H), 7.1-7.5 (m, 7H), 7.0-7.1 (m, 2H), 3.2-3.3 (m, 2H), 2.9-3.1 (m, 1H), 1.52 (s, 6H), 1.31 (s, 9H), 1.03 (d, J = 6.6 Hz, 6H) |
| 2-39 | (ii) | mixture of P-1 and P-3 | 8:2 | δ 9.76 (s, 1H), 7.2-8.1 (m, 10H), 6.9-7.0 (m, 2H), 3.1-3.3 (m, 2H), 2.4-2.8 (m, 1H), 1.60 (s, 6H), 0.87 (d, J = 6.9 Hz, 6H) |
| | | | | δ 9.6-9.7 (m, 1H), 7.2-8.1 (m, 10H), 7.14 (d, J = 8.0 Hz, 2H), 3.1-3.3 (m, 2H), 2.4-2.8 (m, 1H), 1.55 (s, 6H), 0.96 (d, J = 6.6 Hz, 6H) |
| 2-40 | (ii) | mixture of P-1 and P-3 | 6:4 | δ 9.72 (s, 1H), 7.1-7.4 (m, 7H), 6.8-6.9 (m, 2H), 3.14 (s, 2H), 2.85 (sep, J = 5.5 Hz, 1H), 2.57 (t, J = 6.7 Hz, 2H), 1.52 (s, 6H), 1.5-1.7 (m, 2H), 1.2-1.4 (m, 6H), 1.0-1.2 (m, 6H), 0.8-1.0 (m, 3H) |
| | | | | δ 9.3-9.4 (m, 1H), 7.1-7.4 (m, 7H), 7.0-7.1 (m, 2H), 3.19 (s, 2H), 2.9-3.1 (m, 1H), 2.57 (t, J = 6.7 Hz, 1H), 1.52 (s, 6H), 1.5-1.7 (m, 2H), 1.2-1.4 (m, 6H), 1.0-1.2 (m, 6H), 0.8-1.0 (m, 3H) |
| 2-43 | (ii) | mixture of P-1 and P-3 | 7:3 | δ 9.68 (s, 1H), 6.8-7.4 (m, 9H), 3.77 (s, 3H), 3.13 (s, 2H), 2.82 (sep, J = 6.6 Hz, 1H), 1.52 (s, 6H), 1.01 (d, J = 6.8 Hz, 6H) |
| | | | | δ 9.27 (s, 1H), 6.8-7.4 (m, 9H), 3.77 (s, 3H), 3.20 (s, 2H), 2.9-3.1 (m, 1H), 1.52 (s, 6H), 1.05 (d, J = 7.0 Hz, 6H) |
| 2-44 | (ii) | mixture of P-1 and P-3 | 7:3 | δ 9.73 (s, 1H), 6.7-7.5 (m, 8H), 6.02 (s 2H), 3.12 (s, 2H), 2.83 (sep, J = 6.8 Hz, 1H), 1.51 (s, 6H), 1.01 (d, J = 6.8 Hz, 6H) |
| | | | | δ 9.33 (s, 1H), 6.7-7.5 (m, 8H), 6.02 (s 2H), 3.19 (s, 2H), 2.9-3.1 (m, 1H), 1.51 (s, 6H), 1.0-1.2 (m, 6H) |
| 2-45 | (ii) | mixture of P-1 and P-3 | 7:3 | δ 9.68 (s, 1H), 6.8-7.4 (m, 9H), 4.0-4.2 (m, 2H), 3.6-3.8 (m, 2H), 3.51 (q, J = 6.9 Hz, 2H), 3.13 (s, 2H), 2.82 (sep, J = 6.9 Hz, 1H), 1.52 (s, 6H), 1.14 (t, J = 6.9 Hz, 3H), 1.00 (d, J = 6.9 Hz, 6H) |
| | | | | δ 9.27 (s, 1H), 6.8-7.4 (m, 9H), 4.0-4.2 (m, 2H), 3.6-3.8 (m, 2H), 3.51 (q, J = 6.9 Hz, 2H), 3.20 (s, 2H), 2.94 (sep, J = 8.8 Hz, 1H), 1.52 (s, 6H), 1.14 (t, J = 6.9 Hz, 3H), 1.05 (d, J = 6.9 Hz, 6H) |
| 2-46 | (ii) | mixture of P-1 and P-3 | 7:3 | δ 9.91 (s, 1H), 7.1-7.5 (m, 7H), 6.8-6.9 (m, 2H), 3.36 (s, 3H), 3.13 (s, 2H), 2.8-2.95 (m, 1H), 1.52 (s, 6H), 1.02 (d, J = 6.9 Hz, 6H) |
| | | | | δ 9.55 (s, 1H), 7.1-7.5 (m, 7H), 7.0-7.1 (m, 2H), 3.31 (s, 3H), 3.20 (s, 2H), 2.95-3.1 (m, 1H), 1.52 (s, 6H), 1.06 (d, J = 6.9 Hz, 6H) |
| 2-47 | (ii) | P-1 | | δ 10.0-10.2 (br, 1H), 7.4-7.8 (m, 2H), 7.1-7.4 (m, 4H), 6.8-7.1 (m, 2H), 3.15 (s, 2H), 2.8-3.1 (m, 1H), 1.53 (s, 6H), 1.05 (d, J = 6.6 Hz, 6H) |
| 2-48 | (ii) | mixture of P-1 and P-3 | 6:4 | δ 10.05 (s, 1H), 6.8-7.5 (m, 8H), 3.14 (s, 2H), 2.8-3.1 (m, 1H), 1.51 (s, 6H), 1.08 (d, J = 6.6 Hz, 6H) |
| | | | | δ 9.61 (s, 1H), 6.8-7.5 (m, 8H), 3.22 (s, 2H), 2.8-3.1 (m, 1H), 1.51 (s, 6H), 1.13 (d, J = 6.8 Hz, 6H) |
| 2-49 | (ii) | mixture of P-1 and P-3 | 7:3 | δ 10.41 (s, 1H), 6.9-8.1 (m, 9H), 3.29 (s, 2H), 2.24 (s, 3H), 1.49 (s, 6H) |
| | | | | δ 10.3-10.4 (br, 1H), 6.9-8.1 (m, 9H), 3.1-3.4 (m, 2H), 2.12 (s, 3H), 1.49 (s, 6H) |
| 2-50 | (ii) | mixture of P-1 and P-3 | 8:2 | δ 10.09 (s, 1H), 6.8-7.9 (m, 9H), 3.15 (s, 2H), 2.8-3.0 (m, 1H), 1.54 (s, 6H), 1.05 (s, 6H) |
| | | | | δ 9.7-9.8 (br, 1H), 6.8-7.9 (m, 9H), 3.1-3.3 (m, 2H), 3.0-3.1 (m, 1H), 1.54 (s, 6H), 1.03 (s, 6H) |
| 3-01 | (i) | P-2 | | δ 7.60 (dd, J = 6.8, 2.1 Hz, 2H), 7.20-7.30 (m, 5H), 6.91 (dd, J = 6.8, 2.4 Hz, 2H), 3.8 (s, 3H), 3.60 (s, 2H), 1.94 (s, 6H) |
| 3-02 | (i) | P-2 | | δ 7.15-7.35 (m, 5H), 3.20 (s, 2H), 2.68 (sep, J = 6.8 Hz, 1H), 1.86 (s, 6H), 1.17 (d, J = 6.8 Hz, 6H) |
| 3-03 | (i) | P-2 | | δ 7.62-7.70 (m, 2H), 7.20-7.45 (m, 8H), 3.63 (s, 2H), 1.95 (s, 6H) |

TABLE 21-continued

| No. | measuring conditions | tautomers | mixing ratio | $^1$H NMR chemical shift or melting point |
|---|---|---|---|---|
| 3-04 | (i) | P-2 | | δ 7.15-7.34 (m, 8H), 6.98-7.10 (m, 2H), 3.08 (s, 2H), 2.79 (s, 2H)., 1.84 (s, 6H), 1.18 (s, 6H) |
| 3-05 | (i) | P-2 | | δ 7.04 (d, J = 8.0 Hz, 2H), 6.98 (d, J = 8.0 Hz, 2H), 3.13 (s, 2H), 3.05 (s, 2H), 2.59 (sep, J = 6.8 Hz, 1H), 2.30 (s, 3H), 1.50 (s, 6H), 1.09 (d, 6.8 Hz, 6H) |
| 3-06 | (i) | P-2 | | δ 7.55 (dd, J = 6.8, 2.1 Hz, 2H), 7.03 (s, 4H), 6.91 (d, J = 8.6 Hz, 2H), 3.84 (s, 3H), 3.14 (s, 2H), 3.56 (s, 2H), 2.28 (s, 3H), 1.56 (s, 6H) |
| 3-07 | (i) | P-2 | | δ 7.18~7.42 (m, 4H), 7.00 (s, 4H), 3.21 (s, 2H), 3.16 (sep, J = 7.2 Hz, 1H), 2.61 (t, J = 7.5 Hz, 2H), 2.29 (s, 3H), 1.62 (s, 6H), 1.54~1.58 (m, 2H), 1.26~1.36 (m, 6H), 1.07 (d, J = 7.2 Hz, 6H), 0.87~0.92 (m, 3H) |
| 3-08 | (i) | P-2 | | δ 6.91~7.42 (m, 9H), 3.22 (sep, J = 7.2 Hz, 1H), 2.4~2.7 (m, 2H), 1.55 (s, 6H), 1.53~1.57 (m, 2H), 1.23~1.35 (m, 6H), 1.12 (d, J = 7.2 Hz, 6H), 0.8~0.9 (m, 3H) |
| 3-09 | | | | m.p. 144.6~145.5° C. |
| 3-10 | (i) | P-2 | | δ 6.91-7.33 (m, 9H), 3.06 (s, 2H), 3.05 (s, 2H), 2.73 (s, 2H), 2.31 (s, 3H), 1.49 (s, 6H), 1.10 (s, 6H) |
| 3-11 | (i) | P-2 | | δ 7.55-7.66 (m, 2H), 7.25-7.42 (m, 3H), 7.03 (s, 4H), 3.58 (s, 2H), 3.14 (s, 2H), 2.28 (s, 3H), 1.58 (s, 6H) |
| 3-12 | (i) | P-2 | | δ 7.35 (d, J = 8.6 Hz, 2H), 6.98 (d, J = 8.6 Hz, 2H), 3.14 (s, 2H), 3.06 (s, 2H), 2.59 (sep, J = 6.8 Hz, 1H), 1.50 (s, 6H), 1.10 (d, J = 7.1 Hz, 6H) |
| 3-13 | (i) | P-1 | | δ 7.83 (d, J = 7.4 Hz, 2H), 7.38 (t, J = 7.4 Hz, 2H), 7.15-7.33 (m, 4H), 7.08 (d, J = 7.1 Hz, 2H), 5.91 (s, 1H), 3.60 (s, 3H), 1.98 (s, 6H) |
| 3-14 | (i) | P-1 | | δ 7.73 (d, J = 7.4 Hz, 2H), 7.41 (t, J = 7.4 Hz, 2H), 7.16-7.36 (m, 4H), 3.16 (s, 3H), 2.10 (s, 3H), 1.98 (s, 6H) |
| 3-16 | (i) | P-2 | | δ 7.12~7.62 (m, 10H), 3.59 (s, 2H), 3.19 (s, 2H), 1.59 (s, 6H) |
| 3-17 | (i) | P-2 | | δ 7.09-7.25 (m, 5H), 3.13 (s, 2H), 3.09 (s, 2H), 2.58 (sep, J = 7.2 Hz, 1H), 1.52 (s, 6H), 1.09 (d, J = 6.9 Hz, 6H) |
| 3-18 | (i) | mixture of P-1 and P-2 | 4:6 | δ 6.94-7.46 (m, 8H), 6.17 (br, 1H), 3.18 (s, 2H), 3.13-3.17 (m, 1H), 2.55-2.66 (m, 2H), 2.35 (s, 3H), 1.64 (s, 6H), 1.50-1.64 (m, 2H), 1.11 (d, J = 6.9 Hz, 6H), 0.95-1.20 (m, 6H), 0.75-0.95 (m, 3H)<br>δ 6.94-7.46 (m, 8H), 4.17 (s, 1H), 3.30 (s, 2H), 2.55-2.66 (m, 2H), 2.40-2.60 (m, 1H), 2.36 (s, 3H), 1.55 (s, 6H), 1.50-1.64 (m, 2H), 1.11 (d, J = 7.2 Hz, 6H), 0.95-1.20 (m, 6H), 0.75-0.95 (m, 3H) |
| 3-19 | (i) | P-2 | | δ 7.25-7.15 (m, 1H), 6.95-7.05 (m, 1H), 6.85-7.05 (m, 2H), 3.13 (s, 2H), 3.05 (s, 2H), 2.59 (sep, J = 7.2 Hz, 1H), 2.29 (s, 3H), 1.51 (s, 6H), 1.09 (d, J = 6.9 Hz, 6H) |
| 3-20 | (i) | mixture of P-1 and P-2 | 5:5 | δ 6.88-7.47 (m, 8H), 6.14 (br, 1H), 3.21 (s, 2H), 3.13-3.20 (m, 1H), 2.52-2.65 (m, 2H), 2.26 (s, 3H), 1.64 (s, 6H), 1.49-1.63 (m, 2H), 1.21-1.39 (m, 6H), 0.95-1.05 (m, 6H), 0.82-0.93 (m, 3H)<br>δ 6.88-7.47 (m, 8H), 4.12 (s, 1H), 2.52-2.65 (m, 2H), 2.40-2.55 (m, 1H), 2.30 (s, 3H), 1.55 (s, 6H), 1.49-1.63 (m, 2H), 1.21-1.39 (m, 6H), 1.05-1.15 (m, 6H), 0.82-0.93 (m, 3H) |
| 3-21 | (i) | P-1 | | 7.95-8.0 (m, 2H), 7.6-7.7 (m, 1H), 7.45-7.55 (m, 2H), 7.0-7.1 (m, 1H), 6.9-7.0 (m, 1H), 6.6-6.7 (m, 1H), 6.56 (s, 1H), 66.03 (s, 1H), 3.09 (s, 2H), 2.92 (sep, J = 6.9 Hz, 1H), 2.22 (s, 3H), 1.64 (s, 6H), 1.25 (d, J 6.9 Hz, 6H) |
| 3-22 | (i) | P-2 | | δ 7.2-7.3 (m, 2H), 7.0-7.1 (m, 2H), 3.14 (s, 2H), 3.06 (s, 2H), 2.50-2.65 (m, 1H), 1.52 (s, 6H), 1.29 (s, 9H), 1.08 (d, J 6.9 Hz, 6H) |
| 3-23 | (i) | mixture of P-1 and P-2 | 5:5 | δ 6.90-7.47 (m, 8H), 6.13 (br, 1H), 3.20 (s, 2H), 3.05-3.19 (m, 1H), 2.52-2.67 (m, 2H), 1.65 (s, 6H), 1.52-1.63 (m, 2H), 1.22-1.41 (m, 6H), 1.27 (s, 9H), 0.94-1.09 (m, 6H), 0.83-0.93 (m, 3H)<br>δ 6.90-7.47 (m, 8H), 4.13 (s, 1H), 3.05-3.19 (m, 2H), 2.52-2.67 (m, 2H), 2.39-2.51 (m, 1H), 1.65 (s, 6H), 1.52-1.63 (m, 2H), 1.22-1.41 (m, 6H), 1.31 (s, 9H), 0.94-1.09 (m, 6H), 0.83-0.93 (m, 3H) |
| 3-24 | (i) | P-2 | | δ 7.12-7.30 (m, 5H), 3.63 (d, J = 7.2 Hz, 1H), 3.10 (s, 2H), 2.50-2.65 (m, 1H), 1.56 (s, 3H), 1.40 (s, 3H), 1.26 (d, J = 7.2 Hz, 3H), 1.08 (d, J = 7.2 Hz, 3H), 1.56 (d, J = 6.9 Hz, 3H) |
| 3-25 | (i) | mixture of P-1 and P-2 | 5:5 | δ 6.88-7.45 (m, 9H), 6.07 (br, 1H), 3.93-4.06 (m, 1H), 3.11 (sep, J = 7.2 Hz, 1H), 2.52-2.65 (m, 2H), 1.81-1.20 (m, 8H), 1.59 (s, 6H), 0.83-1.20 (m, 12H)<br>δ 6.88-7.45 (m, 9H), 4.11 (s, 1H), 3.68-3.77 (m, 1H), 2.52-2.65 (m, 2H), 2.35-2.52 (m, 1H), 1.81-1.20 (m, 8H), 1.59 (s, 6H), 0.83-1.20 (m, 12H) |
| 3-27 | (ii) | mixture of P-1 and P-3 | 9:1 | δ 9.63 (s, 1H), 7.36 (d, J = 7.7 Hz, 2H), 7.05-7.3 (m, 5H), 6.98 (d, J = 7.4 Hz, 2H), 2.45-2.6 (m, 2H), 1.84 (s, 6H), 1.7-1.9 (m, 1H), 1.45-1.65 (m, 2H), 1.2-1.35 (m, 6H), 0.7-1.05 (m, 7H)<br>δ 9.45-9.55 (br, 1H), 7.5-7.6 (m, 2H), 7.05-7.3 (m, 5H), 6.98 (d, J = 7.4 Hz, 2H), 2.45-2.6 (m, 2H), 1.84 (s, 6H), 1.7-1.9 (m, 1H), 1.45-1.65 (m, 2H), 1.2-1.35 (m, 6H), 0.7-1.05 (m, 7H) |
| 3-28 | (ii) | mixture of P-1 and P-3 | 1:9 | δ 9.7-9.8 (br, 1H), 7.34 (d, J = 8.6 Hz, 2H), 7.1-7.3 (m, 4H), 7.00 (d, J = 8.5 Hz, 2H), 3.05-3.2 (m, 1H), 2.4-2.6 (m, 2H), 1.82 (s, 6H), 1.5-1.6 (m, 2H), 1.2-1.35 (m, 6H), 1.14 (d, J = 6.8 Hz, 6H), 0.75-0.9 (m, 3H)<br>δ 9.56 (s, 1H), 7.34 (d, J = 8.6 Hz, 2H), 7.1-7.3 (m, 4H), 7.00 (d, J = 8.5 Hz, 2H), 2.95-3.05 (m, 1H), 2.4-2.6 (m, 2H), 1.87 (s, 6H), 1.5-1.6 (m, 2H), 1.2-1.35 (m, 6H), 1.14 (d, J = 6.8 Hz, 6H), 0.75-0.9 (m, 3H) |
| 3-29 | (ii) | mixture of P-1 and P-3 | 9:1 | δ 9.67 (s, 1H), 7.3-7.4 (m, 4H), 7.17 (d, J = 7.5 Hz 2H), 7.00 (d, J = 8.5 Hz, 2H), 2.4-2.6 (m, 2H), 1.7-1.9 (m, 1H) 1.83 (s, 6H), 1.45-1.65 (m, 2H), 1.2-1.35 (m, 6H), 0.7-1.1 (m, 7H)<br>δ 9.45-9.55 (br, 1H), 7.5-7.6 (m, 2H), 7.3-7.4 (m, 2H), 7.17 (d, J = 7.5 Hz 2H), 7.00 (d, J = 8.5 Hz, 2H), 2.4-2.6 (m, 2H), 1.7-1.9 (m, 1H) 1.83 (s, 6H), 1.45-1.65 (m, 2H), 1.2-1.35 (m, 6H), 0.7-1.1 (m, 7H) |

TABLE 21-continued

| No. | measuring conditions | tautomers | mixing ratio | $^1$H NMR chemical shift or melting point |
|---|---|---|---|---|
| 3-30 | (ii) | P-1 | | δ 9.88 (br, 1H), 7.66 (d, J = 7.4 Hz, 2H), 7.59 (d, J = 7.7 Hz, 2H), 7.3-7.55 (m, 7H), 7.1-7.2 (m, 6H), 2.4-2.6 (m, 2H), 1.96 (s, 6H), 1.5-1.65 (m, 2H), 1.2-1.4 (m, 6H), 0.85 (t, J = 6.9 Hz, 3H) |
| 3-31 | (ii) | P-1 | | δ 9.70 (s, 1H), 7.65-8.05 (m, 6H), 7.0-7.6 (m, 7H), 2.4-2.55 (m, 2H), 1.91 (s, 6H), 1.3-1.55 (m, 2H), 1.1-1.3 (m, 6H), 0.7-0.9 (m, 3H) |
| 3-32 | (ii) | P-1 | | δ 9.80 (s, 1H), 7.25-7.4 (m, 6H), 7.05-7.15 (m, 6H), 2.45-2.6 (m, 2H), 1.93 (s, 6H), 1.45-1.65 (m, 2H), 1.2-1.35 (m, 6H), 1.26 (s, 9H), 0.8-0.9 (m, 3H) |
| 3-33 | (ii) | mixture of P-1 and P-3 | 7:3 | δ 9.75 (s, 1H), 7.15-7.4 (m, 6H) 6.83 (d, J = 8.4 Hz, 2H), 3.12 (s, 2H), 2.84 (sep, J = 6.8 Hz, 1H), 2.57 (t, J = 7.5 Hz 2H), 1.53 (s, 6H), 1.4-1.65 (m, 2H), 1.2-1.4 (m, 6H), 1.00 (d, J = 6.8 Hz, 6H), 0.8-0.9 (m, 3H) <br> δ 9.31 (s, 1H), 7.15-7.4 (m, 6H) 7.05 (d, J = 8.3 Hz, 2H), 3.20 (s, 2H), 2.9-3.05 (m, 1H), 2.57 (t, J = 7.5 Hz 2H), 1.51 (s, 6H), 1.4-1.65 (m, 2H), 1.2-1.4 (m, 6H), 1.05 (d, J = 7.1 Hz, 6H), 0.8-0.9 (m, 3H) |
| 3-34 | (ii) | mixture of P-1 and P-3 | 7:3 | δ 9.88 (s, 1H), 7.40 (d, J = 8.0 Hz, 2H), 7.15-7.3 (m, 4H), 6.85 (d, J = 8.3 Hz, 2H), 3.12 (s, 2H), 2.57 (t, J = 7.4 Hz, 2H), 1.65-1.75 (m, 1H), 1.55-1.65 (m, 2H), 1.49 (s, 6H), 1.2-1.4 (m, 6H), 0.87 (t, J = 6.8 Hz, 3H), 0.55-0.75 (m, 4H) <br> δ 9.06 (s, 1H), 7.63 (d, J = 8.0 Hz, 2H), 7.15-7.3 (m, 4H), 7.07 (d, J = 8.0 Hz, 2H), 3.22 (s, 2H), 2.57 (t, J = 7.4 Hz, 2H), 1.65-1.75 (m, 1H), 1.55-1.65 (m, 2H), 1.43 (s, 6H), 1.2-1.4 (m, 6H), 0.87 (t, J = 6.8 Hz, 3H), 0.55-0.75 (m, 4H) |
| 3-35 | (ii) | mixture of P-1 and P-3 | 6:4 | δ 9.51 (s, 1H), 7.14 (d, J = 8.3 Hz, 2H), 6.72 (d, J = 8.2 Hz, 2H), 3.06 (s, 2H), 2.69 (sep, J = 6.9 Hz, 1H), 2.15-2.3 (m, 2H), 1.46 (s, 6H), 1.4-1.6 (m, 2H), 1.05 (d, J = 6.9 Hz, 6H), 0.88 (t, J = 7.1 Hz, 3H) <br> δ 8.78 (s, 1H), 7.22 (d, J = 8.5 Hz, 2H), 7.00 (d, J = 8.5 Hz, 2H), 3.16 (s, 2H), 2.69 (sep, J = 6.9 Hz, 1H),, 2.05-2.15 (m, 2H), 1.42 (s, 6H), 1.4-1.6 (m, 2H), 1.05 (d, J = 6.9 Hz, 6H), 0.88 (t, J = 7.1 Hz, 3H) |
| 3-36 | (ii) | P-1 | | δ 10.14 (s, 1H), 7.63 (d, J = 7.7 Hz, 2H), 7.52 (d, J = 8.5 Hz, 2H), 7.1-7.5 (m, 11H), 6.97 (d, J = 8.2 Hz, 2H), 3.24 (s, 2H), 2.45-2.65 (m, 2H), 1.61 (s, 6H), 1.5-1.65 (m, 2H), 1.2-1.4 (m, 6H), 0.8-0.9 (m, 3H) |
| 3-37 | (ii) | mixture of P-1 and P-3 | 9:1 | δ 10.04 (s, 1H), 7.0-7.65 (m, 10H), 6.94 (d, J = 8.5 Hz, 2H), 3.21 (s, 2H), 2.45-2.65 (m, 2H), 1.59 (s, 6H), 1.45-1.6 (m, 2H), 1.2-1.35 (m, 6H), 1.22 (s, 9H), 0.8-0.95 (m, 3H) <br> δ 9.85-9.95 (m, 1H), 6.9-7.65 (m, 10H), 3.21 (s, 2H), 2.45-2.65 (m, 2H), 1.59 (s, 6H), 1.45-1.6 (m, 2H), 1.2-1.35 (m, 6H), 1.23 (s, 9H), 0.8-0.95 (m, 3H) |
| 3-38 | (ii) | mixture of P-1 and P-3 | 8:2 | δ 9.66 (s, 1H), 7.1-7.25 (m, 4H) 6.76 (d, J = 8.5 Hz, 2H), 6.70 (d, J = 8.2 Hz, 2H), 3.68 (s, 3H), 3.06 (s, 2H), 2.75-2.9 (m, 1H), 2.57 (t, J = 7.4 Hz, 2H), 1.5-1.65 (m, 2H), 1.50 (s, 6H), 1.2-1.4 (m, 6H), 1.02 (d, J = 6.9 Hz, 6H), 0.87 (t J = 6.9 Hz, 3H) <br> δ 9.25-9.35 (br, 1H), 7.25-7.35 (m, 4H), 6.85-6.95 (m, 4H), 3.68 (s, 3H), 3.12 (s, 2H), 2.9-3.05 (m, 1H), 2.57 (t, J = 7.4 Hz 2H), 1.5-1.65 (m, 2H), 1.50 (s, 6H), 1.2-1.4 (m, 6H), 1.07 (d, J = 7.1 Hz, 6H), 0.87 (t J = 6.9 Hz, 3H) |
| 3-39 | (ii) | P-2 | | δ 7.4-7.55 (m, 2H) 7.20 (d, J = 8.1 Hz, 2H), 6.84 (d, J = 8.3 Hz, 2H), 6.73 (d, J = 8.6 Hz, 2H), 3.69 (s, 3H), 3.08 (s, 2H), 2.5-2.6 (m, 2H), 1.65-1.8 (m, 1H), 1.55-1.65 (m, 2H), 1.45 (s, 6H), 1.2-1.4 (m, 6H), 0.8-1.0 (m, 3H), 0.7-0.8 (m, 2H), 0.6-0.7 (m, 2H) |
| 3-40 | (ii) | P-1 | | δ 10.0-10.1 (m, 1H), 7.75 (d, J = 8.5 Hz, 2H), 6.85-7.7 (m, 13H), 6.76 (d, J = 8.8 Hz, 2H), 3.71 (s, 3H), 3.05-3.25 (m, 2H), 2.45-2.65 (m, 2H), 1.45-1.65 (m, 8H), 1.15-1.35 (m, 6H), 0.8-0.9 (m, 3H) |
| 3-41 | (ii) | mixture of P-1 and P-3 | 7:3 | δ 10.85 (s, 1H), 6.75-7.3 (m, 12H), 3.73 (s, 3H), 3.05-3.25 (m, 2H), 2.45-2.65 (m, 2H), 1.56 (s, 6H), 1.4-1.65 (m, 2H), 1.2-1.4 (m, 6H), 1.24 (s, 9H), 0.8-0.9 (m, 3H) <br> δ 9.9-10.0 (m, 1H), 6.75-7.65 (m, 12H), 3.67 (s, 3H), 3.05-3.25 (m, 2H), 2.45-2.65 (m, 2H), 1.56 (s, 6H), 1.4-1.65 (m, 2H), 1.2-1.4 (m, 6H), 1.24 (s, 9H), 0.8-0.9 (m, 3H) |
| 3-43 | (i) | P-1 | | δ 7.9-8.0 (m, 2H), 7.6-7.7 (m, 1H), 7.45-7.55 (m, 2H), 7.20 (d, J = 8.3 Hz, 2H), 6.74 (d, J = 8.2 Hz, 1H), 6.04 (d, 1H), 3.10 (s, 2H), 2.83-3.00 (m, 1H), 1.64 (s, 6H), 1.25 (s, 9H), 1.24 (d, J = 7.2 Hz, 6H) |
| 3-44 | (i) | mixture of P-1 and P-2 | 1:9 | δ 7.01-7.40 (m, 5H), 5.84 (br, 1H), 3.0-3.25 (m, 2H), 2.75-2.91 (m, 1H), 2.2-2.3 (m, 2H), 1.52 (s, 6H), 1.45-1.91 (m, 2H), 1.01-1.44 (m, 6H), 0.83-1.01 (m, 3H) <br> δ 7.01-7.40 (m, 5H), 3.00-3.28 (m, 3H), 2.45-2.65 (m, 1H), 1.52 (s, 6H), 1.45-1.91 (m, 2H), 1.01-1.44 (m, 6H), 0.83-1.01 (m, 3H) |
| 3-45 | (i) | P-1 | | δ 7.85-7.95 (m, 2H), 7.35-7.45 (m, 2H), 7.1-7.3 (m, 5H), 3.94 (br, 1H), 3.2-3.3 (m, 1H), 3.05-3.15 (m, 1H), 1.85-2.0 (m, 2H), 1.57 (s, 3H), 1.55 (s, 3H), 1.33 (s, 9H), 0.95-1.19 (m, 8h), 0.74-0.82 (m, 3H) |
| 3-46 | (i) | P-2 | | δ 7.05-7.2 (m, 1H), 6.95-7.05 (m, 1H), 6.85-6.95 (m, 2H), 4.64 (s, 1H), 2.92-3.13 (m, 2H), 2.73-2.89 (m, 1H), 2.30 (s, 3H), 1.46-1.61 (m, 6H), 1.06-1.19 (m, 6H) |
| 3-47 | (i) | P-2 | | 7.06-7.29 (m, 5H), 4.64 (s, 1H), 3.12 (d, J = 13.4 Hz, 1H), 3.03 (d, J = 13.4 Hz, 1H), 2.73-2.88 (m, 1H), 1.53 (s, 3H), 1.52 (s, 3H), 1.16 (d, J = 6.9 Hz, 3H), 1.13 (d, J = 7.2 Hz, 3H) |
| 3-48 | (i) | mixture of P-1 and P-2 | 5:5 | δ 6.89-7.47 (m, 8H), 6.13 (br, 1H), 3.20 (s, 2H), 3.12-3.19 (m, 1H), 2.49-2.65 (m, 4H), 1.63 (s, 6H), 1.45-1.62 (m, 4H), 1.20-1.43 (m, 12H), 0.96-1.19 (m, 6H), 0.81-0.93 (m, 6H) <br> δ 6.89-7.47 (m, 8H), 4.11 (s, 1H), 3.11 (s, 2H), 2.49-2.65 (m, 4H), 2.35-2.50 (m, 1H), 1.54 (s, 6H), 1.45-1.62 (m, 4H), 1.20-1.43 (m, 12H), 0.96-1.19 (m, 6H), 0.81-0.93 (m, 6H) |
| 3-49 | (i) | P-1 | | δ 7.13-7.19 (m, 3H), 6.73-6.82 (m, 2H), 5.95 (s, 1H), 3.07 (s, 2H), 2.87 (sep, J = 6.9 Hz, 1H), 2.15 (s, 3H), 1.58 (s, 6H), 1.21 (d, J = 7.2 Hz, 6H) |
| 4-01 | (i) | P-2 | | δ 7.18-7.34 (m, 5H), 3.75 (s, 3H), 3.48 (s, 2H), 3.41 (s, 2H), 1.87 (s, 6H) |

TABLE 21-continued

| No. | measuring conditions | tautomers | mixing ratio | $^1$H NMR chemical shift or melting point |
|---|---|---|---|---|
| 4-03 | (i) | P-1 | | δ 7.08-7.30 (m, 7H), 6.87-6.76 (m, 2H), 3.25 (s, 3H), 3.11 (s, 2H), 2.95 (sep, J = 6.9 Hz, 1H), 2.62 (t, J = 7.6 Hz, 2H), 1.63 (s, 6H), 1.51-1.70 (m, 2H), 1.21-1.42 (m, 6H), 1.15 (d, J = 6.8 Hz, 6H), 0.89 (t, J = 6.8 Hz, 3H) |
| 4-12 | (ii) | mixture of P-1 and P-3 | 8:2 | δ 9.26 (s, 1H), 7.1-7.3 (m, 3H), 6.89 (d, J = 6.9 Hz, 2H), 2.82 (sep, J = 6.9 Hz, 1H), 2.20 (t, J = 7.8 Hz, 2H), 1.82 (s, 6H), 1.37 (m, 2H), 1.19 (d, J = 7.3 Hz, 6H), 0.8-0.9 (m, 3H)<br>δ 9.23 (s, 1H), 7.1-7.3 (m, 3H), 7.04 (d, J = 7.0 Hz, 2H), 2.8-3.0 (m, 1H), 2.0-2.15 (m, 2H), 1.79 (s, 6H), 1.37 (m, 2H), 1.21 (d, J = 6.9 Hz, 6H), 0.8-0.9 (m, 3H) |
| 4-13 | (ii) | P-1 | | δ 9.87 (s, 1H), 7.66 (d, J = 7.7 Hz, 2H), 7.59 (d, J = 8.3 Hz, 2H), 7.1-7.5 (m, 10H), 2.5-2.6 (m, 2H), 1.97 (s, 6H), 1.5-1.6 (m, 2H), 1.2-1.4 (m, 6H), 0.7-0.9 (m, 3H) |
| 4-14 | (ii) | mixture of P-1 and P-2 | 6:4 | δ 9.68 (s, 1H), 7.0-8.0 (m, 14H), 2.4-2.6 (m, 2H), 1.92 (s, 6H), 1.0-1.5 (m, 8H), 0.7-0.9 (m, 3H)<br>δ 7.0-8.0 (m, 14H), 3.31 (s, 1H), 2.4-2.6 (m, 2H), 1.87 (s, 6H), 1.0-1.5 (m, 8H), 0.7-0.9 (m, 3H) |
| 4-15 | (ii) | P-1 | | δ 9.78 (s, 1H), 7.05-7.35 (m, 13H), 2.5-2.6 (m, 2H), 1.95 (s, 6H), 1.5-1.6 (m, 2H), 1.28 (s, 9H), 1.2-1.4 (m, 6H), 0.7-0.9 (m, 3H) |
| 4-16 | (ii) | P-1 | | δ 9.59 (s, 1H), 7.55 (d, J = 8.6 Hz, 2H), 7.41 (d, J = 8.6 Hz, 2H), 7.1-7.35 (m, 3H), 7.00 (d, J = 7.0 Hz, 2H), 2.4-2.5 (m, 2H), 1.90 (s, 6H), 1.8-1.9 (m, 2H), 1.05-1.45 (m, 6H), 1.31 (s, 9H), 0.7-0.9 (m, 3H) |
| 4-17 | (ii) | mixture of P-1 and P-3 | 1:6 | δ 9.63 (s, 1H), 7.54 (d, J = 8.0 Hz, 2H), 7.35-7.45 (m, 4H), 7.41 (d, J = 8.6 Hz, 2H), 2.4-2.5 (m, 2H), 1.88 (s, 6H), 1.8-1.9 (m, 2H), 1.0-1.4 (m, 6H), 1.30 (s, 9H), 0.7-0.8 (m, 3H)<br>δ 9.7-9.8 (m, 1H), 7.83 (d, J = 8.5 Hz, 2H), 7.1-7.6 (m, 6H), 2.4-2.5 (m, 2H), 1.88 (s, 6H), 1.8-1.9 (m, 2H), 1.0-1.4 (m, 6H), 1.30 (s, 9H), 0.7-0.8 (m, 3H) |
| 4-18 | (ii) | mixture of P-1 and P-3 | 8:2 | δ 9.96 (s, 1H), 7.3-7.7 (m, 9H), 7.19 (d, J = 8.4 Hz, 2H), 6.87 (d, J = 8.4 Hz, 2H), 3.20 (s, 2H), 2.45-2.6 (m, 2H), 1.56 (s, 6H), 1.35-1.55 (m, 2H), 1.2-1.35 (m, 6H), 0.8-0.9 (m, 3H)<br>δ 9.45 (br, 1H), 7.78 (d, J = 8.6 Hz, 2H), 7.1-7.7 (m, 11H), 3.26 (s, 2H), 2.45-2.6 (m, 2H), 1.50 (s, 6H), 1.35-1.55 (m, 2H), 1.2-1.35 (m, 6H), 0.8-0.9 (m, 3H) |
| 4-19 | (ii) | mixture of P-1 and P-3 | 8:2 | δ 9.87 (s, 1H), 6.8-7.9 (m, 8H), 3.17 (s, 2H), 2.4-2.55 (m, 2H), 1.53 (s, 6H), 1.28 (s, 9H), 1.0-1.5 (m, 8H), 0.7-0.9 (m, 3H)<br>δ 9.3-9.4 (m, 1H), 6.8-7.9 (m, 8H), 3.23 (s, 2H), 2.2-2.4 (m, 2H), 1.47 (s, 6H), 1.25 (s, 9H), 1.0-1.5 (m, 8H), 0.7-0.9 (m, 3H) |
| 4-20 | (ii) | mixture of P-1 and P-3 | 6:4 | δ 9.90 (s, 1H), 7.3-7.7 (m, 9H), 6.80 (d, J = 8.4 Hz, 2H), 6.70 (d, J = 8.3 Hz, 2H), 3.67 (s, 3H), 3.13 (s, 2H), 2.4-2.6 (m, 2H), 1.54 (s, 6H), 1.4-1.6 (m, 2H), 1.0-1.2 (m, 6H), 0.7-0.9 (m, 3H)<br>δ 9.4-9.5 (m, 1H), 6.6-7.8 (m, 13H), 3.68 (s, 3H), 3.17 (s, 2H), 2.4-2.6 (m, 2H), 1.48 (s, 6H), 1.28 (s, 9H), 1.4-1.6 (m, 2H), 1.0-1.2 (m, 6H), 0.7-0.9 (m, 3H) |
| 4-21 | (ii) | mixture of P-1 and P-3 | 7:3 | δ 9.80 (s, 1H), 6.6-7.9 (m, 8H), 3.67 (s, 3H), 3.11 (s, 2H), 2.4-2.6 (m, 2H), 1.51 (s, 6H), 1.28 (s, 9H), 1.0-1.6 (m, 8H), 0.7-0.9 (m, 3H)<br>δ 9.35 (m, 1H), 6.6-7.9 (m, 8H), 3.68 (s, 3H), 3.15 (s, 2H), 2.2-2.4 (m, 2H), 1.45 (s, 6H), 1.0-1.6 (m, 8H), 1.25 (s, 9H), 0.7-0.9 (m, 3H) |
| 4-22 | (ii) | mixture of P-1 and P-3 | 6:4 | δ 9.43 (s, 1H), 6.66 (s, 4H), 3.67 (s, 3H), 3.01 (s, 2H), 2.6-2.8 (m, 2H), 2.2-2.3 (m, 2H), 1.44 (s, 6H), 1.3-1.5 (m, 2H), 1.07 (d, J = 6.8 Hz, 6H), 0.89 (t, J = 7.3 Hz, 3H)<br>δ 8.78 (s, 1H), 6.91 (d, J = 8.3 Hz, 2H), 6.73 (d, J = 8.3 Hz, 2H), 3.68 (s, 3H), 3.08 (s, 2H), 2.7-2.9 (m, 2H), 2.0-2.2 (m, 2H), 1.39 (s, 6H), 1.3-1.5 (m, 2H), 1.07 (d, J = 6.8 Hz, 6H), 0.89 (t, J = 7.3 Hz, 3H) |
| 4-23 | (i) | mixture of P-1 and P-2 | 9:1 | δ 8.0-8.1 (m, 2H), 7.6-7.7 (m, 2H), 7.15-7.3 (m, 3H), 7.05-7.15 (m, 2H), 6.37 (br, 1H), 3.92 (s, 3H), 3.27 (s, 2H), 3.12-3.19 (m, 1H), 1.65 (s, 6H), 1.08 (d, J = 7.2 Hz, 6H)<br>δ 8.0-8.1 (m, 2H), 7.6-7.7 (m, 2H), 7.15-7.3 (m, 3H), 7.05-7.15 (m, 2H), 4.2-4.3 (m, 1H), 3.92 (s, 3H), 3.1-3.2 (m, 2H), 2.35-2.5 (m, 1H), 1.65 (s, 6H), 0.95-1.05 (m, 6H) |
| 4-27 | (i) | P-1 | | δ 9.71 (s, 1H), 7.13-7.33 (m, 3H)., 7.05-7.12 (m, 2H), 4.31 (q, J = 7.1 Hz, 2H), 3.23 (sep, J = 6.9 Hz, 1H), 1.94 (s, 6H), 1.36 (t, J = 7.3 Hz, 3H), 1.30 (d, J = 6.8 Hz, 6H) |
| 4-28 | (ii) | mixture of P-1 and P-3 | 6:4 | δ 9.66 (s, 1H), 6.9-8.3 (m, 11H), 3.60 (s, 2H), 2.82 (sep, J = 6.7 Hz, 1H), 2.58 (t, J = 8.0 Hz, 2H), 1.60 (s, 6H), 1.5-1.7 (m, 2H), 1.2-1.4 (m, 6H), 0.97 (d, J = 5.9 Hz, 6H), 0.87 (t, J = 7.0 Hz, 3H)<br>9.29 (s, 1H), 6.9-8.3 (m, 11H), 3.69 (s, 2H), 2.95 (sep, J = 6.6 Hz, 1H), 2.58 (t, J = 8.0 Hz, 2H), 1.57 (s, 6H), 1.5-1.7 (m, 2H), 1.2-1.4 (m, 6H), 0.99 (d, J = 6.3 Hz, 6H), 0.87 (t, J = 7.0 Hz, 3H) |
| 4-29 | (ii) | mixture of P-1 and P-3 | 7:3 | δ 9.66 (s, 1H), 6.9-8.3 (m, 11H), 3.60 (s, 2H), 2.82 (sep, J = 6.5 Hz, 1H), 2.58 (t, J = 7.7 Hz, 2H), 1.59 (s, 6H), 1.5-1.7 (m, 2H), 1.2-1.4 (m, 10H), 0.97 (d, J = 6.6 Hz, 6H), 0.86 (t, J = 6.4 Hz, 3H)<br>δ 9.29 (s, 1H), 6.9-8.3 (m, 11H), 3.69 (s, 2H), 2.85-3.0 (m, 1H), 2.58 (t, J = 7.7 Hz, 2H), 1.59 (s, 6H), 1.5-1.7 (m, 2H), 1.2-1.4 (m, 10H), 0.97 (d, J = 6.6 Hz, 6H), 0.86 (t, J = 6.4 Hz, 3H) |
| 4-30 | (ii) | mixture of P-1 and P-3 | 7:3 | δ 9.68 (s, 1H), 6.8-8.3 (m, 11H), 3.59 (s, 2H), 2.82 (sep, J = 6.7 Hz, 1H), 1.65-1.8 (m, 5H), 1.59 (s, 6H), 1.1-1.5 (m, 6H), 0.98 (d, J = 6.6 Hz, 6H)<br>δ 9.29 (s, 1H), 6.8-8.3 (m, 11H), 3.69 (s, 2H), 2.85-3.0 (m, 1H), 1.65-1.8 (m, 5H), 1.59 (s, 6H), 1.1-1.5 (m, 6H), 1.04 (d, J = 6.6 Hz, 6H) |
| 4-31 | (ii) | mixture of P-1 and P-3 | 7:3 | δ 10.17 (s, 1H), 6.3-8.3 (m, 10H), 3.62 (s, 2H), 2.95 (sep, J = 5.2 Hz, 1H), 1.57 (s, 6H), 1.03 (d, J = 5.3 Hz, 6H) |

TABLE 21-continued

| No. | measuring conditions | tautomers | mixing ratio | $^1$H NMR chemical shift or melting point |
|---|---|---|---|---|
| | | | | δ 9.69 (s, 1H), 6.3-8.3 (m, 10H), 3.71 (s, 2H), 3.24 (sep, J = 5.2 Hz, 1H), 1.54 (s, 6H), 1.09 (d, J = 5.3 Hz, 6H) |
| 4-32 | (ii) | mixture of P-1 and P-3 | 5:5 | δ 9.81 (s, 1H), 8.0-8.15 (m, 1H), 7.7-7.85 (m, 2H), 6.9-7.6 (m, 8H), 3.62 (s, 2H), 2.58 (t, J = 7.9 Hz, 2H), 2.3-2.45 (m, 2H), 1.57 (s, 6H), 1.0-1.4 (m, 16H), 0.85-1.0 (m, 3H), 0.7-0.85 (m, 3H) |
| | | | | δ 9.72 (s, 1H), 8.25-8.35 (m, 1H), 7.85-7.95 (m, 2H), 6.9-7.6 (m, 8H), 3.72 (s, 2H), 2.58 (t, J = 7.9 Hz, 2H), 2.3-2.45 (m, 2H), 1.54 (s, 6H), 1.0-1.4 (m, 16H), 0.85-1.0 (m, 3H), 0.7-0.85 (m, 3H) |
| 4-33 | (ii) | mixture of P-1 and P-3 | 8:2 | δ 9.61 (s, 1H), 6.8-8.3 (m, 11H), 3.59 (s, 2H), 2.58 (t, J = 7.5 Hz, 2H), 2.4-2.55 (m, 1H), 1.59 (s, 6H), 1.0-1.7 (m, 18H), 0.8-0.9 (m, 3H) |
| | | | | δ 9.28 (s, 1H), 6.8-8.3 (m, 11H), 3.69 (s, 2H), 2.58 (t, J = 7.5 Hz, 2H), 2.4-2.55 (m, 1H), 1.59 (s, 6H), 1.0-1.7 (m, 18H), 0.8-0.9 (m, 3H) |
| 4-34 | (ii) | P-1 | | δ 10.25 (s, 1H), 8.1-8.2 (m, 1H), 7.8-7.9 (m, 1H), 7.77 (d, J = 7.9 Hz, 1H), 7.45-7.55 (m, 3H), 7.35 (t, J = 8.1 Hz, 1H), 7.15-7.25 (m, 4H), 7.07 (d, J = 7.1 Hz, 1H), 6.3-6.4 (m, 1H), 5.95-6.05 (m, 1H), 3.71 (s, 2H), 2.59 (t, J = 7.8 Hz, 2H), 1.63 (s, 6H), 1.45-1.7 (m, 2H), 1.2-1.45 (m, 6H), 0.8-0.9 (m, 3H) |
| 4-35 | (ii) | mixture of P-1 and P-3 | 8:2 | δ 9.74 (s, 1H), 7.1-7.35 (m, 5H), 6.8-6.95 (m, 1H), 6.6-6.7 (m, 1H), 3.42 (s, 2H), 2.89 (sep, J = 6.5 Hz, 1H), 2.57 (t, J = 7.7 Hz, 2H), 1.57 (s, 6H), 1.45-1.65 (m, 2H), 1.2-1.4 (m, 6H), 1.06 (d, J = 6.5 Hz, 6H), 0.8-0.9 (m, 3H) |
| | | | | δ 9.41 (s, 1H), 7.1-7.35 (m, 5H), 6.8-6.95 (m, 1H), 6.7-6.8 (m, 1H), 3.48 (s, 2H), 2.95-3.1 (m, 1H), 2.57 (t, J = 7.7 Hz, 2H), 1.57 (s, 6H), 1.45-1.65 (m, 2H), 1.2-1.4 (m, 6H), 1.06 (d, J = 6.5 Hz, 6H), 0.8-0.9 (m, 3H) |
| 4-36 | (ii) | mixture of P-1 and P-3 | 8:2 | δ 9.74 (s, 1H), 7.1-7.35 (m, 5H), 6.8-6.95 (m, 1H), 6.6-6.7 (m, 1H), 3.43 (s, 2H), 2.8-2.95 (m, 1H), 2.57 (t, J = 7.7 Hz, 2H), 1.52 (s, 6H), 1.5-1.65 (m, 2H), 1.2-1.4 (m, 10H), 1.06 (d, J = 6.2 Hz, 6H), 0.85 (t, J = 6.9 Hz, 3H) |
| | | | | δ 9.45-9.55 (m, 1H), 7.1-7.35 (m, 5H), 6.8-6.95 (m, 1H), 6.7-6.8 (m, 1H), 3.47 (s, 2H), 2.95-3.1 (m, 1H), 2.57 (t, J = 7.7 Hz, 2H), 1.52 (s, 6H), 1.5-1.65 (m, 2H), 1.2-1.4 (m, 10H), 1.06 (d, J = 6.2 Hz, 6H), 0.85 (t, J = 6.9 Hz, 3H) |
| 4-37 | (ii) | mixture of P-1 and P-3 | 7:3 | δ 9.76 (s, 1H), 7.1-7.35 (m, 5H), 6.8-6.95 (m, 1H), 6.6-6.8 (m, 1H), 3.42 (s, 2H), 2.89 (sep, J = 6.5 Hz, 1H), 2.4-2.55 (m, 1H), 1.65-1.9 (m, 5H), 1.52 (s, 6H), 1.1-1.5 (m, 5H), 1.07 (d, J = 6.6 Hz, 6H) |
| | | | | δ 9.41 (s, 1H), 7.1-7.35 (m, 5H), 6.8-6.95 (m, 1H), 6.6-6.8 (m, 1H), 3.4-3.5 (m, 2H), 2.95-3.1 (m, 1H), 2.4-2.55 (m, 1H), 1.65-1.9 (m, 5H), 1.52 (s, 6H), 1.1-1.5 (m, 5H), 1.07 (d, J = 6.6 Hz, 6H) |
| 4-38 | (ii) | mixture of P-1 and P-3 | 7:3 | δ 10.15 (s, 1H), 7.61 (s, 1H), 7.26 (d, J = 3.8 Hz, 1H), 6.6-6.95 (m, 2H), 6.50 (s, 1H), 6.32 (d, J = 5.4 Hz, 1H), 3.42 (s, 2H), 3.02 (sep, J = 5.2 Hz, 1H), 1.52 (s, 6H), 1.12 (d, J = 5.2 Hz, 6H) |
| | | | | δ 9.82 (s, 1H), 7.59 (s, 1H), 7.29 (d, J = 3.7 Hz, 1H), 6.6-6.95 (m, 2H), 6.50 (s, 1H), 6.32 (d, J = 5.4 Hz, 1H), 3.50 (s, 2H), 3.02 (sep, J = 5.2 Hz, 1H), 1.50 (s, 6H), 1.19 (d, J = 5.3 Hz, 6H) |
| 4-39 | (ii) | P-1 | | δ 9.84 (s, 1H), 7.1-7.5 (m, 5H), 6.8-6.95 (m, 1H), 6.6-6.8 (m, 1H), 3.4-3.6 (m, 2H), 2.56 (t, J = 7.7 Hz, 2H), 2.3-2.45 (m, 2H), 1.50 (s, 6H), 1.05-1.65 (m, 16H), 0.75-0.9 (m, 6H) |
| 4-40 | (ii) | mixture of P-1 and P-3 | 7:3 | δ 9.70 (s, 1H), 7.1-7.35 (m, 5H), 6.8-6.95 (m, 1H), 6.6-6.8 (m, 1H), 3.42 (s, 2H), 2.57 (t, J = 7.6 Hz, 2H), 2.4-2.55 (m, 1H), 1.52 (s, 6H), 1.05-1.75 (m, 18H), 0.8-0.9 (m, 3H) |
| | | | | δ 9.34 (s, 1H), 7.1-7.35 (m, 5H), 6.8-6.95 (m, 1H), 6.6-6.8 (m, 1H), 3.48 (s, 2H), 2.57 (t, J = 7.6 Hz, 2H), 2.4-2.55 (m, 1H), 1.52 (s, 6H), 1.05-1.75 (m, 18H), 0.8-0.9 (m, 3H) |
| 4-41 | (ii) | P-1 | | δ 10.30 (s, 1H), 7.53 (s, 1H), 7.28 (d, J = 5.2 Hz, 1H), 7.20 (s, 4H), 6.90 (t, J = 3.5 Hz, 1H), 6.73 (s, 1H), 6.38 (s, 1H), 6.07 (s, 1H), 3.50 (s, 2H), 2.59 (t, J = 7.5 Hz, 2H), 1.58 (s, 6H), 1.5-1.65 (m, 2H), 1.2-1.4 (m, 6H), 0.8-0.9 (m, 3H) |
| 4-42 | (ii) | mixture of P-1 and P-3 | 9:1 | δ 9.57 (s, 1H), 7.1-7.25 (m, 4H), 2.87 (sep, J = 7.1 Hz, 1H), 2.56 (t, J = 8.0 Hz, 2H), 1.62 (s, 6H), 1.45-1.85 (m, 13H), 1.25-1.4 (m, 12H), 1.10 (d, J = 6.8 Hz, 6H), 0.8-0.9 (m, 3H) |
| | | | | δ 9.60 (s, 1H), 7.1-7.25 (m, 4H), 3.0-3.15 (m, 1H), 2.56 (t, J = 8.0 Hz, 2H), 1.62 (s, 6H), 1.45-1.85 (m, 13H), 1.25-1.4 (m, 12H), 1.21 (d, J = 7.1 Hz, 6H), 0.8-0.9 (m, 3H) |
| 4-43 | (ii) | P-1 | | δ 9.57 (s, 1H), 7.17 (s, 4H), 2.8-2.95 (m, 1H), 2.56 (t, J = 7.8 Hz, 2H), 1.62 (s, 6H), 1.2-1.9 (m, 29H), 1.10 (d, J = 6.7 Hz, 6H), 0.86 (t, J = 7.2 Hz, 3H) |
| 4-44 | (ii) | P-1 | | δ 9.58 (s, 1H), 7.19 (dd, J = 8.2 Hz, 13.4 Hz, 4H), 2.8-2.95 (m, 1H), 2.4-2.55 (m, 1H), 1.61 (s, 6H), 1.15-1.9 (m, 27H), 1.11 (d, J = 6.8 Hz, 6H) |
| 4-45 | (ii) | mixture of P-1 and P-3 | 8:2 | δ 9.94 (s, 1H), 7.58 (s, 1H), 6.4-6.5 (m, 1H), 6.27 (d, J = 2.4 Hz, 1H), 3.02 (sep, J = 5.2 Hz, 1H), 1.64 (s, 6H), 1.3-1.85 (m, 17H), 1.13 (d, J = 5.1 Hz, 6H) |
| | | | | δ 9.94 (s, 1H), 7.56 (s, 1H), 6.67 (d, J = 2.2 Hz, 1H), 6.4-6.5 (m, 1H), 3.35-3.45 (m, 1H), 1.64 (s, 6H), 1.3-1.85 (m, 17H), 1.26 (d, J = 5.3 Hz, 6H) |
| 4-46 | (ii) | P-1 | | δ 9.64 (s, 1H), 7.36 (d, J = 7.8 Hz, 2H), 7.13 (d, J = 8.7 Hz, 2H), 2.45-2.65 (m, 4H), 1.59 (s, 6H), 1.05-1.85 (m, 33H), 0.7-0.9 (m, 6H) |
| 4-47 | (ii) | P-1 | | δ 9.53 (s, 1H), 7.1-7.2 (m, 4H), 2.56 (t, J = 8.0 Hz, 2H), 2.45-2.55 (m, 1H), 1.61 (s, 6H), 1.1-1.8 (m, 35H), 0.86 (t, J = 6.8 Hz, 3H) |
| 4-48 | (ii) | P-1 | | δ 10.04 (s, 1H), 7.56 (s, 1H), 7.17 (s, 4H), 6.40 (s, 1H), 6.09 (d, J = 2.9 Hz, 1H), 2.58 (t, J = 7.7 Hz, 2H), 1.75-1.9 (m, 6H), 1.65 (s, 6H), 1.2-1.7 (m, 19H), 0.8-0.95 (m, 3H) |
| 4-49 | (ii) | mixture of P-1 and P-3 | 6:4 | δ 10.21 (s, 1H), 7.2-7.4 (m, 7H), 7.05 (d, J = 4.9 Hz, 2H), 2.93 (s, 2H), 2.8-2.9 (m, 1H), 2.5-2.6 (m, 2H), 1.5-1.65 (m, 2H), 0.9-1.35 (m, 16H), 0.86 (t, J = 5.3 Hz, 3H) |

TABLE 21-continued

| No. | measuring conditions | tautomers | mixing ratio | $^1$H NMR chemical shift or melting point |
|---|---|---|---|---|
| | | | | δ 9.73 (s, 1H), 7.2-7.4 (m, 7H), 6.96 (d, J = 4.6 Hz, 2H), 2.99 (s, 2H), 2.9-3.05 (m, 1H), 2.5-2.6 (m, 2H), 1.5-1.65 (m, 2H), 0.9-1.35 (m, 16H), 0.86 (t, J = 5.3 Hz, 3H) |
| 4-50 | (ii) | mixture of P-1 and P-3 | 6:4 | δ 10.21 (s, 1H), 7.1-7.3 (m, 7H), 7.05 (d, J = 4.8 Hz, 2H), 2.93 (s, 2H), 2.8-2.9 (m, 1H), 2.5-2.6 (m, 2H), 1.5-1.6 (m, 2H), 0.9-1.35 (m, 20H), 0.86 (t, J = 5.4 Hz, 3H) |
| | | | | δ 9.72 (s, 1H), 7.1-7.3 (m, 7H), 6.95 (d, J = 4.3 Hz, 2H), 2.99 (s, 2H), 2.9-3.0 (m, 1H), 2.5-2.6 (m, 2H), 1.5-1.6 (m, 2H), 0.9-1.35 (m, 20H), 0.86 (t, J = 5.4 Hz, 3H) |
| 4-51 | (ii) | mixture of P-1 and P-3 | 6:4 | δ 10.21 (s, 1H), 7.1-7.3 (m, 7H), 7.05 (d, J = 4.6 Hz, 2H), 2.93 (s, 2H), 2.8-2.9 (m, 1H), 2.4-2.6 (m, 1H), 1.75-1.85 (m, 4H), 0.95-1.5 (m, 16H) |
| | | | | δ 9.74 (s, 1H), 7.1-7.3 (m, 7H), 6.9-7.0 (m, 2H), 2.98 (s, 2H), 2.9-3.0 (m, 1H), 2.4-2.6 (m, 1H), 1.65-1.75 (m, 4H), 0.95-1.5 (m, 16H) |
| 4-52 | (ii) | mixture of P-1 and P-3 | 6:4 | δ 10.57 (s, 1H), 7.53 (s, 1H), 7.1-7.25 (m, 5H), 7.04 (d, J = 4.6 Hz, 1H), 6.62 (d, J = 2.4 Hz, 1H), 6.45-6.5 (m, 1H), 2.92 (s, 2H), 2.9-3.05 (m, 1H), 1.0-1.25 (m, 8H), 0.85-1.0 (m, 2H) |
| | | | | δ 10.21 (s, 1H), 7.59 (s, 1H), 7.1-7.25 (m, 5H), 6.97 (d, J = 4.5 Hz, 1H), 6.4-6.5 (m, 1H), 6.28 (d, J = 2.4 Hz, 1H), 2.98 (s, 2H), 2.75-2.85 (m, 1H), 1.0-1.25 (m, 8H), 0.85-1.0 (m, 2H) |
| 4-53 | (ii) | mixture of P-1 and P-3 | 7:3 | δ 10.41 (s, 1H), 6.95-7.45 (m, 9H), 2.95-3.1 (m, 2H), 2.55 (t, J = 5.8 Hz, 2H), 2.40 (d, J = 5.8 Hz, 2H), 1.5-1.65 (m, 2H), 1.0-1.4 (m, 16H), 0.75-0.95 (m, 8H) |
| | | | | δ 9.80 (s, 1H), 6.95-7.45 (m, 9H), 2.95-3.1 (m, 2H), 2.55 (t, J = 5.8 Hz, 2H), 2.40 (d, J = 5.8 Hz, 2H), 1.5-1.65 (m, 2H), 1.0-1.4 (m, 16H), 0.75-0.95 (m, 8H) |
| 4-54 | (ii) | mixture of P-1 and P-3 | 6:4 | δ 10.22 (s, 1H), 7.1-7.3 (m, 7H), 7.0-7.1 (m, 2H), 2.92 (s, 2H), 2.56 (t, J = 5.8 Hz, 2H), 2.45-2.7 (m, 1H), 1.5-1.65 (m, 8H), 1.25-1.5 (m, 8H), 1.0-1.25 (m, 4H), 0.8-0.95 (m, 5H) |
| | | | | δ 9.69 (s, 1H), 7.1-7.3 (m, 7H), 6.9-7.0 (m, 2H), 2.98 (s, 2H), 2.56 (t, J = 5.8 Hz, 2H), 2.45-2.7 (m, 1H), 1.5-1.65 (m, 8H), 1.25-1.5 (m, 8H), 1.0-1.25 (m, 4H), 0.8-0.95 (m, 5H)) |
| 4-55 | (ii) | P-1 | | δ 10.21 (s, 1H), 7.53 (s, 1H), 7.05-7.35 (m, 9H), 6.40 (s, 1H), 6.08 (s, 1H), 3.10 (s, 2H), 2.57 (t, J = 5.8 Hz, 2H), 1.5-1.65 (m, 2H), 1.2-1.4 (m, 6H), 0.9-1.0 (m, 2H), 0.8-0.9 (m, 5H) |
| 4-56 | (ii) | mixture of P-1 and P-3 | 7:3 | δ 9.68 (s, 1H), 7.1-7.35 (m, 4H), 6.85-7.1 (m, 2H), 6.65-6.85 (m, 2H), 3.09 (s, 2H), 2.86 (sep, J = 6.8 Hz, 1H), 2.57 (t, J = 7.4 Hz, 2H), 2.22 (s, 3H), 1.50 (s, 6H), 1.4-1.65 (m, 2H), 1.15-1.4 (m, 10H), 1.02 (d, J = 6.2 Hz, 6H), 0.8-0.95 (m, 3H) |
| | | | | δ 9.29 (s, 1H), 7.1-7.35 (m, 4H), 6.85-7.1 (m, 4H), 3.14 (s, 2H), 2.95-3.05 (m, 1H), 2.57 (t, J = 7.4 Hz, 2H), 2.22 (s, 3H), 1.50 (s, 6H), 1.4-1.65 (m, 2H), 1.15-1.4 (m, 10H), 1.0-1.1 (m, 6H), 0.8-0.95 (m, 3H) |
| 4-57 | (ii) | mixture of P-1 and P-3 | 7:3 | δ 9.69 (s, 1H), 7.15-7.2 (m, 4H), 6.85-7.0 (m, 2H), 6.73 (d, J = 7.9 Hz, 2H), 3.09 (s, 2H), 2.85 (sep, J = 6.7 Hz, 1H), 2.45-2.55 (m, 1H), 2.22 (s, 3H), 1.65-1.9 (m, 5H), 1.50 (s, 6H), 1.15-1.5 (m, 5H), 1.02 (d, J = 6.8 Hz, 6H) |
| | | | | δ 9.29 (s, 1H), 7.30 (d, J = 7.9 Hz, 2H), 7.15-7.2 (m, 4H), 6.85-7.0 (m, 4H), 3.14 (s, 2H), 2.95-3.05 (m, 1H), 2.45-2.55 (m, 1H), 2.22 (s, 3H), 1.65-1.9 (m, 5H), 1.50 (s, 6H), 1.15-1.5 (m, 5H), 1.06 (d, J = 7.1 Hz, 6H) |
| 4-58 | (ii) | mixture of P-1 and P-3 | 7:3 | δ 10.11 (s, 1H), 7.61 (s, 1H), 6.96 (d, J = 5.6 Hz, 2H), 6.74 (d, J = 5.7 Hz, 2H), 6.50 (s, 1H), 6.32 (s, 1H), 3.10 (s, 2H), 2.98 (sep, J = 5.3 Hz, 1H), 2.22 (s, 3H), 1.49 (s, 6H), 1.07 (d, J = 5.2 Hz, 6H) |
| | | | | δ 9.70 (s, 1H), 7.59 (s, 1H), 6.85-7.05 (m, 4H), 6.50 (s, 1H), 6.32 (s, 1H), 3.17 (s, 2H), 2.98 (sep, J = 5.3 Hz, 1H), 2.22 (s, 3H), 1.46 (s, 6H), 1.15 (d, J = 4.6 Hz, 6H) |
| 4-59 | (ii) | mixture of P-1 and P-3 | 5:5 | δ 9.79 (s, 1H), 7.1-7.3 (m, 4H), 6.9-7.05 (m, 2H), 6.77 (d, J = 7.7 Hz, 2H), 3.18 (s, 2H), 2.57 (t, J = 7.5 Hz, 2H), 2.35-2.5 (m, 2H), 2.22 (s, 3H), 1.49 (s, 6H), 1.55-1.65 (m, 2H), 1.2-1.45 (m, 8H), 1.05-1.2 (m, 6H), 0.85-0.9 (m, 3H), 0.7-0.85 (m, 3H) |
| | | | | δ 9.71 (s, 1H), 7.42 (d, J = 7.9 Hz, 2H), 7.1-7.3 (m, 4H), 6.9-7.05 (m, 2H), 3.11 (s, 2H), 2.57 (t, J = 7.5 Hz, 2H), 2.35-2.5 (m, 2H), 2.22 (s, 3H), 1.46 (s, 6H), 1.55-1.65 (m, 2H), 1.2-1.45 (m, 8H), 1.05-1.2 (m, 6H), 0.85-0.9 (m, 3H), 0.7-0.85 (m, 3H) |
| 4-60 | (ii) | mixture of P-1 and P-3 | 7:3 | δ 9.64 (s, 1H), 7.15-7.25 (m, 4H), 6.85-7.05 (m, 2H), 6.65-6.8 (m, 2H), 3.09 (s, 2H), 2.58 (t, J = 7.8 Hz, 2H), 2.4-2.65 (m, 1H), 2.22 (s, 3H), 1.45-1.75 (m, 8H), 1.50 (s, 6H), 1.25-1.4 (m, 8H), 1.05-1.25 (m, 2H), 0.8-0.95 (m, 3H) |
| | | | | δ 9.2-9.3 (m, 1H), 7.15-7.35 (m, 4H), 6.85-7.05 (m, 4H), 3.1-3.2 (m, 2H), 2.58 (t, J = 7.8 Hz, 2H), 2.4-2.65 (m, 1H), 2.22 (s, 3H), 1.45-1.75 (m, 8H), 1.50 (s, 6H), 1.25-1.4 (m, 8H), 1.05-1.25 (m, 2H), 0.8-0.95 (m, 3H) |
| 4-61 | (ii) | P-1 | | δ 10.23 (s, 1H), 7.52 (s, 1H), 7.20 (m, 4H), 7.00 (d, J = 7.4 Hz, 2H), 6.86 (d, J = 7.8 Hz, 2H), 6.37 (d, J = 1.6 Hz, 1H), 6.03 (d, J = 2.82 Hz, 1H), 3.19 (s, 2H), 2.59 (t, J = 7.8 Hz, 2H), 2.22 (s, 3H), 1.54 (s, 6H), 1.45-1.7 (m, 2H), 1.2-1.45 (m, 6H), 0.8-0.9 (m, 3H) |
| 4-62 | (ii) | P-1 | | δ 7.22 (d, J = 8.1 Hz, 2H), 7.11 (d, J = 8.2 Hz, 2H), 6.99 (d, J = 7.7 Hz, 2H), 6.69 (d, J = 7.9 Hz, 2H), 4.11 (q, J = 7.1 Hz, 2H), 3.01 (s, 2H), 2.9-3.0 (m, 1H), 2.58 (t, J = 7.8 Hz, 2H), 2.23 (s, 3H), 1.45-1.65 (m, 2H), 1.51 (s, 6H), 1.2-1.4 (m, 6H), 1.09 (d, J = 6.9 Hz, 6H), 1.07 (t, J = 7.1 Hz, 3H). 0.8-0.9 (m, 3H) |
| 4-71 | (i) | P-1 | | δ 7.15-7.63 (m, 8H), 6.90-6.98 (m, 2H), 3.17 (s, 2H), 2.60-2.74 (m, 1H), 1.64 (s, 6H), 0.96 (d, J = 6.9 Hz, 6H) |
| 4-72 | | | | m.p. 117~119° C. |
| 4-73 | | | | m.p. 69~71° C. |

TABLE 21-continued

| No. | measuring conditions | tautomers | mixing ratio | $^1$H NMR chemical shift or melting point |
|---|---|---|---|---|
| 4-74 | | | | m.p. 113~115° C. |
| 4-75 | | | | m.p. 102~104° C. |
| 4-76 | | | | m.p. 101~103° C. |
| 4-80 | | | | m.p. 88~90° C. |
| 4-81 | | | | m.p. 58~60° C. |
| 4-82 | | | | m.p. 133~135° C. |
| 4-83 | | | | m.p. 109~111° C. |
| 4-84 | | | | m.p. 108~110° C. |
| 4-85 | | | | m.p. 88~90° C. |
| 4-86 | | | | m.p. 140~142° C. |
| 4-87 | | | | m.p. 108~110° C. |
| 4-88 | (i) | P-1 | | δ 12.7-13.1 (br, 1H), 7.12-7.21 (m, 3H), 6.84-6.94 (m, 2H), 3.11 (s, 2H), 3.04-3.15 (m, 1H), 2.42 (s, 3H), 1.58 (s, 6H), 1.27 (d, J = 6.9 Hz, 6H) |
| 4-89 | (i) | P-1 | | δ 10.7-11.4 (br, 1H), 7.12-7.22 (m, 3H), 6.84-6.95 (m, 2H), 3.87 (s, 3H), 3.16 (s, 2H), 2.98-3.12 (m, 1H), 2.25 (s, 3H), 1.57 (s, 6H), 1.21 (d, J = 6.8 Hz, 6H) |
| 4-90 | | | | m.p. 149~151° C. |
| 4-91 | (ii) | P-1 | | δ 9.6-9.9 (br, 1H), 7.1-7.25 (m, 3H), 6.8-6.9 (m, 2H), 4.02 (t, J = 6.6 Hz, 2H), 3.11 (s, 2H), 3.07 (sep, J = 7.5 Hz, 1H), 2.11 (s, 3H), 1.5-1.7 (m, 2H), 1.49 (s, 6H), 1.2-1.4 (m, 6H), 1.09 (d, J = 6.8 Hz, 6H), 0.87 (t, J = 6.8 Hz, 3H) |

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| Total | 1000 mg |

A compound represented by the formula (1) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| Total | 100 mg |

A compound represented by the formula (1) and lactose are sifted through a 60-mesh sieve. Corn starch is sifted through a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| Total | 150 mg |

A compound represented by the formula (1) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| Total | 150 mg |

A compound represented by the formula (1), lactose, microcrystalline cellulose and CMC—Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Compound represented by the formula (I) | 100 mg |
| Saturated Fatty Acid Glyceride | 1000 mL |

Solutions having the above-mentioned composition are usually administered to a patient intravenously at a rate of 1 mL per 1 minute.

Assay Example

Next, usefulness of compounds of the present invention as inhibitors of myeloma cell growth will be demonstrated specifically with reference to the following assay example, but the present invention is by no means restricted thereto. The $CO_2$ concentration (%) in a $CO_2$ incubator is expressed by the ratio of $CO_2$ in the atmosphere in vol %.

Aassay Example

Cell Proliferation Assay

Myeloma cell strain RPMI8226 (DS Pharma Biomedical Co., Ltd.) was incubated in liquid culture in a $CO_2$ incubator (5% $CO_2$) in RPMI1640 medium containing 10% (v/v) fetal calf serum. The resulting cells were suspended in RPMI640 medium(GIBCO) containing 10% (v/v) fetal calf serum and plated in 96-well flat-bottomed microplates (Corning Incorporated) in 100 μl/mL (400000 cells/well) per well. Furtheremore, each of the compounds prepared in Synthetic Examples was dissolved in dimethylsulfoxide and added at 0.1% (v/v) to final concentrations of 0.1 to 10 μg/mL. As the negative control, dimethyl sulfoxide was added at 0.1% (v/v).

After 4 days of incubation at 37° C. in liquid culture in a $CO_2$ incubator (5% $CO_2$), the viable cells were counted by the WST assay. A 10-μl aliquot of Cell Counting Kit-8 reagent solution (Dojindo Molecular Technologies, Inc.) was added to each well and incubated in a $CO_2$ incubator (5% $CO_2$) for 4 hours for color reaction, and light absorbance was measured at 450 nm by using a microplate reader. As the cell growth inhibitory activities in the presence of the test compounds relative to that in the absence of them (negative control), the concentrations (IC50) yielding 50% inhibition of cell proliferation were calculated. The results indicate that the compounds of the present invention greatly inhibited growth of RPMI8226 cells and confirm that the compounds of the present invention have growth inhibitory activities on myeloma cells.

The IC50 values (μg/mL) for test compounds against RPMI8226 cells were shown in Table 22.

TABLE 22

| No. | IC50 (μg/mL) |
| --- | --- |
| 1-03 | 4.0 |
| 1-07 | 8.1 |
| 3-01 | 11.1 |
| 3-02 | 11.6 |
| 3-03 | 6.4 |
| 3-07 | 8.8 |
| 2-01 | 10.6 |
| 2-03 | 6.3 |
| 2-05 | 5.3 |

TABLE 22-continued

| No. | IC50 (μg/mL) |
| --- | --- |
| 2-06 | 10.8 |
| 2-07 | 7.4 |
| 2-09 | 8.9 |
| 2-10 | 8.4 |
| 2-12 | 4.9 |
| 2-14 | 6.6 |
| 2-15 | 5.8 |
| 2-16 | 11.2 |
| 2-19 | 13.4 |
| 2-20 | 38.8 |
| 2-21 | 6.8 |
| 2-22 | 4.2 |
| 2-23 | 0.16 |
| 2-24 | 6.8 |
| 2-25 | 6.2 |
| 2-28 | 68.6 |
| 2-29 | 14.5 |
| 2-31 | 5.7 |
| 2-32 | 4.1 |
| 2-33 | 12.3 |
| 2-49 | 3.6 |
| 2-34 | 6.7 |
| 2-35 | 5.6 |
| 2-36 | 17.7 |
| 2-37 | 3.9 |
| 2-39 | 4.4 |
| 2-40 | 6.5 |
| 2-43 | 7.9 |
| 2-44 | 7.7 |
| 2-45 | 20.7 |
| 2-46 | 3.9 |
| 2-47 | 3.3 |
| 2-48 | 6.4 |
| 2-50 | 3.9 |
| 3-05 | 4.9 |
| 3-06 | 7.7 |
| 3-07 | 5.3 |
| 3-09 | 4.3 |
| 3-10 | 7.6 |
| 3-11 | 4.8 |
| 3-12 | 5.4 |
| 3-13 | 5.4 |
| 3-14 | 7.9 |
| 3-16 | 3.5 |
| 3-17 | 4.4 |
| 3-18 | 7.4 |
| 3-19 | 4.3 |
| 3-20 | 6.6 |
| 3-21 | 4.5 |
| 3-22 | 3.9 |
| 3-23 | 8.5 |
| 3-24 | 4.2 |
| 3-25 | 7.4 |
| 3-27 | 7.7 |
| 3-28 | 4.9 |
| 3-29 | 5.5 |
| 3-30 | 24.9 |
| 3-31 | 6.4 |
| 3-32 | 27.1 |
| 3-33 | 5.9 |
| 3-34 | 3.2 |
| 3-35 | 3.8 |
| 3-38 | 4.2 |
| 3-39 | 0.4 |
| 3-40 | 76.7 |
| 3-41 | 17.0 |
| 3-43 | 8.0 |
| 3-44 | 3.3 |
| 3-45 | 5.6 |
| 3-46 | 3.3 |
| 3-47 | 3.3 |
| 3-49 | 4.3 |
| 4-01 | 11.1 |
| 4-03 | 6.4 |
| 4-12 | 5.6 |
| 4-13 | 8.3 |
| 4-14 | 3.8 |

TABLE 22-continued

| No. | IC50 (μg/mL) |
|---|---|
| 4-15 | 10.2 |
| 4-16 | 4.2 |
| 4-17 | 5.6 |
| 4-18 | 5.6 |
| 4-19 | 21.6 |
| 4-20 | 4.8 |
| 4-21 | 6.1 |
| 4-22 | 4.1 |
| 4-23 | 6.3 |
| 4-27 | 5.5 |
| 4-28 | 19.5 |
| 4-30 | 43.2 |
| 4-31 | 3.3 |
| 4-33 | 54.6 |
| 4-34 | 18.7 |
| 4-35 | 10.5 |
| 4-36 | 13.5 |
| 4-37 | 8.5 |
| 4-38 | 3.4 |
| 4-39 | 10.0 |
| 4-40 | 9.9 |
| 4-41 | 12.5 |
| 4-45 | 3.9 |
| 4-48 | 8.5 |
| 4-49 | 3.4 |
| 4-50 | 3.3 |
| 4-51 | 3.2 |
| 4-52 | 8.4 |
| 4-53 | 4.5 |
| 4-54 | 36.1 |
| 4-55 | 11.7 |
| 4-56 | 30.2 |
| 4-57 | 10.0 |
| 4-58 | 3.3 |
| 4-59 | 22.5 |
| 4-60 | 38.6 |
| 4-61 | 6.4 |
| 4-71 | 3.2 |
| 4-72 | 4.3 |
| 4-73 | 5.9 |
| 4-74 | 6.6 |
| 4-75 | 3.2 |
| 4-76 | 3.6 |
| 4-80 | 9.6 |
| 4-81 | 5.4 |
| 4-82 | 6.7 |
| 4-83 | 7.1 |
| 4-84 | 3.2 |
| 4-85 | 5.4 |
| 4-86 | 3.3 |
| 4-87 | 9.9 |
| 4-88 | 3.7 |
| 4-89 | 4.7 |
| 4-90 | 5.5 |
| 4-91 | 57.7 |

INDUSTRIAL APPLICABILITY

The pyrazole compounds of the present invention show excellent growth inhibition activity on myeloma cells and are extremely useful for treatment of multiple myeloma.

The entire disclosures of Japanese Patent Application No. 2010-268758 filed on Dec. 1, 2010 and Japanese Patent Application No. 2011-217818 filed on Sep. 30, 2011 including specifications, claims and summaries are incorporated herein by reference in their entireties.

The invention claimed is:

1. A pyrazole compound of formula (1), a tautomer of the compound, or a pharmaceutically acceptable salt or solvate thereof:

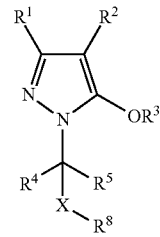

(1)

wherein $R^1$ is a hydrogen atom, $C_1$-$C_{10}$ alkyl, $C_1$-$C_{10}$ alkyl substituted with $R^{17}$, $C_1$-$C_{10}$ haloalkyl, $C_3$-$C_{10}$ cycloalkyl, $C_3$-$C_{10}$ halocycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, —C($R^{12}$)=NO$R^{13}$, D1 to D23, cyano, phenyl, phenyl substituted with ($R^{11}$)$_a$, benzyl or benzyl having a benzene ring which may be substituted with ($R^{11}$)$_a$, in which when a is an integer of at least 2, each $R^{11}$ may be identical with or different from one another, and when there are two neighboring $R^{11}$, the two neighboring $R^{11}$ may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —$_{CH2}$CH$_2$N($R^{y}$)—, —CH$_2$N($R^{y}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{y}$)CH=CH—, —OCH=N—, —SCH=N—, —N($R^{y}$)CH=N—, —N($R^{y}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{11}$, a 5-membered or 6-membered ring which may have a hydrogen atom on the ring-constituting carbon atoms replaced by a Z which may be identical with or different from one another, if two or more Z's are present, $R^2$ is a hydrogen atom, a halogen atom, cyano, $C_1$-$C_{10}$ alkyl, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, —C($R^{12}$)=NO$R^{13}$, D1 to D23, benzyl, benzyl having a benzene ring optionally substituted with ($R^{21}$)$_e$, phenyl or phenyl optionally substituted with ($R^{21}$)$_e$, in which when e is an integer of at least 2, each $R^{21}$ may be identical with or different from one another, and when there are two neighboring $R^{21}$, the two neighboring $R^{21}$ may form —CH$_2$CH$_2$CH$_2$—, —CH$_2$CH$_2$O—, —CH$_2$OCH$_2$, —OCH$_2$O—, —CH$_2$CH$_2$S—, —CH$_2$SCH$_2$—, —CH$_2$CH$_2$N($R^{y}$)—, —CH$_2$N($R^{y}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{y}$)CH=CH—, —OCH=N—, —SCH=N—, —N($R^{y}$)CH=N—, —N($R^{y}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present, $R^3$ is a hydrogen atom, $C_1$-$C_6$ alkyl, $C_3$-$C_6$ cycloalkyl, $C_1$-$C_6$ alkoxy$C_1$-$C_6$ alkyl, $C_2$-$C_6$ alkenyl, $C_2$-$C_6$ alkenyl optionally substituted with $R^{31}$, $C_2$-$C_6$ alkynyl, $C_2$-$C_6$ alkynyl optionally substituted with $R^{31}$, —C(O)$R^{12}$, —C(O)O$R^{12}$, —C(O)N($R^{12}$)$R^{13}$, —Si($R^{32}$)($R^{33}$)$R^{34}$, benzyl or benzyl having a benzene ring which may be substituted with $(R^{15})_g$, in which when g is an integer of at least 2, each $R^{15}$ may be identical with or different from one another, X is a single bond or —$(CR^6R^7)_n$—

$R^4$ and $R^5$ are each independently $C_1$-$C_6$ alkyl or $C_3$-$C_6$ cycloalkyl, and $R^4$ and $R^5$ may form —$CH_2CH_2$—, —$CH_2CH_2CH_2$—, —$CH_2CH_2CH_2CH_2$— or —$CH_2CH_2CH_2CH_2CH_2$— to form a 3-membered, 4-membered, 5-membered or 6-membered ring together with the carbon atoms attached to $R^4$ and $R^5$, $R^6$ and $R^7$ are each independently a hydrogen atom or $C_1$-$C_6$ alkyl, $R^8$ is D1 to D23, E1 to E8, M1 to M9, $C_3$-$C_{10}$ cycloalkyl, F1, F2, $C_3$-$C_{10}$ cycloalkenyl, phenyl or phenyl optionally substituted with $(R^{81})_k$, in which when k is an integer of at least 2, each $R^{81}$ may be identical with or different from one another, and when there are two neighboring $R^{81}$, the two neighboring $R^{81}$ may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH=CH$—, —$OCH=CH$—, —$SCH=CH$—, —$N(R^y)CH=CH$—, —$OCH=N$—, —$SCH=N$—, —$N(R^y)CH=N$—, —$N(R^y)N=CH$—, —$CH=CHCH=CH$—, —$OCH_2CH=CH$—, —$N=CHCH=CH$—, —$N=CHCH=N$— or —$N=CHN=CH$— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present, D1 to D23 are aromatic heterocyclic rings of structural formulae, respectively,

D1

D2

D3

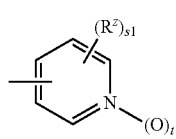

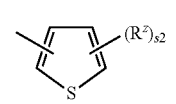

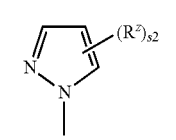

-continued

D4

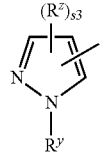

D5

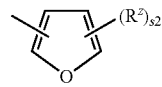

D6

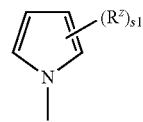

D7

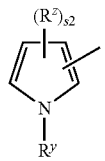

D8

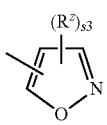

D9

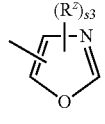

D10

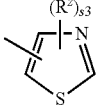

D11

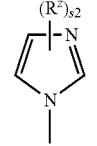

D12

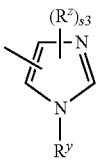

D13

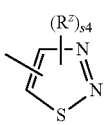

D14

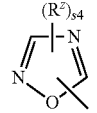

-continued
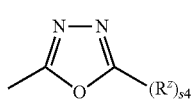 D15
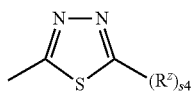 D16
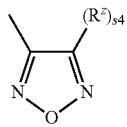 D17
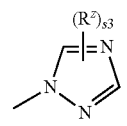 D18
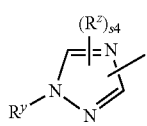 D19
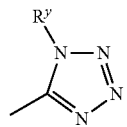 D20
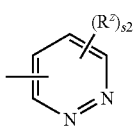 D21
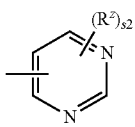 D22
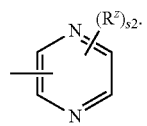 D23
E1 to E8 are saturated heterocyclic rings of structural formulae, respectively,
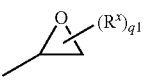 E1
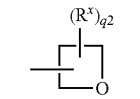 E2
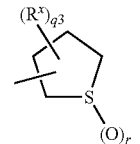 E3
-continued
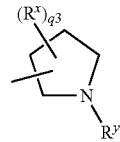 E4
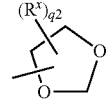 E5
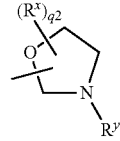 E6
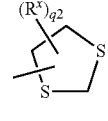 E7
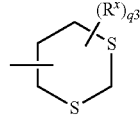 E8
M1 to M9 are partially unsaturated aromatic heterocyclic rings of formulae, respectively,
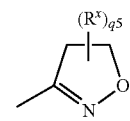 M1
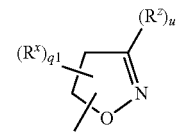 M2
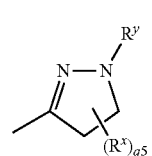 M3
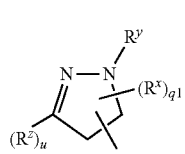 M4
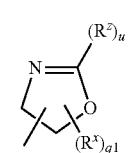 M5

-continued

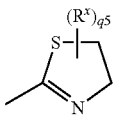
M6

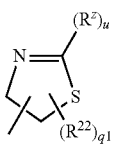
M7

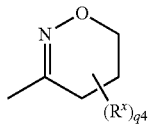
M8

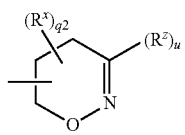
M9

F1 and F2 are rings of formulae, respectively,

F1

F2

$R^x$ is a hydrogen atom, $C_1$-$C_6$ alkyl, $C_1$-$C_6$ haloalkyl, $C_3$-$C_6$ cycloalkyl, $C_3$-$C_6$ halocycloalkyl, —$OR^{82}$, —C(O) $R^{12}$, —C(O)$OR^{12}$, phenyl, phenyl which may be substituted with $(R^{15})_d$, benzyl or benzyl having a benzene ring which may be substituted with $(R^{15})_d$, in which when d is an integer of at least 2, each $R^{15}$ may be identical with or different from one another, $R^y$ is $C_1$-$C_{10}$ alkyl, $C_1$-$C_{10}$ haloalkyl, $C_3$-$C_{10}$ cycloalkyl, $C_3$-$C_{10}$ halocycloalkyl, phenyl, phenyl which may be substituted with $(R^{15})_d$, benzyl or benzyl having a benzene ring which may be substituted with $(R^{15})_d$, in which when d is an integer of at least 2, each $R^{15}$ may be identical with or different from one another, $R^z$ is a halogen atom, cyano, nitro, $C_1$-$C_{10}$ alkyl, $C_1$-$C_{10}$ haloalkyl, $C_1$-$C_{10}$ alkoxy, $C_1$-$C_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —C(O)$NH_2$, —C(S)$NH_2$, —S(O)$_2$$NH_2$, phenoxy, phenyl or phenyl which may be substituted with $(R^{16})_m$, and when m is an integer of at least 2, each $R^{16}$ may be identical with or different from one another, in which when s1, s2 or s3 is an integer of at least 1, each $R^z$ may be identical with or different from one another, and when there are two neighboring $R^z$, the two neighboring $R^z$, may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)$$CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH=CH$—, —$OCH=CH$—, —$SCH=CH$—, —$N(R^y)CH=CH$—, —$OCH=N$—, —$SCH=N$—, —$N(R^y)CH=N$—, —$N(R^y)N=CH$—, —$CH=CHCH=CH$—, —$OCH_2CH=CH$—, —$N=CHCH=CH$—, —$N=CHCH=N$— or —$N=CHN=CH$— to form, together with the carbon atoms attached to the two neighboring $R^z$, a 5-membered or 6-membered ring which may have a hydrogen atom on the ring-constituting carbon atoms replaced by a Z which may be identical with or different from one another, if two or more Z's are present, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, $C_1$-$C_6$ alkoxy($C_1$-$C_6$) alkyl, $C_1$-$C_6$ alkoxy($C_1$-$C_6$) alkoxy, nitro, cyano or phenyl, $R^{12}$ and $R^{13}$ are each independently a hydrogen atom, $C_1$-$C_{10}$ alkyl, $C_3$-$C_{10}$ cycloalkyl, $C_1$-$C_{10}$ haloalkyl, $C_3$-$C_{10}$ halocycloalkyl, D1 to D23, benzyl, benzyl having a benzene ring which may optionally be substituted with $(R^{14})_b$, phenyl or phenyl which may optionally be substituted with $(R^{14})_b$, in which when b is an integer of at least 2, each $R^{14}$ may be identical with or different from one another, and when there are two neighboring $R^{14}$, the two neighboring $R^{14}$ may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)$$CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH=CH$—, —$OCH=CH$—, —$SCH=CH$—, —$N(R^y)CH=CH$—, —$OCH=N$—, —$SCH=N$—, —$N(R^y)CH=N$—, —$N(R^y)N=CH$—, —$CH=CHCH=CH$—, —$OCH_2CH=CH$—, —$N=CHCH=CH$—, —$N=CHCH=N$— or —$N=CHN=CH$— to form, together with the carbon atoms attached to the two $R^{14}$, a 5-membered or 6-membered ring which may have a hydrogen atom on the ring-constituting carbon atoms replaced by a Z which may be identical with or different from one another, if two or more Z's are present, $R^{14}$ is a halogen atom, nitro, cyano, $C_1$-$C_{10}$ alkyl, $C_1$-$C_{10}$ haloalkyl, $C_1$-$C_{10}$ alkoxy, $C_1$-$C_{10}$ haloalkoxy, phenoxy or phenyl, $R^{15}$ is a halogen atom, $C_1$-$C_6$ alkyl, $C_1$-$C_6$ alkoxy, $C_1$-$C_6$ haloalkyl, $C_1$-$C_6$ haloalkoxy, $C_3$-$C_6$ cycloalkyl, $C_3$-$C_6$ cycloalkoxy, $C_3$-$C_6$ halocycloalkyl, $C_3$-$C_6$ halocycloalkoxy, nitro, cyano or phenyl, $R^{16}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, nitro, cyano or phenyl, and when there are two neighboring $R^{16}$, the two neighboring $R^{16}$ may form —$OCH_2O$— to form a 5-membered ring together with the carbon atoms to the two R16, $R^{17}$ is —C(O)$OR^{12}$, phenyl or phenyl substituted with $(R^{11})_a$, in which when a is an integer of at least 2, each $R^{11}$ may be identical with or different from one another, $R^{21}$ is a halogen atom, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_6$ alkoxy($C_1$-$C_6$) alkyl, —$OR^{23}$, —C(O)$R^{24}$, —C(O)OR$^{24}$, —NR$^{24}$R$^{25}$, —C(O)NR$^{24}$R$^{25}$, —S(O)$_2$NR$^{24}$R$^{25}$, phenyl or phenyl which may be substituted with (R$^{22}$)$_f$, in which when f is an integer of at least 2, each R$^{22}$ may be identical with or different from one other, and when there are two neighboring R$^{22}$, the two neighboring R$^{22}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^y$)—, —CH$_2$N(R$^y$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^y$)CH=CH—, —OCH=N—, —SCH=N—, —N(R$^y$)CH=N—, —N(R$^y$)N=CH—, —CH=CHCH=CH—, —OCH$_2$CH=CH—, —N=CHCH=CH—, —N=CHCH=N— or —N=CHN=CH— to form, together with the carbon atoms attached to the two R$^{22}$, a 5-membered or 6-membered ring which may have a hydrogen atom on the ring-constituting carbon atoms replaced by a Z which may be identical with or different from one another, if two or more Z's are present, R$^{22}$ is a halogen atom, C$_1$-C$_{10}$ alkyl, C$_1$-C$_{10}$ alkoxy, C$_1$-C$_{10}$ haloalkyl, C$_1$-C$_{10}$ haloalkoxy, C$_3$-C$_{10}$ cycloalkyl, C$_3$-C$_{10}$ cycloalkoxy, C$_3$-C$_{10}$ halocycloalkyl, C$_3$-C$_{10}$ halocycloalkoxy, nitro, cyano or phenyl, R$^{23}$ is a hydrogen atom, C$_1$-C$_{10}$ alkyl, C$_1$-C$_{10}$ haloalkyl, C$_3$-C$_{10}$ cycloalkyl, C$_3$-C$_{10}$ halocycloalkyl, C$_1$-C$_6$ alkoxy (C$_1$-C$_6$) alkyl, phenyl, phenyl which may be substituted with (R$^{22}$)$_f$, benzyl or benzyl having a benzene ring which may be substituted with (R$^{22}$)$_f$, in which when f is an integer of at least 2, each R$^{22}$ may be identical with different from one another, R$^{24}$ and R$^{25}$ are each independently a hydrogen atom, C$_1$-C$_{10}$ alkyl, C$_3$-C$_{10}$ cycloalkyl, C$_1$-C$_{10}$ haloalkyl, C$_3$-C$_{10}$ halocycloalkyl, benzyl, benzyl having a benzene ring which may optionally be substituted with (R$^{14}$)$_b$, 1-phenethyl, 1-phenethyl having a benzene ring which may optionally be substituted with (R$^{14}$)$_b$, 2-phenethyl, 2-phenethyl having a benzene ring which may optionally be substituted with (R$^{14}$)$_b$, phenyl or phenyl which may optionally be substituted with (R$^{14}$)$_b$, in which when b is an integer of at least 2, each R$^{14}$ may be identical with or different from one another, R$^{31}$ is a halogen atom or phenyl, R$^{32}$, R$^{33}$ and R$^{34}$ are each independently C$_1$-C$_{10}$ alkyl, C$_3$-C$_{10}$ cycloalkyl, benzyl, benzyl having a benzene ring which may optionally be substituted with (R$^{14}$)$_b$, phenyl or phenyl which may optionally be substituted with (R$^{14}$)$_b$, in which when b is an integer of at least 2, each R$^{14}$ may be identical with or different from one another, R$^{81}$ is a halogen atom, nitro, cyano, C$_1$-C$_{10}$ alkyl, C$_1$-C$_{10}$ haloalkyl, C$_3$-C$_{10}$ cycloalkyl, C$_3$-C$_{10}$ halocycloalkyl, C$_1$-C$_6$ alkoxy(C$_1$-C$_6$) alkyl, —OR$^{23}$, —C(R$^{83}$)=NR$^{84}$, —C(R$^{83}$)=NOR$^{84}$, —C(O)R$^{24}$, —C(O)OR$^{24}$, —S(O)cR$^{24}$, —OS(O)$_2$R$^{24}$, —NR$^{24}$R$^{25}$, —C(O)NR$^{24}$R$^{25}$, —C(S)NH$_2$, —S(O)$_2$NR$^{24}$R$^{25}$, phenyl or phenyl which may be substituted with (R$^{22}$)$_m$, in which when m is an integer of at least 2, each R$^{22}$ may be identical with or different from one another, R$^{82}$ is a hydrogen atom, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy (C$_1$-C$_6$) alkyl, phenyl, phenyl which may be substituted with (R$^{15}$)$_d$, benzyl or benzyl having a benzene ring which may be substituted with (R$^{15}$)$_d$, in which when d is an integer of at least 2, each R$^{15}$ may be identical with or different from one another, R$^{83}$ and R$^{84}$ are each independently a hydrogen atom, C$_1$-C$_6$ alkyl, C$_1$-C$_6$ haloalkyl, C$_3$-C$_6$ cycloalkyl, C$_3$-C$_6$ halocycloalkyl, phenyl, phenyl which may be substituted with (R$^{15}$)$_d$, benzyl or benzyl having a benzene ring which may be substituted with (R$^{15}$)$_d$, in which when d is an integer of at least 2, each R$^{15}$ may be identical with or different from one another, Z is a halogen atom, cyano, nitro, C$_1$-C$_{10}$ alkyl, C$_1$-C$_{10}$ haloalkyl, C$_1$-C$_{10}$ alkoxy, C$_1$-C$_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —C(O)NH$_2$, —C(S)NH$_2$, or —S(O)$_2$NH$_2$, a, b, d, e, f, g, k and m are each independently an integer of from 1 to 5, c is an integer of from 0 to 2, q1 is an integer of from 0 to 3, q2 is an integer of from 0 to 5, q3 is an integer of from 0 to 7, q4 is an integer of from 0 to 6, q5 is an integer of from 0 to 4, r is an integer of from 0 to 2, s1 is an integer of from 0 to 4, s2 is an integer of from 0 to 3, s3 is an integer of from 0 to 2, s4 is an integer of 0 or 1, n is an integer of 1, t is an integer of 0 or 1, and u is an integer of 0 or 1.

2. The pyrazole compound according to claim 1, a tautomer of the compound, or a pharmaceutically acceptable salt or solvate thereof, wherein X is —(CR$^6$R$^7$)$_n$.

3. The pyrazole compound according to claim 2, a tautomer of the compound, or a pharmaceutically acceptable salt or solvate thereof, wherein R$^1$ is C$_1$-C$_{10}$ alkyl, C$_1$-C$_{10}$ alkyl substituted with R$^{17}$, C$_1$-C$_6$ haloalkyl, C$_3$-C$_6$ cycloalkyl, —C(O)R$^{12}$, —C(O)OR$^{12}$, —C(O)N(R$^{13}$)R$^{12}$, —C(R$^{12}$)=NR$^{13}$, —C(R$^{12}$)=NOR$^{13}$, D1 to D12, D18, D19, D21 to D23, phenyl or phenyl substituted with (R$^{11}$)a, in which when there are two neighboring R$^{11}$, the two neighboring R$^{11}$ may form —OCH$_2$O—, —OCH$_2$CH$_2$O—, —OCH=CH—, —CH=CHCH=CH— or —N=CHCH=CH— to form, together with the carbon atoms attached to the two R$^{11}$, a 5-membered or 6-membered ring which may have a hydrogen atom on the ring-constituting carbon atoms optionally replaced by a Z which may be identical with or different from one another, if two or more Z's are present, R$^2$ is a hydrogen atom, a halogen atom, C$_1$-C$_6$ alkyl, C$_3$-C$_6$ cycloalkyl, D1, D2, D4 to D12, D18, D19, D21 to D23, —C(O)R$^{12}$, —C(O)OR$^{12}$, benzyl, benzyl having a benzene ring optionally substituted with (R$^{21}$)$_e$, phenyl or phenyl optionally substituted with (R$^{21}$)$_e$, in which when there are two neighboring R$^{21}$, the two neighboring R$^{21}$ may form —OCH$_2$O—, —OCH$_2$CH$_2$O—, —OCH=CH— or —CH=CHCH=CH—, to form, together with the carbon atoms attached to the two R$^{21}$, a 5-membered or 6-membered ring which may have a hydrogen atom on the ring-constituting carbon atoms replaced by one or more Z's which may be identical with or different from one another, if two or more Z's are present, R$^3$ is a hydrogen atom, C$_1$-C$_4$ alkyl, C$_3$-C$_4$ cycloalkyl, C$_1$-C$_4$ alkoxy(C$_1$-C$_4$) alkyl, —C(O)R$^{12}$, —C(O)OR$^{12}$, —C(O)N($R^{12}$)$R^{13}$, —Si($R^{32}$)($R^{33}$)$R^{34}$, benzyl or benzyl having a benzene ring which may be substituted with ($R^{15}$)$_g$, $R^4$ and $R^5$ are each independently $C_1$-$C_4$ alkyl, each of $R^6$ and $R^7$ is a hydrogen atom, $R^8$ is D1, D2, D4, D5, D7 to D12, D19, D22, D23, E1 to E8, F1, F2, $C_3$-$C_{10}$ cycloalkyl, phenyl or phenyl optionally substituted with ($R^{81}$)$_k$, and in which when there are two neighboring $R^{81}$, the two neighboring $R^{81}$ may form —OCH$_2$O—, —CH$_2$CH$_2$CH$_2$—, —OCH$_2$CH$_2$O—, —OCH=CH—, —CH=CHCH=CH— or —N=CHCH=CH—, to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present, $R^x$ is a hydrogen atom, $C_1$-$C_6$ alkyl, $C_1$-$C_6$ haloalkyl or phenyl, $R^y$ is $C_1$-$C_6$ alkyl, $C_3$-$C_6$ cycloalkyl, phenyl or phenyl which may be substituted with ($R^{15}$)$_d$, $R^z$ is a halogen atom, $C_1$-$C_6$ alkyl, phenoxy, phenyl or phenyl which may be substituted with ($R^{16}$)$_m$, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl, $R^{12}$ and $R^{13}$ are each independently a hydrogen atom, $C_1$-$C_6$ alkyl, $C_3$-$C_6$ cycloalkyl, $C_1$-$C_6$ haloalkyl, $C_1$-$C_6$ halocycloalkyl, D2, D4, D5, D7, D21, D22, D23, benzyl, benzyl having a benzene ring which may optionally be substituted with ($R^{14}$)$_b$, phenyl or phenyl which may optionally be substituted with $R^{14}$)$_b$, in which when there are two neighboring $R^{14}$, the two neighboring $R^{14}$ may form —OCH$_2$O—, —OCH$_2$CH$_2$O—, —OCH=CH—, —CH=CHCH=CH— or —N=CHCH=CH—, to form together with the carbon atoms attached to the two $R^{14}$, a 5-membered or 6-membered ring which may have a hydrogen atom on the ring-constituting carbon atoms replaced by a Z which may be identical with or different from one another, if two or more Z's are present, $R^{14}$ is a halogen atom, nitro, cyano, $C_1$-$C_6$ alkyl, $C_1$-$C_6$ haloalkyl, $C_1$-$C_6$ alkoxy, $C_1$-$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy, and when there are two neighboring $R^{16}$, the two neighboring $R^{16}$ may form —OCH$_2$O—, to form a 5-membered ring together with the carbon atoms to the two $R^{16}$, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with ($R^{22}$)$_f$, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$, the two neighboring $R^{22}$ may form —OCH$_2$O—, to form, together with the carbon atoms attached to the two $R^{22}$, a 5-membered ring, $R^{32}$, $R^{33}$ and $R^{34}$ are each independently $C_1$-$C_6$ alkyl, $C_3$-$C_6$ cycloalkyl, benzyl, benzyl having a benzene ring which may optionally be substituted with ($R^{14}$)$_b$, phenyl or phenyl which may optionally be substituted with ($R^{14}$)$_b$), $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl.

4. The pyrazole compound according to claim 3, a tautomer of the compound, or a pharmaceutically acceptable salt or solvate thereof, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —C(O)OR$^{12}$, D2, D4, D5, D7, D21, D22, D23, phenyl or phenyl substituted with ($R^{11}$), in which when there are two neighboring $R^{11}$, the two neighboring $R^{11}$ may form —CH=CHCH=CH— to form, together with the carbon atoms attached to the two $R^{11}$, a 6-membered ring which may have a hydrogen atom on the ring-constituting carbon atoms replaced by a Z which may be identical with or different from one another, if two or more Z's are present, $R^2$ is a hydrogen atom, a halogen atom, $C_1$-$C_6$ alkyl, $C_3$-$C_6$ cycloalkyl, D2, D7, benzyl, benzyl having a benzene ring optionally substituted with ($R^{21}$)$_e$, phenyl or phenyl optionally substituted with ($R^{21}$)$_e$, in which when there are two neighboring $R^{21}$, the two neighboring $R^{21}$ may form —OCH$_2$O—, —OCH$_2$CH$_2$O—, —OCH=CH— or —CH=CHCH=CH— to form, together with the carbon atoms attached to the two $R^{21}$, a 5-membered or 6-membered ring which may have a hydrogen atom on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)OR$^{12}$, —C(O)N($R^{12}$)$R^{13}$, —Si($R^{32}$)($R^{33}$)$R^{34}$ or benzyl, $R^8$ is D2, D7, D23, F1, F2, phenyl or phenyl optionally substituted with ($R^{81}$)$_k$, in which when there are two neighboring $R^{81}$, the two neighboring $R^{81}$ may form —OCH$_2$O—, —CH$_2$CH$_2$CH$_2$— or —CH=CHCH=CH— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with ($R^{16}$)$_m$, $R^{12}$ and $R^{13}$ are each independently a hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, $R^{17}$ is —C(O)OR$^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, $R^{32}$, $R^{33}$ and $R^{34}$ are each independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy.

5. The pyrazole compound according to claim 4, a tautomer of the compound, or a pharmaceutically acceptable salt or solvate thereof, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with ($R^{11}$)$_a$, $R^2$ is a hydrogen atom, a halogen atom, $C_1$-$C_6$ alkyl, D2, benzyl, benzyl having a benzene ring optionally substituted with $(R^{21})_e$, phenyl or phenyl optionally substituted with $(R^{21})_e$,
  in which when there are two neighboring $R^{21}$, the two neighboring $R^{21}$ may form —OCH$_2$O—, —OCH$_2$CH$_2$O— or —CH=CHCH=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present,
$R^3$ is a hydrogen atom,
$R^8$ is D2, F1, F2, phenyl or phenyl optionally substituted with $(R^{81})_k$,
  in which when there are two neighboring $R^{81}$, the two neighboring $R^{81}$ may form —OCH$_2$O—, —CH$_2$CH$_2$CH$_2$— or —CH=CHCH=CH— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present,
$R^z$ is a halogen atom, $C_1$-$C_6$ alkyl, phenoxy or phenyl,
$R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro,
$R^{12}$ is $C_1$-$C_6$ alkyl,
$R^{17}$ is —C(O)OR$^{12}$ or phenyl,
$R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and
$R^{81}$ is a halogen atom, $C_1$-$C_6$ alkyl, $C_1$-$C_6$ haloalkyl, $C_1$-$C_6$ alkoxy, phenyl or phenoxy.

6. The pyrazole compound according to claim 1, a tautomer of the compound, or a pharmaceutically acceptable salt or solvate thereof, wherein $R^2$ is a hydrogen atom, a halogen atom, cyano, $C_1$-$C_{10}$ alkyl, $C_1$-$C_{10}$ alkyl substituted with $R^{17}$, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)R$^{12}$, —C(O)OR$^{12}$, —C(R$^{12}$)=NR$^{13}$, —C(R$^{12}$)=NOR$^{13}$, D1 to D23, benzyl, benzyl having a benzene ring optionally substituted with $(R^{21})_e$, phenyl or phenyl optionally substituted with $(R^{21})_e$,
  in which when there are two neighboring $R^{21}$'s, the two neighboring $R^{21}$'s may form —CH$_2$CH$_2$CH$_2$—, —CH$_2$CH$_2$O—, —CH$_2$OCH$_2$—, OCH$_2$O—, —CH$_2$CH$_2$S—, —CH$_2$SCH$_2$—, —CH$_2$CH$_2$N(R$^{y'}$)—, —CH$_2$N(R$^{y'}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{y'}$)CH=CH—, —OCH=N—, —SCH=N—, —N(R$^{y'}$)CH=N—, —N(R$^{y'}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present, and
X is a single bond.

7. The pyrazole compound according to claim 6, a tautomer of the compound, or a pharmaceutically acceptable salt or solvate thereof, wherein $R^1$ is $C_1$-$C_{10}$ alkyl, $C_1$-$C_{10}$ alkyl substituted with $R^{17}$, $C_1$-$C_6$ haloalkyl, $C_3$-$C_6$ cycloalkyl, —C(O)R$^{12}$, —C(O)OR$^{12}$, —C(O)N(R$^{13}$)R$^{12}$, —C(R$^{12}$)=NOR$^{13}$, D1 to D12, D18, D19, D21 to D23, phenyl or phenyl substituted with $(R^{11})_a$,
  in which when there are two neighboring $R^{11}$, the two neighboring $R^{11}$ may form —OCH$_2$O—, —OCH$_2$CH$_2$O—, —OCH=CH—, —CH=CHCH= CH— or —N=CHCH=CH— to form, together with the carbon atoms attached to the two $R^{11}$, a 5-membered or 6-membered ring which may have a hydrogen atom on the ring-constituting carbon atoms replaced by Z which may be identical with or different from one another, if two or more Z's are present,
$R^2$ is $C_1$-$C_6$ alkyl, $C_3$-$C_6$ cycloalkyl, D1, D2, D4 to D12, D18, D19, D21 to D23, benzyl, benzyl having a benzene ring optionally substituted with $(R^{21})_e$, phenyl or phenyl optionally substituted with $(R^{21})_e$,
  in which when there are two neighboring $R^{21}$, the two neighboring $R^{21}$ may form —OCH$_2$O—, —OCH$_2$CH$_2$O—, —OCH=CH— or —CH=CHCH=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present,
$R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)R$^{12}$, —C(O)OR$^{12}$, —C(O)N(R$^{12}$)R$^{13}$, —Si(R$^{32}$)(R$^{33}$)R$^{34}$, benzyl or benzyl having a benzene ring which may be substituted with $(R^{15})_g$,
$R^4$ and $R^5$ are each independently $C_1$-$C_4$ alkyl,
$R^8$ is D1, D2, D4, D5, D7 to D12, D19, D22, D23, E1 to E9, F1, F2, $C_3$-$C_{10}$ cycloalkyl, phenyl or phenyl optionally substituted with $(R^{81})_k$,
  in which when there are two neighboring $R^{81}$, the two neighboring $R^{81}$ may form —OCH$_2$O—, —CH$_2$CH$_2$CH$_2$—, —OCH$_2$CH$_2$O—, —OCH=CH—, —CH=CHCH=CH— or —N=CHCH=CH— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present,
$R^x$ is a hydrogen atom, $C_1$-$C_6$ alkyl, $C_1$-$C_6$ haloalkyl or phenyl,
$R^y$ is $C_1$-$C_6$ alkyl, $C_3$-$C_6$ cycloalkyl, phenyl or phenyl which may be substituted with $(R^{15})_d$, benzyl or benzyl having a benzene ring which may be substituted with $(R^{15})_d$,
$R^z$ is a halogen atom, $C_1$-$C_6$ alkyl, phenoxy, phenyl or phenyl which may be substituted with $(R^{16})_m$,
$R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl,
$R^{12}$ and $R^{13}$ are each independently a hydrogen atom, $C_1$-$C_6$ alkyl, $C_3$-$C_6$ cycloalkyl, $C_1$-$C_6$ haloalkyl, $C_3$-$C_6$ halocycloalkyl, D2, D4, D5, D7, D21, D22, D23, benzyl, benzyl having a benzene ring which may optionally be substituted with $(R^{14})_b$,
  in which when there are two neighboring $R^{14}$, the two neighboring $R^{14}$ may form —OCH$_2$O—, —OCH$_2$CH$_2$O—, —OCH=CH—, —CH=CHCH= CH— or —N=CHCH=CH— to form, together with the carbon atoms attached to the two $R^{14}$, a 5-membered or 6-membered ring which may have a hydrogen atom on the ring-constituting carbon atoms replaced by a Z which may be identical with or different from one another, if two or more Z's are present, $R^{14}$ is a halogen atom, nitro, cyano, $C_1$-$C_6$ alkyl, $C_1$-$C_6$ haloalkyl, $C_1$-$C_6$ alkoxy, $C_1$-$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{16}$, the two neighboring $R^{16}$ may form —OCH$_2$O— to form a 5-membered ring together with the carbon atoms to the two $R^{16}$, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with $(R^{22})_p$, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$, the two neighboring $R^{22}$ may form —OCH$_2$O— to form, together with the carbon atoms attached to the two $R^{22}$, a 5-membered ring, each of $R^{32}$, $R^{33}$ and $R^{34}$ are each independently $C_1$-$C_6$ alkyl, $C_3$-$C_6$ cycloalkyl, benzyl, benzyl having a benzene ring which may optionally be substituted with $(R^{14})_b$, phenyl or phenyl which may optionally be substituted with $(R^{14})_b$, $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl.

8. The pyrazole compound according to claim 7, a tautomer of the compound, or a pharmaceutically acceptable salt or solvate thereof, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —C(O)OR$^{12}$, D2, D4, D5, D7, D21, D23, phenyl or substituted with a $(R^{11})_a$, in which when there are two neighboring $R^{11}$, the two neighboring $R^{11}$ may form —CH=CHCH=CH— to form, together with the carbon atoms attached to the two $R^{11}$'s, a 5-membered or 6-membered ring which may have a hydrogen atom on the ring-constituting carbon atoms replaced by a Z which may be identical with or different from one another, if two or more Z's are present, $R^2$ is $C_1$-$C_6$ alkyl, $C_3$-$C_6$ cycloalkyl, D2, D7, benzyl, benzyl having a benzene ring optionally substituted with $(R^{21})_e$, phenyl or phenyl optionally substituted with $(R^{21})_e$, in which when there are two neighboring $R^{21}$, the two neighboring $R^{21}$ may form —OCH$_2$O—, —OCH$_2$CH$_2$O—, —OCH=CH— or —CH=CHCH=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)R$^{12}$, —C(O)OR$^{12}$, —C(O)N(R$^{12}$)R$^{13}$, —Si(R$^{32}$)(R$^{33}$)R$^{34}$ or benzyl, $R^8$ is D2, D7, D23, F1, F2, phenyl or phenyl optionally substituted with $(R^{81})_k$, in which when there are two neighboring $R^{81}$, the two neighboring $R^{81}$ may form —OCH$_2$O—, —CH$_2$CH$_2$CH$_2$— or —CH=CHCH=CH— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with $(R^{16})_m$, $R^{12}$ and $R^{13}$ are each independently a hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ loalkyl or $C_1$-$C_6$ haloalkoxy, $R^{17}$ is —C(O)OR$^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, $R^{32}$, $R^{33}$ and $R^{34}$ are each independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl or phenoxy.

9. The pyrazole compound according to claim 8, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with $(R^{11})_a$, $R^2$ is $C_1$-$C_6$ alkyl, D2, benzyl, benzyl having a benzene ring optionally substituted with $(R^{21})_e$, phenyl or phenyl optionally substituted with $(R^{21})_e$, in which when there are two neighboring $R^{21}$, the two neighboring $R^{21}$ may form —OCH$_2$O—, —OCH$_2$CH$_2$O— or —CH=CHCH=CH— to form, together with the carbon atoms attached to the two $R^{21}$, a 5-membered or 6-membered ring which may have a hydrogen atom on the ring-constituting carbon atoms replaced by a Z which may be identical with or different from one another, if two or more Z's are present, $R^3$ is a hydrogen atom, $R^8$ is D2, F1, F2, phenyl or phenyl optionally substituted with $(R^{81})_k$, in which when there are two neighboring $R^{81}$, the two neighboring $R^{81}$ may form —OCH$_2$O—, —CH$_2$CH$_2$CH$_2$— or —CH=CHCH=CH— to form, together with the carbon atoms attached to the two $R^{81}$, a 5-membered or 6-membered ring which may have a hydrogen atom on the ring-constituting carbon atoms replaced by a Z which may be identical with or different from one another, if two or more Z's are present, $R^z$ is a halogen atom, $C_1$-$C_6$ alkyl, phenoxy or phenyl, $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, $R^{12}$ is $C_1$-$C_6$ alkyl, $R^{17}$ is —C(O)OR$^{12}$ or phenyl, $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and $R^{81}$ is a halogen atom, $C_1$-$C_6$ alkyl, $C_1$-$C_6$ haloalkyl, $C_1$-$C_6$ alkoxy or phenoxy.

10. A therapeutic agent for multiple myeloma comprising the pyrazole compound according to claim 1, a tautomer of the compound or a pharmaceutically acceptable salt or solvate thereof as an active ingredient.

* * * * *